US008173133B2

(12) United States Patent
Bauer et al.

(10) Patent No.: US 8,173,133 B2
(45) Date of Patent: May 8, 2012

(54) ACYL PSEUDODIPEPTIDES WHICH CARRY A FUNCTIONALIZED AUXILIARY ARM

(75) Inventors: Jacques Bauer, St. Prex (CH); Olivier Martin, Orleans (FR); Sylvain Rodriguez, St. Prex (CH)

(73) Assignee: OM Pharma, Meyrin/Geneva (CH)

( * ) Notice: Subject to any disclaimer, the term of this patent is extended or adjusted under 35 U.S.C. 154(b) by 130 days.

(21) Appl. No.: 12/640,527

(22) Filed: Dec. 17, 2009

(65) Prior Publication Data

US 2010/0215685 A1 Aug. 26, 2010

Related U.S. Application Data

(63) Continuation of application No. 10/169,053, filed as application No. PCT/FR00/03650 on Dec. 21, 2000, now Pat. No. 7,799,762, which is a continuation of application No. PCT/IB99/02038, filed on Dec. 22, 1999.

(51) Int. Cl.
 *A61K 39/00* (2006.01)
(52) U.S. Cl. ............... 424/191.1; 424/184.1; 424/185.1; 424/193.1; 424/204.1; 424/234.1; 424/262.1; 424/274.1; 560/195; 560/196
(58) Field of Classification Search ............... 424/184.1, 424/185.1, 193.1, 204.1, 234.1, 265.1, 274.1; 560/195, 196
See application file for complete search history.

(56) References Cited

U.S. PATENT DOCUMENTS

| 5,700,910 | A | 12/1997 | Metzger et al. |
| 7,157,092 | B1 | 1/2007 | Bauer et al. |

FOREIGN PATENT DOCUMENTS

| DE | 41 23 365 | 1/1993 |
| DE | 41 23 366 | 1/1993 |
| EP | 519 327 | 12/1992 |
| EP | 668 289 | 3/1995 |
| WO | WO95/14026 | 5/1995 |
| WO | WO 99/32428 | 7/1999 |
| WO | WO 00/00462 | 1/2000 |

OTHER PUBLICATIONS

McGahren W. J et al, (Beta-Lysyloxy)myoinositol guanidino glycoside antibiotics), Journal of Organic Chemistry, vol. 46, No. 4, pp. 792-799.
Moon Byung Jo et al, Synthesis of Enkephalin Degrading Peptidase Inhibitors,Bulletin of Korean Chemistry Society, vol. 18, No. 7, 1997, pp. 778-781; (w/English Translation).
Restovtseva Li et al, Mass Spectrometry in the investigation of Beta Lysine containing peptides, Organic Mass Spectrometry, vol. 6, No. 1, 1972, pp. 1-8; (w/English Translation).

(Continued)

*Primary Examiner* — Deborah D Carr
(74) *Attorney, Agent, or Firm* — Law Offices of Albert Wai-Kit Chan, PLLC

(57) ABSTRACT

The present invention is directed in particular to dipeptide-like compounds derived from functionally substituted amino acids, having fatty acid chains bound thereto through amidification of the amine functional groups of said dipeptide-like compounds, one end portion of which bears an accessory functional side chain spacer, with the other end portion being an acid group either in neutral or charged state.
Compounds of the present invention have immunomodulating properties like adjuvants, In addition, compounds of the invention can be grafted on a given antigen in order to modulate or tune the immune response or can be equally grafted on a pharmaceutical carrier to enhance the therapeutic effect or targeting thereof. Accordingly, compounds of the invention find use in human and veterinary medicine both as immunogens and diagnostic tools.

20 Claims, 86 Drawing Sheets

OTHER PUBLICATIONS

Rostovtseva Li et al, Peptides of L Beta- Lysine IV, structure and the synthesis of the . . . Streptothrycin D, Zhurnal Obshchei Khimil, vol. 41, No. 7, pp. 1611-1616; (w/English Translation).

Rostovtseva Li et al, Peptides of L. Beta-Lysine III, Synthesis and mass spectrometric . . . of L. Beta- Lysine, Zhurna Obshchei Khimil, vol. 41, No. 7, pp. 1664-1611; (w/Eglish Transiation).

PCT International Search Report for OM Pharma International Application No. PCT/FR00/08659, Filed Dec. 21, 2000, Dated May 2, 2001.

PCT nternational Preliminary Examination Renort for OM Pharma International Application No. PCT/FR00/03659, Filed Dec. 21, 2000, Dated Oct. 25, 2001.

Savoy Fabienne et al, "Synthetic triacylated lipid A derivative activates antigen presenting cells via the TLR4 pathway and . . . in vivo", Immunology, 211(2006), 767-777.

Mascarell, Laurent et al, "A Synthetic triacylated pseudo-dipeptide molecue promotes Th1/TReg immune responses and enhances . . . sublingual route", Vaccine (2007)26, 108-118.

Byl B et al, "OM197-MP-AC induces the maturation of human dendritic cells and promotes a primary T cell response", International Immunopharmacology 3(2003), 417-425.

Fagan Maura et al, "Acyciic Analogue of Lipid A Stimulates TNF-a and Arachidonate Release . . . LPS signaling pathway", Journal Of Immunology, 1994(153) pp. 5230-5238.

Fagan Maura et al, "Acyclic Analogue of Lipid A Stimulates TNF-a and Arachidonate Release . . . LPS signaling pathway", Journal Of Immunology, 1994(153): pp. 5230-5238.

Annotated Patent Selections—Pulmonary Allergy Dermatological Gastrointestinal & Arthritis, Expert Opinion Ther. Patents(2007), 17(12)pp. 1477-1487.

Yohko Kawai et al, "A typical bacterial omithine containing lipid N alpha -(D)-[3-(hexadecanoyloxy) . . . adjuvant", FEMS Immunol Med Microbiol, 1999, 23(1) pp. 67-73 abstract.

Bulusu Murty A.R.C et al, "Synthesis of Diamino Acids-Potential Lipopolysaccharide Antagonists" Tetrahedron Letters, vol. 33, No. 14, pp. 1859-1862, 1992.

OM-197-MC-Succ

OM-197-N'(C10-2OC8)-MC-AC

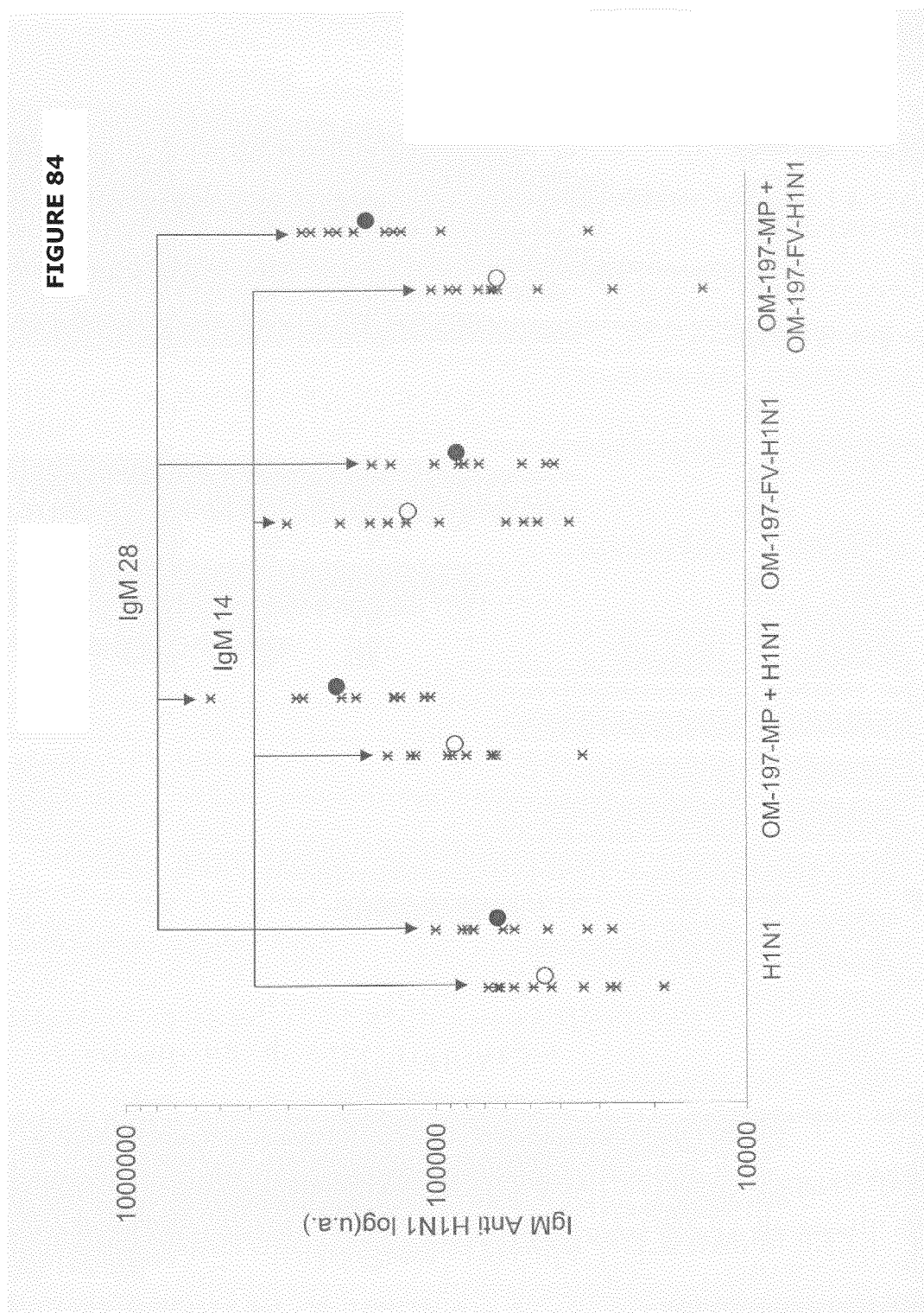

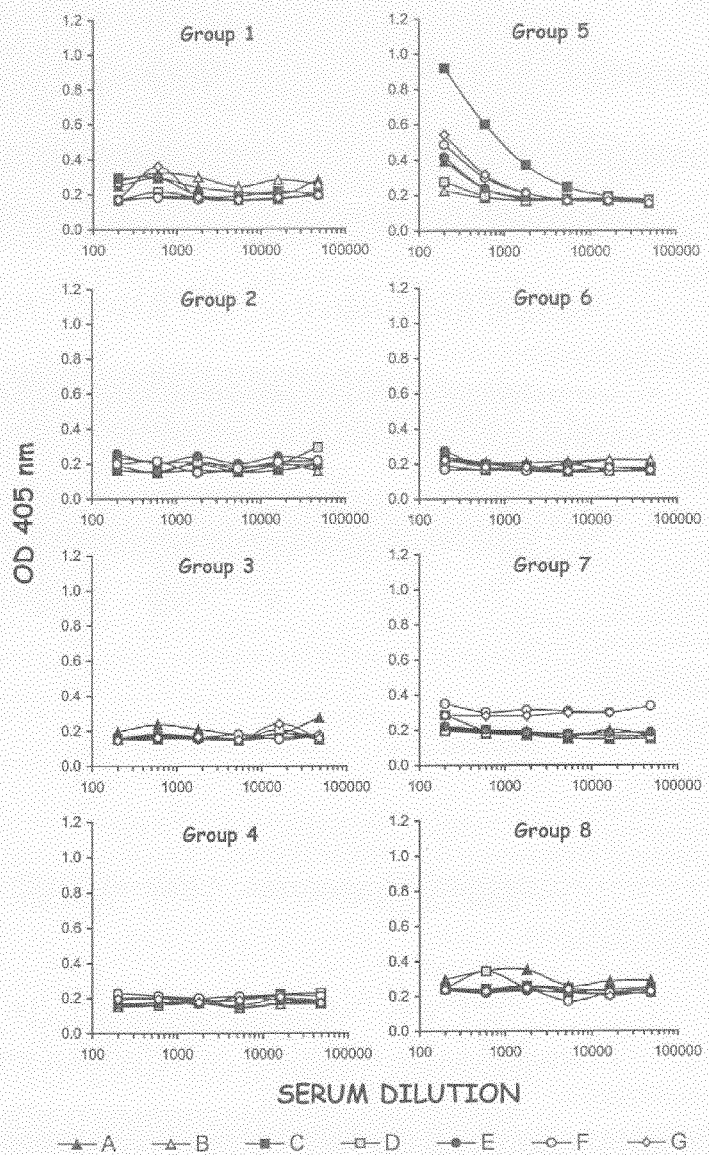

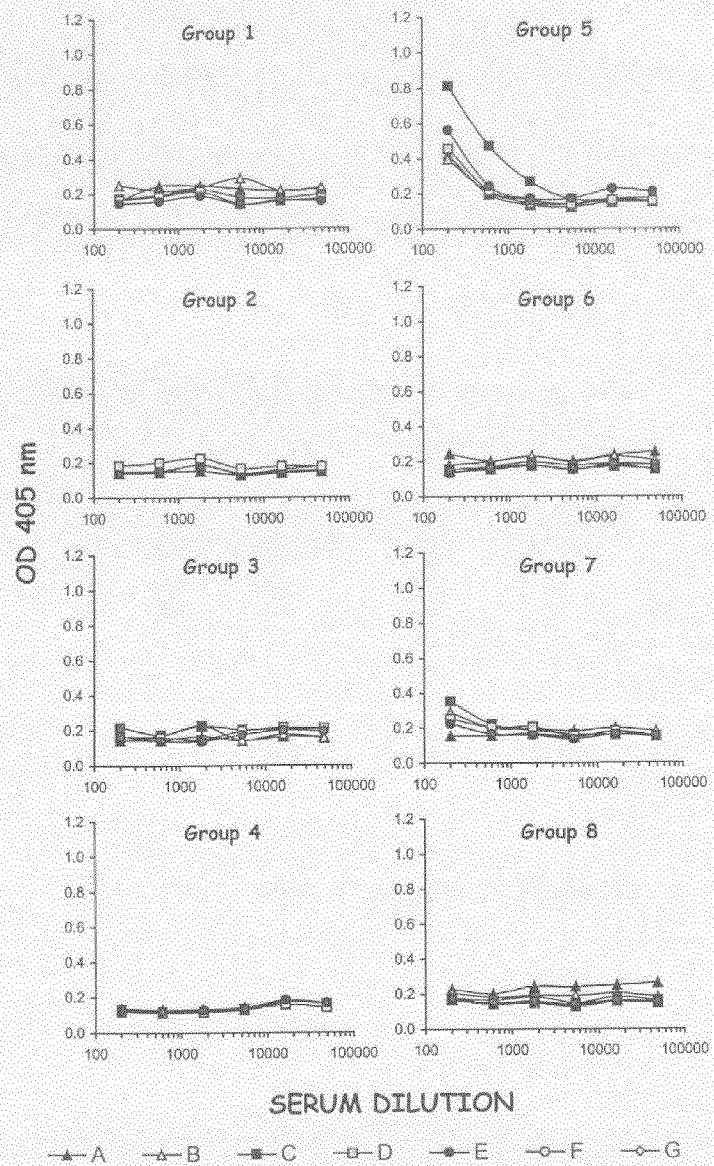

US 8,173,133 B2

ACYL PSEUDODIPEPTIDES WHICH CARRY A FUNCTIONALIZED AUXILIARY ARM

This application is a Continuation of U.S. Ser. No. 10/169,053, filed Aug. 28, 2002, which is the National Stage of Int'l App'l No. PCT/FR2000/003650, filed Dec. 21, 2000, which claims priority of International Application No. PCT/IB1999/002038, filed Dec. 22, 1999. The entire contents and disclosures of the preceding applications are incorporated by reference into this application.

BACKGROUND ART

The present invention relates to the field of chemistry and more specifically to the field of peptide chemistry. More precisely, it is directed to acyl-dipeptide-like compounds bearing an accessory functionally substituted side chain spacer which can optionally be grafted in the form of conjugates, the accessory side chain spacer of which further imparts original properties to the molecule in terms of biological activity and physical chemical characteristics. Depending on the chemical species involved, the accessory side chain spacer gives the acyl-dipeptide-like compound added functional ability by finely tuning its original properties and by conferring novel ones thereto as well. These molecules bearing an accessory functional side chain spacer can be conjugated to a pharmaceutical carrier, an antigen or a vehicle. Bioconjugation involves coupling two or more chemical species to form a novel molecular complex having properties differing from those of the individual components. Natural or synthetic products, having inherent pharmacological properties, can be mutually combined to make new species having original or improved pharmacological and chemical physical properties as compared to starting compounds. Bioconjugates have a wide range of applications in all fields of human medicine and animal care as well as diagnostics.

A great number of homo- or heterobifunctional coupling agents have already been described and may be used in coupling molecules ranging from amino acids, to peptides, protein, sugars, oligosaccharides, polysaccharides, nucleic acids, oligonucleotides, polynucleotides, lipids, and nearly every single molecule bearing a functional group capable of bonding. Considerable effort has been made in recent years regarding the synthesis of antigenic constructs made from two molecules bearing different messages. Good et al. [(1987), *Science*, 235: 1059-1062], have for instance reported the synthesis of a peptide containing both T helper and B lymphocyte recognition epitopes. Bessler and Jung [(1992) *Res. Immunol.*, 5: 548-553] have disclosed conjugates composed of a peptide and an immunostimulant. Hoffmann et al. [(1997) *FEMS Immunol. Med. Microbiol.*, 17: 225-234] have disclosed conjugates of a lipopeptide and a mellitin derived-synthetic peptide. Ulrich and Meyers [(1995) *Vaccine Design*, Plenum Press, New York, 495-524], have observed that immune response was inefficient unless the hapten and MPL adjuvant (Monophosphoryl Lipid A) were found in the same liposome. They suggested the possible existence of a covalent bond between MPL and the hapten. In fact, a hapten-adjuvant conjugate may prove to be highly efficient when used as a vaccine adjuvant. Ikeda et al. [(1999) Chem. Pharm. Bull., 47 (4), 563-568] have reported synthesis of a structural analog of Lipid A coupled to a peptide tumour-derived antigen and demonstrated it has in vitro mitogenic activity.

The conjugation concept may equally apply to protein or even protein polysaccharide conjugates. Indeed, it is well known that use of polysaccharides alone as a vaccine does only give rise to a weak immune response in children aged below 5, as no T cell-mediated response is involved. [Gotschlich et al. (1977); *Antibodies in Human Diagnosis and Therapy*, Peltola et al., (1977), *Pediatrics* 60: 730-737]. By contrast, linking polysaccharides to protein carriers does result in a much stronger immune response. This phenomenon was discovered in 1931 by Avery and Goebel [(1931), *J. Exp. Med.*, 54: 437-447]. A variety of recently developed vaccines reflect progress accomplished so far in this field. Mention should be made of vaccines to *Haemophilus influenzae* and different serotypes of *Streptococcus pneumoniae* [Powell and Newman, (1995), *Vaccine Design*, Plenum Press, New York]. In the latter case, a multivalent vaccine has been developed [Sood et Fatton, (1998), *Exp. Opin. Invest. Drugs*, 7: (3), 333-347].

A complex composed of an adjuvant bound to a polysaccharide-protein unit raises new opportunities. Chemical synthesis technology as applied to bioconjugates is currently well developed and one can carry out a number of projects which were inconceivable just a few years ago, relying on the wide range of homo- or heterobifunctional reagents now available and using conjugation procedures extensively reported in the literature [Hermanson, (1996), Bioconjugate Techniques, Academic Press, New York].

Thus, mention can be made, for instance, of the reductive amination method [Roy et al., (1984), *Canad. J. Biochem. Cell Biol.*, 62: 270-279, Hermansson, p. 472] allowing conjugation of a carrier molecule to an aldehyde functional group, having a primary amine on a peptide or protein molecule, with a protein-polysaccharide conjugate or with a pharmaceutical carrier. This reaction results in the formation of a very stable dialkylamine compound.

BRIEF DESCRIPTION OF THE DRAWINGS

FIG. 84 shows the induction of anti-H1N1 IgM antibody 14 days and 28 days after injection of H1N1, the mixture of H1N1 and OM-197-MP, the conjugate OM-197-FV-H1N1, or of the mixture OM-197-FV-H1N1 and OM-197-MP;

FIG. 85 are graphs showing the determination of the antigenic properties of acylated pseudodipeptides conjugated with T-epitope portion of *Plasmodium yoelii* 2 weeks after the second injection in mice;

FIG. 86 are graphs showing the determination of the antigenic properties of acylated pseudodipeptides conjugated with T-epitope portion of *Plasmodium yoelii* 2 weeks after the third injection in mice;

DISCLOSURE OF THE INVENTION

Figure 1:
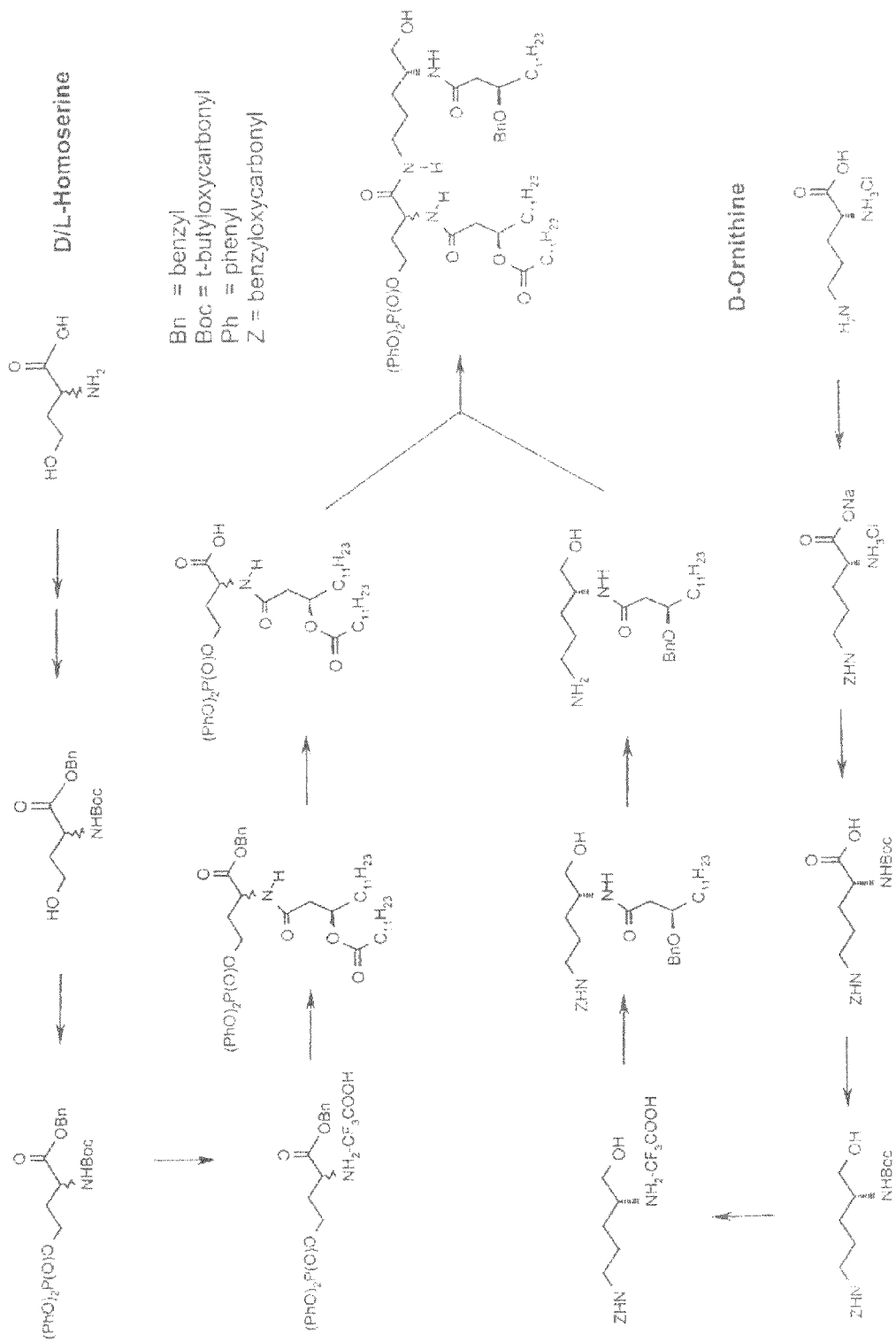
FIG. 1 shows the synthesis of the intermediate pseudodipeptide from DL-homoserine and D-ornithine.

The present invention is more specifically directed to dipeptide-like compounds derived from functionally substituted amino acids, the free amino functional groups of which are amidified by fatty acids and one end portion of which bears an accessory functional side chain spacer.

More precisely, the invention relates to N-acyl-dipeptide-like compounds bearing an acid group in neutral or charged state at one end portion thereof and an accessory functional side chain spacer at the other end portion thereof, having the general formula I:

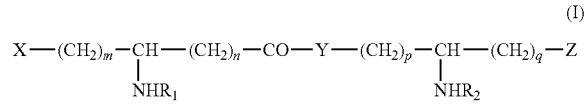
(I)

wherein R$_1$ and R$_2$ each designate an acyl group derived from a saturated or unsaturated, straight or branched chain-carboxylic acid having from 2 to 24 carbon atoms, which is unsubstituted or bears one or more substituents selected among hydroxyl, alkyl, alkoxy, acyloxy, amino, acylamino, acylthio and (C$_{1-24}$)alkylthio groups, subscripts m, n are integers ranging from 0 to 10,
subscripts p, q are integers ranging from 1 to 10,
Y designates O or NH,
X and Z designate an accessory functional side chain spacer or an acid group either in neutral or charged state selected among the following groups
carboxyl
  carboxy[(C$_{1-5}$)alkoxy]
  carboxy[(C$_{1-5}$)alkylthio]
  phosphono[(C$_{1-5}$)alkoxy]
  phosphono[(C$_{1-5}$)alkylthio]
  dihydroxyphosphoryloxy[C$_{1-5}$)alkoxy]
  dihydroxyphosphoryloxy[C$_{1-5}$)alkylthio]
  dihydroxyphosphoryloxy
  hydroxysulfonyloxy
  hydroxysulfonyl[(C$_{1-5}$)alkoxy]
  hydroxysulfonyl[(C$_{1-5}$)alkylthio]
  hydroxysulfonyloxy[(C$_{1-5}$)alkoxy]
  hydroxysulfonyloxy[(C$_{1-5}$)alkylthio
  [carboxy(C$_{1-5}$)alkyl]aminocarbonyl
  [dicarboxy(C$_{1-5}$)alkyl]aminocarbonyl
  [ammonio(C$_{1-5}$)alkyl]aminocarbonyl
  {carboxy[amino(C1-C5)alkyl]aminocarbonyl
  provided that at least one of substituents X or Z designates an accessory functional side chain spacer.

The accessory group denoted by X or Z has the general formula (II):

(II)

where A designates either O, S or NH
subscript r is an integer ranging from 0 to 1,
subscript s is an integer ranging from 1 to 10,
W is selected among the following groups
  formyl
  acetyl
  cyano
  halo
  amino
  bromo- or iodo-acetamido
  acylamido
  diacylimido
  sulfhydril
  alkylthio
  hydroxyl
  1,2-dihydroxyethyl
  alkoxy
  acyloxy
  vinyl
  ethynyl
  free carboxyl
  esterified carboxyl or in the form of a mixed anhydride, amide or hydrazide,
  azido
  thiocyano.

The invention is especially directed to novel N-acyl dipeptide-like compounds bearing an acid group either in neutral or charged satete, at one end portion thereof and bearing an accessory functional side chain spacer at the other, having the general formula I:

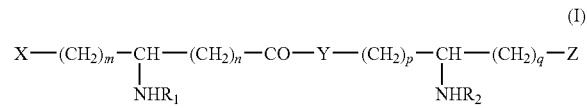
(I)

wherein R$_1$ and R$_2$ each designate an acyl group derived from a saturated or unsaturated straight or branched chain-carboxylic acid having from 2 to 24 carbon atoms, which is unsubstituted or bears one or more substituents selected among hydroxyl, alkyl, alkoxy, acyloxy, amino, acylamino, acylthio and ($C_{1-24}$)alkylthio groups,
subscripts m, n are integers ranging from 0 to 10,
subscripts p, q are integers ranging from 1 to 10,
X and Z each designate an acid group either in neutral or charged state or an accessory functional side chain spacer, provided that at least one of substituents X or Z designates an accessory functional side chain spacer,
Y designates O or NH,
The acid group X or Y is preferably selected among the following groups:
carboxyl
carboxy[($C_{1-5}$)alkoxy]
carboxy[($C_{1-5}$)alkylthio]
phosphono[($C_{1-5}$)alkoxy]
phosphono[($C_{1-5}$)alkylthio]
dihydroxyphosphoryloxy[$C_{1-5}$)alkoxy]
dihydroxyphosphoryloxy
hydroxysulfonyloxy
hydroxysulfonyl[($C_{1-5}$)alkoxy]
hydroxysulfonyl[($C_{1-5}$)alkylthio]
hydroxysulfonyloxy[($C_{1-5}$)alkoxy]
hydroxysulfonyloxy[($C_{1-5}$)alkylthio]
and the accessory group denoted by X or Z has the general formulae II, excluding a dihydroxyethyl radical.

Where substituents X or Z designate an acid group in neutral state, reference is made to the free carboxylic, sulphonic, phosphonic or phosphoric compound. Where the acid group is in a charged state, reference is made to the carboxylic, sulphonic, phosphonic or phosphoric salt form, namely by addition of an organic or mineral base, preferably one intended for therapeutic use. As for bases not intended for therapeutic use, such bases provide a means for easy identification, purification and separation.

Salt forming bases intended for therapeutic use mainly include alkaline bases such as sodium, potassium or lithium hydroxides, ammonium salts, alkali earth metal bases such as calcium or strontium hydroxide, magnesium salts, ferrous metal salts and the like, organic bases such as those derived from primary, secondary, tertiary amines of basic amino acids such as lysine and ornithine or amino sugars. Examples of bases not intended for therapeutic use are brucine, strychnine, N methylglucosamine or N-methylmorpholin. As previously stated, salts derived therefrom will serve as separation, identification or purification means.

When m is equal to 1 and n is equal to 0, the molecule of interest derives from serine or aspartic acid. Where m is equal to 2 and n is equal to 0, the molecule being considered mainly derives from homoserine or glutamic acid.
Where Y=NH, p is equal to 3 and q is equal to 1, the product of interest may be a citrulline, ornithine or arginine compound.
Where p is equal to 4 and q is equal to 1, reference is made to a homoarginine or lysine compound.

Where substituents X or Z designate the accessory group of general formula (III)

$$O-CO-(CH_2)_s-W \quad (III)$$

subscript s is an integer ranging from 1 to 10, being, in particular, equal to 4, 5 or 6
W is preferably selected among the following groups:
formyl
amino
hydroxyl
1,2-dihydroxyethyl
carboxyl.

Among dipeptide-like compounds which are herein included, special attention is devoted to compounds of general formula IV which are currently preferred:

$$X-(CH_2)_m-\underset{NHR_1}{CH}-(CH_2)_n-CO-NH-(CH_2)_p-\underset{NHR_2}{CH}-(CH_2)_q-Z \quad (IV)$$

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from the group comprised of hydroxyl, alkyl, alkoxy, acyloxy, amino, acylamino, acylthio and ($C_{1-24}$)alkylthio groups,
subscripts m and n are integers ranging from 0 to 10,
subscripts p and q are integers ranging from 1 to 10,
and wherein one of substituents X or Z is a carboxyl or a dihydroxyphosphoryloxy radical or a carboxy[($C_{1-5}$)alkoxy] radical or a carboxy[($C_{1-5}$)alkylthio] radical or a carboxy [($C_{1-5}$)alkyl]aminocarbonyl or a [dicarboxy($C_{1-5}$)alkyl]aminocarbonyl or a {carboxy[amino($C_{1-5}$)alkyl]-aminocarbonyl radical and wherein the other substituent is an acyloxy radical chosen among one of 6-aminohexanoyloxy, 6-oxohexanoyloxy, 6-hydroxyhexanoyloxy, 6,7-dihydroxyheptanoyloxy or 3-carboxypropanoyloxy groups.

$R_1$ and $R_2$ are meant to include saturated or unsaturated, branched or straight chain-acyl derivatives having a variable size chain from 2 to 24 carbon atoms, of distinct or identical nature, which can bear one or more substituents selected from the group comprised of alkyl, amino, acylamino, hydroxyl, alkoxy, acyloxy acylthio and alkylthio groups. Among acyl groups herein of interest, mention should be made of those derived from lauric acid, 2-hydroxyoctanoic acid, 2-decanoyloxyoctanoic acid, 3-lauryloxymyristic acid, 3-hydroxymyristic acid, 3-myristoylmyristic acid and 3-palmitoylmyristic acid which are currently preferred.

The invention relates in particular to the following dipeptide-like compounds listed in the table below as being preferred compounds:

$$X-(CH_2)_m-\overset{*}{\underset{NHR_1}{CH}}-(CH_2)_n-CO-Y-(CH_2)_p-\overset{**}{\underset{NHR_2}{CH}}-(CH_2)_q-Z$$

$$Z = OR_3 \text{ or}$$
$$Z = A-(CO)_r-(CH_2)_s-W$$

| EX# | X | *,** | Y | m,n,p,q | $R_1$ | $R_2$ | $R_3$ | A | r | s | W |
|---|---|---|---|---|---|---|---|---|---|---|---|
| 1.2 | HOOC | R,R | NH | 1,0,3,1 | 3($C_{12}$O)$C_{14}$ | 3(HO)$C_{14}$ | H | — | — | — | — |
| 1.3 | HOOC | R,R | NH | 1,0,3,1 | 3($C_{12}$O)$C_{14}$ | 3(HO)$C_{14}$ | P(O)(OH)$_2$ | — | — | — | — |
| 2.1 | (HO)$_2$P(O)—O | R,R | NH | 2,0,3,1 | 3($C_{12}$O)$C_{14}$ | 3(HO)$C_{14}$ | — | O | 1 | 4 | CHOHCH$_2$OH |
| 2.2 | (HO)$_2$P(O)—O | R,R | NH | 2,0,3,1 | 3($C_{12}$O)$C_{14}$ | 3(HO)$C_{14}$ | — | O | 1 | 4 | CHO |
| 2.3 | HOOC | R,R | NH | 1,0,3,1 | 3($C_{12}$O)$C_{14}$ | 3(HO)$C_{14}$ | — | O | 1 | 4 | CHOHCH$_2$OH |

-continued

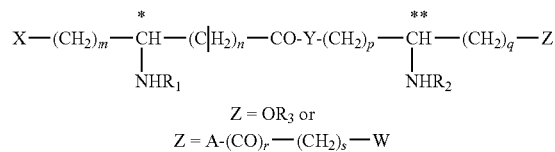

$Z = OR_3$ or
$Z = A\text{-}(CO)_r\text{—}(CH_2)_s\text{—}W$

| EX# | X | *,** | Y | m,n,p,q | $R_1$ | $R_2$ | $R_3$ | A | r | s | W |
|---|---|---|---|---|---|---|---|---|---|---|---|
| 2.4 | HOOC | R,R | NH | 1,0,3,1 | $3(C_{12}O)C_{14}$ | $3(HO)C_{14}$ | — | O | 1 | 4 | CHO |
| 2.5 | HOOC | R,R | NH | 1,0,3,1 | $3(C_{12}O)C_{14}$ | $3(HO)C_{14}$ | — | O | 1 | 5 | OH |
| 2.6 | $(HO)_2P(O)$—O | RS,R | NH | 2,0,3,1 | $3(C_{12}O)C_{14}$ | $3(HO)C_{14}$ | — | O | 1 | 5 | $NH_2$ |
| 2.7 | $(HO)_2P(O)$—O | R,R | NH | 2,0,3,1 | $3(C_{12}O)C_{14}$ | $3(HO)C_{14}$ | — | O | 1 | 5 | $NH_2$ |
| 2.8 | $(HO)_2P(O)$—O | S,R | NH | 2,0,3,1 | $3(C_{12}O)C_{14}$ | $3(HO)C_{14}$ | — | O | 1 | 5 | $NH_2$ |
| 2.9 | $(HO)_2P(O)$—O | R,R | NH | 2,0,3,1 | $3(C_{12}O)C_{14}$ | $3(HO)C_{14}$ | — | O | 1 | 5 | OH |
| 2.10 | $(HO)_2P(O)$—O | RS,R | O | 2,0,3,1 | $3(C_{12}O)C_{14}$ | $3(HO)C_{14}$ | — | NH | 0 | 5 | CHO |
| 2.11 | $HOOCCH_2O$ | R,R | NH | 1,0,3,1 | $3(C_{12}O)C_{14}$ | $3(HO)C_{14}$ | — | O | 1 | 4 | CHO |
| 2.12 | $HOOCCH_2S$ | S,R | NH | 1,0,3,1 | $3(C_{12}O)C_{14}$ | $3(HO)C_{14}$ | — | O | 1 | 6 | $NH_2$ |
| 2.13 | $(HOOC)_2CHCH_2O$ | R,R | NH | 1,0,3,1 | $3(C_{12}O)C_{14}$ | $3(HO)C_{14}$ | — | O | 1 | 4 | CHO |
| 2.14 | $(HO)_2P(O)$—O | RS,R | NH | 2,0,3,1 | $3(C_{12}O)C_{14}$ | $3(HO)C_{14}$ | — | O | 1 | 5 | $NHC(O)CH_2Br$ |
| 2.15 | $(HO)_2P(O)O$ | RS,R | NH | 2,0,3,1 | $3(HO)C_{14}$ | $3(C_{12}O)C_{14}$ | — | O | 1 | 4 | CHO |
| 2.16 | HOOC | R,R | NH | 1,0,3,1 | $3(C_{12}O)C_{14}$ | $3(HO)C_{14}$ | — | O | 1 | 5 | $NH_2$ |
| 2.17 | HOOC | R,R | NH | 1,0,3,1 | $3(C_{12}O)C_{14}$ | $3(HO)C_{14}$ | — | O | 1 | 5 | $NHCO(CH_2)_2COOH$ |
| 2.18 | HOOC | R,R | NH | 1,0,3,1 | $3(C_{12}O)C_{14}$ | $3(HO)C_{14}$ | — | O | 1 | 1 | $NH_2$ |
| 2.19 | HOOC | R,R | NH | 1,0,3,1 | $3(C_{12}O)C_{14}$ | $3(HO)C_{14}$ | — | O | 1 | 2 | COOH |
| 2.20 | $H_2N(CH_2)_3NHCO$ | R,R | NH | 1,0,3,1 | $3(C_{12}O)C_{14}$ | $3(HO)C_{14}$ | H | — | — | — | — |
| 2.21 | $H_2N(CH_2)_4CH(COOH)NHCO$ | R,R | NH | 1,0,3,1 | $3(C_{12}O)C_{14}$ | $3(HO)C_{14}$ | H | — | — | — | — |
| 2.22 | $H_2N(CH_2)_4CH(COOH)NHCO$ | R,R | NH | 1,0,3,1 | $3(C_{12}O)C_{14}$ | $3(HO)C_{14}$ | — | O | 1 | 5 | $NH_2$ |
| 2.23 | $HOOCCH_2CH(COOH)$—NHCO | R,R | NH | 1,0,3,1 | $3(C_{12}O)C_{14}$ | $3(HO)C_{14}$ | H | — | — | — | — |
| 2.24 | $HOOCCH_2CH(COOH)$—NHCO | R,R | NH | 1,0,3,1 | $3(C_{12}O)C_{14}$ | $3(HO)C_{14}$ | — | O | 1 | 5 | $NH_2$ |
| 2.25 | HOOC | R,R | NH | 1,0,3,1 | $C_2$ | $3(HO)C_{14}$ | — | O | 1 | 5 | $NH_2$ |
| 2.26 | HOOC | R,R | NH | 1,0,3,1 | $2(C_{10}O)C_8$ | $3(HO)C_{14}$ | — | O | 1 | 5 | $NH_2$ |

The invention relates in particular to the following as being currently preferred compounds:

N—[(R)-3-dodecanoyloxytetradecanoylamino]-D-aspartic acid, α-N-{(4R)-5-hydroxy-4-[(R)-3-hydroxytetradecanoylamino]pentyl}amide and addition salts with a mineral or an organic base thereof (Ex 1.2)

3-[(R)-3-dodecanoyloxytetradecanoylamino]-4-oxo-5-aza-9-[(R)-3 hydroxytetradecanoylamino]-decan-1,10-diol 1-dihydrogenphosphate 10-(6,7-dihydroxyheptanoate) and addition salts with a mineral or an organic base thereof (Ex 2.1)

3-[(R)-3-dodecanoyloxytetradecanoylamino]-4-oxo-aza-9-[(R)-3 hydroxytetradecanoylamino]-dedan-1,10-diol 1-dihydrogenphosphate 10-(6-oxohexanoate) and addition salts with a mineral or an organic base thereof (Ex. 2.2)

N—[(R)-3-dodecanoyloxytetradecanoylamino]-D-aspartic acid, α-N-{-(4R)-5-hydroxy-4-[(R)-3-hydroxytetradecanoylamino]pentyl}amide 5-O-(6,7-dihydroxyheptanoate) and addition salts with a mineral or an organic base thereof (Ex. 2.3)

N—[(R)-3-dodecanoyloxytetradecanoylamino]-D-aspartic acid, α-N-{(4R)-5-hydroxy-4-[(R)-3-hydroxytetradecanoylamino]pentyl}amide 5-O-(6-oxohexanoate) and addition salts with a mineral or an organic base thereof (Ex. 2.4.)

(3RS,9R), (3R,9R) and (3S,9R)-3-[(R)-3-dodecanoyloxytetradecanoylamino]-4-oxo-5-aza-9-[(R)-3-hydroxy-tetra-decanoylamino]-decan-1,10-diol 1-dihydrogenphosphate 10-(6-aminohexanoate) and addition salts with a mineral or an organic base thereof (Ex. 2.6, 2.7 and 2.8)

3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6-hydroxyhexanoate) and addition salts with a mineral or an organic base thereof (Ex. 2.9)

{2-[(R)-3-hydroxytetradecanolamino]-5-(6-oxohexyl) amino}pentyl 2-[(R)-3-dodecanoyloxytetradecanoylamino]-4-(dihydroxyphosphoryloxy)-butanoate and addition salts with a mineral or an organic base thereof (Ex 2.10)

N—[(R)-3-dodecanoyloxytetradecanoyl]-D-aspartic acid, α-N-{(4R)-5-(6-aminohexanoyloxy)-4-[(R)-3-hydroxytetradecanoylamino]pentyl}amide and addition salts with a mineral or an organic base thereof (Ex. 2.16)

N—[(R)-3-dodecanoyloxytetradecanoyl]-D-aspartic acid, α-N-{(4R)-5-succinyloxy-4-[(R)-3-hydroxytetradecanoylamino]pentyl}amide and addition salts with a mineral or an organic base thereof (Ex. 2.19)

N—[(R)-3-dodecanoyloxytetradecanoyl]-D-aspartic acid, α-N-{(4R)-5-(6-aminohexanoyloxy)-4-[(R)-3-hydroxytetradecanoylamino]pentyl}amide β-N-[(1S)-1-carboxy-5-aminopentyl]amide and addition salts with a mineral or an organic base thereof (Ex. 2.22)

N—[(R)-3-dodecanoyloxytetradecanoyl]-D-aspartic acid, α-N-{(4R)-5-(6-aminohexanoyloxy)-4-[(R)-3-hydroxytetradecanoylamino]pentyl}amide β-N-[(1S)-1,2-dicarboxyethyl]amide and addition salts with a mineral or an organic base thereof (Ex. 2.24)

These compounds have distinctive interesting pharmacological properties, mainly with regard to immunomodulation. They are particularly relevant in the preparation of vaccine compositions in admixture formulations or as covalent conjugates with polypeptide or polysaccharide antigens or with compounds made of polysaccharide-conjugated polypeptides. They can be used mainly in prevention of protozoal, viral and microbial infections or in treatment of certain autoimmune disease.

Other applications include use as vectors for molecules of therapeutic interest due to their ability to form non covalent complexes based on the variably hydrophilic or hydrophobic character of their accessory side chain spacer. Their chemical properties allow coupling thereof with molecules of therapeutic interest. Likewise, their amphophilic character enhances formulation and transport of molecules associated therewith to the membrane receptors, as well as to the cell membranes and cytoplasm.

Other applications include use as vectors for molecules of therapeutic interest due to their ability to form non covalent complexes based on the variably hydrophilic or hydrophobic character of their accessory side chain spacer. Their chemical properties allow coupling thereof with molecules of therapeutic interest. Likewise, their amphophilic character enhances formulation and transport of molecules associated therewith to the membrane receptors, as well as to the cell membranes and cytoplasm.

They can be used alone or either in covalent linkage or not with a molecule of therapeutic interest by means of administration through oral, parenteral, rectal, topical, subcutaneous or submucosal route.

They can be used solely or either in covalent linkage or not with a molecule of therapeutic interest by carrying out extemporaneous incubation ex vivo with blood cells in order to promote formation of immunocompetent cells before injecting them back in vivo using parenteral administration.

The molecules of interest display similar properties, as adjuvants for the immune system when used for example in vaccination, either in covalent association or not with the appropriate antigens, against disease of viral, parasitic, microbial or fungal origin. These optionally conjugated molecules can further be used in treatment of certain autoimmune disease.

In contrast, some compounds according to the invention show following covalent association or not utterly different properties regarding their capacity to induce cytokine production or maturation of immunocompetent stem cells derived from hematopoietic and lymphoid organs.

Some compounds in accordance with the invention promote maturation and differentiation of monocytes into functional dendritic cells, in presence or absence of the appropriate antigen and act in promoting humoral and cell mediated immunity.

Certain compounds herein contemplated promote differentiation of cells which are part of the hematopoietic system especially within the bone marrow and result in improvement or correction of certain immune system disorders. They display in particular antiviral properties.

The compounds in accordance with the invention are particularly interesting due to their low toxicity. They are used either in covalent association or not with antigens in prevention or treatment of infectious disease in humans and animals at doses ranging from 0.005 mg to 100 mg per unit dosage and from 0.005 to 200 mg daily depending on the particular indication and the individual's body weight.

The present invention is equally directed to a method for obtaining N-acyl dipeptide-like compounds bearing an acid group either in neutral or charged state at one end portion thereof and bearing an accessory functional side chain spacer at the other, having the general formula I which comprises the steps of blocking amine functional groups in position (q+1) and YH in position ω of an ω-functionally derivatized amino acid by transverse blocking reagents, reacting the still free carboxylic functional group with a reducing agent to yield a corresponding alcohol, freeing the amine functional group in position (q+1) and then acylating the same by means of a carboxylic acid functional derivative of formula $R_2OH$, wherein $R_2$ is as defined above, and subsequently freeing the terminal amine functional group, to yield the functionally derivatized amino alcohol of general formula V

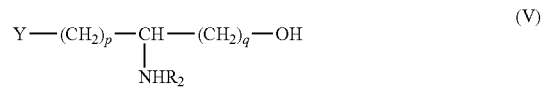

wherein Y designates HO or preferably $NH_2$, $R_2$ designates an acyl group derived from a saturated or unsaturated carboxylic acid having from 2 to 24 carbon atoms, which is unsubstituted or bears one or more substituents as defined above, p and q each designate an integer ranging from 1 to 10, which amino alcohol is condensed in presence of a peptide condensing agent in an inert solvent, together with a ω-functionally derivatized amino acid compound of general formula VI

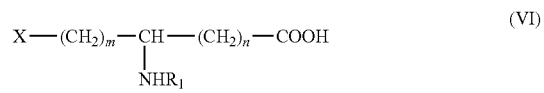

wherein $R_1$ is an acyl group derived from a saturated or unsaturated carboxylic acid having from 2 to 24 carbon atoms, which is unsubstituted or bears one or more substituents as specified above, m and n are integers ranging from 0 to 10, and X is an acid group as defined above which can be in the form of an ester, to yield the dipeptide-like compound of general formula VII

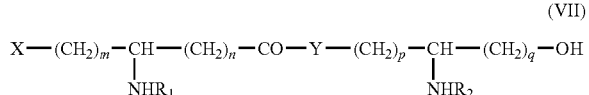

wherein substituents $R_1$ and $R_2$ and subscripts m, n, p and q are as specified above, the free terminal alcohol functional group of which can be, if needed, alkyl-, acyl or otherwise substituted by an alkyl-, acyl- or an otherwise substitution reagent of general formula VIII, $$A\text{-}(CO)_r\text{---}(CH_2)_s\text{---}W \qquad (VIII)$$

with A being a leaving group, an OH, SH or $NH_2$ functional group subscript r preferably being equal to 1, or optionally equal to 0, subscript s preferably ranging from 2 to 6, optionally being included between 1 and 10

W being preferably chosen among the following groups, formyl, -acetyl, -cyano, halo, amino, -bromo- or iodoacetamido, -acylamido, -diacylimido, -sulfhydril, -alkylthio, -hydroxyl, -1,2-dihydroxyethyl, -acyloxy, -vinyl, ethynyl, free or esterified carboxyl or in the form a mixed anhydride, amide or hydrazide, -azido, -thiocyano or precursors thereof, if needed, in the presence of a coupling agent, and subjecting the product to a catalytic hydrogenation or some other deprotection process in order to obtain the derivative of general formula I:

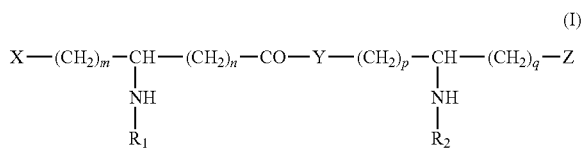

(I)

wherein substituents and subscripts X, Y, Z, $R_1$, $R_2$, n, m, p and q have the same meanings as those given above.

The invention is also directed to a method for obtaining phosphodipeptide-like compounds of general formula IV

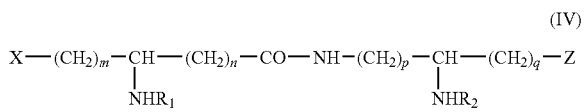

(IV)

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from the group comprised of hydroxyl, alkyl, alkoxy, acyloxy, amino, acylamino, acylthio and $(C_{1\text{-}24})$alkylthio groups,
subscripts m, p and q are integers ranging from 1 to 10,
subscript n is an integer ranging from 0 to 10,
X and Z each designate an acid group in neutral or charged state or an accessory functional side chain spacer,
characterized in that it consists in blocking amine functional groups in positions (q+1) and ω of a diamino acid of formula $H_2N(CH_2)_p CHNH_2(CH_2)_{q-1}COOH$ by blocking reagents which readily undergo acidolysis and hydrogenolysis, respectively, reacting the still free carboxylic functional group with a reducing agent to yield a corresponding alcohol, freeing the amine functional group in position (q+1) and then acylating the same by means of a carboxylic acid functional derivative of formula $R_2OH$ wherein $R_2$ is as defined above, then freeing the terminal amine functional group by hydrogenolysis to obtain an amino alcohol of general formula IX

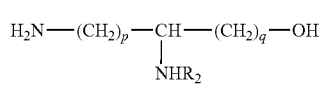

(IX)

wherein $R_2$ designates an acyl group derived from a saturated or unsaturated carboxylic acid having from 2 to 24 carbon atoms, which is unsubstituted or bears one or more substituents as specified above, p and q designate an integer ranging from 1 to 10 which amino alcohol is condensed in presence of a peptide condensing agent in an inert solvent, together with an co-hydroxy amino acid derivative of general formula VI:

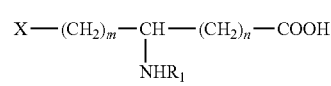

(VI)

wherein $R_1$ is an acyl group derived from a saturated or unsaturated carboxylic acid having from 2 to 24 carbon atoms, which is unsubstituted or bears one or more substituents,
m is an integer ranging from 1 to 10,
n is an integer ranging from 0 to 10,
and X is a dialkyloxy- or diaryloxy-phosphoryloxy radical of formula
wherein substituents $R_1$, $R_2$, and subscripts m, n, p and q are as defined above, and R is a radical which readily undergoes hydrogenolysis, the free terminal alcohol functional group of which can be—if desired—alkyl- or acyl- or otherwise substituted by an alkyl- or acyl- or otherwise substitution reagent of general formula VIII $$A\text{-}(CO)_r\text{---}(CH_2)_s\text{---}W \qquad (VIII)$$

where A can be a leaving group, an OH, SH or $NH_2$ functional group
subscript r is an integer preferably equal to 1, optionally equal to 0,
subscript s is an integer ranging from 2 to 6, optionally ranging from 1 to 10,
W is preferably selected among the following groups
-formyl, -acetyl, -cyano, -halo, -amino, -bromo- or iodo-acetamido, -acylamido, -diacylimido, -sulfhydril, -alkylthio, -hydroxyl, 1,2-dihydroxyethyl, -acyloxy, -vinyl, -ethynyl, -free or esterified carboxyl or in the form of a mixed anhydride, amide or hydrazide, azido, -thiocyano or precursors thereof,
if needed, in presence of a coupling agent, and subjecting the same to a catalytic hydrogenation or some other deprotection process so as to obtain the derivative of general formula XI

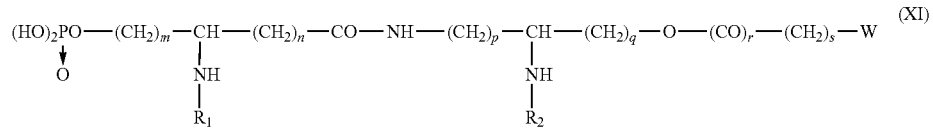

(XI)

wherein substituents W, $R_1$, $R_2$ and subscripts m, n, p, q, r, s have the same meanings as above.

The invention still relates to a method for obtaining phosphodipeptide-like compounds of general formula XII

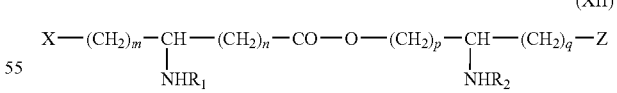

(XII)

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from the group comprised of hydroxyl, alkyl, alkoxy, acyloxy, amino, acylamino, acylthio and $(C_{1\text{-}24})$alkylthio groups,
subscripts m, p and q are integers ranging from 1 to 10,
subscript n is an integer ranging from 0 to 10,
and wherein X and Z each designate an acid group or an accessory functional side chain spacer, which consists in blocking amine functional groups in positions (q+1) and ω of a diamino acid of formula $H_2N(CH_2)_p CHNH_2(CH_2)_{q-1}COOH$ by blocking reagents which readily undergo acidolysis and hydrogenolysis, respectively, reacting the still free carboxylic functional group with a reducing agent to yield a corresponding alcohol, freeing the amine functional group in position (q+1) and then acylating the same by means of a carboxylic acid functional derivative of formula $R_2OH$ wherein $R_2$ is as defined above, then freeing the terminal amine functional group by hydrogenolysis and thereafter alkyl substituting the amine functional group by an ω-functionally derivatized alkyl triflate to obtain an amino alcohol of general formula XIII

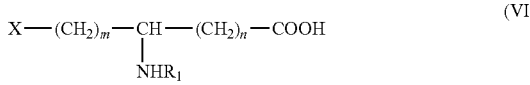

wherein $R_2$ designates an acyl group derived from a saturated or unsaturated carboxylic acid having from 2 to 24 carbon atoms, which is unsubstituted or bears one or more substituents as specified above, p and q designate an integer ranging from 1 to 10, subscript s is preferably included between 2 and 7, but may range from 1 to 10, which amino alcohol is condensed in presence of a condensing agent in an inert solvent, together with an ω-hydroxy amino acid derivative of general formula VI:

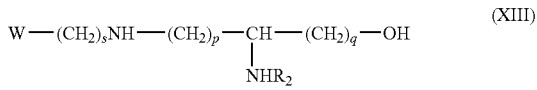

wherein $R_1$ is an acyl group derived from a saturated or unsaturated carboxylic acid having from 2 to 24 carbon atoms, which is unsubstituted or bears one or more substituents, m is an integer ranging from 1 to 10, n is an integer ranging from 0 to 10, and X is a dialkyloxy- or diaryloxy-phosphoryloxy radical of formula

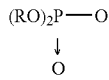

to yield the dipeptide-like compound of general formula XIV

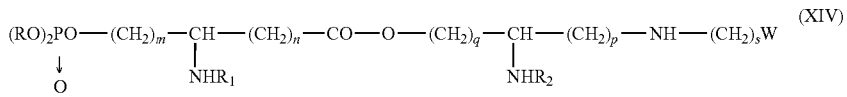

wherein substituents $R_1$, $R_2$, and subscripts m, n, p, q and s are as defined above, and R is a radical which readily undergoes hydrogenolysis, and then subjecting the product to a catalytic hydrogenation or some other deprotection process so as to obtain the derivative of general formula XV:

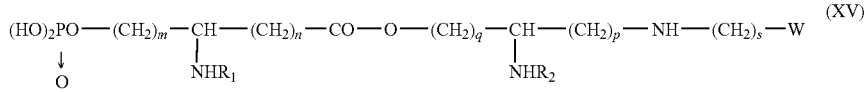

wherein substituents W, $R_1$, $R_2$, and subscripts m, n, p, q, r and are as specified above, W being chosen among the following groups, formyl, -acetyl, -cyano, -halo, -bromo- or iodoacetamido, -acylamido, -diacylimido, -acyloxy, -vinyl, ethynyl, free or esterified carboxyl or having the form of a mixed anhydride, amide or hydrazide, -azido, -thiocyano or precursors thereof.

The invention further relates to a method for producing carboxydipeptide-like compounds of general formula IV

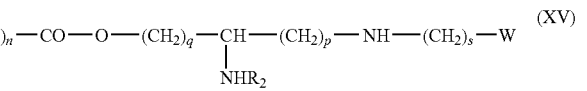

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from the group comprised of hydroxyl, alkyl, alkoxy, acyloxy, amino, acylamino, acylthio and $(C_{1-24})$alkylthio groups, subscripts m, p and q are integers ranging from 1 to 10, subscript n is an integer ranging from 0 to 10, and wherein X and Z each designate an acid group or an accessory functional side chain spacer, which consists in blocking amine functional groups in positions (q+1) and ω of a diamino acid of formula $H_2N(CH_2)_p CHNH_2(CH_2)_{q-1}COOH$ by blocking reagents which readily undergo acidolysis and hydrogenolysis, respectively, reacting the still free carboxylic functional group with a reducing agent to yield a corresponding alcohol, freeing the amine functional group in position (q+1) and then acylating the same by means of a carboxylic acid functional derivative of formula $R_2OH$ wherein $R_2$ is as defined above, then freeing the terminal amine functional group by hydrogenolysis to obtain an amino alcohol of formula IX

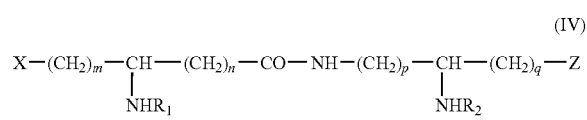

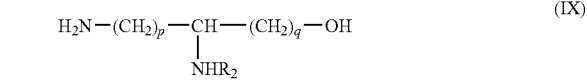

wherein $R_2$ designates an acyl group derived from a saturated or unsaturated carboxylic acid having from 2 to 24 carbon atoms, which is unsubstituted or bears one or more substituents as specified above, p and q designate an integer ranging from 1 to 10
which amino alcohol is condensed in presence of a peptide condensing agent in an inert solvent, together with an ω-carboxy amino acid functional derivative of general formula VI:

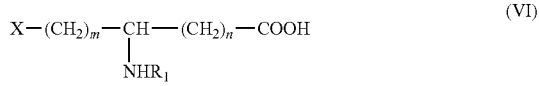

(VI)

wherein $R_1$ is an acyl group derived from a saturated or unsaturated carboxylic acid having from 2 to 24 carbon atoms, which is unsubstituted or bears one or more substituents, m is an integer ranging from 1 to 10,
n is an integer ranging from 0 to 10,
and X is an RO—CO-radical
to form the dipeptide-like compound of general formula XVI

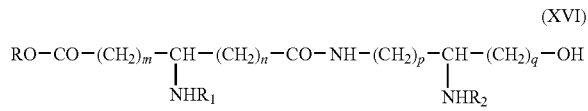

(XVI)

wherein substituents $R_1$, $R_2$ and subscripts m, n, p and q have the same meanings as above, and R is a group which readily undergoes hydrogenolysis, such as a benzyl group for instance. The free terminal alcohol functional group of which may be, if needed, alkyl or acyl or otherwise substituted by an alkyl or acyl or otherwise substitution reagent of general formula VIII,

A-(CO)$_r$—(CH$_2$)$_s$—W (VIII)

where A is a leaving group, an OH, SH or NH$_2$ functional group, subscript r is an integer preferably equal to 1, optionally equal to 0,
subscript s is an integer ranging from 2 to 6, optionally ranging from 1 to 10,
W is preferably selected among the following groups-formyl, -acetyl, -cyano, -halo, amino, -bromo- or iodoacetamido, -acylamido, -diacylimido, -sulfhydril, -alkylthio, -hydroxyl, -1,2-dihydroxyethyl, -acyloxy, -vinyl, -ethynyl, -free or esterified carboxyl or in the form of some other derivative
if needed, in presence of a coupling agent, and subjecting the same to a catalytic hydrogenation or some other deprotection process so as to obtain the derivative of general formula XI wherein substituents W, $R_1$, $R_2$, and subscripts m, n, p, q, r and are as specified above.

The invention still relates to a method for obtaining phosphodipeptide-like compounds of general formula IV

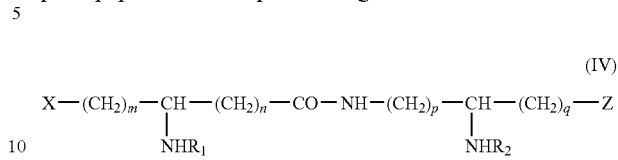

(IV)

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from the group comprised of hydroxyl, alkyl, alkoxy, acyloxy, amino, acylamino, acylthio and ($C_{1-24}$)alkylthio groups, subscripts m, p and q are integers ranging from 1 to 10,
subscript n is an integer ranging from 0 to 10,
and wherein X and Z each designate an acid group or an accessory functional side chain spacer,
which consists in deprotecting the esterified carboxyl functional group of a dipeptide-like compound of formula XVI

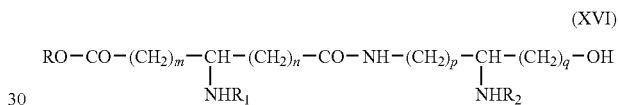

(XVI)

wherein substituents $R_1$, $R_2$ and subscripts m, n, p and q have the same meanings as above, and R is a group which readily undergoes hydrogenolysis such as a benzyl group for instance, then subjecting the resulting acid to a peptide coupling reaction with a partially protected amino acid or diaminoalkane such as, for example, 3-benzyloxycarbonylamino-1-aminopropane, dibenzyl L-aspartate or ε-N-benzyloxycarbonyl-L-lysine, in presence of a peptide coupling agent, and thereafter subjecting, if needed, the coupling reaction product to an acyl-, alkyl- or otherwise substitution reaction with a reagent of general formula VIII

A-(CO)$_r$—(CH$_2$)$_s$—W (VIII)

where A can be a leaving group, an OH, SH or NH$_2$ functional group,
subscript r is an integer equal to 1 or 0,
subscript s is an integer ranging in general from 1 to 10, preferably from 2 to 6,
W is selected among the following groups-formyl, -acetyl, -cyano, -halo, -amino, -bromo- or iodo-acetamido, -acylamido, -diacylimido, -sulfhydril, -alkylthio, -hydroxyl, 1,2-dihydroxyethyl-, -acyloxy, -vinyl, -ethynyl, -free or esterified or otherwise derivatized carboxyl group,

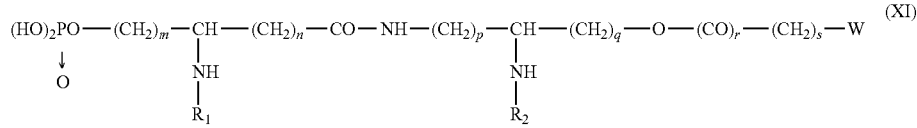

(XI)

if needed, in presence of an activating agent, and deprotecting the resulting product, for example by hydrogenolysis, so as to obtain the product of general formula XVIII

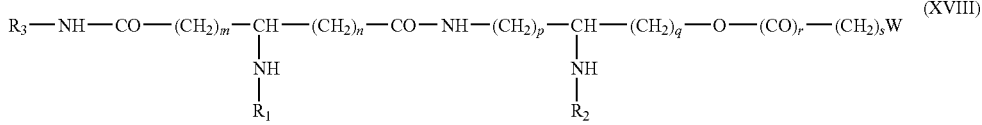

wherein substituents W, $R_1$, $R_2$, and subscripts m, n, p, q, r and are as specified above and group $R_3$ designates an aminoalkyl, carboxyalkyl, dicarboxyalkyl or aminocarboxyalkyl group.

Stereochemistry of chiral centers bearing acylamino groups is determined by initially used amino acid configuration whereas stereochemistry of acylamino groups depends on initially used fatty acid configuration. One can start from a diamino acid having L or D configuration or of a racemic mixture. One can start from a hydroxylated amino acid of L, D configuration or of a racemic mixture. All such stereoisomers or diastereoisomers of compounds of general formulae I or IV or XII or still XVI are included in the scope of the invention.

Generally, the compounds of the invention are prepared by coupling an acid functional group of an N-acyl-, ω-functionally substituted amino acid with the amine functional group of an amino alcohol resulting from the reduction of a carboxyl group of a mono-N-acyl-diamino acid, followed by O-acyl or -alkyl substitution of the still free alcohol functional group in order to introduce an accessory functional side chain spacer, which can be optionally modified after binding to expose a reactive functional group. Deprotection of the final product frees an acid functional group.

In a currently preferred method for preparing the compounds of the invention (FIG. 1), the ω-functionally derivatized amino acid is an α-amino ω-hydroxyl acid such as serine or homoserine, which is subjected to a series of N-protection reactions (for example, in the form of a t-butoxycarbonyl derivative), benzyl ester formation by O-alkyl substitution of a carboxylate and phosphorylation of the OH functional group in order to introduce a protected phosphate group. Typical protective groups of phosphates may be phenyl, benzyl or o-xylyl groups. A phenyl group is the currently preferred one. Next, the amine functional group is freed by removal of the protective group (for example by treatment of the t-butyoxycarbonyl derivative with trifluoroacetic acid), then acyl-substituted by an activated fatty acid derivative, preferably a derivative of 3-hydroxytetradecanoic acid such as 3-dodecanoyloxytetradecanoic acid. The activated form may be an acyl chloride, an activated ester, a mixed anhydride or any other species allowing formation of an amide bond. Next, benzyl ester is removed by selective hydrogenolysis to yield a carboxylic acid bearing an acylamido group in α position and a $(RO)_2P(O)O$—-group in ω position.

The peptide coupling reaction partner is obtained in preference from an α,ω-diaminoacid such as ornithine or lysine through a series of protective reaction steps which are selective of the amine functional group in ω position, for example in the form a benzyloxycarbonyl derivative, by means of a copper complex according to the method disclosed in [*Organic Preparations and Procedures International*, 23 (1992): 191-194], removal of the copper complex and protection of the amine functional group in α position, for example in the form of a t-butyoxycarboxyl derivative. Other protective groups could be used. The free carboxylic functional group is converted by reduction into a primary alcohol using for example the borane-dimethylsulfide complex or by treatment of a preformed mixed anhydride by sodium borohydride, according to a method disclosed in [Tetrahedron Letters, 32 (1991) 923-926]. The amine functional group in α position is freed in acidic medium (for example through treatment by trifluoroacetic acid), then N-acyl-substituted by an activated fatty acid derivative, preferably a 3-hydroxytetradecanoic acid derivative such as 3-benzyoxytetradecanoic acid. If needed, the free OH functional group is protected at this stage, for example in the form of a benzyloxymethyl ether. The ω-amino functional group is freed by treatment with a reagent compatible with other protective groups still present, for example by selective hydrogenolysis in an alcohol type solvent containing triethylamine if the protective group is a benzyloxycarbonyl one.

Figure 5:
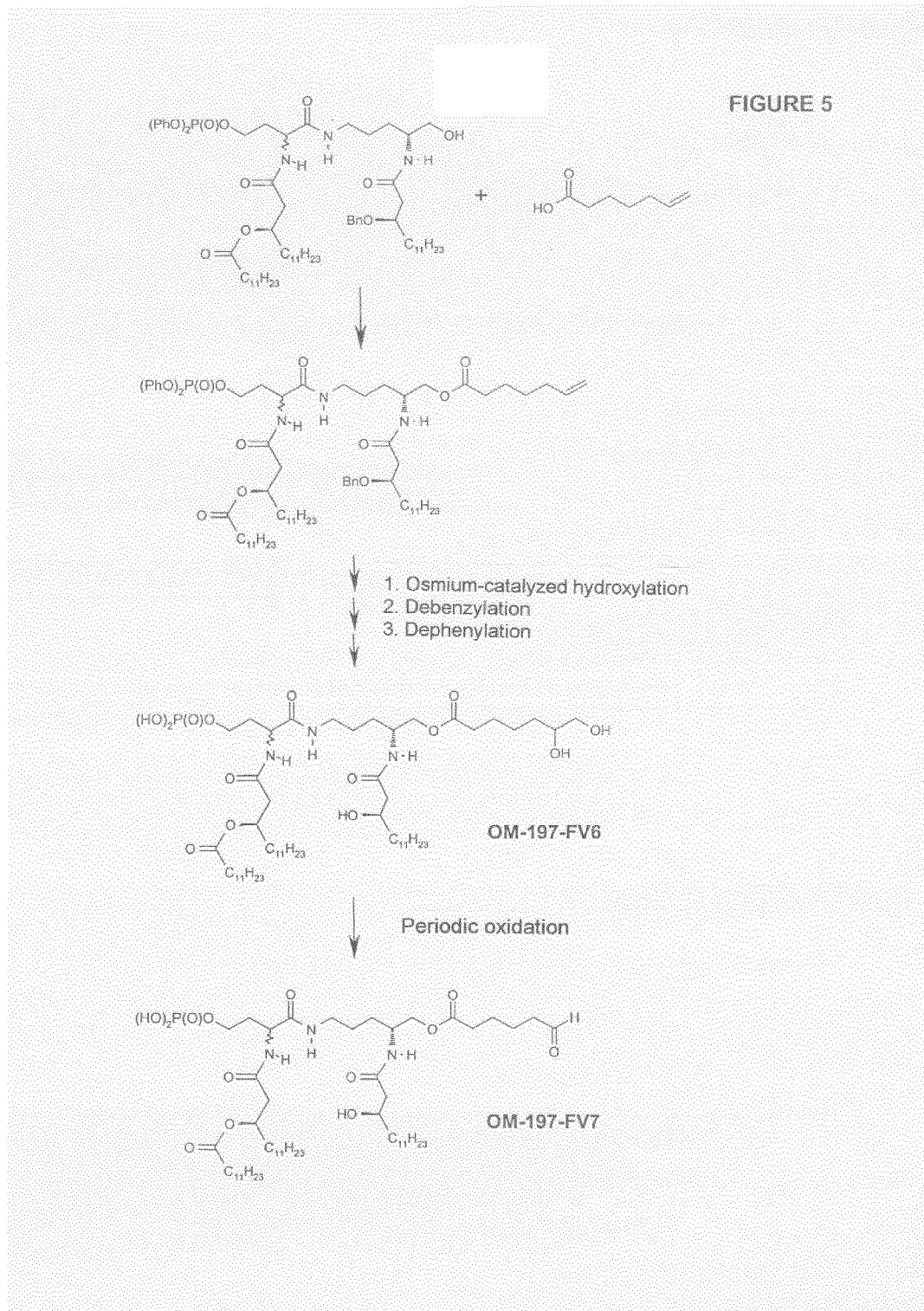
FIG. 5 shows the synthesis of the peptide conjugate OM-197-FV7.

In the currently preferred synthesis method, the amine thus obtained is coupled by means of an α-acylamine-, ω-phosphoryl-carboxylic acid prepared as described above in presence of IIDQ or another peptide coupling reagent, to yield a protected phosphorylated dipeptide-like compound. This product is O-acyl substituted at the still free hydroxyl functional group with an co-functionally derivatized acid such as 6-heptenoic acid in presence of EDCI or another esterifying reagent (FIG. 5). The alkenyl functional group of this ester is subjected to a dihydroxylation reaction in presence of osmium tetraoxide either in catalytic or stoichiometric amount, then the protective groups of the phosphate and the hydroxyl functional group optionally present in the form of a benzyl ether, are removed by hydrogenolysis in presence of a suitable catalyst (EX 2.1.). In the last step, the vicinal diol group is subjected to an oxidation reaction such as for example using periodic acid to generate a reactive aldehyde functional group (E.x. 2.2) Reduction of the aldehyde functional group into a primary alcohol results in a derivative bearing an ω-hydroxyacyl group (Ex. 2.9).

Figure 2:
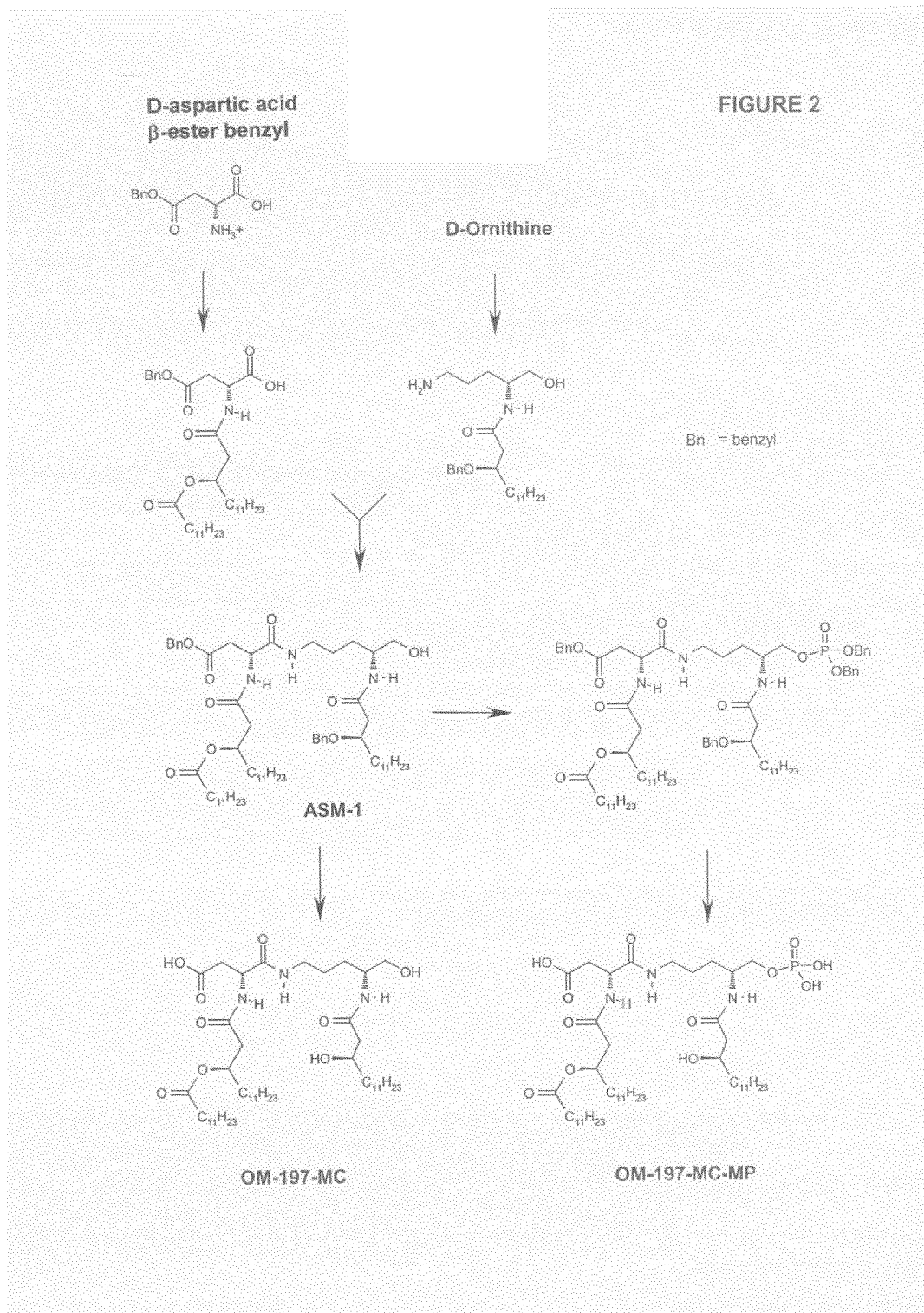
FIG. 2 shows the synthesis of the pseudodipeptide OM-197-MC and OM-197-MC-MP.
Figure 11:
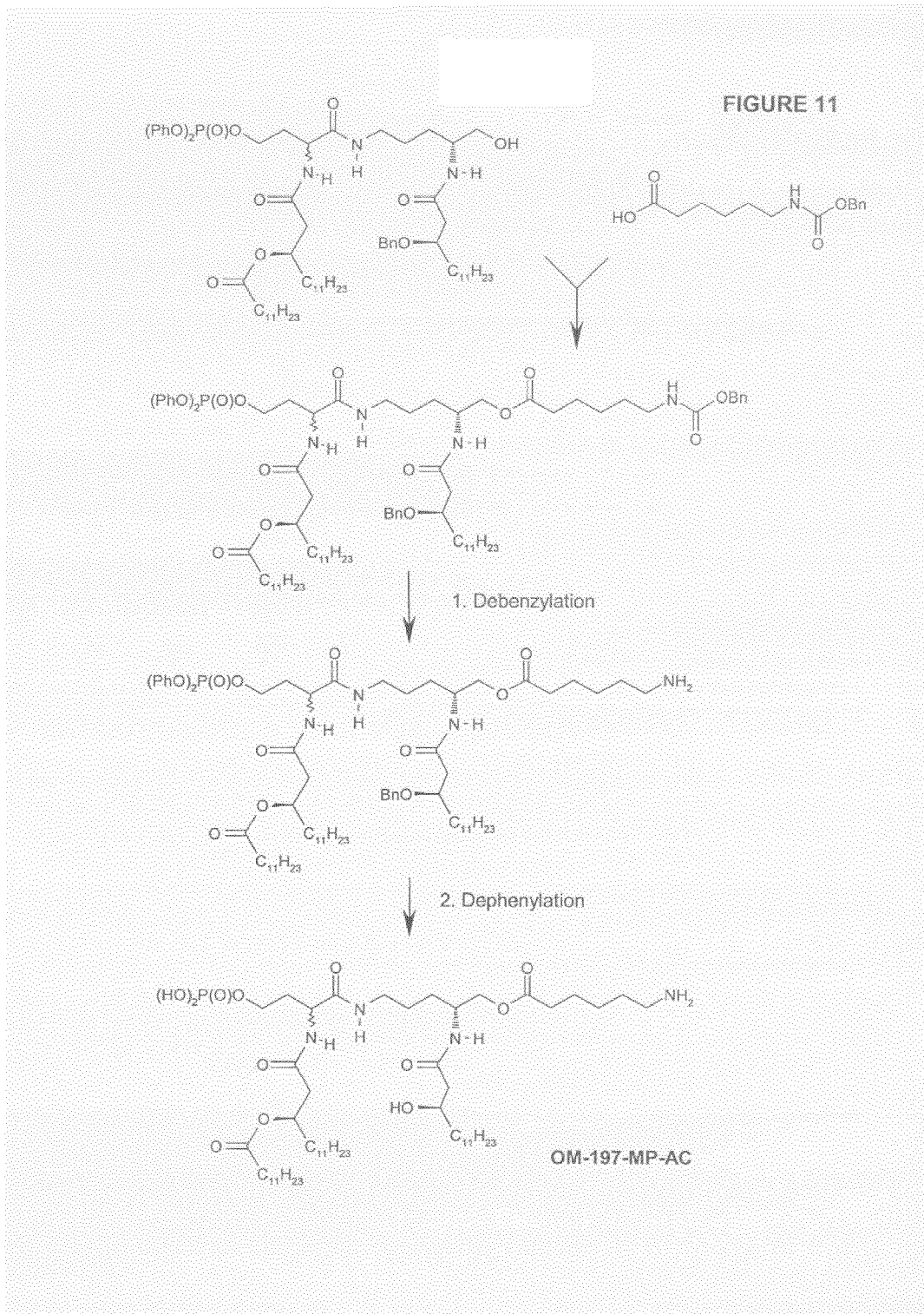
FIG. 11 shows the synthesis of the peptide conjugate OM-197-MP-AC.

As one alternative to this method, the resulting peptide conjugate product is O-acyl substituted using an ω-aminoalkanoic acid derivative, such as 6-benzyloxycarbanoylaminohexanoic acid (FIG. 11). The product thus obtained is subjected to a full deprotection reaction by hydrogenolysis in presence of a suitable catalyst to provide a dipeptide-like compound bearing an aminoalkanoyl accessory side chain spacer (Ex. 2.6).

n a second preferred method, the peptide coupling reaction acid partner is a D- or L-aspartic acid or optionally a D- or L-glutamic acid derivative (FIG. 2). The aspartic acid derivative is obtained by N-acylation of the amine functional group of this amino acid β-benzyl ester by reaction with a fatty acid, preferably a 3-hydroxy fatty acid derivative such as 3-dodecanoyloxytetradecanoic acid, in presence of an acyl substitution agent. This product is coupled to the amino alcohol of the previously mentioned type, and the dipeptide-like compound thus obtained is then subjected either to a hydrogenolysis reaction in presence of a catalyst such as palladium on carbon or a platinium coated substrate to provide the dipeptide-like compound bearing the carboxylic acid functional group (Ex. 1.2) or to a phosphorylation reaction, for example by the phosphoramidite method, followed by a hydrogenolysis reaction to yield the dipeptide-like compound bearing a carboxylic acid and a phosphoric acid functional group (Ex 1.3.).

Alternatively, the hydroxyl functional group of the previously obtained dipeptide-like compound (FIG. 2) is acylated by an ω-functionally substituted acid. Preferably, this ω-functionally substituted acid is an ω-alcenoic acid or an ω-aminoalkanoic acid. In case heptenoic acid is used (FIG. 8), the dipeptide-like compound finally results in an O-heptenoyl derivative which is sequentially subjected to dihydroxylation reactions in presence of osmium tetraoxide, and thereafter to deprotection (Ex 2.3) and periodic oxidation reactions (Ex. 2.4), whereby reduction of the thus formed aldehyde functional group with a reducing agent such as for example sodium borohydride yields the dipeptide-like compound bearing an ω-hydroxyalkanoyl functional group (Ex. 2.5). In case ω-aminoalkanoic acid such as N-benzyloxycarbonyl 6-aminohexanoic acid or glycine derivative is used (FIG. 24), acylation of the dipeptide-like compound results in protected O-aminoacyl derivatives which are thereafter subjected to a deprotection reaction through hydrogenolysis (Ex. 2.13 and 2.18).

In a second variant to this procedure (FIG. 13), the intermediate dipeptide-like compound described in FIG. 2 is subjected to a protection reaction at the free hydroxyl functional group, preferably in the form of a tetrahydropyranyl ether, then the esterified carboxyl functional group is successively deprotected by hydrogenolysis or some other deprotection method, reduced, preferably after activation into a mixed anhydride, with a reducing agent such as sodium borohydride; the resulting hydroxyl functional group is subjected to a phosphorylation reaction, preferably by the phosphoramidite method, and thereafter the tetrahydropyranyl ether is hydrolyzed in acidic conditions and the hydroxyl functional group thereby regenerated is subjected to an acylation reaction with an ω-functionally substituted carboxylic acid. In preference, the ω-functionally substituted acid is an ω-alcenoic acid or an ω-aminoalkanoic acid. In the case of 6-benzyloxycarbonylaminohexanoic acid, the dipeptide-like compound results into a protected O-aminoacyl derivative which is subsequently subjected to a hydrogenolysis reaction (Ex. 2.7, Ex. 2.8). Alternatively, the monophosphorylated intermediate of the previous section can be obtained (FIG. 15) by peptide coupling of an N-acyl aspartic acid β-benzylester derivative (FIG. 2) with a protected species, for example in the form of either benzyloxymethyl or tetrahydrofuranyl ether or still silyl-ornithine-aminoalcohol derivative (FIG. 1), followed by freeing the acid functional group in the form of a benzyl ester, reducing the same into a primary alcohol, phosphorylating said functional group and deprotecting the protected alcohol functional group in the form of either benzyloxymethyl, tetrahydropyranyl or silyl ether.

In a third variant to this procedure, the intermediate dipeptide-like compound described in FIG. 2 is subjected to an O-acylation reaction (FIG. 27) using a dicarboxylic acid derivative, preferably succinic anhydride, in presence of a base or a coupling agent, then the newly formed ester is subjected to a deprotection reaction by hydrogenolysis (Ex. 2.19) Treatment of deprotected O-aminoacyl derivatives with succinic anhydride gives dipeptide-like compounds bearing a succinylaminoacyl group (Ex. 2.17).

Figure 17:
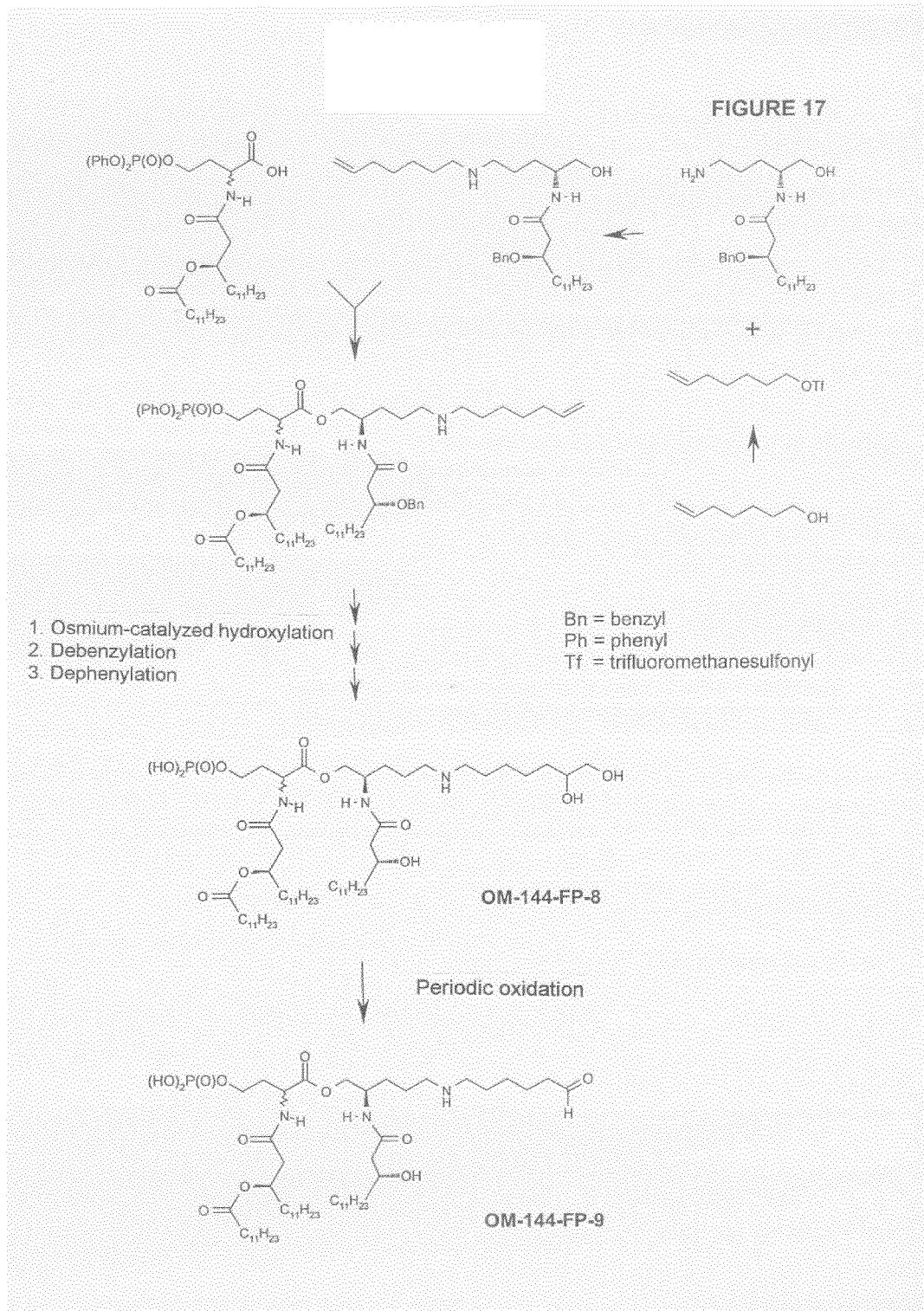
FIG. 17 shows the synthesis of the conjugate OM-144-FP-8 and OM-144-FP-9.

According to a third preferred method, the amino alcohol obtained from ornithine or lysine as described above, is alkyl-substituted by an ω-alkenyl triflate, such as hept-6-enyl triflate (FIG. 17). The coupling of this amino alcohol bearing a secondary amine with α-acylamine ω-phosphoryl acid described above in presence of EDCI or another acylating agent gives an ester. The alkenyl group is then subjected to a dihydroxylation reaction in presence of osmium tetraoxide, and then the protective groups are removed by hydrogenolysis in presence of appropriate catalysts, and the vicinal diol functional group is oxidized by sodium periodate to form a reactive aldehyde functional group (Ex. 2.10).

According to a fourth preferred method (FIG. 19), an N-protected serine derivative, for example a p-methoxybenzyloxycarbonyl derivative prepared according to a method disclosed in Synthesis (1989), 36-37 is O-alkyl substituted with benzyl bromoacetate. The protective group of the amine functional group is removed, for example by treatment with trifluoroacetic acid in dichloromethane, and the amine functional group is N-acylated, preferably with a 3-hydroxy fatty acid derivative such as 3-dodecanoyloxytetradecanoic acid, in presence of an acylating agent or using an acid chloride or any other activated form of the fatty acid. The N-acyl O-alkyl serine derivative thus obtained is coupled with the amino alcohol described above (FIG. 1) in presence of a peptide coupling agent such as IIDQ, and the free OH functional group is then acyl substituted with an ω-functionally derivatized alkanoic acid in presence of a reagent such carbodiimide. Preferably, this functionally derivatized acid is an co-alcenoic acid or an co-aminoalkanoic acid derivative. For instance, using hept-6-enoic acid, the dipeptide-like compound finally results in an O-(6-heptenoyl) derivative which is subjected in succession to dihydroxylation reactions in presence of osmium tetraoxide, followed by hydrogenolysis and periodic oxidation deprotection reactions (Ex 2.11.).

Figure 20:
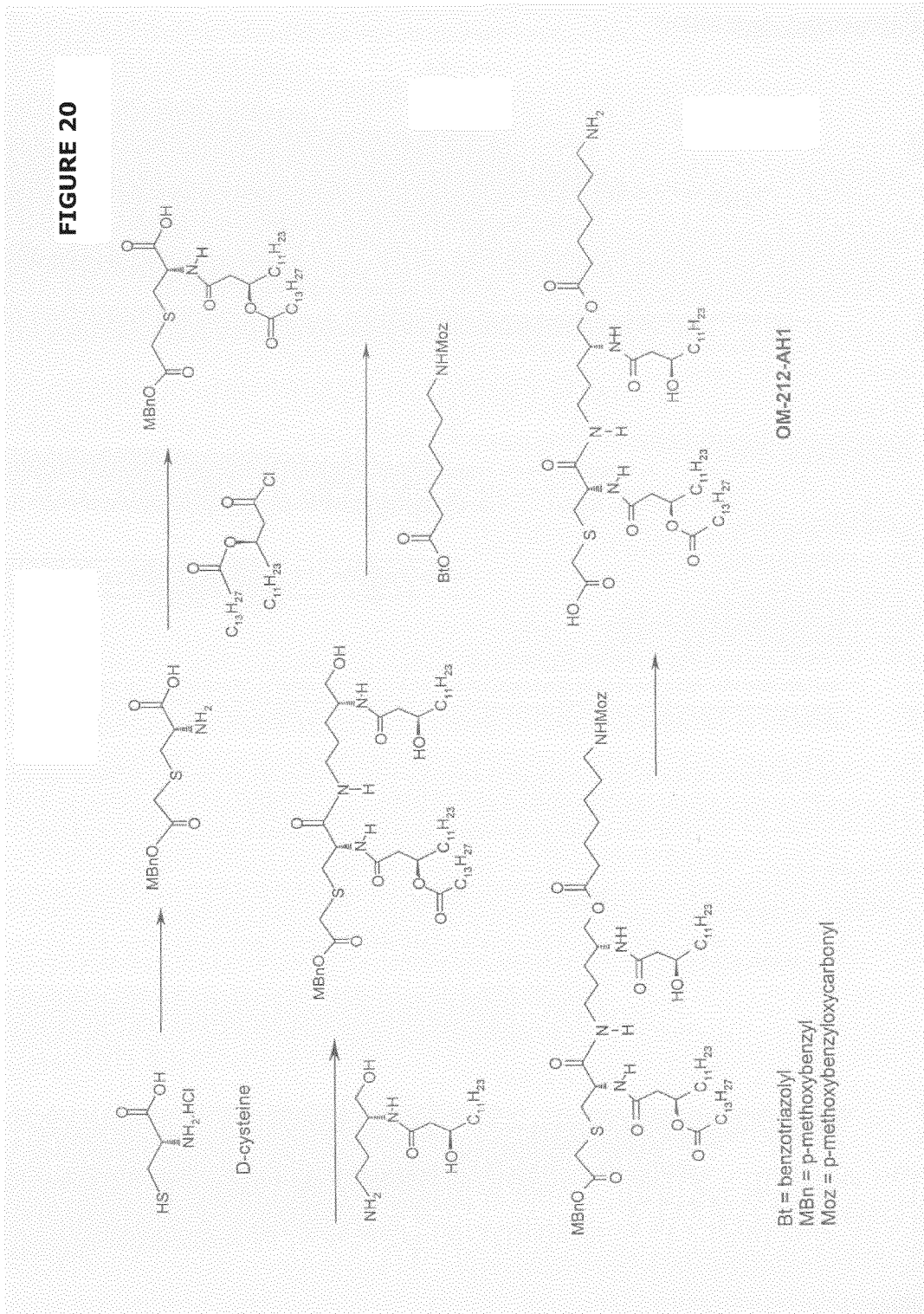
FIG. 20 shows the synthesis of peptide conjugate OM-212-AH1.

According to a fifth currently preferred method, the starting amino acid is cysteine or homocysteine (FIG. 20). For example, cysteine is S-alkyl substituted with p-methoxybenzyl bromoacetate, then N-acyl substituted, preferably with a 3-hydroxy fatty acid derivative such as 3-tetradecanoyloxytetradecanoic acid, in presence of an acylating agent or using acid halide or any other activated form of such a fatty acid. The S-alkyl N-acyl-cysteine derivative thus obtained is coupled to 5-amino-2-[(R)-3-hydroxytetradecanoylamino]pentan-1-ol in presence of IIDQ or another peptide coupling agent. The free OH functional group is then O-acyl substituted with an ω-functionally derivatized alkanoic acid, used in the form of an activated ester such as O-benzotriazolyl ester. Preferably, this acid is an ω-aminoalkanoic acid such as 7-(p-methoxy-benzyloxycarbonylamino)heptanoic acid. The product thus obtained is subjected to a full deprotection reaction in an aqueous acidic environment to thereby provide a dipeptide-like compound bearing a 7-aminoheptanoyl accessory side chain spacer (Ex. 2.12).

In another preferred method (FIG. 21), the serine N-p-methoxybenzyloxycarbonyl derivative is O-alkyl substituted with dibenzyl methylenemalonate in alkaline conditions. The amino protective group is removed by acid treatment, then the amine functional group thus freed is N-acyl substituted, preferably with a 3-acylhydroxy fatty acid derivative such as 3-dodecanoyloxytetradecanoic acid, in presence of an acylating agent or a functional fatty acid derivative such as acid chloride or any other activated form of such a fatty acid. The N-acyl O-alkyl serine derivative thus obtained is coupled to the amino alcohol described above (FIG. 1) in presence of IIDQ or any other peptide coupling agent. The dipeptide-like compound is then O-acyl substituted at the free OH functional group with an ω-functionally derivatized alkanoic acid. In preference, this acid is an ω-alcenoic acid or an ω-aminoalkanoic acid derivative, for example, using the hept-6-enoic acid. The dipeptide-like compound accordingly results in the O-(6-heptenoyl) derivative which is sequentially subjected to dihydroxylation reactions in presence of osmium tetraoxide, then to deprotection reactions by hydrogenolysis and periodic oxidation reaction, to finally yield a derivative having a 6-oxohexanoyl accessory side chain spacer as well as a malonyl group (Ex. 2.13).

In an equally preferred alternative method (FIG. 22), the 6-aminohexanoyl derivative mentioned above (FIG. 11), is N-acylated with a bromoacetamido group using for example bromoacetic acid O-succinimidyl ester as an acylating agent. This reaction provides a derivative bearing a 6-(bromoacetamido)hexanoyl accessory side chain spacer. (Ex 2.14.).

According to an eighth preferred method (FIG. 23), the O-phosphoryl-serine benzyl ester (see FIG. 1) is N-acyl substituted with 3-benzyloxytetradecanoic acid, preferably using the mixed anhydride prepared from 3-benzyloxytetradecanoic acid and isobutyl chloroformate. The benzyl ester is then subjected to selective hydrogenolysis as stated above. The ω-N-benzyloxycarbonyl diamino alcohol derived from ornithine (see FIG. 1) is $N_\alpha$-acyl substituted with 3-dodecanoyloxytetradecanoic acid, in presence of a coupling agent or using an activated ester or some other activated form of the fatty acid, and the ω-amino functional group is freed by selective hydrogenolysis. This amine is coupled to the N-(3-benzyloxytetradecanoyl) O-(diphenyl-oxyphosphoryl)homoserine derivative in presence of IIDQ or another peptide coupling agent. The dipeptide-like compound thus obtained is O-acyl substituted with an ω-functionally derivatized alkanoic acid, for example in presence of carbodiimide. Preferably, this acid is an ω-alcenoic acid or an ω-aminoalkanoic acid derivative. For example, using hept-6-enoic acid, the dipeptide-like compound results in an O-(6-heptenoyl) derivative which is sequentially subjected to dihydroxylation reactions in presence of osmium tetraoxide, then to a deprotection process by hydrogenolysis in presence of suitable catalysts and to a periodic oxidation reaction, to ultimately provide the derivative bearing a 6-oxohexanoyl accessory group.

According to a ninth preferred method (FIGS. 29, 31 and 34), the intermediate dipeptide-like compound described in FIG. 2 is subjected to a deprotection reaction at the esterified carboxyl functional group, and then this carboxyl functional group is coupled to a functionally substituted aminoalkane, in presence of a coupling agent. Preferably, the functionally substituted aminoalkane is an α,ω-diaminoalkane or amino acid derivative. In case of 1-amino-3-benzyloxycarbonylaminopropane (FIG. 29), the coupling reaction product is thereafter subjected to a hydrogenolysis reaction (Ex. 2.20). In case of $N^\epsilon$, Z-lysine benzyl ester, (FIG. 31), and α,β-dibenzyl aspartate (FIG. 34), the coupling reaction product is subjected either to a deprotection reaction, preferably by hydrogenolysis (Ex. 2.21 and 2.23), or an O-acylation reaction by means of an ω-functionally substituted alkanoic acid, preferably the N-benzyloxycarbonyl 6-aminohexanoic acid derivative. The resulting ester is then deprotected by hydrogenolysis or some other deprotection method (Ex. 2.22 and 2.24).

The invention further relates to intermediates of general formulae V, VI, IX, XIII and XVI either in the form of a pure enantiomer and/or stereoisomer or a mixture of stereoisomers.

The invention still relates to pharmaceutical compositions containing as an active ingredient at least one compound of general formula I, either in neutral or charged state, in combination or in admixture with a non toxic, pharmaceutically acceptable, inert vehicle or excipient.

The invention relates more specifically to pharmaceutical compositions containing as an active ingredient at least one salt of a compound of general formula I, together with an organic or mineral base intended for therapeutic use.

The invention still further relates to pharmaceutical compositions based on a compound of general formula I, either in the form of a pure enantiomer or in the form of a mixture of stereoisomers, in combination or in admixture with a pharmaceutical excipient or vehicle.

Among pharmaceutical formulations herein contemplated, mention should be made of those which are suitable to administration by mucosal, transcutaneous, topical, parenteral, digestive route or inhalation such as for instance coated or uncoated tablets, capsules, injection solutes or suspensions, spray, gels, plasters or rapid absorption solutes.

In preference, the compounds according to the invention can be grafted on an antigen to modulate the immune response or also be grafted on a pharmaceutical carrier to enhance therapeutic effect or targeting thereof and be administered by injection as conjugates in aqueous solutions or suspensions, optionally neutralized by an amine or a hydroxyalkylamine. For instance, mention is made of H1N1 antigen, SYVPSAEQI (SEQUENCE ID 1) nonapeptide antigen of *Plasmodium* and pharmaceutical carriers such as AZT, d4T as well as antibiotics such as macrolids and substances which act on the central nervous system CNS.

The following non limiting examples are intended to further illustrate the invention. They are outlined in FIGS. 1 to 86.

EXAMPLES

1$^{st}$ Series of Examples Preparation of Synthesis Intermediates

Example 1.1

1-(diphenyloxyphosphoryloxy)-3-[(R)-dodecanoyloxytetra-decanoyl-amino]-4-oxo-5-aza-9-[(R)-3-benzyloxytetradecanoylamino]-decan-10-ol (FIG. 1)

1.1.1. 4-(diphenyloxyphosphoryloxy)-2-[(R)-3-dodecanoyloxy-tetra-decanoyl-amino]butanoic acid a. N-Terbutyloxycarbonyl-DL-homoserine To a solution of homoserine bromohydrate (2 g; 16.78 mmol.) in H$_2$O (20 ml), addition was made in succession of a 1 M NaOH solution (16.78 ml) and cesium carbonate (3.01 g; 9.23 mmol.). After stirring for 5 minutes, the solution was cooled in an ice/water bath. Dioxane (60 ml) and t-butyl pyrocarbonate were then added. The reaction mixture was kept under stirring in an ice-cold water bath for 1 hour and thereafter at room temperature for 5 hours. The solvent was subsequently evaporated under vacuum and the dry residue was directly used in the next step.

b. Benzyl N-t-butyloxycarbonyl-DL-homoserinate

To the residue of the previous step, dimethylformamide (20 ml) was added and the solvent was evaporated to dryness. Then, to the reaction mixture, dimethylformamide (60 ml) and benzyl bromide (4.5 ml; 20.13 mmol) were added. At this point, a white precipitate formed. The mixture was kept under stirring for 16 hours. The solvent was then driven away under vacuum and the residue was extracted with ethyl acetate (2×20 ml). The organic layer was successively washed with H$_2$O (20 ml) and with brine (20 ml). After drying over MgSO$_4$, the solvent was evaporated and the residue was used as such in the next step.

c. Benzyl N-t-butyloxycarbonyl-O-(diphenyloxyphosphoryl)-DL-homoserinate

To the dried residue of the previous step dissolved in $CH_2Cl_2$ (60 ml), 4-N,N-dimethylaminopyridine (DMAP) (4.11 g; 33.56 mmol) was added. The reaction mixture was stirred for 10 minutes, and pyridine (12 ml) and diphenylchlorophosphate (6.95 ml; 33.56 mmol) were then added. The solution was stirred at room temperature for 18 hours and then washed successively with 1N HCl (5×20 ml), $H_2O$ (30 ml) and brine (30 ml). The organic layer was dried over $MgSO_4$ and the solvent was driven away under vacuum. By performing flash chromatography purification on a silica gel (elution with 4/1 hexane/ethyl acetate mixture), the phosphorylated product (7.49 g 82.4%) was recovered as a crystalline solid. Melting point: 63.5-64.0° C.

d. Benzyl O-(diphenyloxyphosphoryl)-DL-homoserinate, trifluoroacetic salt

The phosphorylated product of the previous step (7.88 g; 15.4 mmol) dissolved in trifluoroacetic acid (15 ml) was kept under stirring at room temperature for 2.5 hours. The solvent was then driven away under high vacuum and a purification step by flash chromatrography on a silica gel (10/1 MeOH/$CH_2Cl_2$ eluent) was conducted to recover the deprotected amine trifluoroacetic salt (7.17 g; 88.9%) as a crystalline solid. m.p.=73.0-73.5° C.

e. Benzyl 2-[(R)-3-Dodecanoyloxytetradecanoyl amino]-4(diphenyloxyphosphoryloxy)butanoate (R)-3-dodecanoyloxytetradecanoic acid (4.284 g; 10.07 mmol, 1 eq.) prepared according to the method disclosed in [*Bull. Chem. Soc. Jpn.*, 60 (1987), 2205-2214], was dissolved in tetrahydrofurane THF (30 ml) and the solution was cooled down to −15° C. N-methylmorpholin (1.108 ml; 10.07 mmol, 1 eq.) and isobutyl chloroformate (1.31 ml; 10.07 mmol; 1 eq.) were then added. The reaction mixture was kept under stirring for 30 minutes at 15° C. To the reaction mixture, there was next added benzyl O-(diphenyloxyphosphoryl)-DL-homoserinate (5.724 g; 10.07 mmol 1 eq.) in a THF/$Et_3N$ mixture (30 ml/5 ml). After stirring for 18 hours at room temperature, the solvent was driven away under vacuum. The residue was diluted with $H_2O$ (20 ml) and then extracted with ethyl acetate (2×30 ml). The organic layers were pooled, washed in succession with water (20 ml) and brine (20 ml) and dried over $MgSO_4$ before evaporating the solvent. By running flash chromatography purification on a silica gel (2/1 hexane/ethyl acetate eluent), the required benzyl ester was recovered (7.455 g 87%) as a crystalline solid. m.p.=31.0°-32.1° C., $^1$H-NMR (CDCl$_3$, 250 MHz), δ in ppm: 7.4-7.1 (m, 15H), 6.90 (2d, 1H, $^3J$=7.6 Hz, NH), 5.3-5.1 (m, 3H), 4.7 (m, 1H), 4.35 (m, 2H), 2.45 (m, 2H), 2.4-2.1 (m, 4H), 1.6 (m, 4H), 1.4-1.1 (m, 34H), 0.9 (t, 6H). $^{13}$C-NMR (CDCl$_3$, 63 MHz), δ in ppm: 173.01, 171.08, 169.66, 150.18, (d, $^2J_{P,C}$=7.1 Hz), 135.01, 129.60, 128.33, 128.14, 127.96, 125.21, 119.80 (d, $^3J_{P,C}$=5.0 Hz), 70.69, 67.05, 65.19 (d, $^2J_{P,C}$=5.6 Hz), 49.13, 40.97, 40.77 (2 diast.), 34.20, 33.98, 33.82, 31.70, 29.42, 29.34, 29.14, 28.94, 25.01, 24.77, 22.47, 13.91.

f. 4-(diphenyloxyphosphoryloxy)-2-[(R)-3-dodecanoyloxytetradecanoylamino]-butanoic acid A solution of the benzyl ester obtained in the previous step (2. 23 g 2.6 mmol) in HPLC-grade methanol MeOH (300 ml) in a three neck-round flask was hydrogenated in presence of carbon—10% palladium (1 g) at room temperature and under atmospheric pressure hydrogen for 1 hour. The catalyst was then filtered off and the filtrate was concentrated to obtain a colorless liquor. This product was homogeneous as assessed by thin layer chromatography and NMR, and was used directly with no further purification treatment in the coupling step; Rf=0.75 ($CH_2Cl_2$-MeOH-$Et_3N$, 10/1/0.5). $^1$H-NMR (CDCl$_3$, 250 MHz), δ in ppm: 7.4-7.1 (m, 10H), 6.85 (2d, 1H, NH), 5.15 (m, 1H), 4.6 (m, 1H), 4.35 (m, 2H), 2.45 (m, 2H), 2.4-2.15 (m, 4H), 1.6 (m, 4H), 1.4-1.1 (m, 34H), 0.9 (t, 6H). $^{13}$C-NMR (CDCl$_3$, 63 MHz), δ in ppm: 173.35, 173.30 (2 diast.), 172.75, 170.37, 150.0 (d, $^2J_{P,C}$=7.5 Hz), 129.55, 125.28, 119.71 (d, $^3J_{P,C}$=4.4 Hz), 70.78, 65.65, (d, $^2J_{P,C}$=5.9 Hz), 49.00, 40.77, 40.63 (2 diast.), 34.13, 33.86, 33.76, 31.59, 29.31, 29.25, 29.03, 28.82, 24.88, 24.68, 22.36, 13.76.

1.1.2 (2R)-5-amino-2-[(R)-3-benzyloxytetradecanoylamino]-pentan-1-ol a. Copper Salt of D-Ornithine

To a solution of D-ornithine (5.25 g; 30 mmol) in 1M NaOH (30 ml), a solution of cupric sulfate pentahydrate (3.814 g; 15.3 mmol) in water (50 ml) was added. After stirring for 2 hours at room temperature, the solvent was evaporated to dryness. Methanol (60 ml) was added to the residue to form a purple-colored solid which was separated, washed in succession with dioxane and methanol to be directly used in the next step.

b. Copper (2R)-2-Amino-5-(benzyloxycarbonylamino)pentanoate

The purple-colored solid was dissolved in 1N NaOH (40 ml) and dioxane (70 ml), The reaction mixture was cooled in an ice-cold water bath and benzyl chloroformate (5.14 ml; 36 mmol) was then added. After stirring in an ice-cold water bath for 3 hours and thereafter at room temperature for 15 hours, the purple-colored precipitate was recovered by filtration and sequentially washed with 95% EtOH (40 ml), $H_2O$ (50 ml) and EtOH (60 ml). The precipitate was dried in an oven (T<45° C., under vacuum); the yield of the two-step process was 8.27 g, i.e. 93% of the predicted yield. (Reference: *Organic Preparations and Procedures international*, 23: (1992) 191-194).

c. (2R)-5-(benzyloxycarbonylamino)-2(terbutyloxycarbonylamino) pentanoic acid The copper salt obtained in the previous step was dissolved in 2 N HCl (400 ml) and ethylenediaminetetraacetic acid (EDTA) was added (8.15 g, 27.8 mmol.) thereto. The mixture was stirred for 2.5 hours, and neutralized to pH 7 by adding NaOH 5N (about 160 ml). A white precipitate was formed at this point. The mixture was then stirred for 2.5 hours in an ice-cold water bath. The precipitate was filtered, washed with cold water until washing effluents were colorless, then dried in an oven below 60° C. This solid was dissolved in 1N NaOH (156 ml) and the solution was cooled down into an ice-cold water bath. To this solution, t-butyl pyrocarbonate (7.7 g; 35.2 mmol.) in dioxane (160 ml) was added. The mixture was stirred at 0° C. for 45 minutes and thereafter for 16 hours at room temperature. The organic solvent was evaporated and ethyl acetate (70 ml) was added to dissolve the residue. The aqueous layer was then acidified by adding 2N HCl down to pH≈3, washed with AcOEt (100 ml). The organic layers were combined and washed with H₂O (30 ml) and with brine (30 ml), then evaporated under vacuum. By conducting flash chromatography purification on a silica gel (20/1 CH₂Cl₂/MeOH eluent), the required product was recovered as a colorless oil (Yield: 8.42 g in two steps i.e. 76.6% of the predicted yield) (Rf=0.19, 20/1 CH₂Cl₂/MeOH)

d. (2R)-5-(Benzyloxycarbonylamino)-2-(terbutyloxycarbonylamino)pentan-1-ol

To a cold solution (−15° C.) of the diamino pentanoic acid derivative obtained previously (5.45 g; 14.8 mmol) in THF (60 ml), N-methylmorpholin (1.654 ml; 14.8 mmol) and isobutyl chloroformate (IBCF) (9.6 ml; 14.8 mmol) were added. The reaction mixture was stirred at −15° C. for 1 minute followed by addition of sodium borohydride (5.1 g; 44.6 mmol) in 10 ml of water. After further stirring for 10 minutes at −15° C., H₂O (400 ml) was added to the mixture to stop the reaction. The solution was subsequently washed with ethyl acetate AcOEt (100 ml×2). The organic layers were combined and washed with H₂O (50 ml) and with brine (60 ml) then dried over MgSO₄. The solvent was removed and the residue recrystallized from an ethyl acetate/hexane mixture to provide the expected crystalline product (4.94 g; 94.9% yield) m.p.=47.5-48° C.

e. (2R)-5-(benzyloxycarbonylamino-2-amino-pentan-1-ol, trifluoroacetic salt

A solution of (2R)-5-(benzyloxycarbonylamino)-2-(terbutyloxy-carbonylamino)-pentan-1-ol (6.32 g; 18 mmol) as obtained above in trifluoroacetic acid (25 ml) was prepared then subjected to stirring for 2.5 hours at room temperature. The solvent was thereafter evaporated and the residue purified by flash chromatrography on a silica gel (10/1 MeOH/CH₂Cl₂ eluent) to recover the trifluoroacetic salt as an oil (5.45 g 82.7%). The hydrochloride compound melts at 133.0°-134.3° C. (recrystallization from methanol).

f. (2R)-5-(Benzyloxycarbonylamino)-2-[(R)-3-benzyloxy-tetra-decanoylamino]pentan-1-ol To a solution of (R)-3-benzyloxytetradecanoic acid (5.27 g; 15. 8 mmol) [*Bull. Chem. Soc. Jpn.*, 60: (1987), 2197-2204] in THF (30 ml) which had been cooled down to −15° C., addition was made of N-methylmorpholin (1.89 ml 15.8 mmol) and of isobutyl chloroformate (2.21 ml, 15.8 mmol). After stirring the reaction mixture at −15° C. for 30 minutes, there was added a trifluoroacetate salt solution as obtained above (15.25 g, 14.4 mmol.) in a THF/Et₃N mixture (30 ml, 1.44 ml). Stirring was continued at room temperature for 16 hours and then the reaction mixture was diluted with H₂O (30 ml) and AcOEt (60 ml). The organic layer was separated and the aqueous layer was washed with ethyl acetate AcOEt (60 ml). The organic layers were pooled and washed with H₂O (30 ml) and with brine (30 ml) then dried over MgSO₄ before carrying out solvent evaporation under vacuum. The residue was recrystallized from an ethyl acetate/hexane mixture to finally yield the expected product in a crystalline state (5.8 g; 71.2% yield), m.p.=117.5-118° C. Rf=0.32, 3/1 ethyl acetate-petroleum ether. ¹H-NMR (CDCl₃, 250 MHz), δ in ppm: 7.4-7.2 (m, 10H), 6.5 (d, 1H, NH), 5.1 (s, 2H), 4.9 (m, 1H, NH), 4.5 (2d, AB, 2H), 3.8 (m, 2H), 3.5 (m, 2H), 3.1 (m, 2H), 2.4 (m, 2H) 1.6-1.4 (m, 6H), 1.4-1.2 (m, 18H), 0.9 (t, 3H). ¹³C-NMR (CDCl₃, 63 MHz), δ in ppm: 172.24, 156.49, 138.06, 136.53, 128.46, 128.04, 127.87, 76.76, 71.39, 66.60, 65.44, 51.54, 41.43, 40.65, 33.76, 31.87, 29.61, 29.30, 28.01, 26.47, 25.05, 22.65, 14.09.

g. (2R)-5-Amino-2-[(R)-3-benzyloxytetradecanoylamino]pentan-1-ol

In a three-neck flask, the catalyst (150 mg of 20% palladium/carbon) was added to the solution of (2R)-5-(benzyloxycarbonylamino)-2-[(R)-3-benzyloxytetradecanoylamino]pentan-1-ol (3.0 g; 5.27 mmol) in a mixture of triethylamine Et₃N (6 ml)/HPLC-grade ethanol EtOH (300 ml). Air was discharged under vacuum then the flask was loaded with hydrogen. The reaction mixture was hydrogenated at room temperature for 2 hours then the catalyst was filtered off and the filtrate was concentrated to provide the desired product as a homogenous white solid. Rf=0.2, 5/1 0/0.5 CH₂Cl₂-MeOH-Et₃N, m.p.=47-48° C.
¹H-NMR (CDCl₃, 250 MHz), δ in ppm: 7.4-7.2 (m, 5H), 6.75 (d, 1H, NH) 4.5 (2d, AB, 2H), 3.9 (m, 2H), 3.5 (m, 2H), 2.3-2.6 (m, 7H), 1.7-1.2 (m, 24H), 0.9 (t, 3H). ¹³C-NMR (CDCl₃, 63 MHz), δ in ppm: 171.86, 138.13, 128.37, 127.87, 127.75, 76.81, 71.50, 64.57, 51.38, 41.51, 41.17, 33.89, 31.82, 29.26, 28.57, 28.03, 25.07, 22.60, 14.04.

1.1.3. 1-(Diphenyloxyphosphoryloxy)-3-[(R)-3-dodcanoyloxy-tetra-decanoylaminol]-4-oxo-5-aza-9-[(R)-3-benzyloxytetradecanoylamino]-decan-10-ol IIDQ (2-isobutoxy-1-isobutoxycarbonyl-1,2-dihydroquinoline) 364 g; 1.2 mmol., 1.2 eq.) was added to a solution of (2RS)-4-(diphenyloxyphosphoryloxy)-2-[(R)-3-dodecanoyloxy-tetra-decanoylamino]-butanoic acid (850 g; 1.0 mmol; 1 eq.) in anhydrous methylene chloride CH₂Cl₂ (20 ml) at room temperature and under argon flow. After stirring for 15 minutes, addition was made of a solution of (2R)-5-amino-2-[(R)-3-benzyloxytetradecanoylamino]pentan-1-ol (757; 1.0 mmol.; 1 eq.) in anhydrous CH₂Cl₂ (10 ml). After stirring for 4 hours, the solution was evaporated to dryness. By running a flash chromatography purification on a silica gel (5/2 CH₂Cl₂/acetone eluent), there was recovered the phosphorylated dipeptide-like compound (620 mg; 53%) as an amorphous solid. (Rf=0.49, in dichloromethane-methanol-triethylamine, 10/1/0.5). ¹H-NMR (CDCl₃, 250 MHz), δ in ppm: 7.40-7.15 (m, 15H), 7.00 (m, 1H), 6.90 and 6.80 (2d, 2 diast., 1H), 6.65 (d, 1H) (3×NH), 5.15 (m, 1H), 4.50 (m, 3H), 4.30 (m, 2H), 3.85 (m, 2H), 3.45 (m, 2H), 3.15 (m, 2H), 2.41-2.14 (m, 8H), 1.6-1.4 (m, 8H), 1.4-1.1 (m, 54H), 0.9 (t, 9H, 3CH₃). ¹³C-NMR (CDCl₃, 63 MHz), δ in ppm: 173.11, 171.68, 170.52 (2 diast.), 169.94 (2 diast), 150.0 (d, ²J$_{P,C}$=7.2 Hz), 138.0 (2 diast.), 129.58, 127.99, 127.49, 127.26, 125.24, 119.73 (t, ³J$_{P,C}$=5.0 Hz), 76.48, 71.12, 70.71, 65.86 (broad spin), 64.22, 50.96, 49.71 (broad spin), 41.46, 41.05, 39.07, 34.13, 34.00, 32.70, 31.61, 29.34, 29.06, 28.87, 27.98, 25.25, 24.92, 24.72, 22.38, 13.80.

Example 1.2

N—[(R)-3-dodecanoyloxytetradecanoyl]-D-aspartic acid, α-N-{(4R)-5-hydroxy-4[(R)-3-hydroxytetradecanoylamino]-pentyl}amide (=OM-197-MC) (FIG. 2)

1.2.1 N—[(R)-3-dodecanoyloxytetradecanoyl]-D-aspartic acid, β-benzyl ester

To a solution of (R)-3-dodecanoyloxytetradecanoic acid (3.35 g; 7.85 mmol.) in anhydrous THF (25 ml) at −15° C. and under argon flow, there were added in succession N-methylmorpholin (0.86 ml; 7.85 mmol; 1 eq.) and isobutyl chloroformate (1.02 ml; 7.85 mmol.; 1 eq.). Rapid formation of a N-methylmorpholin hydrochloride precipitate was observed. After stirring for 30 minutes at −15° C., a commercially available solution of H-D-Asp(OBn)-OH (Senn Chemicals AG, Switzerland-Dielsdorf) (1.75 g; 7.85 mmol.; 1 eq.) in a 3.5/1 $CH_3CN/H_2O$ mixture (85 ml) containing $Et_3N$ (3.7 ml) was added. The reaction mixture was then stirred overnight at room temperature. The organic solvent was then evaporated and the aqueous layer was cooled down to 0° C., acidified with a 10% aqueous solution of citric acid down to pH=3 and extracted with AcOEt (2×). The organic layer was dried over $MgSO_4$, filtered and evaporated. By running a flash chromatography purification on a silica gel (2/1 petroleum ether/AcOEt eluent containing 2% of acetic acid) followed by coevaporation of toluene, there was recovered [(R)-3-dodecanoyloxytetradecanoylamino]-D-aspartic acid β-benzyl ester (4.00 g; 81%) as a white crystalline solid (Rf=0.42 in 1/1 petroleum ether/EtOAc containing 2% of acetic acid; phosphomolybdinium compound and U.V. color development agent). m.p.=67-69° C.

1.2.2. N—[(R)-3-dodecanoyloxytetradecanoyl]-D-aspartic acid, α-N-{(4R)-5-hydroxy-4-[(R)-3-benzyloxytetradecanoylamino pentyl}amide β-benzyl ester (ASM-1)

To a solution of β-benzyl ester as obtained above (363 mg; 0.57 mmol.) and (2R)-5-amino-2-[(R)-3-benzyloxy-tetradecanoylamino]pentan-1-ol (Section 1.1.2) (250 mg; 0.57 mmol.; 1.0 eq) in anhydrous $CH_2Cl_2$ (6 ml) at 0° C. (ice/water bath), addition was made in succession under argon flow of commercially available HOAt (1-hydroxy-7-azabenzotriazol) (94 mg, 0.69 mmol., 1.2 eq.) and commercially available N,N'-diisopropylcarbodiimide (109 μl, 0.69 mmol., 1.2 eq.). The reaction mixture was stirred for 1 hour at 0° C. and thereafter overnight at room temperature. The reaction mixture was subsequently washed with water, a 1N HCl solution, and a saturated solution of $NaHCO_3$ followed by layer separation. The organic layer was dried on $MgSO_4$, filtered and evaporated. By running a flash chromatography purification on a silica gel (3/1 $CH_2Cl_2$/acetone eluent), there was recovered the coupling reaction product (436 mg; 72%) as a white crystalline solid (Rf=0.27 in 5/1 $CH_2Cl_2$-acetone; phosphomolybdinium compound and U.V. color development agent). m.p.=106-108° C.; $^{13}C$-NMR (62.89 MHz, $CDCl_3$), δ in ppm: 173.66; 172.09 171.73; 170.33; 170.12; 138.23; 135.28; 128.53; 128.37; 128.13; 127.81; 127.71; 125.81; 76.71; 71.40; 71.16; 66.77; 65.01; 51.36; 49.39; 41.66; 39.25; 34.40; 33.98; 31.85; 29.58; 29.47; 29.29; 29.11; 28.00; 25.57; 25.17; 25.08; 24.94; 22.62; 14.05.

1.2.3. N—[(R)-3-dodecanoyloxytetradecanoylamino]-D-aspartic acid, α-N{(4R)-5-hydroxy-4-[(R)-3-benzyloxytetradecanoylamino pentyl}amide (=OM-197-MC)

Figure 3:
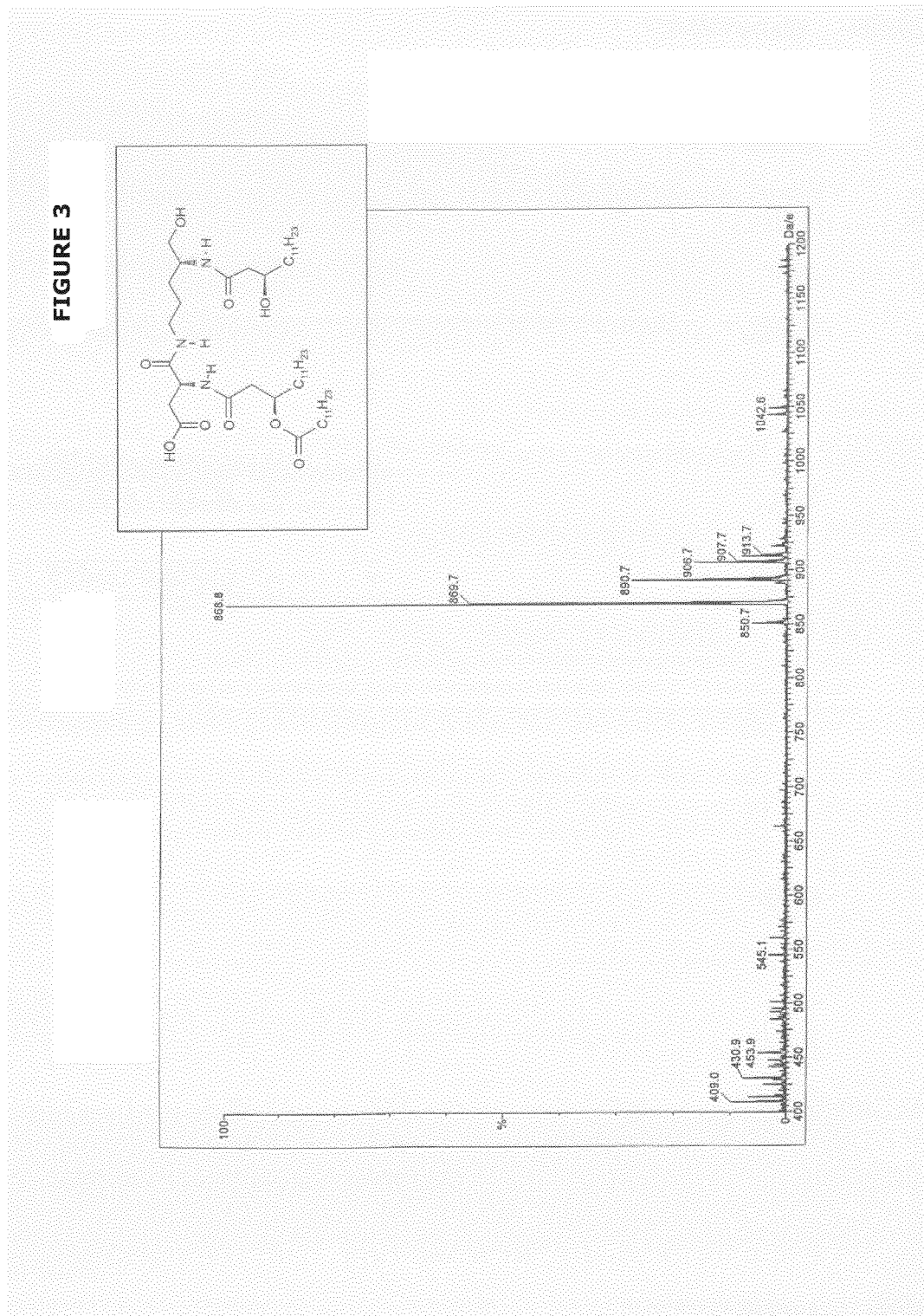
FIG. 3 shows the ionic cloud by LC/ES mass spectra analysis of the conjugate OM-197-MC.

A solution of N—[(R)-3-dodecanoyloxytetradecanoyl]-D-aspartic acid β-benzyl ester, α-N-{(4R)-5-hydroxy-4-[(R)-3-benzyloxytetradecanoylamino pentyl}amide (417 mg; 0.40 mmol.) in a 1/1 MeOH/EtOAc mixture (36 ml) was hydrogenated in presence of 10% Pd/carbon (20 mg) at room temperature and under atmospheric pressure hydrogen for 3 hours. The catalyst was filtered off, washed with a 4/1 $CH_2Cl_2$/MeOH mixture (50 ml) and the filtrate was evaporated to dryness by suction from a vacuum pump to yield the free acid (345 mg; 100%) as a white crystalline solid (Rf=0.30 in 9/1 $CH_2Cl_2$/MeOH containing 0.5% of acetic acid; phosphomolybdinium compound color developer). m.p. 135-137° C. ES/MS: m/z ratio 868.7 $[M+H]^+$, 890.7 $[M+Na]^+$, 868.7 $[M+K]^+$ 912.7 $[M-H+2Na]^+$ (FIG. 3).

1.2.4. N—[(R)-3-dodecanoyloxytetradecanoyl]-L-aspartic acid, α-N-{(4R)-5-hydroxy-4-[(R)-3-benzyloxytetradecanoylamino pentyl}amide The same reaction scheme was followed using commercially available H-L-Asp(Obn)-OH (Fluka, Buchs, Switzerland) to finally obtain an epimer product of L-aspartic series.

Example 1.3

N—[(R)-3-dodecanoyloxytetradecanoyl]-D-aspartic acid, α-N-{(4R)-5-dihydroxyphosphoryloxy-4-[(R)-3-hydroxytetradecanoyl-amino]pentyl}amide (=OM-197-MC-MP) (FIG. 2)

1.3.1. N—[(R)-3-dodecanoyloxytetradecanoyl]-D-aspartic acid, α-N-{(4R)-5-dibenzyloxyphosphoryloxy-4-[(R)-3-benzyloxytetradecanoylamino pentyl}amide β-benzyl ester To a solution of N—[(R)-3-dodecanoyloxytetradecanoyl]-D-aspartic acid, α-N-{(4R)-5-hydroxy-4-[(R)-3-benzyloxytetradecanoylamino]-pentyl}amide β-benzyl ester as obtained above (300 mg; 0.29 mmol.) and 1H-tetrazol (60 mg; 0.86 mmol.) in anhydrous THF (12 ml) at room temperature and under argon flow, there was added 85% dibenzyldiethyl phosphoramidite (231 μl; 0.66 mmol.). Rapid formation of white crystals in the reaction medium was observed. After stirring for 30 minutes, the reaction mixture was cooled down to −20° C. then a solution of mCPBA (57-86%; 183 mg; 1.06 mmol.) in $CH_2Cl_2$ (8 ml) was added. Disappearance of crystals was noted. After stirring for 45 minutes at room temperature, a saturated solution of $Na_2S_2O_3$ was added then the reaction mixture was stirred again for 10 minutes. The solution was diluted with ether, then the organic layer was separated and washed with a saturated solution of $Na_2S_2O_3$ (5×), a saturated solution of $NaHCO_3$ (2×) and a solution of 1M HCl (1×). The organic layer was dried over $MgSO_4$, filtered and evaporated. By running a flash chromatography purification on a silica gel (5/1 $CH_2Cl_2$/acetone eluent), there was recovered the phosphotriester (294 mg; 79%) as a white solid (Rf=0.27 in 5/1 $CH_2Cl_2$-acetone; phosphomolybdinium compound and U.V. color development agent) $^{13}C$-NMR (62.89 MHz, $CDCl_3$), δ in ppm: 173.66; 171.73; 171.01; 170.60; 170.03; 138.22; 135.50; 135.40; 135.28; 128.40; 128.33; 128.16; 128.08; 127.94; 127.82; 127.76; 127.53; 127.41; 76.43; 71.03; 70.90; 69.28; 66.47; 49.09; 48.37; 41.62; 41.36; 41.24; 39.02; 38.88; 25.05; 24.94; 24.82; 22.48; 13.90.

1.3.2. N—[(R)-3-dodecanoyloxytetradecanoyl]-D-aspartic acid, α-N-{(4R)-5-dihydroxyphosphoryloxy-4-[(R)-3-hydroxytetradecanoyl-amino] pentyl}amide (=OM-197-MC-MP)

Figure 4:
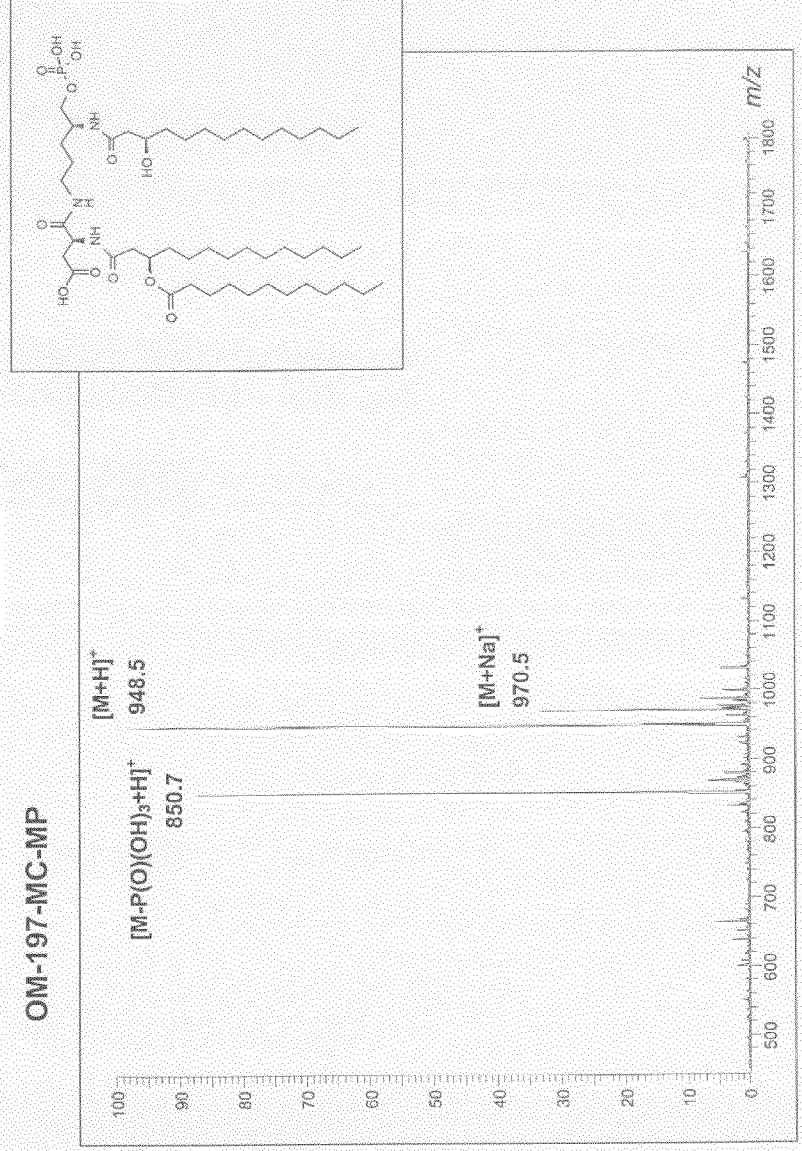
FIG. 4 shows the ionic cloud by LC/ES mass spectra analysis of the monoconjugate OM-197-MC-MP.

A solution of dibenzylphosphate as prepared above (249 mg; 190 μl) in HPLC-grade EtOH (12 ml) is hydrogenated in presence of 10% Pd/carbon (30 mg) at room temperature and under atmospheric pressure hydrogen for 4 hours. The catalyst is filtered off on a millipore filter and the filtrate is evaporated to dryness then the residue is dried by a vacuum pump to obtain the crude free phosphate (180 mg; 100%). ES/MS: m/z 850.7 [M+H−P(O)(OH)$_3^+$], 948.5 [M+H]$^+$ 970.5 [M+Na]$^+$ (FIG. 4).

Example 1.1

Determining Epimerization Rate of Synthesis Intermediates

Stereochemistry of chiral centers bearing acylamino groups is determined by initially used amino acid configuration. However, peptide coupling performed between the aspartic or glutamic acid derivative and the aminoalcohol obtained from ornithine or lysine can lead, under certain conditions, to epimerization at $C_\alpha$ of the acid partner involved in the coupling reaction. In order to assess epimerization rate of such a reaction, the following method was followed for compounds derived from aspartic acid.

The sample (30 μg) was evaporated into a microvial, then redissolved in 40 μl of 6M HCl Hydrolysis was allowed to proceed for 24 hours at 110° C. under argon atmosphere. The sample was then evaporated to dryness, and thereafter redissolved in 100 ml of 0.1 M tetraborate buffer, pH 9.2. A pre-column derivatization was subsequently run with OPA-IBLC reagent (o-phtaldialdehyde-N-isobutyryl-L-cysteine) in the following proportions:
5 μl of a 0.1 M sodium tetraborate buffer solution, pH 9.2
2 μl of a methanol 170 mM OPA, 260 mM IBLC solution
2 μl of the solution to be assayed
By running an HPLC separation on Hypersil ODS column (250×4.6 mm, 5 μm, Supelco), both derivatives arising from L- and D-forms of aspartic acid present in the initial sample were quantified (Bruckner et al., 1995, J. Chromatography. A 711, 201-215). HPLC operating conditions used were as follows:
Column: Hypersil ODS (250×4.6, 5 μm, Supelco)
Mobile phase: A: 23 mM sodium acetate, pH 5.9
B: Methanol-acetonitrile (121)
Injection: 5 μl
Flow rate: 1 ml/min
Elution step: 96:4 to 80:20 A:B gradient within 25 minutes
Detection: UV: 338
Under these chromatographic conditions, retention times of 16.1 and 17.2 minutes were observed for the L- and D-aspartic acid derivatives, respectively.

2$^{nd}$ Series of Examples Preparation of Dipeptide-Like Compounds Bearing an Accessory Functional Side Chain Spacer Example 2.1

3-[(R)-dodecanoyloxytetradecanoylamino]-4oxo-5-aza-9-[(R)-3-hydroxytetradecanoylamino]-decan-1,10-diol 1-dihydrogenphate 10-(6,7-dihydroxyheptanoate) (=OM-197-FV6) (FIG. 5)

2.1.1. 1-(Diphenyloxyphosphoryloxy)-3-[(R)-3-dodecanoyloxytetra-decanoylamino]-4-oxo-5-aza-9-[(R)-3-benzyl-oxytetradecanoylamino]-decan-10-ol (6-heptenoate)

To a solution of 1-(diphenyloxyphosphoryloxy)-3-[(R)-3-dodecanoyloxytetradecanoylamino]-4-oxo-5-aza-9-[(R)-3-benzyloxytetra-decanoylamino]-10-ol (FIG. 1.1) (875 mg; 0.74 mmol.) in anhydrous CH$_2$Cl$_2$ (25 ml), there was added 6-heptenoic acid (141 μl; 1.04 mmol.; 1.4 eq.). The solution was cooled down to 0° C. Next, there was added EDCI (64 mg; 0.33 mmol.; 1.4 eq.) and DMAP (41 mg; 0.33 mmol.; 0.14 eq.) The reaction mixture was stirred for 30 minutes at 0° C. and thereafter 3 hours at room temperature. After dilution with CH$_2$Cl$_2$, the organic layer was washed in succession with H$_2$O, a 1N HCl solution and H$_2$O. The organic layer was then dried over MgSO$_4$, then evaporated at 40° C. under vacuum. By running a flash chromatography purification on a silica gel (petroleum ether/AcOEt 1/1 eluent), there was recovered 1-(Diphenyloxyphosphoryloxy)-3-[(R)-3-dodecanoyloxytetradecanoylamino]-4-oxo-5-aza-9-[(R)-3-benzyloxytetradecanoylamino]-dcan-10-ol 6-heptenoate (820 mg; 85%) as a white foam (Rf=0.18 in 1/1 petroleum ether/AcOEt; phosphomolybdinium acid color developer). $^{13}$C-NMR (62.89 MHz, CDCl$_3$), δ in ppm: 173.30; 171.18; 170.4; 169.91; 169.73; 150.10; 138.21; 138.14; 129.77; 128.25; 127.49; 125.44; 119.88; 114.56; 76.48; 71.11; 70.90; 66.01; 65.52 49.90; 47.80; 41.34; 39.07; 33.92; 33.76; 33.69; 33.61; 33.17; 31.75; 29.47; 29.19; 29.00; 28.46; 28.11 25.34; 25.05; 24.85; 22.52; 13.96.

2.1.2. 1-(Diphenyloxyphosphoryloxy)-3-[(R)-3-dodecanoyloxy-tetradecanoylamino]-4-oxo-5-aza-9-[(R)-3-benzyloxytetradecanoylamino]-10-ol (6,7-dihydroxyheptenoate)

To a solution containing K$_3$Fe(CN)$_6$ (373 mg; 1.13 mmol; 3 eq.) K$_2$CO$_3$ (157 mg; 1.13 mmol.; 3 eq.) and 1,4-diazabicyclo[2.2.2.]octane (DABCO) (10.7 mg; 0.095 mmol.; 0.25 eq.) in a t-butanol/water mixture (5 ml/5 ml), there was added the compound obtained above (486 mg, 0.38 mmol.), then osmium tetraoxide dissolved in 2.5% t-butanol (48 μl; 4.75 μmol.; 0.0125 eq.). The reaction mixture was strongly stirred for 16 hours at room temperature (27° C.). Na$_2$S$_2$O$_5$ (60 mg) was added and stirring was continued for nearly 1 hour until the medium shifted in color from brown to green or blue. The reaction mixture was diluted with ether and the organic layer was separated. The aqueous layer was thoroughly washed with ether and the organic layers were pooled, dried over MgSO$_4$, then evaporated at 40° C. under vacuum. The expected raw diol was thus obtained as a green oil. By running flash chromatography purification on a silica gel (5/2 CH$_2$Cl$_2$/acetone), there was pure 1-(diphenyloxyphosphoryloxy)-3-[(R)-3-dodecanoyloxytetradecanoylamino]-4-oxo-5-aza-9-[(R)-3-benzyloxytetradecanoylamino]-10-ol 6,7-dihydroxyheptanoate (198 mg; 40%) as an amorphous solid (Rf=0.24 in 5/2 CH$_2$Cl$_2$/acetone; phosphomolybdinium acid color developer). $^{13}$C-NMR (62.89 MHz, CDCl$_3$), δ in ppm: 173.46; 173.33; 171.34; 170.58; 170.02; 150.13; 138.23; 129.80; 128.26; 127.87; 127.54; 125.50; 120.01; 119.80; 71.79; 71.23; 70.97; 66.63; 66.03; 65.54; 49.93; 47.90; 41.46; 39.17; 33.98; 33.79; 32.86; 32.45; 31.77; 29.49; 29.21; 29.03; 28.51; 25.50; 25.07; 24.87; 24.77; 24.66; 22.54; 13.99. HPLC (210 nm): T$_R$=32.535 min. (retention time) ES/MS: m/z ratio 1343.0 (M+Na$^+$); 1321.0 (M+H$^+$) 1071.0 (M+H$^+$ monophenyl phosphate).

2.1.3. 1(-Diphenyloxyphosphoryloxy)-3-[(R)-3-dodecanoyloxy-tetradecanoylamino]-4-oxo-5-aza-9-[(R)-3-hydroxytetradecanoylamino]-10-ol (6,7-dihydroxyheptanoate)

A solution of the above diol (198 mg, 0.15 mmol.) in HPLC grade EtOH (20 ml)/AcOEt (1.4 ml) mixture is hydrogenated in presence of Pd on carbon containing 10% Pd (70 mg) at room temperature and under atmospheric pressure hydrogen for 2.5 hours. The catalyst is filtered off. The filtrate is evaporated to dryness and the residue is then dried by suction from a vacuum pump to provide the crude debenzylated product (168 mg 91%) as an amorphous solid. $^{13}$C-NMR (62.89 MHz, CDCl$_3$), δ in ppm 173.15; 173.51; 172.82; 171.04; 170.49; 170.35; 150.05; 129.79; 129.42; 125.53; 119.91; 119.83; 119.72; 71.80; 70.93; 68.58; 66.47; 65.94; 65.52; 50.02; 48.12; 42.59; 41.26; 39.13; 36.92; 34.29; 33.85; 32.32; 31.74; 29.50; 29.18; 29.00; 28.15; 25.47; 25.07; 24.85; 24.73; 24.56; 22.51; 13.99. HPLC (210 nm): $T_R$=30.7 min. ES/MS: m/z ratio 1253.0 [M+Na]$^+$; 1231.0 [M+H]$^+$.

2.1.4. 3-[(R)-3-dodecanoyloxytetradecanoylamino]-4-oxo-5-aza-9-[(R)-3-hydroxytetradecanoylamino]-decan-1,10-diol-1-dihydrogen-phosphate 10-(6,7-dihydroxyheptanoate) (=OM-197-FV6)

Figure 6:
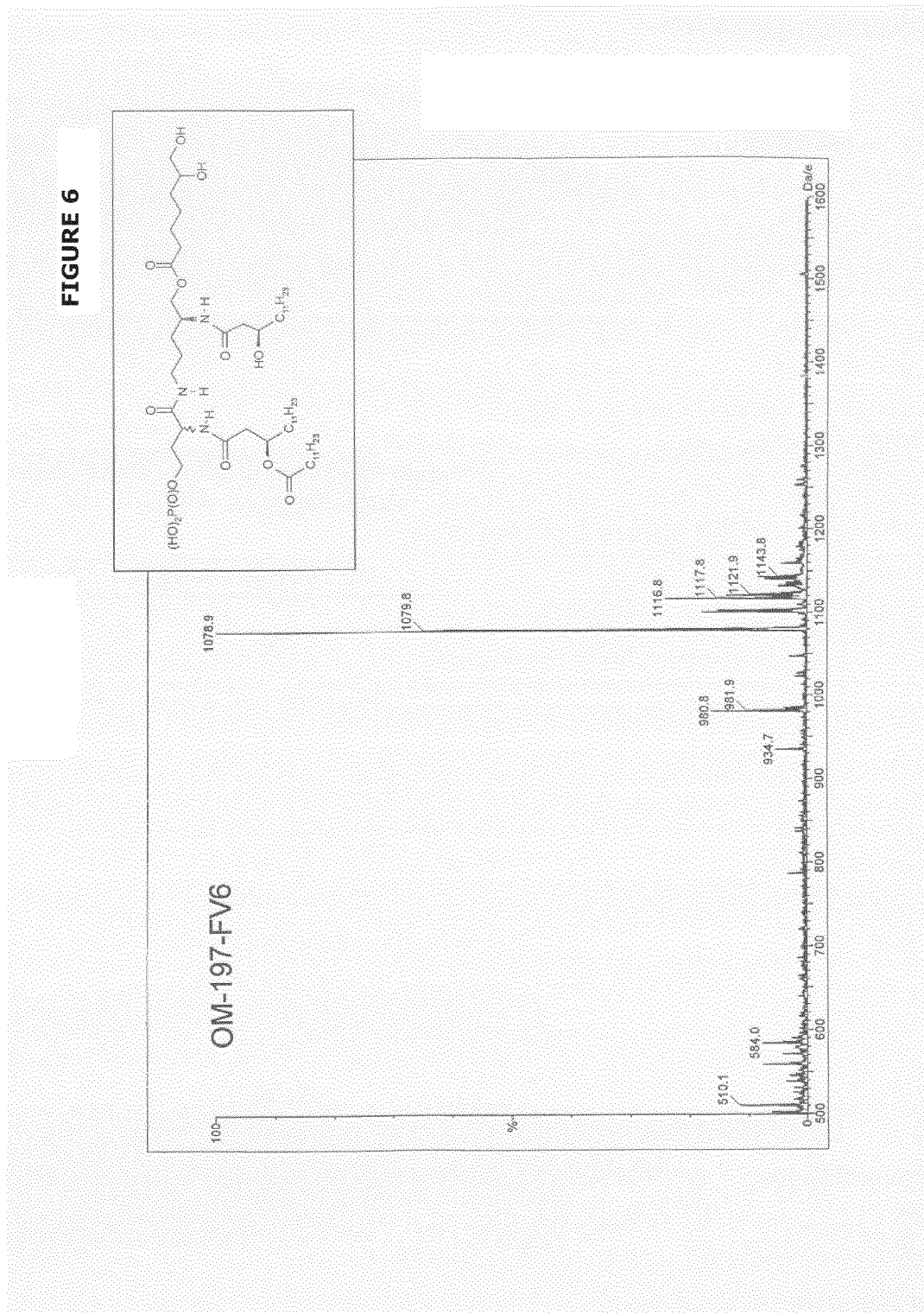
FIG. 6 shows the ionic cloud of LC/ES mass spectra analysis of the peptide conjugate OM-197-FV6.

A suspension of platinium oxide PtO$_2$ (91 mg) (preactivated to yield platinium black under atmospheric pressure hydrogen for 10 min) in HPLC-grade ethanol (1 ml) is added to a solution of the previously obtained trivalent alcohol (168 mg; 0.14 mmol.) in HPLC-grade EtOH (8 ml)/AcOEt mixture (8 ml). The solution is hydrogenated at room temperature (27° C.) under atmospheric pressure hydrogen for 24 hours. The catalyst is filtered off. The filtrate is evaporated to dryness then the residue is dried by suction from a vacuum pump to thereby obtain the crude phosphate product (130 mg; 88%). HPLC (210 nm): $T_R$=23.6 min. ES/MS: m/z ratio 1078.9 [M+H]$^+$, 1100.8 [M+Na]$^+$, 116.8 [M+K]$^+$ (FIG. 6).

Example 2.2

3-[(R)-3-dodecanoyloxytetradecanoylamino]-4-oxo-5-aza-9-[(R)-3-hydroxytetradecanoylamino]-decan-1,10-diol 1-dihydrogen-phosphate 10-(6-oxohexanoate) (=OM-197-FV7)

2.2.1.3-[(R)-3-dodecanoyloxytetradecanoylamino]-4-oxo-5-aza-9-[(R)-3-hydroxytetradecanoylamino]-decan-1,10-diol 1-dihydrogen-phosphate 10-(6-oxohexanoate) (=OM-197-FV7) (FIG. 5)

Figure 7:
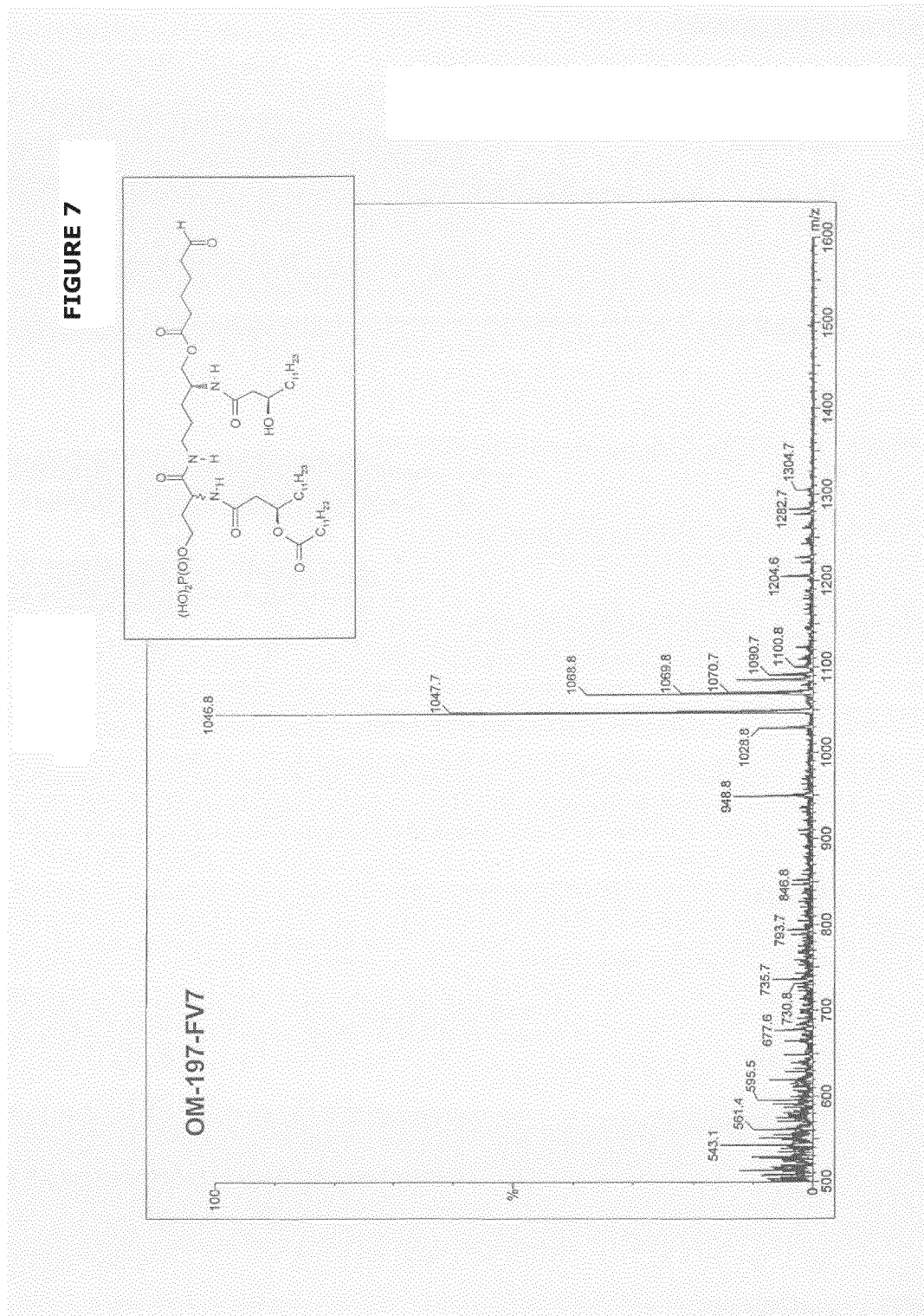
FIG. 7 shows the ionic cloud of LC/ES mass spectra analysis of the conjugate OM-197-FV7.

A periodic oxidation reaction was carried out through addition of 1.86 ml of 0.1 M NaIO$_4$ (39.62 mg, 20 eq.) to 10 mg (9.28 i mol., 1 eq.) of deprotected triol as prepared above in a (1:1) water/isopropanol mixture. The reaction is monitored by LC/UV detection and shows quantitative conversion of the diol functional group into aldehyde two hours later. The expected reaction is shown to occur by observing a 1046.8 m/z ratio molecular ion on the ES/MS spectrum following the periodic oxidation step (FIG. 7). By looking at the spectrum, 1068.8 m/z ratio ([M+Na]$^+$) sodium and 1084.8 m/z ratio ([M+K]$^+$) potassium adducts are clearly visible, as well as a fragment corresponding to the loss of a 948.8 m/z ratio phosphoryl group. The reaction is terminated by adding 1 to 2 drops of ethylene glycol. Purification of the product can be carried out by SPE on a C18 phase with a yield of 90% (5 mg diol analyte)

Example 2.3

Figure 8:
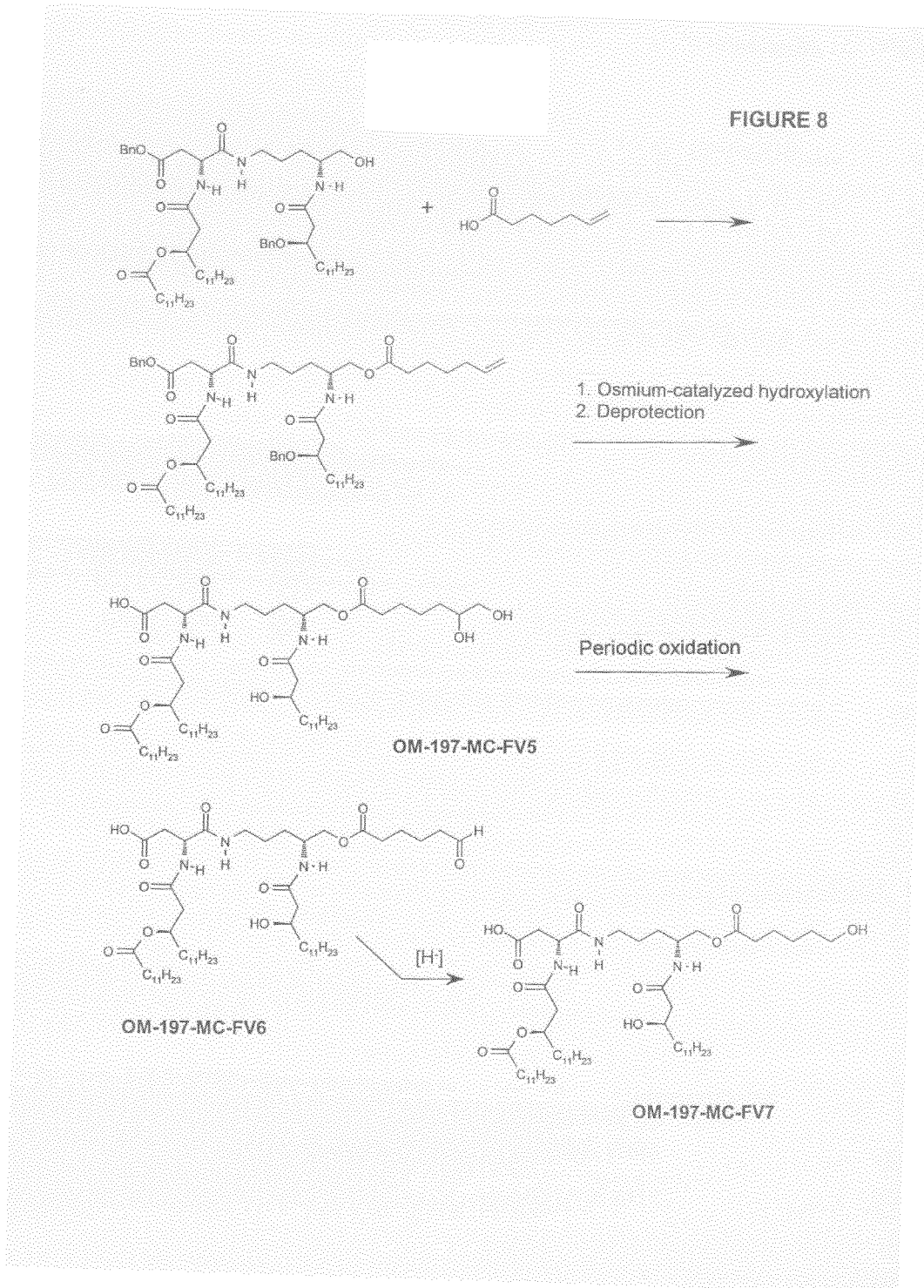
FIG. 8 shows the synthesis of the peptide conjugate OM-197-MC-FV5, OM-197-MC-FV6 and OM-197-MC-FV7.

N—[(R)-3-dodecanoyloxytetradecanoylamino]-D-aspartic acid, α-N-{(4R)-5-hydroxy-4-[(R)-3-hydroxytetra-decanoylamino]-pentyl}amide 5-O-(6,7-dihydroxyheptanoate) (=OM-197-MC-FV5) (FIG. 8)

2.3.1. N—[(R)-3-dodecanoyloxytetradecanoylamino]-D-aspartic acid, α-N-{(4R)-5-hydroxy-4-[(R)-3-benzyloxytetra-decanoylamino]pentyl}-amide-β-benzyl ester, 5-O-(6-heptenoate)

To a solution of N—[(R)-3-dodecanoyloxytetradecanoylamino]-D-aspartic acid, α-N-{(4R)-5-hydroxy-4-[(R)-3-benzyloxy-tetradecanoylamino]pentyl}amide-β-benzyl ester (Section 1.2.2.) (122 mg; 0.116 mmol.) in anhydrous dichloromethane (5 ml), there is added 6-heptenoic acid (22 µl; 0.160 mmol; 1.4 eq.). The solution is cooled down to 0° C. Addition is then made of EDCI (49.3 mg; 0.25 mmol.; 2.1 eq.) and DMAP (5.6 mg; 0.046 mmol.; 0.4 eq.). The reaction mixture is stirred at 0° C. for 30 minutes, and thereafter for 6 hours at room temperature. After CH$_2$Cl$_2$ dilution, the organic layer is washed in succession with H$_2$O, 1N HCl (2×), NaHCO$_3$ (2×) and H$_2$O (2×). The expected heptenoic acid ester is thereby obtained in a pure state (119 mg; 89%) as a white solid (R$_f$=0.62 in 5/1 CH$_2$Cl$_2$/acetone mixture, color developer: phosphomolybdinium acid) $^{13}$C-NMR (62.89 MHz, CDCl$_3$), δ in ppm: 173.63; 173.38, 171.72; 171.11, 170.08; 138.14; 135.28; 128.46, 128.34; 128.24; 128.05; 127.64; 127.53; 114.62; 76.49; 71.14, 66.66; 65.49; 49.17; 47.79; 41.69; 41.35; 39.09; 35.46; 34.33; 33.80; 33.65; 33.21; 31.79, 29.52; 29.23; 29.06; 28.46; 28.16; 22.56; 14.00. HPLC (210 nm): $T_R$=36.9 min. ES/MS: m/z ratio 1159.0 [M+H]$^+$; 1176.0 [M+NH$_4$]$^+$. Mp=81.5-84° C. [α]$_D^{20}$=+7.3 (CHCl$_3$).

2.3.2. N—[(R)-3-dodecanoyloxytetradecanoylamino]-D-aspartic acid, α-N-{(4R)-5-hydroxy-4-[(R)-3-benzyloxytetradecanoylamino]pentyl}amide-β-benzyl ester, 5-O-(6,7-dihydroxyheptanoate)

To a solution of heptenoic acid ester as obtained above (60 mg; 0.052 mmol.) in a (5/3 ml) H$_2$O/acetone mixture, addition is made of N-methylmorpholin oxide (9 mg; 0.076 mmol.; 1.5 eq.), and thereafter of a solution of OsO$_4$ in 2.5% t-butanol (123 µl; 0.012 mmol.; 0.23 eq.) in a dropwise fashion. The reaction mixture is stirred for 24 hours at room temperature. Na$_2$S$_2$O$_5$ (20 mg) is added to the reaction mixture which is stirred thereafter for 1 hr to 2 hr at room temperature. The solution is then extracted several times with ether, and the organic layers are subsequently pooled, dried, over MgSO$_4$ and concentrated. By running a flash chromatography treatment on a silica gel (5/2 CH$_2$Cl$_2$/acetone eluent), there is recovered the expected diol in a pure state (35 mg; 57%) as a white solid (Rf=0.15 in a 5/1 CH$_2$Cl$_2$/acetone mixture; color developer: phosphomolybdinium acid). $^{13}$C-NMR (62.89 MHz, CDCl$_3$), δ in ppm 173.67; 173.39; 171.81; 171.34; 170.27; 170.01; 138.18; 135.27; 128.56; 128.42; 128.18; 127.50; 127.68; 76.68; 71.82; 71.37; 71.17; 66.85; 66.74; 65.66; 49.27; 47.99; 41.88; 41.51; 39.31; 35.60; 34.42; 33.95; 33.51; 31.80; 29.60; 29.49; 29.30; 28.55; 25.65; 25.60; 25.19; 25.12; 24.97; 24.77; 24.14; 22.65; 14.08. HPLC (210 nm): $T_R$=34.16 min. ES/MS: m/z ratio 1193.0 [M+H$^+$]; 1212.0 [M+NH$_4$]$^+$.

2.3.3. N—[(R)-3-dodecanoyloxytetradecanoylamino]-D-aspartic acid, α-N-{(4R)-5-hydroxy-4-[(R)-3-hydroxytetradecanoylamino]pentyl}amide 5-O-(6,7-dihydroxyheptanoate) (=OM-197-MC-FV5)

Figure 9:
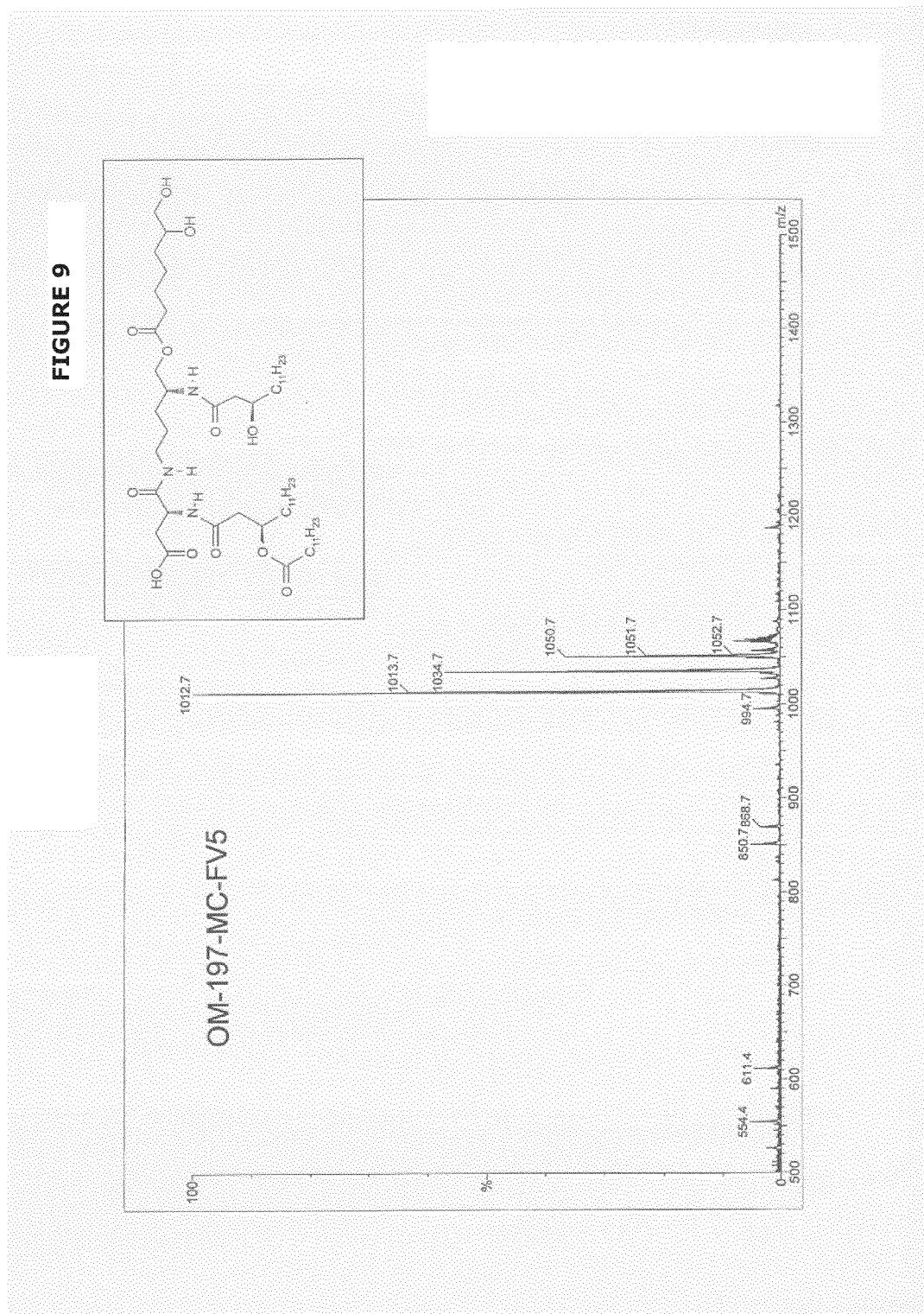
FIG. 9 shows the ionic cloud of LC/ES mass spectra analysis of the peptide conjugate OM-197-MC-FV5.

A solution of the above obtained diol (35 mg; 0.029 mmol.) in a HPLC-grade MeOH (2 ml)/AcOEt (2 ml) mixture is hydrogenated in presence of Pd on carbon containing 10% palladium (10 mg) at room temperature and under atmospheric pressure hydrogen for 2.5 hours. The catalyst is filtered off. The filtrate is evaporated to dryness then the residue is dried by suction from a vacuum pump to obtain crude N—[(R)-3-dodecanoyloxytetradecanoylamino]-D-aspartic acid, α-N-{(4R)-5-hydroxy-4-[(R)-3-hydroxy-tetra-decanoylamino]-pentyl}amide 5-O-(6,7-dihydroxyheptanoate) (26 mg; 88%) as a white solid. HPLC (210 nm): $T_R$=26.90 min. m.p.=94-97° C. $[\alpha]_D^{20}$=+11.1° (CHCl$_3$/MeOH=1:0.1). ES/MS: m/z ratio 1012.7 [M+H]$^+$; 1034, 7 [M+Na]$^+$, 1050.7 [M+K]$^+$ (FIG. 9).

Example 2.4

N—[(R)-3-dodecanoyloxytetradecanoylamino]-D-aspartic acid, α-N-{(4R)-5-hydroxy-4-[(R)-3-hydroxytetradecanoylamino]pentyl}amide 5-O-(6-oxohexanoate) (=OM-197-MC-FV7) (FIG. 8)

Figure 10:
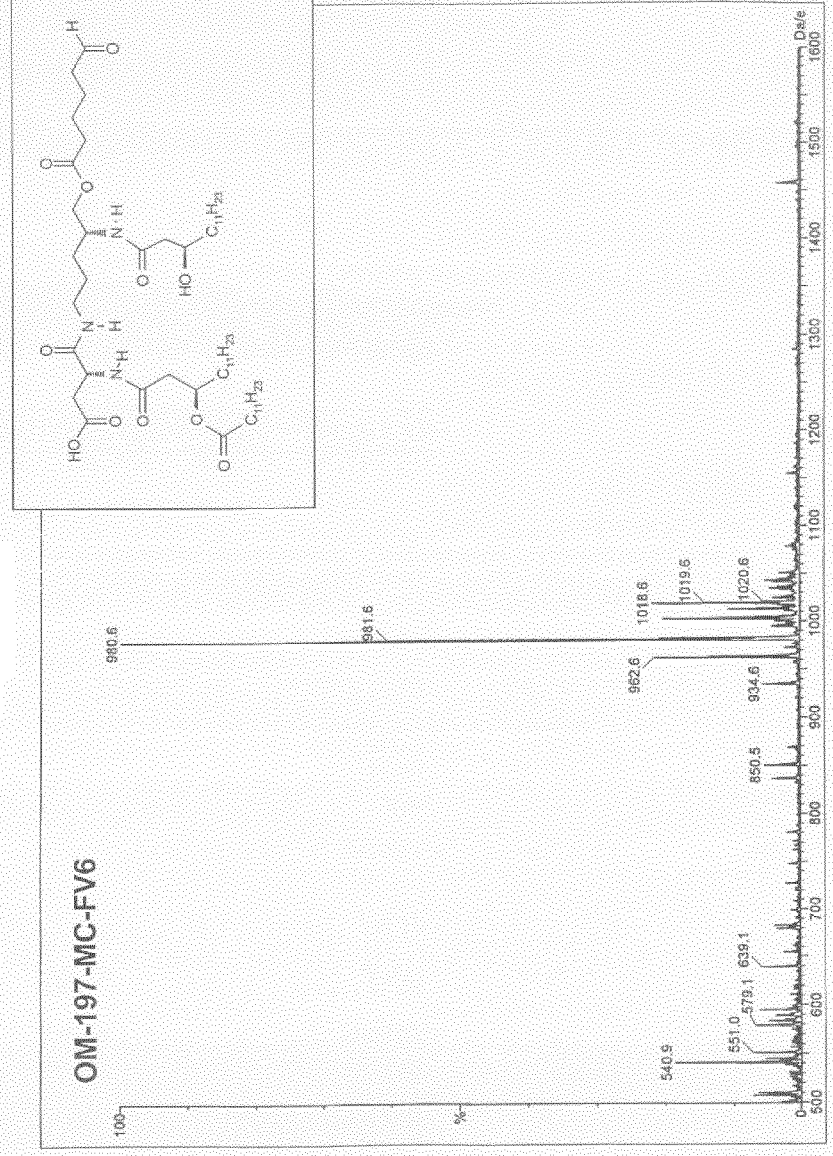
FIG. 10 shows the ionic cloud of LC/ES mass spectra analysis of the monoconjugate OM-197-MC-FV6.

1.98 ml of 0.1 M NaIO$_4$ (42.25 mg, 20 eq.) are added to 10 mg (9.88 μM, 1 eq.) of deprotected triol prepared above (Section 2.3.3.) in a (1:1) isopropanol-water mixture. The solution is stirred for 2 hours at room temperature. The reaction is stopped by adding 1 to 2 drops of ethylene glycol. Upon this periodic oxidation step, an m/z ratio 980.6 [M+H]$^+$ molecular ion is observed on the ES/MS spectrum (FIG. 10), demonstrating the presence of an aldehyde functional group. Peaks corresponding to 1002.8 m/z ratio ([M+Na]$^+$) sodium and 1018.6 m/z ratio ([M+K]$^+$) potassium adducts are also visible. SPE purification on a C18 phase affords recovery of the OM-197-MC-FV6 product with 90% yield.

Example 2.5

N—[(R)-3-dodecanoyloxytetradecanoylamino]-D-aspartic acid, α-N-{(4R)-5-hydroxy-4-[(R)-3-hydroxytetradecanoylamino]pentyl}amide 5-O-(6-hydroxyhexanoate) (=OM-197-MC-FV7) (FIG. 8)

2.5.1. N—[(R)-3-dodecanoyloxytetradecanoylamino]-D-aspartic acid, α-N-{(4R)-5-hydroxy-4-[(R)-3-hydroxytetradecanoylamino]pentyl}amide 5-O-(6-hydroxyhexanoate) (=OM-197-MC-FV7)

To a solution of 6-oxohexanoic acid derivative as obtained above (4.5 mg, 0.0043 mmol.) in 90% isopropanol (20 ml), there is added a NaBH$_4$ solution in methanol (1 mg/ml) (0.2 ml). The mixture is stirred for 3 min. at 25° C., then excess acetic acid (0.2 ml) is added. Purification by preparative HPLC on a C18 column affords recovery of the product OM-197-MC-FV7 (2.3 mg, 51%) dissolved in 90% isopropanol.

Example 2.6

(3RS,9R)-3-[(R)-3-dodecanoyloxytetradecanoylamino]-4oxo-5-aza-9-[(R)-3-hydroxytetradecanoylamino]-decan-10-ol 1-dihydrogen-phosphate(6-aminohexanoate) (=OM-287-AC-RS, R) (FIG. 11)

2.6.1. 1-(Diphenyloxyphosphoryloxy)-3-[(R)-dodecanoyloxytetradecanoylamino]-4-oxo-5-aza-9-[(R)-3-benzyloxy-tetra-decanoylamino]-decan-10-ol(6-benzyloxycarbonyl aminohexanoate)

To a solution of 1-(diphenyloxyphosphoryloxy)-3-[(R)-3-dodecanoyloxytetradecanoylamino]-4-oxo-5-aza-9-[(R)-3-benzyloxy-tetra-decanoylamino]-decan-10-ol (FIG. 1) (230 mg; 0.20 mmol.) in anhydrous CH$_2$Cl$_2$ (8 ml), addition is made of 6-benzyloxycarbanoylaminohexanoic acid (88 mg; 0.33 mmol.; 1.65 eq.). The solution is cooled down to 0° C. This is followed by addition of EDCI (200 mg, 1.04 mmol, 5.2 eq.) and DMAP (13 mg; 0.10 mmol.; 0.5 eq.). The reaction mixture is stirred for 30 minutes at 0° C., and thereafter for 4 hours at room temperature. After dilution with CH$_2$Cl$_2$, the organic layer is separated and washed in succession with H$_2$O, 1N HCl, H$_2$O. The organic layer is then dried over MgSO$_4$, and evaporated at 40° C. under vacuum. By running a flash chromatography purification on a silica gel (7/1.2 CH$_2$Cl$_2$/Acetone eluent), there is recovered the pure ester (115 mg; 41%) as an amorphous solid (Rf=0.77 in 5/2 CH$_2$Cl$_2$/Acetone, phosphomolybdinium acid color developer) $^{13}$C-NMR (62.89 MHz, CDCl$_3$), δ in ppm: 173.27; 171.20; 170.34; 169.88; 156.36; 150.16; 150.13; 138.28; 136.56; 129.80; 128.35; 128.26; 127.90; 127.51; 125.45; 119.97; 119.83; 71.05; 66.37; 65.97; 65.61; 49.94; 47.81; 41.39; 40.66; 39.09; 34.32; 34.25; 33.95; 33.65; 31.78; 29.50; 29.38; 29.22; 29.03; 28.55; 28.44; 25.95; 25.06; 24.87; 24.26; 22.55; 14.00. HPLC (210 nm): T$_R$=33.497 min. ES/MS: m/z ratio 1424.0 [M+H]$^+$; 1174.0 [M+H−(PhO)$_2$OPOH]$^+$.

2.6.2. 1-(Diphenyloxyphosphoryloxy)-3-[(R)-3-dodecanoyloxytetradecanoylamino]-4-oxo-5-aza-9-[(R)-3-hydroxy-tetradecanoylamino]-decan-10-ol 10-(6-aminohexanoate)

A solution of the above obtained product (115 mg; 0.81 μmol.) in an HPLC-grade EtOH (15 ml)/glacial acetic acid (0.4 ml) mixture is hydrogenated in presence of palladium (10% Pd-carbon) (80 mg) at room temperature and under atmospheric pressure hydrogen for 4 hours. The catalyst is filtered off. The filtrate is evaporated to dryness and the residue is then dried by suction from a vacuum pump to obtain the debenzylated product (90 mg, 97%) as an amorphous solid. HPLC (210 nm): T$_R$=29.185 min. ES/MS: m/z ratio 1200.0 [M+H]$^+$; 952.0 [M+H−(PhO)$_2$OPOH]$^+$.

2.6.3. 3-[(R)-3-dodecanoyloxytetra-decanoylamino]-4-oxo-5-aza-9-[(R)-3-hydroxytetradecanoylamino]-1,10-diol-dihydrogenphosphate 10-(6-aminohexanoate) (=OM-197-MP-AC)

Figure 12:
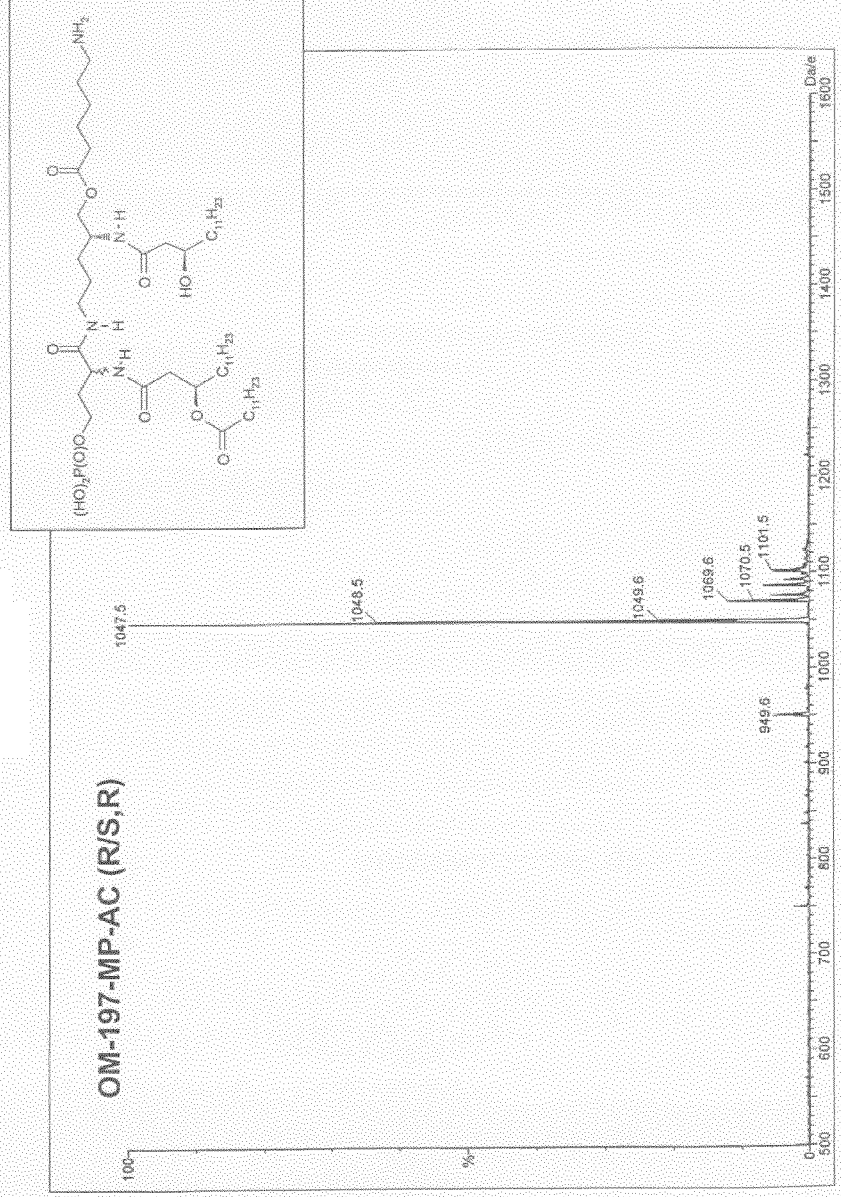
FIG. 12 shows the ionic cloud of LC/ES mass spectra analysis of the conjugate OM-197-MP-AC (R/S, R)

To a solution of platinium oxide PtO$_2$ (30 mg) in (HPLC-grade) ethanol (1 ml) (preactivated to yield platinium black under atmospheric pressure hydrogen for 10 minutes), addition is made of a solution of amino alcohol as obtained above (90 mg, 75 μmol.) in an HPLC-grade EtOH (5 ml)/1N HCl (0.1 ml) mixture. The solution is hydrogenated at room temperature, under atmospheric pressure hydrogen for 24 hours. The catalyst is filtered off. The filtrate is evaporated to dryness and the residue is then dried by suction from a vacuum pump to obtain the desired aminophosphate (60 mg, 79%). HPLC (210 nm): T$_R$=28.51 min. ES/MS: m/z ratio 1047.5 [M+H]$^+$; 1069.6 (M+Na)$^+$, 949.6 [M+H−(HO)$_2$OPOH]$^+$ (FIG. 12).

Example 2.7

Figure 13:
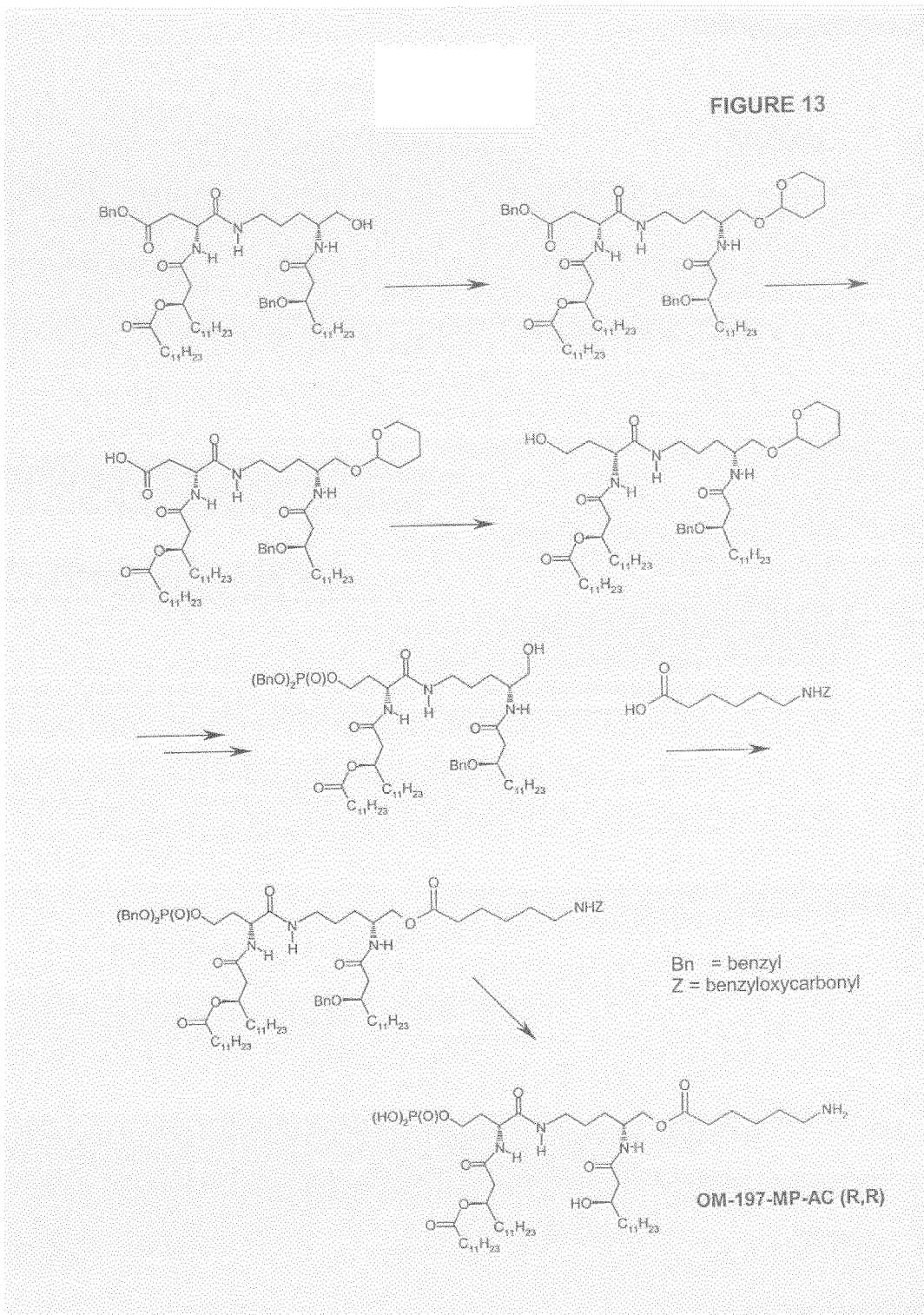
FIG. 13 shows the synthesis of the peptide conjugate OM-197-MP-AC (R, R)

(3R,9R)-3-[(R)-3-dodecanoyloxytetradecanoylamino]-4oxo-5-aza-9-[(R)-3-hydroxytetradecanoylamino]-1,10-diol 1-dihydrogenphosphate 10-(6-aminohexanoate)(OM-197-MP-AC) (FIG. 13)

2.7.1. N—[(R)-3-dodecanoyloxytetradecanoyl]-D-aspartic acid, α-N-{(4R)-5-(2-tetrahydropyranyl) oxy-4-[(R)-3-benzyloxytetradecanoyl-amino] pentyl}amide β-benzyl ester(ASM-O-THP)

To a solution of N—[(R)-3-dodecanoyloxytetradecanoyl]-D-aspartic acid, α-N-{(4R)-5-hydroxy-4-[(R)-3-benzyloxytetradecanoylamino]-pentyl}amide β-benzyl ester (1.5 g; 1.43 mmol.) in anhydrous CH$_2$Cl$_2$ (30 ml), there are added in succession at room temperature and under argon flow 3,4-

Dihydro-2H-pyran (DHP) (327 µl, 3.58 mmol.) and pyridinium p-toluenesulfonate (PPTS) (108 mg, 429 µmol.). After stirring for 18 hours at room temperature, addition is made again of 3,4-Dihydro-2H-pyran (DHP) (130 µl, 1.43 mmol.). The solution is then stirred for further 9 hours at room temperature then diluted with $CH_2Cl_2$ and successively washed with a 5% $NaHCO_3$ solution and $H_2O$. The organic layer is dried over $MgSO_4$, filtered and evaporated. By running flash chromatography purification on a silica gel (successively 6/1 and 7/1 $CH_2Cl_2$/acetone eluent), there is recovered the N—[(R)-3-dodecanoyloxytetradecanoyl]-D-aspartic acid, α-N-{(4R)-5-(2-tetrahydroxypyranyl)oxy-4-[(R)-3-benzyloxytetradecanoylamino]pentyl}-amide β-benzyl ester (1.45 g; 90%) as a white crystalline solid (Rf=0.57 in 5/1 $CH_2Cl_2$/acetone; phosphomolybdinium compound and U.V. color development agent

2.7.2 N—[(R)-3-dodecanoyloxytetradecanoyl]-D-aspartic acid, α-N-{(4R)-5-(2-tetrahydroypyranyl)oxy-4-[(R)-3-benzyloxytetradecanoyl-amino]pentyl}amide A solution of the compound obtained above (250 mg; 0.22 mmol.) in a 1/1 EtOH/EtOAc mixture (16 ml) containing $Et_3N$ (0.4 ml) is hydrogenated in presence of Pd on carbon containing 10% Pd (10 mg) at room temperature and under atmospheric pressure hydrogen for 2 hours. The catalyst is filtered off and the filtrate is evaporated to dryness and then dried by suction from a vacuum pump to recover the acid as a triethylammonium salt (250 mg).

2.7.3.3-[(R)-3-dodecanoyloxytetradecanoylamino]-4-oxo-5-aza-9-[(R)-3-benzyloxytetradecanoylamino]-10-(2-tetrahydropyranyl)oxy-decan-1-ol To a solution of the acid obtained above (≈250 mg) in a 2/1 $CH_2Cl_2$/anhydrous THF mixture (3 ml) at 0° C. and under argon flow, there are added N-methylmorpholin (72 µl; 0.66 mmol.; 3 eq.) then isobutyl chloroformate (86 µl; 0.66 mmol.; 3 eq.). Rapid formation of an N-methylmorpholin hydrochloride precipitate is observed. The reaction progress is monitored by TLC. (Rf=0.90 in 2/1 $CH_2Cl_2$/acetone). After stirring for 30 minutes at room temperature, the reaction mixture is cooled down to 0° C. and a solution of $NaBH_4$ (33 mg; 0.88 mmol.; 4 eq.) in $H_2O$ (1 ml) is then quickly added. As soon as gas emission has ceased (5 min.), the solution is diluted with $H_2O$ (1 ml) and THF (1 ml) and then stirred for 5 minutes at room temperature. The solution is concentrated, diluted with $CH_2Cl_2$ and $H_2O$, followed by layer separation. The organic layer is dried over $MgSO_4$, filtered and evaporated. By running a flash chromatography purification on a silica gel (2/1 $CH_2Cl_2$/acetone eluent), the alcohol is recovered (138 mg; 61% in two steps) as a white crystalline solid. (Rf=0.33 in 3/1 $CH_2Cl_2$/acetone; phosphomolybdinium compound and U.V. color development agent).

2.7.4.3-[(R)-3-dodecanoyloxytetradecanoylamino]-4-oxo-5-aza-9-[(R)-3-benzyloxytetradecanoylamino]-10-(2-tetrahydropyranyl)oxy-decan-1-ol dibenzyl phosphate To a solution of this alcohol as prepared above (210 mg; 0.12 mmol.) and 1H-tetrazole (25 mg; 0.35 mmol.; 3 eq.) in anhydrous THF (5 ml) at room temperature and under argon flow, there is added 85% dibenzyl-diethyl phosphoramidite (95 µl; 0.27 mmol.; 2.3 eq.). Rapid formation of white crystals in the reaction medium can be seen. After stirring for 30 minutes, the reaction mixture is cooled down to −20° C. and an mCPBA solution (57-86%; 75 mg; 0.43 mmol.; 3.7 eq.) in $CH_2Cl_2$ (3 ml) is then added. Disappearance of crystals is noted. After stirring for 45 minutes at room temperature; a saturated $Na_2S_2O_3$ solution (3 ml) is added and the reaction mixture is then stirred for 10 minutes. The solution is next diluted with ether, and the organic layer is then separated and washed with a saturated solution of $Na_2S_2O_3$ (5×), and a saturated solution of $NaHCO_3$ (2×). The organic layer is dried over $MgSO_4$, filtered and evaporated. By running a flash chromatography purification on a silica gel (4/1 then 2/1 $CH_2Cl_2$/acetone eluent), there is recovered the dibenzylphosphate (126 mg; 84%) in the form of an amorphous solid (Rf=0.53 in 3/1 $CH_2Cl_2$/acetone; phosphomolybdinium compound and U.V. color development agent).

2.7.5.3-[(R)-3-dodecanoyloxytetradecanoylamino]-4-oxo-5-aza-9-[(R)-3-benzyloxytetradecanoylamino]-1,10-diol 1-(dibenzyl phosphate)

A solution of 1% HCl in methanol (25 ml) at 0° C. is added to a solution of the compound prepared above (700 mg, 0.54 mmol.) in $CH_2Cl_2$ (2.5 ml). After stirring for 45 minutes at 0° C., the reaction medium is neutralized with a 5% $NaHCO_3$ solution, diluted with $CH_2Cl_2$ and the organic layer is separated. The resulting aqueous phase is then extracted with $CH_2Cl_2$ (3×) and the organic layers are pooled. The organic layer is dried over $MgSO_4$, filtered and evaporated to yield the crude alcohol (640 mg; 98%) (Rf=0.50 in 3/1 $CH_2Cl_2$/acetone; phosphomolybdinium compound and U.V. color development agent).

2.7.6.3-[(R)-3-dodecanoyloxytetradecanoylamino]-4-oxo-5-aza-9-[(R)-3-benzyloxytetradecanoylamino]-decan-1,10-diol 1-dibenzyl phosphate 10-(6-benzyloxycarbonylaminohexanoate)

To a solution of the compound prepared above (640 mg, 0.53 mmol.) and 6-(benzyloxycarbonylamino)hexanoic acid (423 mg, 1.60 mmol.) in dry $CH_2Cl_2$ (25 ml) at 0° C. and under argon flow, there are added in succession commercially available 1-(3-dimethylaminopropyl)-3-ethylcarbodiimide hydrochloride (306 mg, 1.60 mmol.) and 4-dimethylaminopyridine (20 mg, 160 µmol.). The reaction mixture is then stirred for 30 minutes at 0° C. and thereafter overnight at room temperature. The reaction medium is then washed with water and a solution of 1N HCl followed by layer separation. The organic layer is dried over $MgSO_4$, filtered and evaporated. By running a flash chromatography purification on a silica gel (4/1 then 2/1 $CH_2Cl_2$/acetone eluent), there is recovered the coupling reaction product (537 mg; 71%). $^{13}$C-NMR (62.89 MHz, $CDCl_3$), δ in ppm: 173.18, 171.16, 170.38, 169.60, 156.30, 138.23, 136.50, 135.38, 135.28, 128.42, 128.26, 128.17, 127.79, 127.74, 127.44, 76.48, 71.15, 70.84, 69.47, 69.39, 69.31, 66.25, 65.62, 64.37, 49.78, 47.76, 41.41, 41.34, 40.57, 38.97, 34.22, 34.16, 33.96, 33.57, 32.95, 31.70, 29.15, 28.95, 20 28.32, 25.87, 25.46, 25.02, 28.80, 24.18, 22.49, 13.94.

2.7.7.3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6-aminohexanoate) (=OM-197-MP-AC-R, R) (FIG. 13)

Figure 14:
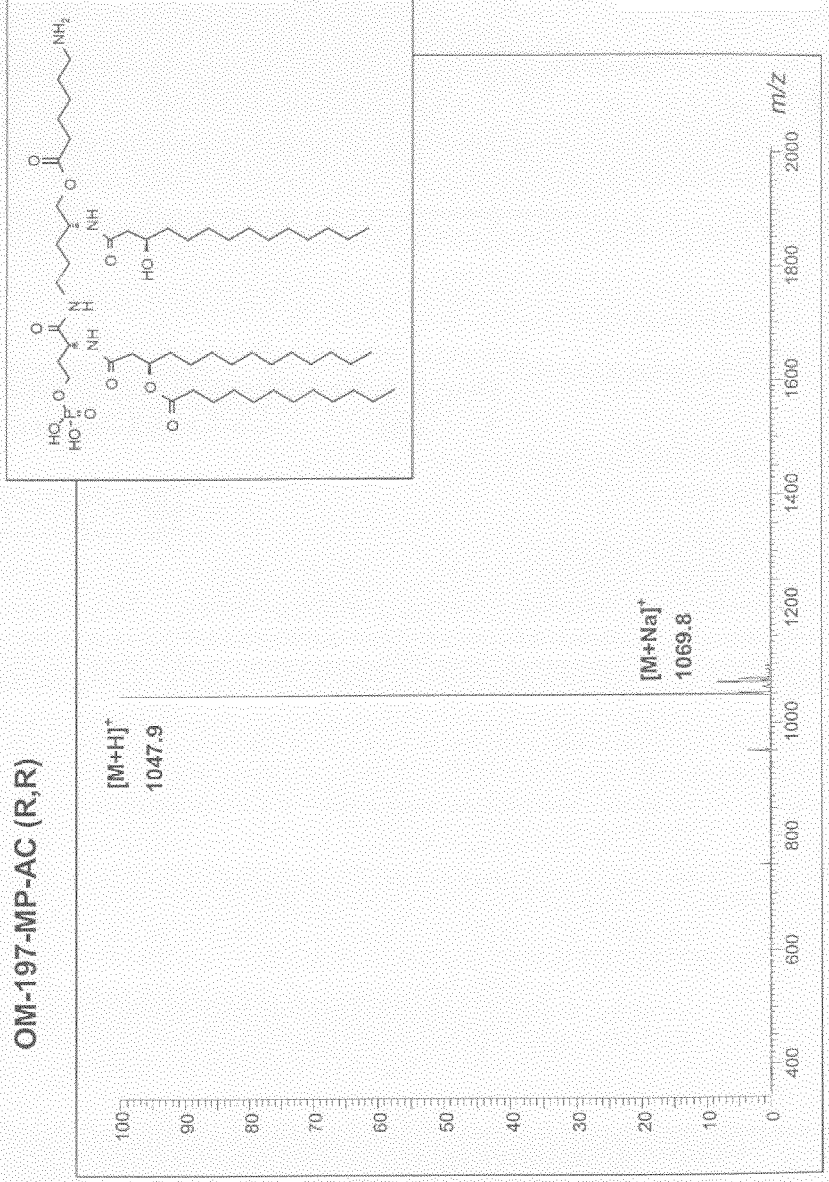
FIG. 14 shows the ionic cloud of LC/ES mass spectra analysis of the conjugate OM-197-MP-AC (R, R)

A solution of the compound as prepared above (500 mg, 0.35 mmol.) in a 5/2 $CH_2Cl_2$/ethanol mixture (70 ml) containing acetic acid (10 ml) is hydrogenated in presence of Pd on carbon containing 10% Pd at room temperature and under atmospheric pressure hydrogen for 12 to 24 hours. The catalyst is filtered off. The filtrate is evaporated to dryness and the residue is then dried by suction from a vacuum pump to obtain 3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6-aminohexanoate) (368 mg, quantitative yield). ES/MS: m/z ratio 1047.9 [M+H]$^+$; 1069.8 (FIG. 14).

Example 2.8

(3S,9R)-3-[(R)-3-dodecanoyloxytetradecanoylamino]-4-oxo-5-aza-9-[(R)-3-hydroxytetradecanoylamino]-1,10-diol 1-dihydrogenphosphate 10-(6-hydroxyhexanoate) (=OM-197-MP-AC-S, R)

Following the same reaction scheme for N—[(R)-3-dodecanoyloxytetradecanoyl]-L-aspartic acid, α-N-{(4R)-5-hydroxyoxy-4-[(R)-3-hydroxytetradecanoylamino]pentyl}amide β-benzyl ester (Section 1.2.4.), synthesis of the product of example 2.8. is finally achieved.

Example 2.9

Figure 15:
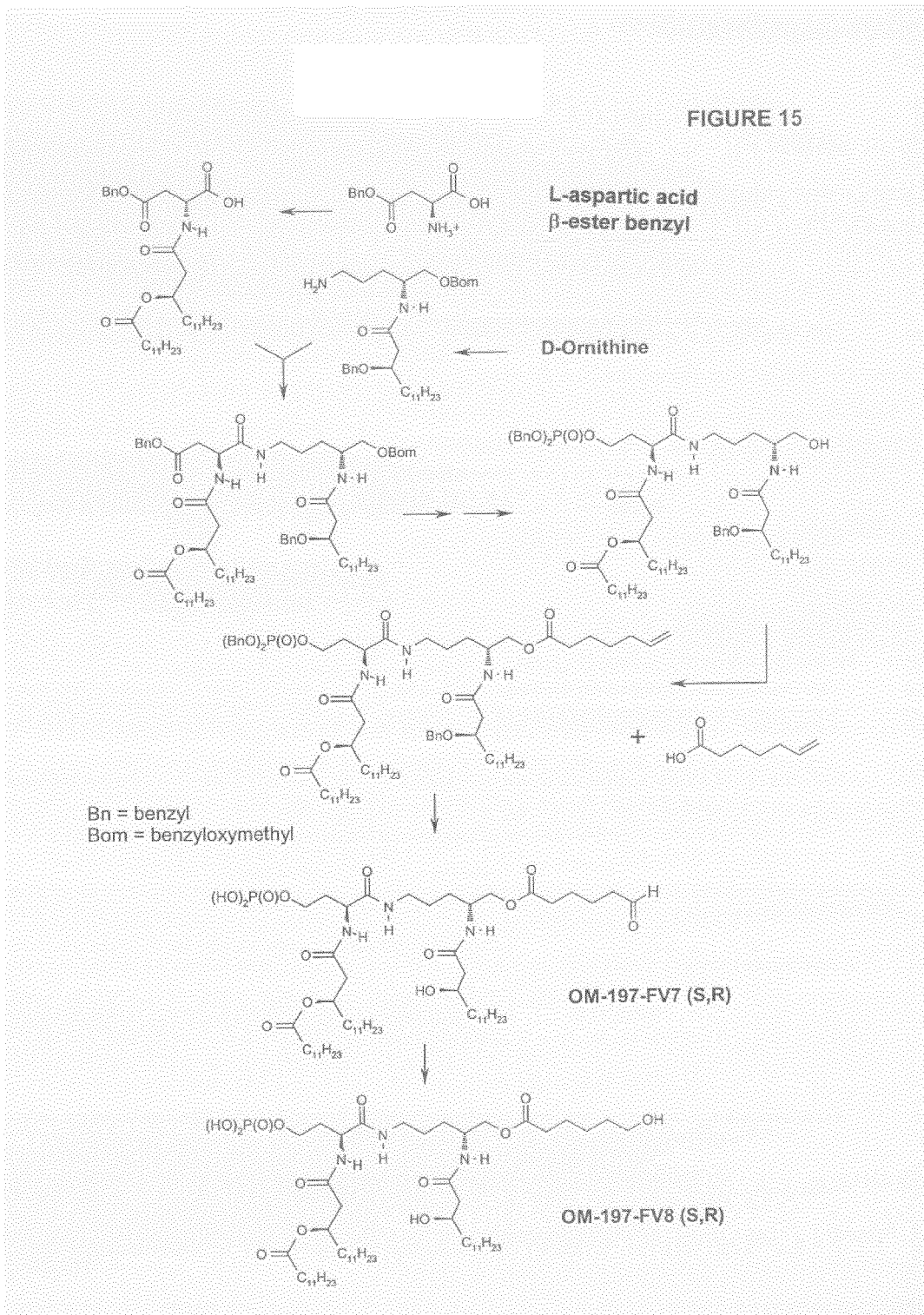
FIG. 15 shows the synthesis of OM-197-FV7 (S, R) and OM-197-FV8 (S, R)

3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6-hydroxyhexanoate) (=OM-197-FV8) (FIG. 15)

2.9.1. (2R)-5-(amino)-2-[(R)-3-benzyloxytetradecanoylamino]-pentan-1-ol benzyloxymethyl ether To a solution of (2R)-5-(benzyloxycarbonylamino)-2-[(R)-3-benzyloxytetradecanoylamino]pentan-1-ol (Section 1.1.2.) (2.05 g; 3.60 mmol.) in anhydrous $CH_2Cl_2$ (40 ml) at room temperature and under argon flow, there are added in succession BOMCl (benzyl chloromethyl ether) (reagent grade 60%, 1.25 ml; 5.41 mmol; 1.5 eq.) and diisopropylethylamine (942 μl; 5.41 mmol.; 1.5 eq.). The reaction mixture is then stirred overnight at room temperature and evaporated thereafter to dryness. By running a flash chromatography purification on a silica gel (2/1 petroleum ether/EtOAc eluent), there is recovered the O-benzyloxymethyl derivative (2.28 g; 92%) as a white crystalline solid. (Rf=0.70 in 1/3 petroleum ether/EtOAc mixture, phosphomolybdinium acid and UV color developer) m.p.=97-100° C. A solution of this product (2.00 g; 2.90 mmol.) in HPLC-grade EtOH (220 ml) containing $Et_3N$ (4 ml) is hydrogenated in presence of 20% $Pd(OH)_2$ on carbon (200 mg) at room temperature and under atmospheric pressure hydrogen for a period of 3 hours. The catalyst is filtered off. The filtrate is evaporated to dryness and the residue is then dried by suction from a vacuum pump to obtain the free amine (1.58 g; 98%) as an amorphous solid. $[α]_D=1°$ (c=1.20; CHCl$_3$) $^1$H-NMR (250 MHz, CDCl$_3$), δ in ppm: 7.45-7.21 (m, 10H, Ar), 6.52 (d, 1H, NH), 4.80-4.45 (m, 6H, 2×CH$_2$-ph, O—CH$_2$—O), 4.10 (m, 1H, H-3'), 3.83 (m, 1H, H-2), 3.62 (dd, 1H, H-1), 3.47 (dd, 1H, H-1), 2.65 (t, 2×H-5), 2.40 (m, 2H, 2×H-2'), 1.80-1.40 (m, 8H, 2×H-4, 2×H-3, 2×H-4', NH$_2$), 1.40-1.20 (m, 18H, 9×CH$_2$), 0.88 (t, 3H, CH$_3$); $^{13}$C-NMR (62.89 MHz, CDCl$_3$), δ in ppm: 170.78; 138.24; 137.63; 128.38; 128.32; 127.66; 127.62; 94.82; 76.70; 71.26; 69.63; 69.44; 48.48; 41.82; 41.47; 33.83; 31.84; 29.88; 29.58; 29.56; 29.51; 29.27; 29.04; 25.11; 22.62; 14.06.

2.9.2. N—[(R)-3-dodecanoyloxytetradecanoylamino]-L-aspartic acid, α-N-{(4R)-5-(benzyloxymethoxy)-4-[(R)-3-benzyloxytetradecanoylamino]-pentyl}amide β-benzyl ester The amine prepared as set forth above is coupled with the N—[(R)-3-dodecanoyloxytetradecanoylamino]-L-aspartic acid β-benzyl ester (prepared from the L-aspartic acid β-benzyl ester, see section 1.2.1) in presence of IIDQ following the same conditions as specified in section 1.2.2. Purification of the product on a silica gel (2:1 then 1:1 petroleum ether/EtOAc) afforded the corresponding amide with a 65% yield. ES/MS: m/z ratio 1169.7 ([M+H]$^+$).

2.9.3. (3S,9R)-3-[(R)-3-dodecanoyloxytetradecanoylamino]-4-oxo-5-aza-9-[(R)-3-benzyloxytetradecanoylamino]-decan-1,10-diol 1-dibenzyl-phosphate A solution of the coupling reaction product obtained above (1.05 g; 0.90 mmol.) in a 1/1 EtOH/EtOAc mixture (65 ml) containing $Et_3N$ (1.5 ml) is hydrogenated in presence of Pd on carbon containing 10% Pd (50 mg) at room temperature and under atmospheric pressure hydrogen for 1 hour. The catalyst is filtered off and the filtrate is evaporated to dryness and then dried by suction from a vacuum pump. The residue is then dissolved in a 1/1 i-PrOH/CH$_2$Cl$_2$ mixture (50 ml) and stirred for minutes at room temperature with an Amberlite IR-120 (H$^+$) resin (3 ml). The resin is filtered off and the filtrate is evaporated to dryness to provide the free acid (956 mg; 99%) as a white crystalline solid.

To a solution of the acid obtained above (855 mg; 0.79 mmol.) in anhydrous THF (5 ml) at 0° C. and under argon flow, there are added N-methylmorpholin (87 μl; 0.79 mmol.; 1 eq.) then isobutyl chloroformate (103 μl; 0.79 mmol.; 1 eq.). Rapid formation of an N-methylmorpholin hydrochloride precipitate is observed. After stirring for 30 minutes at room temperature, the reaction mixture is cooled down to 0° C. and a solution of NaBH$_4$ (60 mg; 1.58 mmol.; 2 eq.) in H$_2$O (2 ml) is then quickly added. As soon as gas emission has ceased (5 min.), the solution is diluted with H$_2$O (2 ml) and THF (2 ml) and then stirred for 5 minutes at room temperature. The solution is concentrated, diluted with CH$_2$Cl$_2$ and H$_2$O, neutralized with a solution of 1M HCl followed by layer separation. The organic layer is dried over MgSO$_4$, filtered and evaporated. By running a flash chromatography purification on a silica gel (4/1 CH$_2$Cl$_2$/acetone eluent), the reduced-state product is recovered (387 mg; 46%) as a white crystalline solid. To a solution of this alcohol (313 mg; 0.29 mmol.) and 1H-tetrazole (62 mg; 0.88 mmol.; 3 eq.) in anhydrous THF (12 ml) at room temperature and under argon flow, there is added 85% dibenzyl-diethyl phosphoramidite (267 μl; 0.67 mmol.; 2.3 eq.). Rapid formation of white crystals in the reaction medium can be seen. After stirring for 30 minutes, the reaction mixture is cooled down to −20° C. and an mCPBA solution (57-85%; 187 mg; 1.08 mmol.; 3.7 eq.) in CH$_2$Cl$_2$ (8 ml) is then added. Disappearance of crystals is noted. After stirring for 45 minutes at room temperature; a saturated Na$_2$S$_2$O$_3$ solution (5 ml) is added and the reaction mixture is then stirred for 10 minutes. The solution is next diluted with ether, and the organic layer is then separated and washed with a saturated solution of Na$_2$S$_2$O$_3$ (5×), a saturated solution of NaHCO$_3$ (2×) and a 1M HCl solution (1×). The organic layer is dried over MgSO$_4$, filtered and evaporated. By running a flash chromatography purification on a silica gel (8/1 then 5/1 CH$_2$Cl$_2$/acetone eluent), there is recovered the phosphotriester (361 mg; 93%) as an amorphous solid.

This product is subjected to a hydrolysis reaction to split the benzyloxymethyl acetal in THF—HCl aqueous medium to thereby obtain (3S,9R)-3-[(R)-3-dodecanoyloxytetradecanoylamino]-4-oxo-5-aza-9-[(R)-3-benzyloxytetradecanoylamino]-decan-1,10-diol 1-dibenzylphosphate.

2.9.4. (3S,9R)-[(R)-3-dodecanoyloxytetradecanoylamino]-4-oxo-5-aza-9-[(R)-3-hydroxytetradecanoylamino]-decan-1,10-diol 1-dihydrogenphosphate 10-(6,7-dihydroxyheptanoate)

The product obtained above is O-acylated on carbon number 10 with hept-6-enoic acid in presence of both EDCI in dichloromethane at 0° C. and DMAP (see section 2.3.1.). This heptenoic acid ester is then subjected to a hydroxylation reaction in presence of (catalytic) osmium tetraoxide and N-methylmorpholin oxide (see section 2.2.2.) to thereby yield the corresponding diol (6,7-dihydroxyheptanoic acid ester). This product is deprotected by hydrogenolysis in ethanol under atmospheric pressure hydrogen in presence of a palladium on carbon catalyst (see section 2.2.3.).

2.9.5. (3S,9R)-3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6-oxohexanoate)

The above deprotected diol is subjected to a periodic oxidation reaction in an isopropanol-water mixture (experimental procedure, see section 2.2.1.)

2.9.6. (3S,9R)-3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6-hydroxyhexanoate) (=OM-197-FV8)

Figure 16:
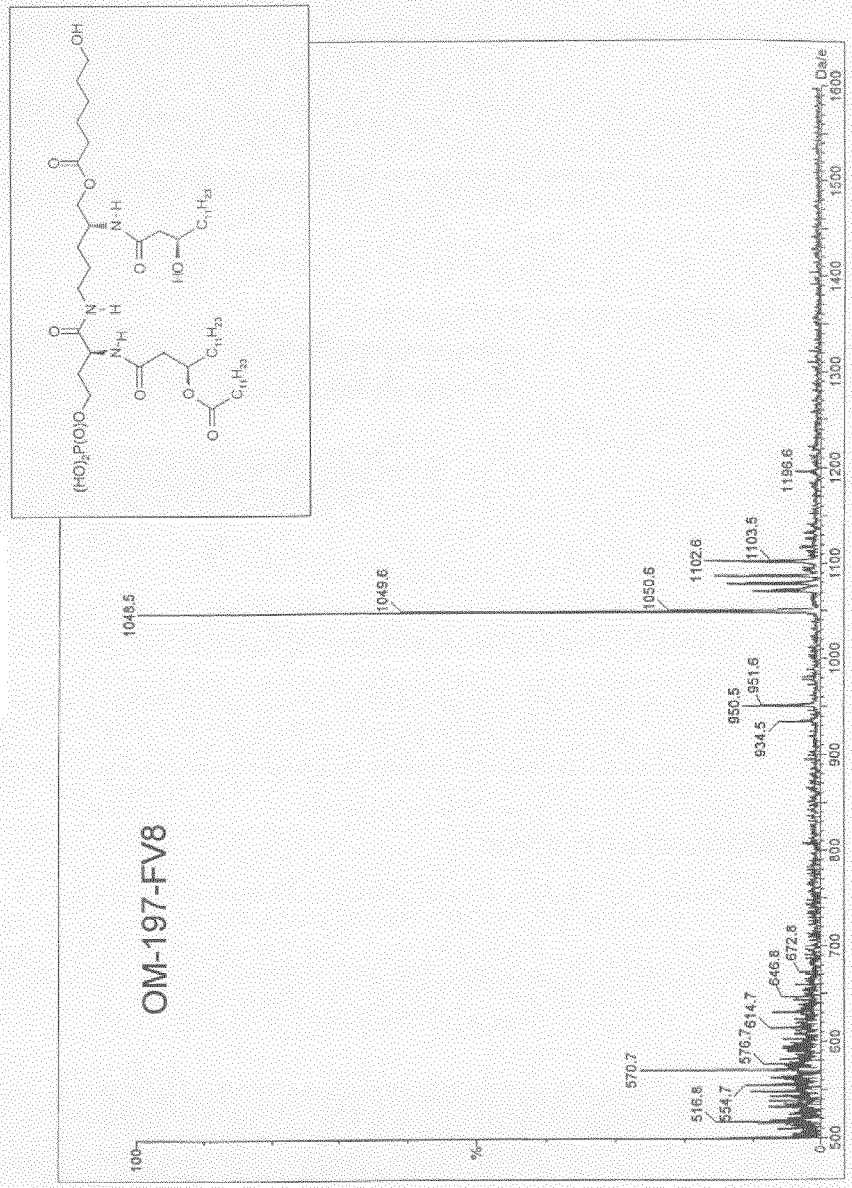
FIG. 16 shows the ionic cloud of LC/ES mass spectra analysis of conjugate OM-197-FV8.

To a solution of 6-oxohexanoic acid derivative as obtained above (4.5 mg, 0.0043 mmol.) in 90% isopropanol (20 ml), there is added a solution of NaBH$_4$ (0.2 ml) in methanol (1 mg/ml). The mixture is stirred for 3 min. at 25° C., then excess acetic acid (0.2 ml) is added. By running a preparative HPLC purification on a C18 column, there is recovered the product OM-197-FV8 (2 mg, 44%), in 90% isopropanol. ES/MS: m/z 1048.5 [M+H]$^+$; 950.5 [M+H−(HO)$_2$OPOH]$^+$ (FIG. 16).

Example 2.10

2-[(R)-3-hydroxytetradecanoylamino]-5-(6-oxo-hexyl)amino}-pentyl 2-((R)-3-dodecanoyloxytetradecanoylamino]-4-(dihydroxy-phosphoryloxy)butanoate (=OM-144-FP9) (FIG. 17)

2.10.1. Hept-6-enyl trifluoromethanesulfonate

Triflic anhydride Tf$_2$O((CF$_3$.SO$_2$)$_2$O, 11 ml; 6.67 mmol.) is added dropwise at −15° C. to a solution of hept-6-en-1-ol (515 mg; 4.51 mmol.) and Et$_3$N (627 μl; 4.51 mmol.) in CH$_2$Cl$_2$ (10 ml) and the mixture is stirred for 30-45 minutes at −15° C. until no alcohol is left. After warming up to room temperature, the medium is diluted with CH$_2$Cl$_2$ and washed in succession with H$_2$O, a saturated aqueous solution of NaHCO$_3$, a saturated aqueous solution of NaCl. The organic layer thus obtained is dried over MgSO$_4$ and concentrated under vacuum to finally yield a residue which is taken up in a (1/2) ethyl acetate/petroleum ether mixture and filtered on a silica gel (removal of triethylamine salts formed during the reaction). After evaporation of the filtrate, the desired triflate compound is obtained with a 87% yield. (956 mg) and is used in the next step with no further purification. Rf=0.8 in 1/2 ethyl acetate/petroleum ether. $^1$H-NMR (CDCl$_3$, 250 MHz), δ in ppm: 5.7, 5.0, 4.45, 2.0, 1.8, 1.4, $^{13}$C-NMR (CDCl$_3$, 62.89 MHz), δ in ppm: 138.21, 114.95, 77.68, 33.40, 29.13, 28.10, 24.53

2.10.2. (2R)-2-[(R)-3-benzyloxytetradecanoylamino]-5-(hept-6-enyl)amino-pentan-1-ol A solution of freshly prepared triflate hereinabove (956 mg; 3.88 mmol.) in CH$_2$Cl$_2$ (10 ml) is added dropwise to a solution of (2R)-5-amino-2-[(R)-3-benzyloxytetradecanoylamino]pentan-1-ol (Section 1.1.2.) (1.69 g; 3.88 mmol) in CH$_2$Cl$_2$ (10 ml) and the mixture is stirred for 4 hours at room temperature under argon flow. After dilution with CH$_2$Cl$_2$, the reaction medium is successively washed with an aqueous saturated solution of NaHCO$_3$ and with H$_2$O. The organic layer thus obtained is dried over MgSO$_4$ and concentrated under vacuum. By running a flash chromatography purification on a silica gel (15/1 CH$_2$Cl$_2$/MeOH eluent), there is recovered the desired secondary amine (862 mg; 43%) Rf=0.3 (8/1 CH$_2$Cl$_2$/MeOH). ES/MS: m/z ratio 532.0 [M+H]$^+$. $^1$H-NMR (CDCl$_3$, 250 MHz), δ in ppm: 7.2-7.4; 7.1; 5.8; 5.0; 4.6; 3.95; 3.5; 2.9; 2.5; 2.1; 1.9-1.5; 1.5-1.2; 0.9. $^{13}$C-NMR (CDCl$_3$, 62.89 MHz), δ in ppm: 172.17; 138.28; 138.21; 128.39; 127.96; 127.71; 114.82; 76.80; 71.40; 63.81; 50.87; 48.30; 47.75; 41.57; 34.10; 33.39; 31.89; 29.66; 29.62; 29.33; 28.19; 28.03; 25.21 26.11; 25.78; 22.82; 22.66; 14.10. $^1$H-NMR (CDCl$_3$, 250 MHz), δ in ppm: 7.2-7.4; 6.75; 5.8; 5.0; 4.5; 3.9; 3.5; 2.5; 2.0; 2.1; 1.7-1.2; 0.9. $^{13}$C-NMR (CDCl$_3$, 62.89 MHz), δ in ppm: 172.77; 138.68; 138.14; 128.23; 127.72; 127.56; 114.22; 76.64; 71.37; 64.58; 51.45; 49.79; 49.37; 41.53; 33.90; 33.53; 31.77; 29.65; 29.20; 28.64; 28.57; 25.00; 26.68; 25.93; 22.53; 13.98 (ammonium salt and free base spectra, respectively).

2.10.3. {2-[(R)-3-benzyloxytetradecanoylamino]-5-(hept-6-enyl)amino}pentyl 2-((R)-3-dodecanoyloxytetradecanoylamino]-4-(diphenyloxyphosphoryloxy)butanoate To a solution of the secondary amine obtained above (163 mg; 0.307 mmol.; 1 eq.) and 4-(diphenyloxyphosphoryloxy)-2-[(R)-3-dodecanoyloxytetradecanoylamino]butanoic acid (Section 1.1.1.) (278 mg; 0.368 mmol.; 1.2 eq.) in CH$_2$Cl$_2$ (25 ml), there is added N,N-diisopropylethylamine (DIEA) (54 μl; 1 eq.). The medium is cooled down to 0° C. and EDCI (71 mg; 1.2 eq.) and 1-hydroxy-7-azabenzotriazole (HOAt) (41 mg; 1 eq.) are then added. The reaction mixture is stirred for 2 hours at 0° C. and thereafter for 90 hours at room temperature. The reaction medium is then washed with H$_2$O and the organic layer is dried over MgSO$_4$ and subsequently evaporated under vacuum at 40° C. By running a silica gel flash chromatography purification (15/1 CH$_2$Cl$_2$/MeOH eluent), recovery of the O-acylated product (126 mg; 32%) is achieved.

2.10.4. {2-[(R)-3-benzyloxytetradecanoylamino]-5-(6,7-dihydroxy-heptyl)amino}pentyl 2-[(R)-3-dodecanoyloxy-tetradecanoyl-amino]-4-(diphenyloxy-phosphoryloxy)-butanoate A freshly prepared 2.5% OsO$_4$ solution in pyridine (1.1 ml; 1.9 eq.) is added dropwise at 25° C. to a solution of the O-acylation reaction product prepared above (70 mg, 0.055 mmol.) in anhydrous pyridine (5 ml). The mixture is stirred for 24 to 48 hours at room temperature and then treated by addition of $Na_2S_2O_5$ and finally diluted with $CH_2Cl_2$, washed in succession with $H_2O$, an aqueous solution of 1N HCl and $H_2O$ again. The resulting organic layer is dried over $MgSO_4$, filtered, evaporated and the residue is subjected to purification by flash chromatography treatment on a silica gel (15/1-10/1 $CH_2Cl_2$/MeOH eluent gradient) to thereby recover the desired diol (27 mg; 38%). HPLC (210 nm): $T_R$=37.25 min0 ES/MS: m/z ratio 1307.0 $[M+H]^+$.

2.10.5. {2-[(R)-3-hydroxytetradecanoylamino]-5-(6,7-dihydroxy-heptyl)amino}pentyl 2-[(R)-3-dodecanoyloxytetradecanoylamino]-4-(dihydroxyphosphoryloxy)butanoate a. Debenzylation To a solution of the above obtained diol (50 mg; 0.038 mmol.) in a HPLC-grade MeOH/AcOH mixture (5/0.2 ml), addition of a catalyst (10% Pd/C) (10 mg) is made. The reaction mixture is stirred for 4 hours under $H_2$ (atmospheric pressure) at room temperature. The catalyst is filtered off on a millipore filter and the filtrate is evaporated to finally recover, with no further purification, the debenzylated product (46 mg; 99%). HPLC (210 nm): $T_R$=35.13 and 35.51 min. (two diastereoisomers were detected). ES/MS: m/z ratio 1217.0 $[M+H]^+$.

b. Dephenylation

Figure 18:
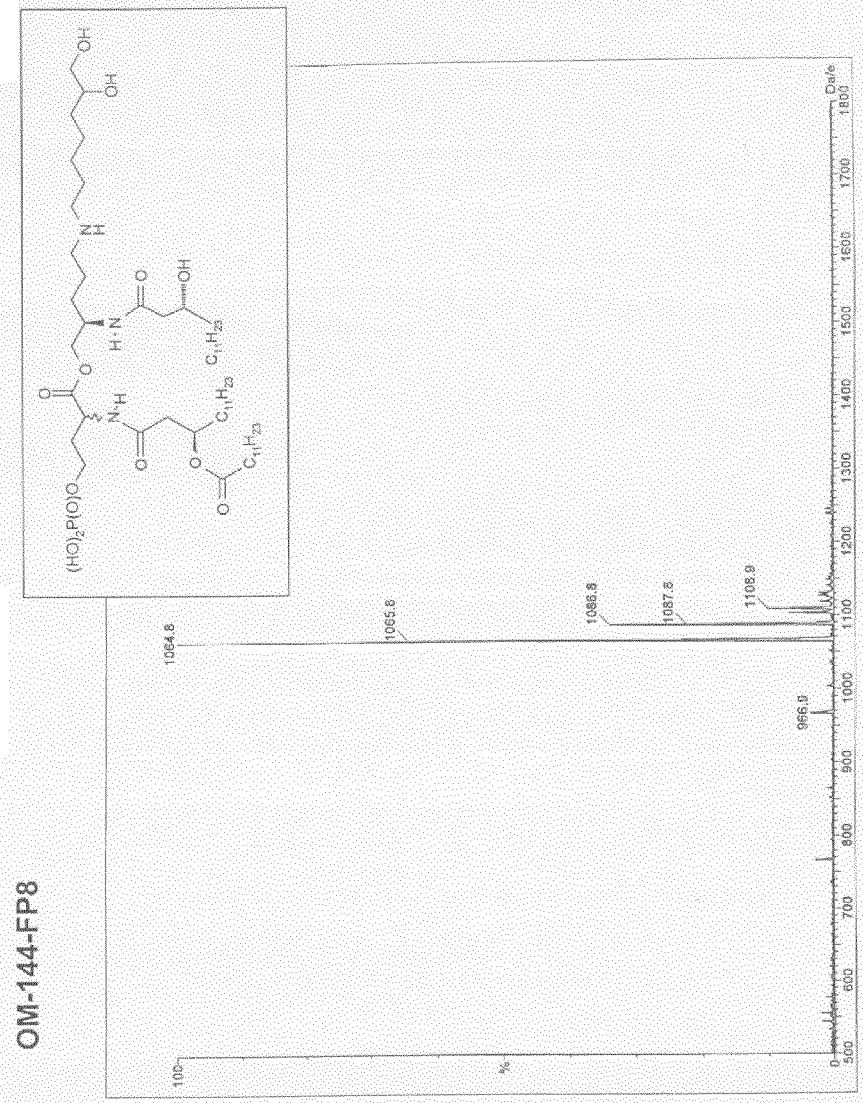
FIG. 18 shows the ionic cloud of LC/ES mass spectra analysis of the conjugate OM-144-FP8.

Preactivation of a catalyst suspension $(PtO_2)$ (25 mg; 3.8 eq.) in HPLC-grade EtOH (0.5 ml) is conducted under $H_2$ for 10 minutes. A solution of the debenzylated product obtained above (35 mg, 0.029 mmol.) in HPLC-grade EtOH (2 ml) from which air was flushed under argon, is added to the catalyst suspension. The reaction mixture is then stirred for 2 hours under $H_2$ at room temperature. The catalyst is filtered off on a millipore filter and the filtrate is evaporated to finally recover, with no further purification, the desired phosphate ester. (26 mg; 87%). HPLC (210 nm): $T_R$=29.3 and 30.9 min. (two diastereoisomers were detected): ES/MS m/z ratio 1064.8 $[M+H]^+$, 1086.8 [M+Na]+, 1108.8 $[M-H+2Na]^+$ (FIG. 18).

2.10.6. {2-[(R)-3-hydroxytetradecanoylamino]-5-(6,7-oxohexyl)amino}pentyl 2-[(R)-3-dodecanoyloxytetradecanoylmino]-4-(dihydroxyphosphoryloxy)butanoate (=OM-144-FP9)

1.87 ml of 0.1 M $NaIO_4$ (40.17 mg, 20 eq.) are added to 10 mg (9.39 µmol., 1 eq.) of the deprotected product prepared above in an isopropanol-water mixture (1:1). The solution is stirred for 2 hours at room temperature. The reaction is stopped by addition of 1 to 2 drops of ethylene glycol. $T_R$=30.0 and 31.5 min. (two diastereoisomers were detected). ES/MS: m/z ratio 1032.8 $[M+H]^+$, 1054.8 $[M+Na]^+$.

Example 2.11

Figure 19:
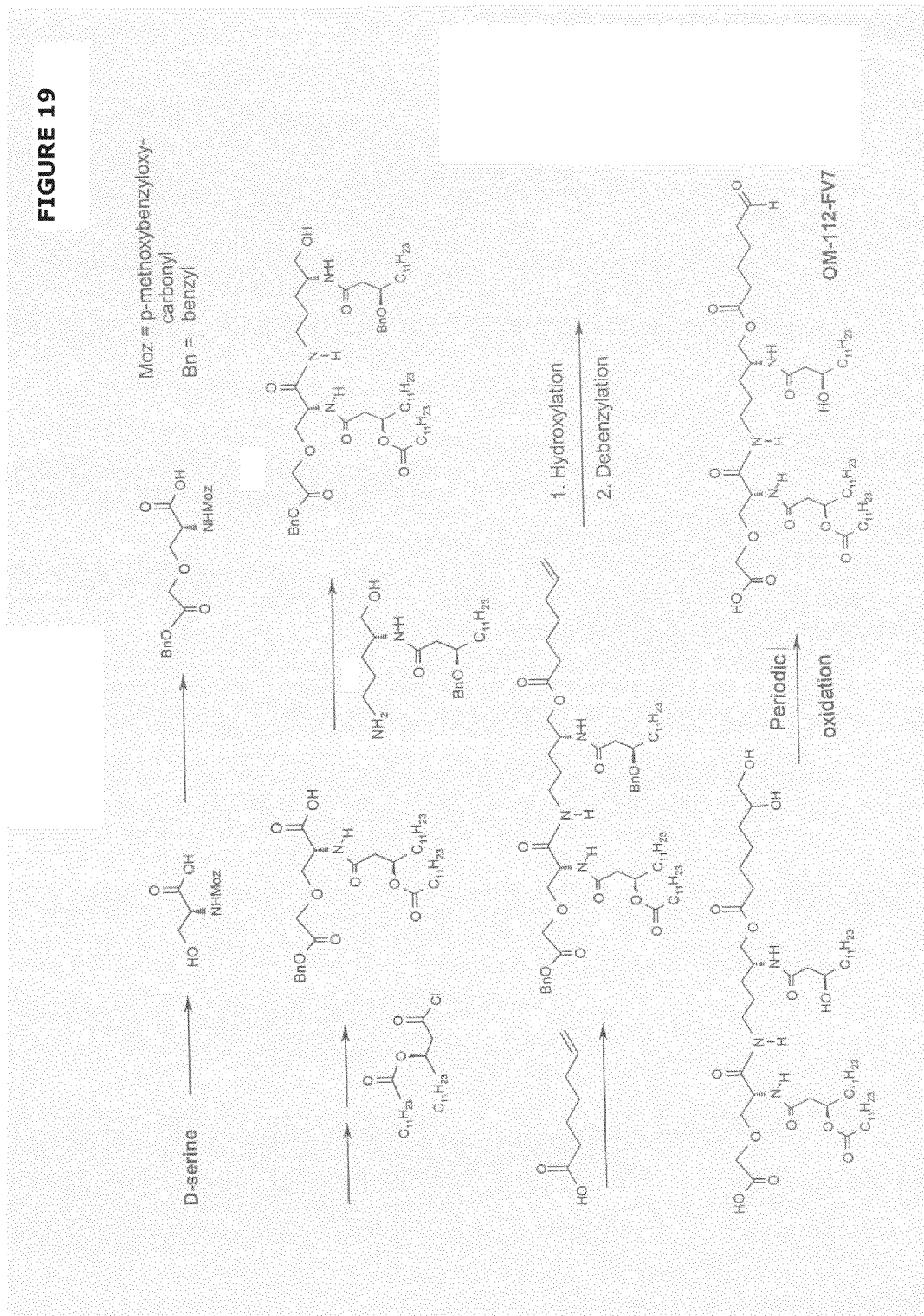
FIG. 19 shows the synthesis of peptide conjugate OM-112-FV7.

(2R,8R)-2-[(R)-3-dodecanoyloxytetradecanoylamino]-3-oxo-4aza-8-[(R)-3-hydroxytetradecanoylamino]-nonan-1,9-diol 1-O-carboxymethyl ether 9-O-(6-oxohexanoate) (=OM-112-FV7) (FIG. 19)

D-serine is protected in the form of an N-(p-methoxybenzyloxycarbonyl) derivative [Reference, Chen, and Wang, Synthesis (1989): 36-37], then the OH functional group is alkyl-substituted with benzyl bromoacetate in presence of NaH (2 eq.). The amine functional group is freed by trifluoroacetic acid treatment in dichloromethane, then acylated with (R)-3-dodecanoyloxytetradecanoic acid chloride treatment in presence of triethylamine. The serine derivative thus obtained is coupled with (2R)-5-amino-2-[(R)-3-benzyloxytetradecanoylamino]pentan-1-ol amine (see section 4.1.1.) in presence of IIDQ to yield the (2R,8R)-2-[(R)-3-dodecanoyloxytetradecanoylamino]-3-oxo-4-aza-8-[(R)-3-benzyloxytetradecanoylamino]nonane-1,9-diol 1-O-benzyloxycarbonylmethylether. This product is then O-acylated with hept-6-enoic acid in presence of EDCI. The double bond of the accessory ester is hydroxylated with osmium tetraoxide (catalytic amount, in presence of N-methylmorpholin N-oxide), and the diol is then deprotected through hydrogenolysis in presence of palladium on carbon in an ethanol solution. The OM-112-FV-7 product is obtained by treatment with sodium periodate in an isopropanol-water mixture. $C_{65}H_{103}N_3O_{12}$. MM: 1010.45.

Example 2.12

(2S,8R)-1-(carboxymethyl)-thio-2-[(R)-3-tetradecanoyloxy-tetradecanoylamino]-3-oxo-4-aza-8-[(R)-3-hydroxy-tetradecanoyl-amino}-nonan-9-ol 9-O-(7-aminoheptanoate) (=OM-212-AH1) (FIG. 20)

D-cysteine is S-alkyl substituted with p-methoxybenzyl bromoacetate in presence of sodium carbonate in a THF-water medium. The S-benzyloxycarbonylmethylcysteine thus obtained is N-acylated with (R)-3-tetradecanoyloxytetradecanoic acid chloride, and the S-alkyl-N-acyl-D-cysteine derivative is then with (2R)-5-amino-2-[(R)-3-hydroxytetradecanoylamino]pentan-1-ol amine {obtained by hydrogenolysis of the (2R)-5-amino-2-[(R)-3-benzyloxy-tetradecanoyl-amino]pentan-1-ol, see 4.1.1.} in presence of IIDQ. The thus obtained product is selectively O-acylated in its primary position with the ester derived from reacting HOBt with 7-(p-methoxybenzyloxy-carbonylamino)heptanoic acid. The two p-methoxybenzyl groups are then removed by treating the ester with aqueous trifluoroacetic acid. $C_{59}H_{112}N_4O_{10}S$. MM 1069.64.

Example 2.13

Figure 21:
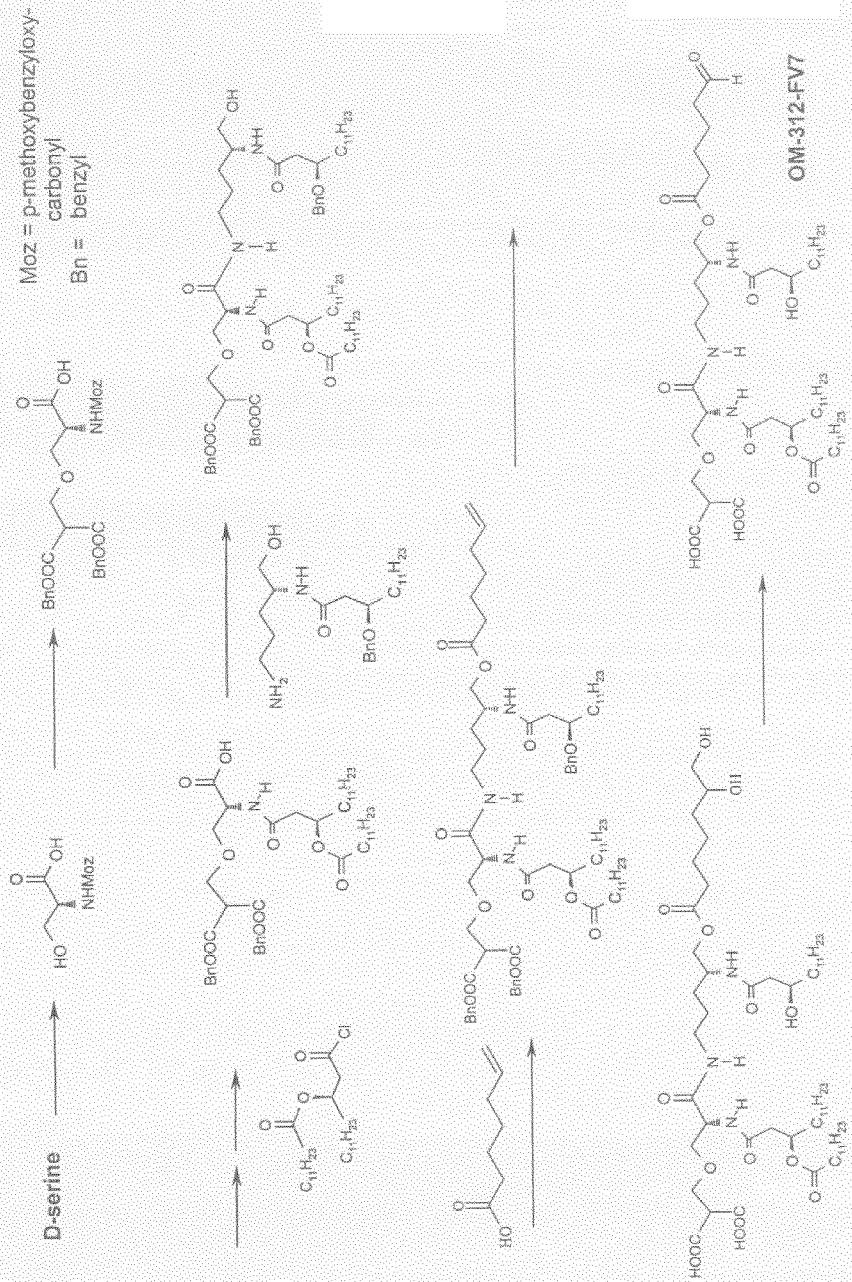
FIG. 21 shows the synthesis of peptide conjugate OM-312-FV7.

(2R,8R)-2-[(R)-3-dodecanoyloxytetradecanoylamino]-3-oxo-4-aza-8-[(R)-3-hydroxytetradecanoylamino]-nonane-1,9-diol 1-O-(2,2-di-carboxyethyl) ether 9-O-(6-oxohexanoate) (=OM-312-FV7) (FIG. 21)

The N-(p-methoxybenzyloxycarbonyl) D-serine derivative is O-alkyl substituted with dibenzyl methylenemalonate in presence of NaH. The amine functional group is freed by trifluoroacetic acid treatment in dichloromethane, and then acylated by (R)-3-dodecanoyloxytetradecanoic acid chloride treatment in presence of triethylamine. The serine derivative thus obtained is coupled with (2R)-5-amino-2-[(R)-3-benzyloxy-tetosm radecanoylamino]pentan-1-ol amine (see section 4.1.1.) in presence of IIDQ to yield the (2R,8R)-2-[(R)-3-dodecanoyloxytetradecanoylamino]-3-oxo-4-aza-8-[(R)-3-benzyloxytetradecanoyl-amino]nonan-1,9-diol 1-O-[2,2-bis-(benzyloxycarbonyl)ethyl]ether. This product is O-acylated with hept-6-enoic acid in presence of EDCI, then the heptenoyl ester is subjected to a hydroxylation reaction with the aid of osmium tetraoxide. The benzyl groups are cleaved by hydrogenolysis in presence of palladium on carbon in an ethanol solution. The OM-312-FV-7 product is obtained by treating the debenzylated product with sodium periodate in an isopropanol-water mixture. $C_{58}H_{105}N_3O_{14}$. MM: 1068.49.

Example 2.14

Figure 22:
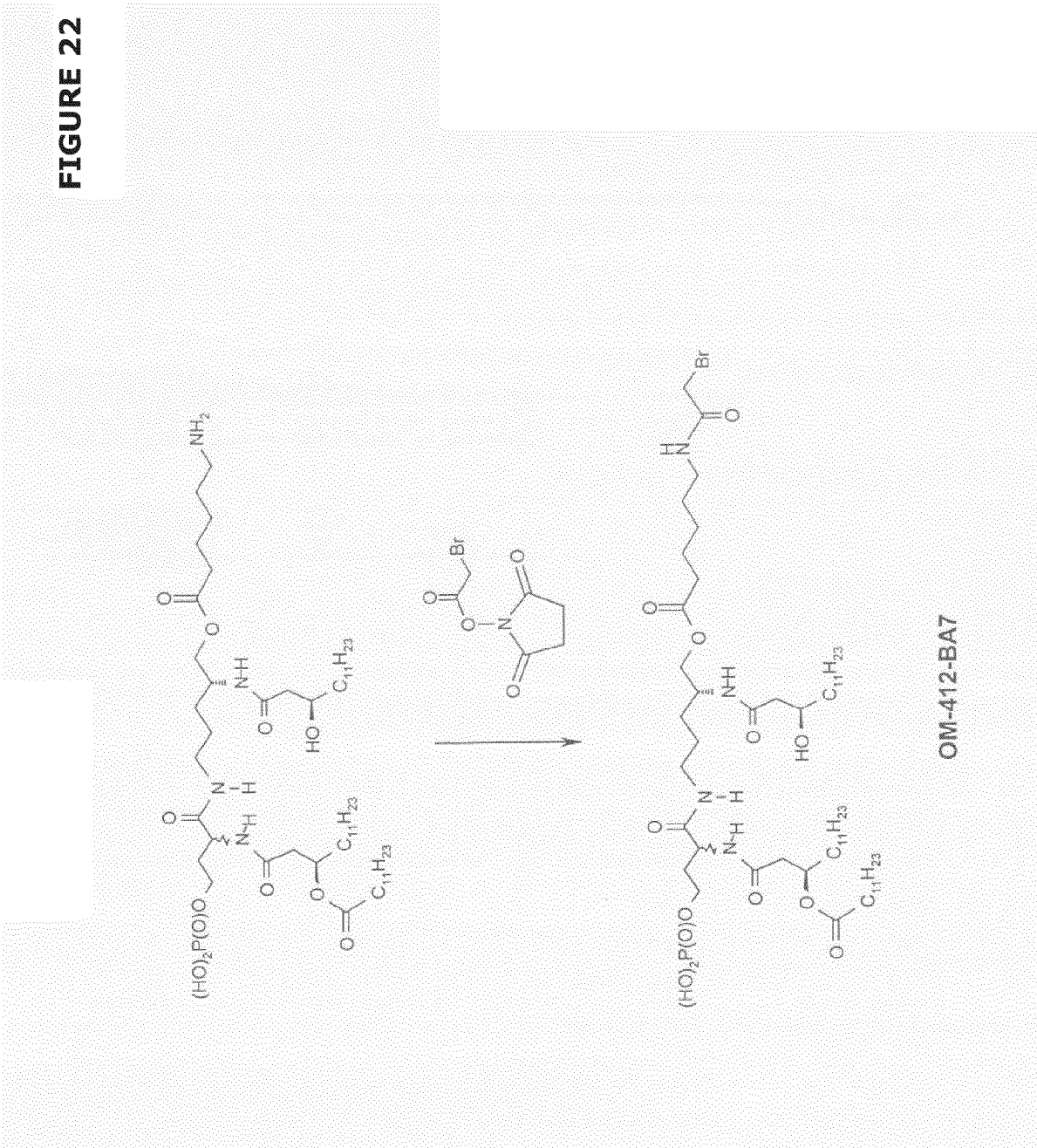
FIG. 22 shows the synthesis of peptide conjugate OM-412-BA7.

3-[(R)-3-dodecanoyloxytetradecanoylamino]-4-oxo-5-aza-9-[(R)-3-hydroxytetradecanoylamino]-1,10-diol-1-dihydrogenphate 10-(6-bromoacetamidohexanoate) (=OM-412-BA7) (FIG. 22).

The 3-[(R)-dodecanoyloxytetradecanoylamino]-4-oxo-5-aza-9-(R)-3 hydroxytetradecanoylamino]-1,10-diol-1-dihydrogenphate 10-(6-aminohexanoate) (see section 4.2.3.3.) is subjected to a bromoacetylation reaction by means of bromoacetic acid succinimidyloxy ester compound in a water-DHF medium in presence of triethylamine. The final product is purified by HPLC. $C_{57}H_{108}BrN_4O_{13}P$. MM: 1168.4.

Figure 23:
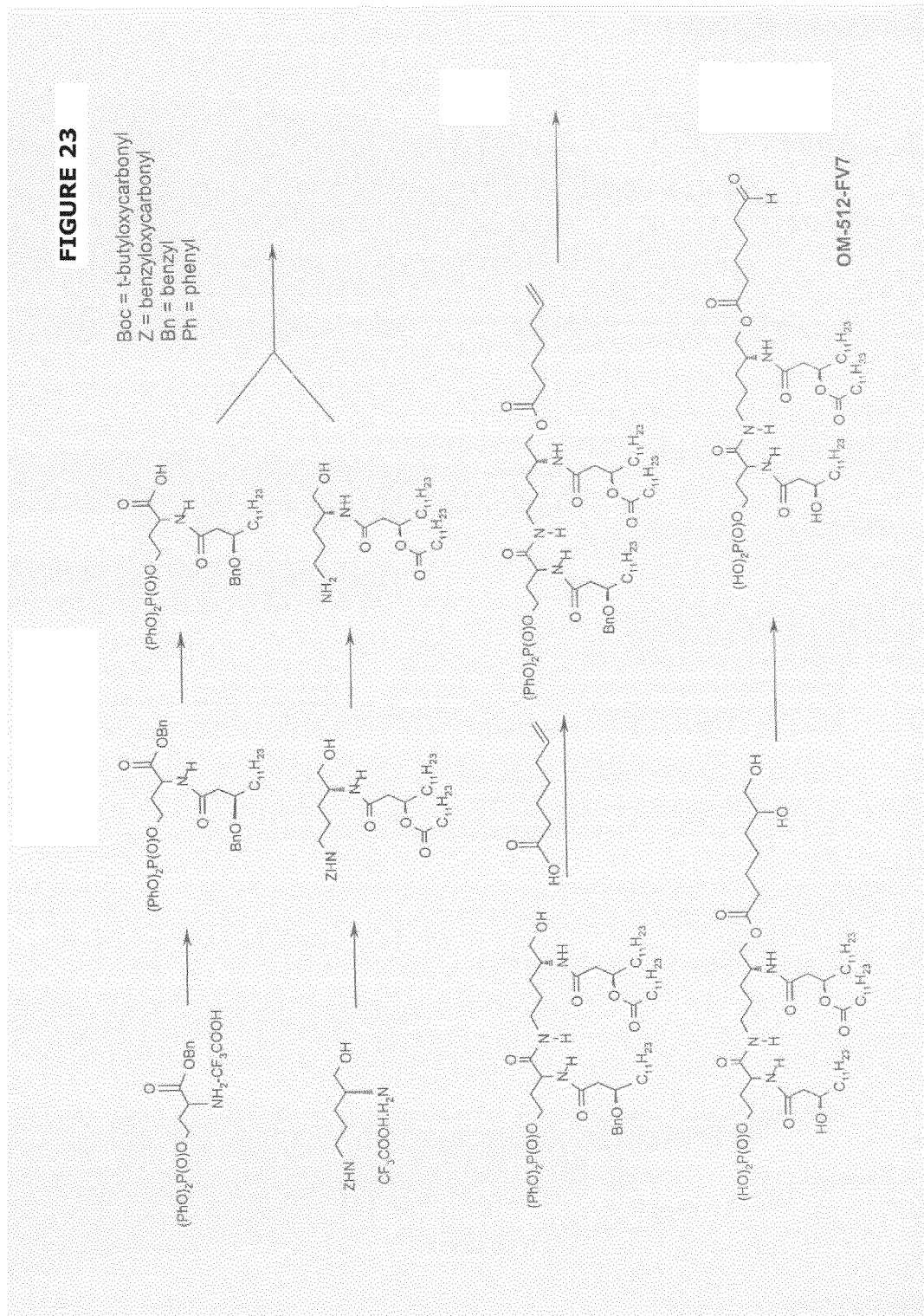
FIG. 23 shows the synthesis of peptide conjugate OM-512-FV7.

(3R,9R)-3-[(R)-hydroxytetradecanoylamino]-4-oxo-5-aza-9-[(R)-dodecanoyloxytetradecanoylamino]-decan-1,10-diol 1-dihydrogenphate 10-O-(6-oxohexanoate)(OM-512-FV7) (FIG. 23)

The 2-[(R)-3-benzyloxytetradecanoylamino]-4-diphenyloxyphosphoryloxy-butanoic acid [obtained by N-acylation of benzyl O-(diphenyloxyphosphoryl)-DL-homoserinate trifluoroacetic salt with (R)-3-benzyloxytetradecanoic acid chloride, then cleavage of the benzyl ester by hydrogenolysis in ethanol in presence of triethylamine and a palladium on carbon catalyst] is coupled with (2R)-5-amino-2-[(R)-3-dodecanoyloxytetradecanoylamino]pentan-1-ol [obtained by N-acylation of (2R)-5-(benzyloxycarbonylamino)-2-aminopentan-ol trifluoroacetic salt with (R)-3-dodecanoyloxytetradecanoic acid chloride, then deprotection of the amino group in $C_5$ position by hydrogenolysis in ethanol in presence of triethylamine and a palladium on carbon catalyst] in presence of IIDQ. The thus formed amide is O-acylated at the free OH functional group with 6-heptenoic acid in presence of EDCI to yield the corresponding ester. The double bond of the additional ester is subjected to a hydroxylation reaction with osmium tetraoxide; and the benzyl group is then removed through hydrogenolysis by using a palladium on carbon catalyst and the phosphate compound is freed through hydrogenolysis over platinium black. The diol functional group is subjected to a periodic oxidation reaction to form the 6-oxohexanoyl derivative OM-512-FV7. $C_{55}H_{104}N_3O_{13}P$. MM: 1046.42.

Example 2.16

Figure 24:
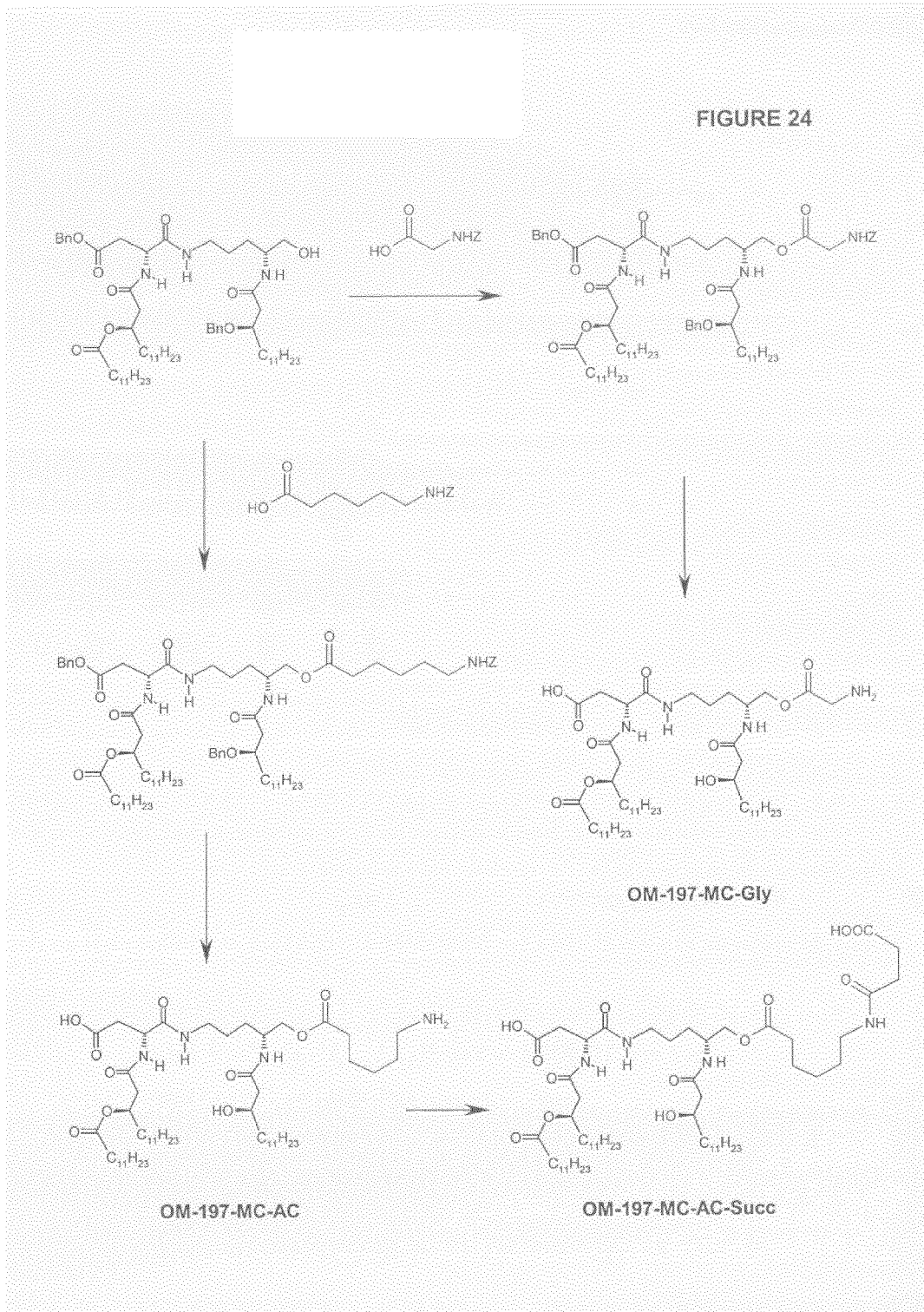
FIG. 24 shows the synthesis of the conjugates OM-197-MC-Gly, OM-197-MC-AC and OM-197-MC-AC-Succ.

N—[(R)-3-dodecanoyloxytetradecanoyl]-D-aspartic acid, α-N-{(4R)-5-(6-benzyloxycarbonylaminohexanoyloxy)-4[(R)-3-hydroxytetradecanoyl-amino] pentyl)amide (=OM-197-MC-AC) (FIG. 24)

2.16.1. N—[(R)-3-dodecanoyloxytetradecanoyl]-D-aspartic acid, α-N-{(4R)-5-(aminohexanoyloxy)-4-[(R)-3-benzyloxytetradecanoyl-amino]pentyl}amide β-benzyl ester To a solution of N—[(R)-3-dodecanoyloxytetradecanoyl]-D-aspartic acid, α-N-{(4R)-5-hydroxy-4-[(R)-3-benzyloxytetradecanoyl-amino]pentyl}amide β-benzyl ester (400 mg, 0.38 mmol.) and 6(benzyloxycarbonylamino)hexanoic acid (220 mg, 0.83 mmol.) in dry $CH_2Cl_2$ (15 ml) at 0° C. and under argon flow, there are added in succession commercially available 1-(3-dimethylaminopropyl)-3-15 ethylcarbodiimide hydrochloride (162 mg, 0.85 mmol.) and 4-dimethylaminopyridine (13 mg, 98 µmol.). The reaction mixture is then stirred for 30 minutes at 0° C. and thereafter overnight at room temperature. The reaction medium is then washed with water and a solution of 1N HCl followed by layer separation. The organic layer is dried over $MgSO_4$, filtered and evaporated. By running a flash chromatography purification on a silica gel (9/1 then 4/1 $CH_2Cl_2$/acetone eluent), there is recovered the coupling reaction product (395 mg; 81%) as a white solid. $^{13}C$-NMR (62.89 MHz, $CDCl_3$), δ in ppm: 173.46, 173.29, 171.83, 171.14, 170.12, 156.38, 138.19, 136.60, 133.30, 128.51, 128.42, 128.31, 127.70, 127.58, 119.97, 76.49, 71.23, 71.06, 66.73, 66.47, 49.21, 47.83, 41.42, 40.73, 39.14, 35.46, 34.86, 33.70, 31.84, 29.57, 29.46, 29.28, 29.10, 26.01, 25.54, 25.17, 25.08, 24.94, 24.31, 22.61, 14.05

Figure 25:
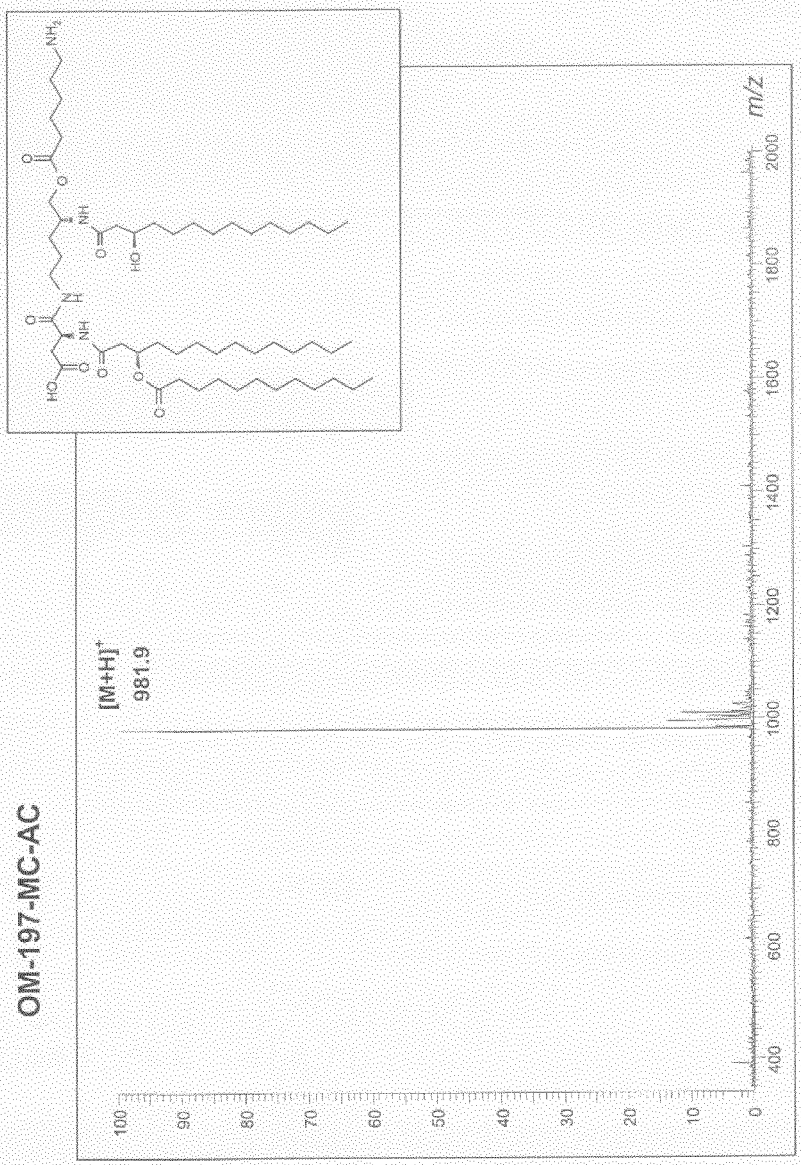
FIG. 25 shows the ionic cloud of LC/ES mass spectra analysis of the conjugate OM-197-MC-AC.

2.16.2. N—[(R)-3-dodecanoyloxytetradecanoyl]-D-aspartic acid, α-N-{(4R)-5-(aminohexanoyloxy)-4-[(R)-3-hydroxytetradecanoylamino]-pentyl}amide A solution of the compound prepared above (340 mg, 0.26 mmol.) in a 5/1 $CH_2Cl_2$/ethanol mixture (24 ml) containing acetic acid (2 ml) is hydrogenated in presence of Pd on carbon containing 10% Pd (40 mg) at room temperature and under atmospheric pressure hydrogen for 12 to 24 hours. The catalyst is filtered off. The filtrate is evaporated to dryness and the residue is then dried by suction from a vacuum pump to obtain N-3-[(R)-3-dodecanoyloxytetradecanoyl]-D-aspartic acid, α-N-{(4R)-5-(6-aminohexanoyloxy)-4-[(R)-3-hydroxytetradecanoylamino]-5 pentyl}amide (238 mg, quantitative yield). $C_{55}H_{104}N_4O_{10}$: ES/MS: m/z ratio 981.9 ([M+H]$^+$); (FIG. 25).

Example 2.17

N—[(R)-3-dodecanoyloxytetradecanoyl]-D-aspartic acid, α-N-{(4R)-5-(6-succinylamidohexanoxyloxy)-4[(R)-3-hydroxy-tetradecanoylamino]pentyl}amide (=OM-197-MC-AC-Succ) (FIG. 24)

To a solution of product of example 2.16. (Section 2.16.2) (50 mg; 0.051 mmol.) in pyridine (3 ml), there are added in succession succinic anhydride (11 mg, 0.11 mmol.) and 4-N, N'-dimethylaminopyridine (7 mg; 0.57 mmol.). After stirring for 6 hours at 50° C. under Ar, methanol (2 ml) is added and the reaction medium is stirred for further 15 min. at room temperature. The solvent is evaporated and the product is purified by a flash chromatography treatment on a silica gel (7:1 then 5:1 $CH_2Cl_2$/MeOH eluent); thereby obtaining the product as a white solid (42 mg; 74%). $C_{59}H_{108}N_4O_{13}$ ES/MS; m/z ratio 1082 ([M+H])$^+$, Rf=0.1 (4:1 $CH_2Cl_2$/MeOH)

Example 2.18

N—[(R)-3-dodecanoyloxytetradecanoyl]-D-aspartic acid, α-N-{(4R)-5-glycinyloxy)-4-[(R)-3-hydroxy-tetradecanoylamino]pentyl}-amide (=OM-197-MC-AC-Gly) (FIG. 24)

2.18.1. N—[(R)-3-dodecanoyloxytetradecanoyl]-D-aspartic acid, α-N-{(4R)-5-(benzyloxycarbonylaminoacetoxy)-4-[(R)-3-benzyloxytetradecanoyl-amino] pentyl}amide β-benzyl ester To a solution of N—[(R)-3-dodecanoyloxytetradecanoyl]-D-aspartic acid, α-N-{(4R)-5-hydroxy-4-[(R)-3-benzyloxytetradecanoylamino]pentyl}-amide β-benzyl ester (300 mg, 0.29 mmol.) and commercially available N-benzyloxycarbonylglycine (101 mg, 0.49 mmol.) in dry $CH_2Cl_2$ (10 ml) at 0° C. and under argon flow, there are added in succession available 1-(3-dimethylaminopropyl)-3-ethylcarbodiimide hydrochloride (93 mg, 0.48 mmol.) and 4-dimethylaminopyridine (6 mg, 49 μmol.). The reaction mixture is then stirred for 30 minutes at 0° C. and thereafter overnight at room temperature. The reaction medium is then washed with water and a solution of 1N HCl followed by layer separation. The organic layer is dried over $MgSO_4$, filtered and evaporated. By running a flash chromatography purification on a silica gel (8/1 then 6/1 $CH_2Cl_2$/acetone eluent), there is recovered the coupling reaction product (313 mg; 88%) as a white solid. $^{13}$C-NMR (62.89 MHz, $CDCl_3$), δ in ppm: 173.71, 173.49, 171.80, 171.68, 171.21, 170.21, 170.06, 169.94, 169.84, 156.41, 138.18, 136.16, 135.26, 128.46, 128.33, 128.26, 128.04, 127.93, 127.65, 127.55, 76.49, 71.14, 71.07, 70.93, 66.90, 66.67, 66.38, 66.26, 49.21, 49.03, 47.72, 47.66, 42.58, 41.83, 41.68, 41.32, 39.02, 35.58, 35.39, 34.34, 33.84, 31.81, 29.52, 29.24, 29.06, 28.31, 28.13, 25.34, 25.12, 25.03, 24.89, 22.57, 14.01.

Figure 26:
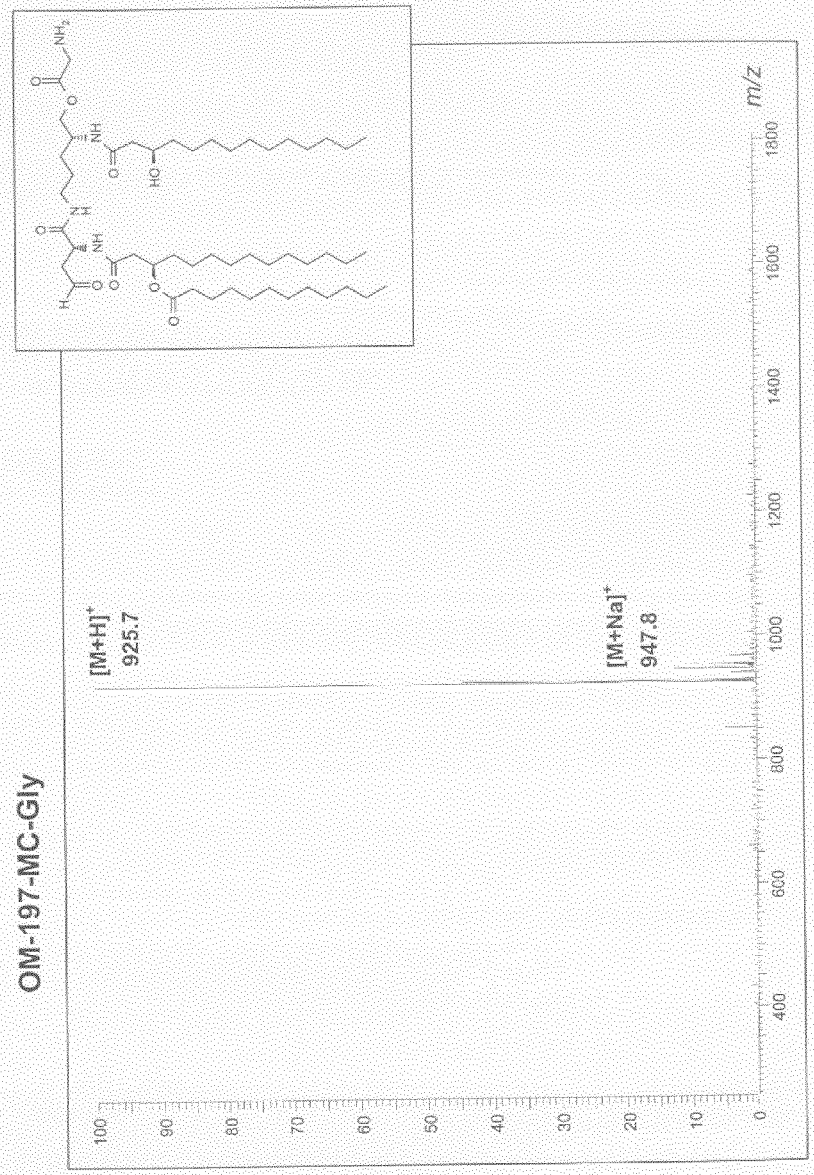
FIG. 26 shows the ionic cloud of LC/ES mass spectra analysis of the conjugate OM-197-MC-Gly.

2.18.2 N-3-[(R)-3-dodecanoyloxytetradecanoyl]-D-aspartic acid, α-N-{(4R)-5-(glycinyloxy)-4-[(R)-3-hydroxytetradecanoylamino]-pentyl}amide A solution of the compound prepared above (268 mg, 0.22 mmol.) in a 5/1 $CH_2Cl_2$/ethanol mixture (12 ml) containing acetic acid (2 ml) is hydrogenated in presence of Pd on carbon containing 10% Pd (30 mg) at room temperature and under atmospheric pressure hydrogen for 12 to 24 hours. The catalyst is filtered off. The filtrate is evaporated to no dryness and the residue is then dried by suction from a vacuum pump to obtain N-3-[(R)-3-dodecanoyloxytetradecanoyl]-D-aspartic acid, α-N-{(4R)-5-(glycinyloxy)-4-[(R)-3-hydroxytetradecanoylamino]-pentyl}amide (200 mg, quantitative yield). $C_{51}H_{104}N_4O_{10}$: ES/MS: m/z ratio 925.7 ([M+H]$^+$), 947.8 ([M+Na]$^+$); (FIG. 26).

Example 2.19

Figure 27:
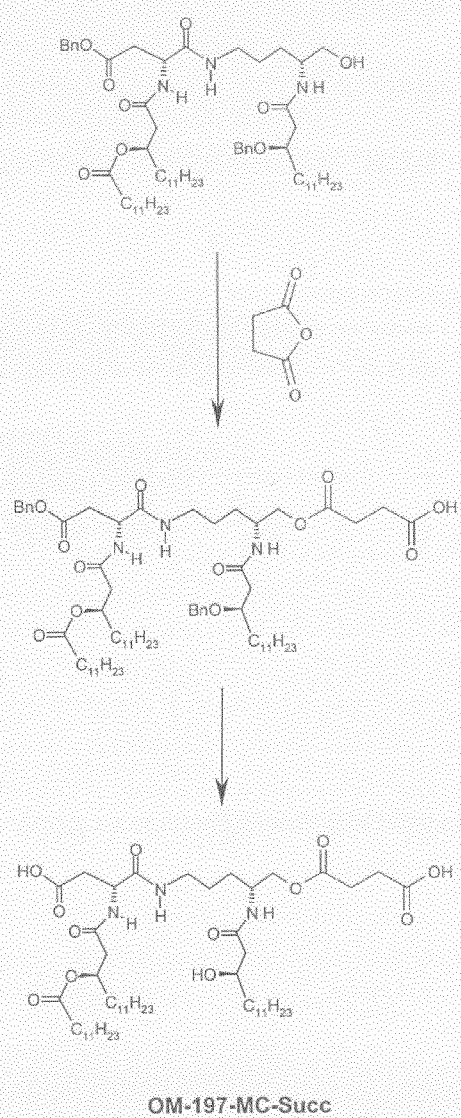
FIG. 27 shows the synthesis of the conjugate OM-197-MC-Succ.

N—[(R)-3-dodecanoyloxytetradecanoyl]-D-aspartic acid, α-N-{(4R)-5-succinyloxy)-4[(R)-3-hydroxytetradecanoylamino]pentyl}-amide (=OM-197-MC-Succ) (FIG. 27)

2.19.1. N—[(R)-3-dodecanoyloxytetradecanoyl]-D-aspartic acid, α-N-{(4R)-5-succinyloxy-4-[(R)-3-benzyloxytetradecanoylamino]pentyl}amide β-benzyl ester To a solution of succinic anhydride (25 mg, 0.25 mmol) in dry $CH_2Cl_2$ (2 ml) in presence of $Et_3N$ (40 μl, 0.29 mmol.) at 0° C., addition is made of a solution of N—[(R)-3-dodecanoyloxytetradecanoyl]-D-aspartic acid, α-N-{(4R)-5-hydroxy-4-[(R)-3-benzyloxytetradecanoylamino]pentyl}-amide β-benzyl ester (Section 1.2.2.) (150 mg, 0.14 mmol) in $CH_2Cl_2$ (5 ml). The reaction mixture is stirred for 10 minutes at 0° C. and thereafter at room temperature. The reaction medium is then diluted with $CH_2Cl_2$, washed with a 1N HCl solution followed by layer separation. The organic layer is dried over $MgSO_4$, filtered and evaporated. By running a flash chromatography purification on a silica gel (9/1 $CH_2Cl_2$/acetone eluent containing 2% acetic acid), there is recovered the acid product (148 mg; 90%) as a white solid. $^{13}$C-NMR (62.89 MHz, $CDCl_3$), δ in ppm: 175.03, 173.55, 173.35, 171.68, 171.92, 171.72, 171.36, 170.97, 170.60, 170.46, 170.41, 138.05, 135.24, 128.85, 128.76, 128.41, 128.27, 128.20, 128.03, 127.59; 76.48, 71.31, 70.77, 66.67, 65.08, 49.20, 48.11, 41.48, 41.31, 39.02, 35.80, 34.26, 34.13, 33.84, 31.77, 29.50, 29.21, 29.03, 25.05, 24.99, 24.83, 22.54, 13.98.

2.19.2 N—[(R)-3-dodecanoyloxytetradecanoyl]-D-aspartic acid, α-N-{(4R)-5-succinyloxy-4-[(R)-3-hydroxytetradecanoylamino]pentyl}amide (=OM-197-MC-Succ) (FIG. 27)

Figure 28:
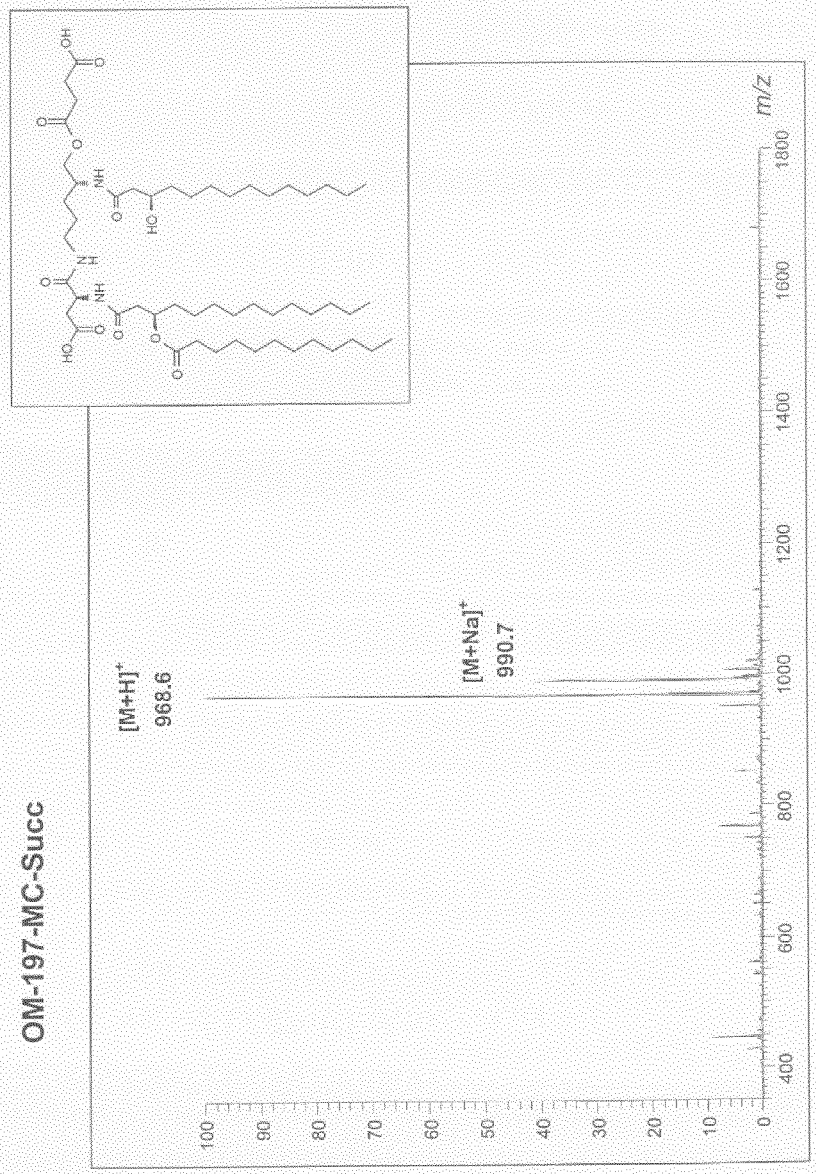
FIG. 28 shows the ionic cloud of LC/ES mass spectra analysis of the conjugate OM-197-MC-Succ.

A solution of the compound prepared above (124 mg, 0.11 mmol.) is dissolved in hot (HPLC-grade) EtOH (12 ml) containing acetic acid (1 ml) and then hydrogenated in presence of Pd on carbon containing 10% Pd (15 mg) at room temperature and under atmospheric pressure hydrogen for 10 hours. The catalyst is filtered off. The filtrate is evaporated to dryness and the residue is then dried by suction from a vacuum pump to recover the diacid product (102 mg, 97%). $C_{53}H_{97}N_3O_{12}$: ES/MS: m/z ratio 968.6 ([M+H]$^+$), 990.7 ([M+Na]$^+$); (FIG. 28).

Example 2.20

Figure 29:
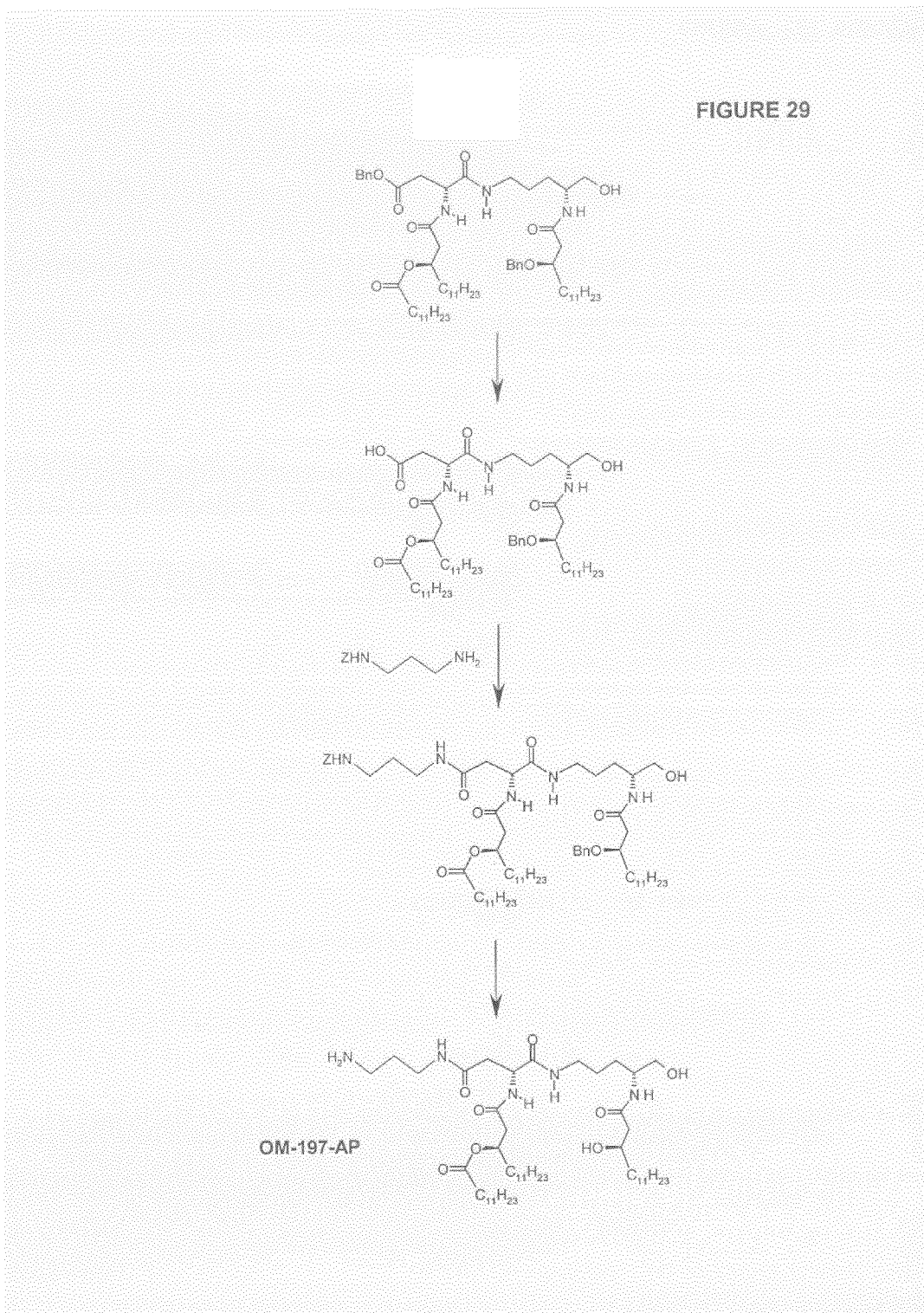
FIG. 29 shows the synthesis of the conjugate OM-197-AP.

N—[(R)-3-dodecanoyloxytetradecanoyl]-D-aspartic acid, α-N-{(4R)-5-hydroxy-4-[(R)-3-hydroxy-tetradecanoylamino]pentyl}-amide β-N-(3-aminopropyl)amide (=OM-197-AP) (FIG. 29)

2.20.1. N—[(R)-3-dodecanoyloxytetradecanoyl]-D-aspartic acid, α-N-{(4R)-5-hydroxy-4-[(R)-3-benzyloxytetradecanoylamino]pentyl}-amide A solution of N—[(R)-3-dodecanoyloxytetradecanoylamino]-D-aspartic acid, α-N-{(4R)-5-hydroxy-4-[(R)-3-benzyloxytetradecanoylamino]-pentyl}amide β-benzyl ester (Section 1.2.2.) (2.53 g; 2.4 mmol.) in a 1/1 EtOH/EtOAc mixture (150 ml) containing $Et_3N$ (4 ml) is hydrogenated in presence of Pd on carbon containing 10% Pd (120 mg) at room temperature and under atmospheric pressure hydrogen for 2 hours. The catalyst is filtered off and the filtrate is evaporated to dryness and then dried by suction from a vacuum pump. The residue is then dissolved in a 1/1 i-PrOH/$CH_2Cl_2$ mixture (100 ml) and stirred for 10 minutes at room temperature with an Amberlite IR-120 (H$^+$) resin (5 ml). The resin is filtered off and the filtrate is evaporated to dryness to provide the free acid (2.25 g; 97%) as a white crystalline solid. (Rf=0.45 in 9/1 $CH_2Cl_2$/MeOH containing 1% of acetic acid, phosphomolybdinium compound and U.V. color development agent). m.p.=115-117° C.

2.20.2 N—[(R)-3-dodecanoyloxytetradecanoyl]-D-aspartic acid, α-N-{(4R)-5-hydroxy-4-[(R)-3-benzyloxytetradecanoylamino]pentyl}amide β-N-(3-benzyloxycarbonylaminopropyl))amide A solution of IIDQ (2-isobutoxy-1-isobutoxycarbonyl-1,2-dihydroquinoline) (98 g; 0.32 mmol.) in anhydrous $CH_2Cl_2$ (3 ml) is added to a solution of the compound prepared above (250 mg, 0.26 mmol.) in anhydrous $CH_2Cl_2$ (15 ml) at 0° C. and under argon flow. The reaction mixture is stirred for 15 minutes at 0° C. and a solution of commercially available 3-benzyloxycarbonylamino-propylamine hydrochloride (70 mg, 0.29 mmol.) in anhydrous $CH_2Cl_2$ (7 ml) containing triethylamine (40 μl, 0.29 mmol.) is added. After stirring for 18 hours, the solution is evaporated to dryness. By running a flash chromatography purification on a silica gel (20/1

CH$_2$Cl$_2$/MeOH eluent), there is recovered the coupling reaction product (217 mg; 78%) as a white solid.

2.20.3. N—[(R)-3-dodecanoyloxytetradecanoyl]-D-aspartic acid, α-N-{(4R)-5-hydroxy-4-[(R)-3-hydroxy-tetradecanoylamino]-pentyl}amide β-N-(3-aminopropyl)amide (=OM-197-AP)

Figure 30:
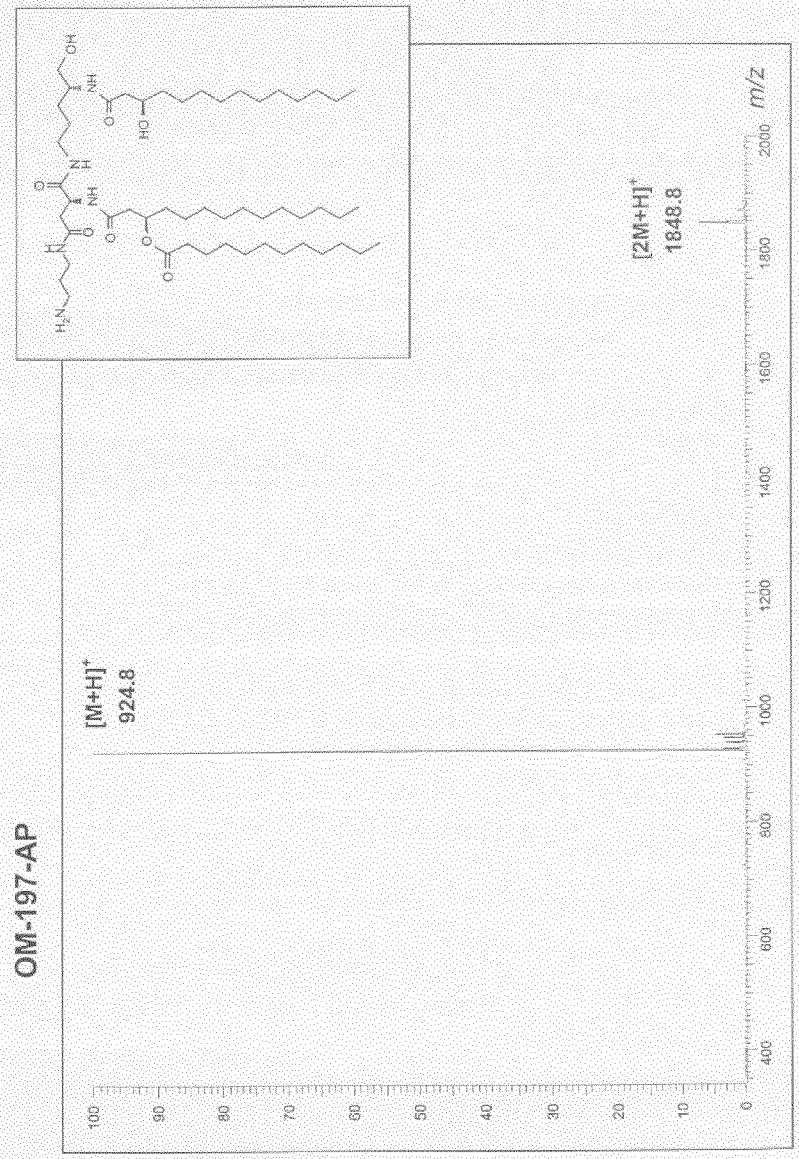
FIG. 30 shows the ionic cloud of LC/ES mass spectra analysis of the conjugate OM-197-AP.

A solution of the compound prepared above (50 mg, 44 mmol.) in a 1/1 CH$_2$Cl$_2$/isopropanol mixture (8 ml) containing acetic acid (1 ml) is hydrogenated in presence of Pd on carbon containing 10% Pd (10 mg) at room temperature and under atmospheric pressure hydrogen for 6 to 8 hours. The catalyst is filtered off. The filtrate is evaporated to dryness and the residue is then dried by suction from a vacuum pump to obtain N—[(R)-3-dodecanoyloxytetradecanoyl]-D-aspartic acid, α-N-{(4R)-5-hydroxy-4-[(R)-3-hydroxytetradecanoylamino]-pentyl}amide β-N-(3-aminopropyl)amide (32 mg, 80%). C$_{52}$H$_{101}$N$_5$O$_8$: ES/MS: m/z ratio 924.8 ([M+H]$^+$); 1848.8 ([2M+H]$^+$); (FIG. 30).

Example 2.21

Figure 31:
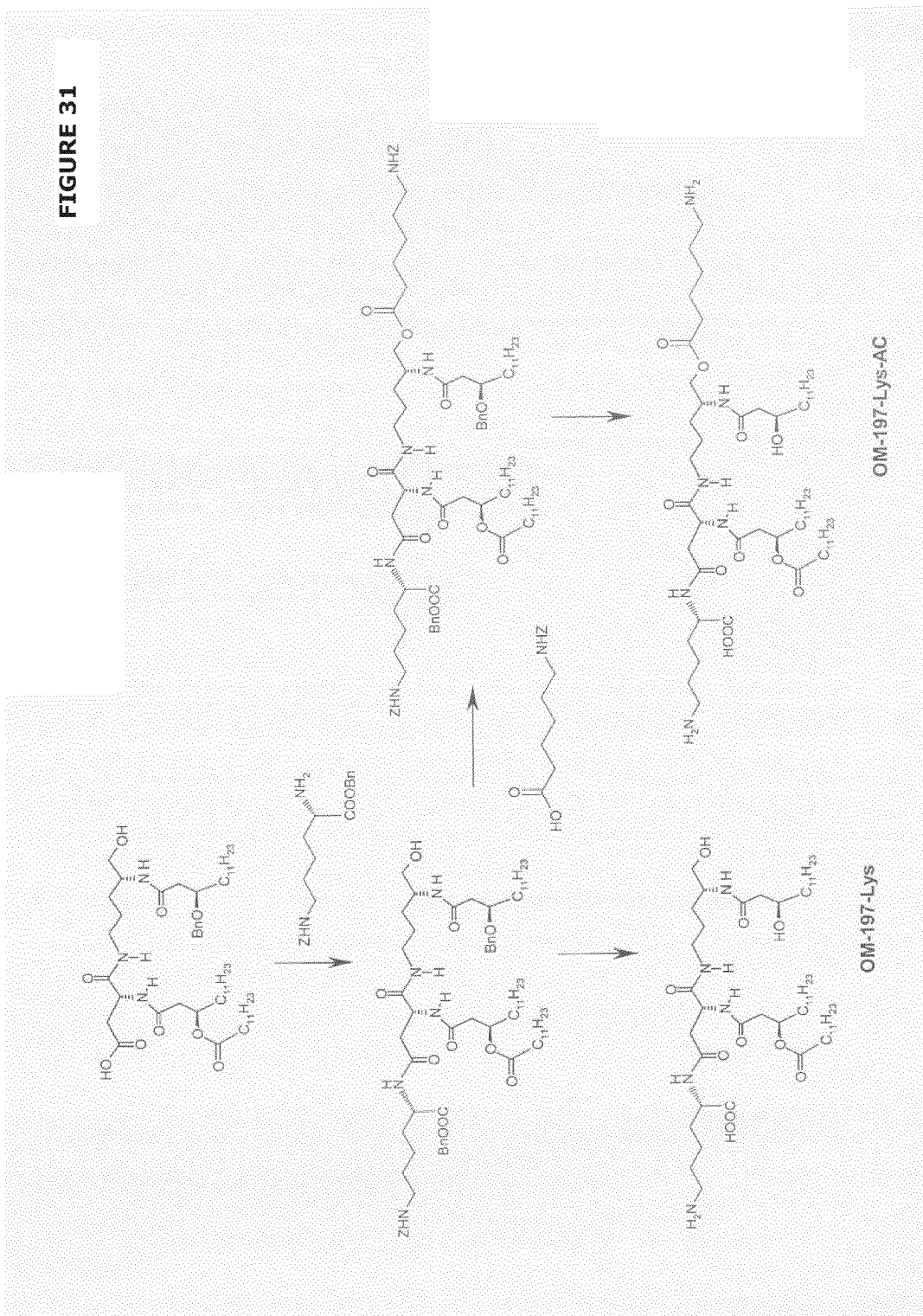
FIG. 31 shows the synthesis of OM-197-Lys and OM-197-Lys-AC.

N—[(R)-3-dodecanoyloxytetradecanoyl]-D-aspartic acid, α-N-{(4R)-5-hydroxy-4[(R)-3-hydroxytetradecanoylamino]pentyl}-amide β-N-[(1S)-1-carboxy-5-aminopentylamide (=OM-197-Lys) (FIG. 31)

2.21.1. N—[(R)-3-dodecanoyloxytetradecanoyl]-D-aspartic acid, α-N-55 (4R)-5-hydroxy-4-[(R)-3-benzyloxytetradecanoylamino]pentyl}-amide β-N-[(1S)-1-benzyloxycarbonyl-5-benzyloxycarbonylaminopentyl]amide A solution of IIDQ (2-isobutoxy-1-isobutoxycarbonyl-1,2-dihydroquinoline) (114 mg; 0.38 mmol.) in anhydrous CH$_2$Cl$_2$ (5 ml) is added to a solution of N—[(R)-3-dodecanoyloxytetradecanoyl]-D-aspartic acid, α-N-{(4R)-5-hydroxy-4-[(R)-3-benzyloxytetradecanoylamino]-pentyl}amide (Section 2.20.1.) (300 mg, 0.31 mmol.) in anhydrous CH$_2$Cl$_2$ (20 ml) at room temperature and under argon flow. The reaction mixture is stirred for 15 minutes at RT then a solution of commercially available ε-N-benzyloxycarbonyl-L-lysine benzyl ester hydrochloride solution (140 mg, 0.31 mmol.) in anhydrous CH$_2$Cl$_2$ (5 ml) containing triethylamine (48 μl, 0.34 mmol.) is added. After stirring for 18 hours, the solution is evaporated to dryness. By running a flash chromatography purification on a silica gel (30/1 then 20/1 CH$_2$Cl$_2$/MeOH eluent), there is recovered the coupling reaction product (317 mg; 77%) as a white solid. $^{13}$C-NMR (62.89 MHz, CDCl$_3$), δ in ppm: 173.68, 172.35, 171.92, 170.74, 170.62, 170.54, 156.75, 156.52, 138.31, 136.54, 135.12, 128.54, 128.40, 128.28, 128.21, 127.96, 127.577, 127.59, 76.67, 71.40, 71.18, 67.20, 67.09, 66.48, 64.67, 52.30, 51.19, 41.64, 40.34, 39.24, 37.58, 34.40, 34.10, 31.83, 29.58, 29.27, 29.09, 25.16, 25.11, 24.93, 22.60, 14.04.

Figure 32:
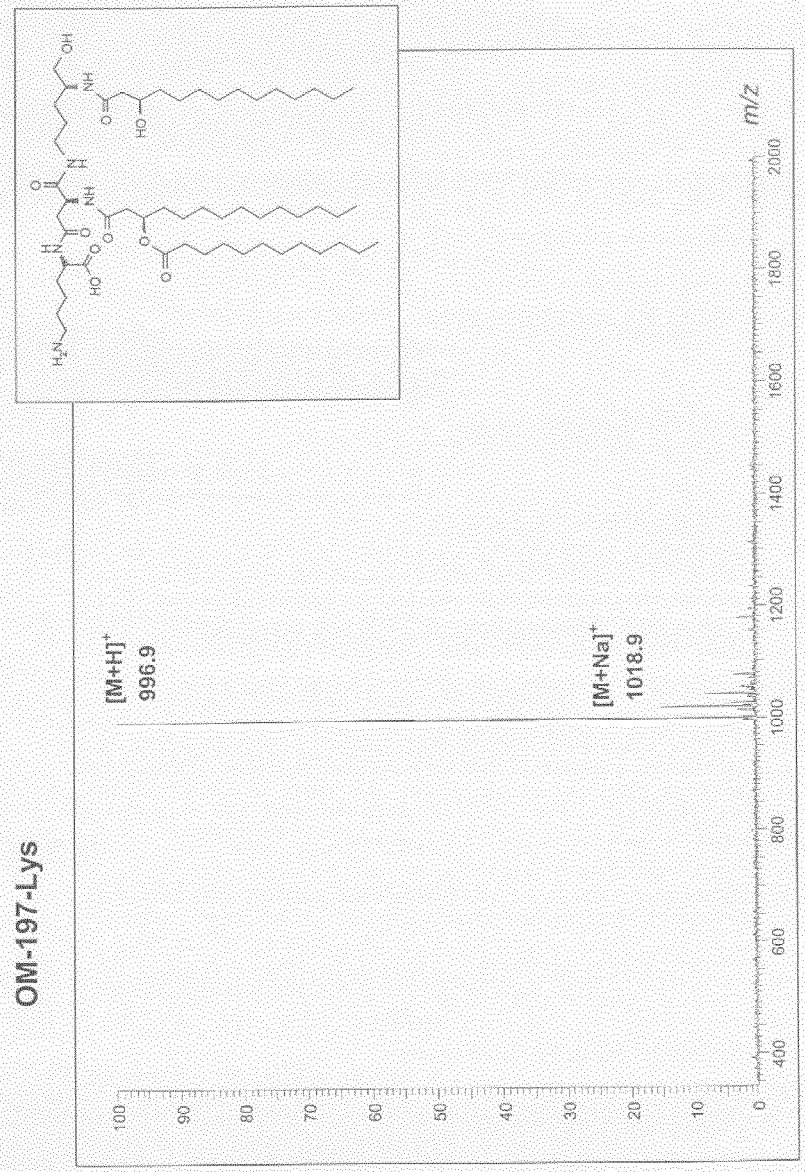
FIG. 32 shows the ionic cloud of LC/ES mass spectra analysis of the conjugate OM-197-Lys.

2.21.2. N—[(R)-3-dodecanoyloxytetradecanoyl]-D-aspartic acid, α-N-{(4R)-5-hydroxy-4-[(R)-3-hydroxytetradecanoylamino]pentyl}-amide β-N-[(1S)-1-carboxy-5-aminopentyl]amide A solution of the above prepared compound (93 mg; 71 μmol.) in a 1/1 CH$_2$Cl$_2$/ethanol mixture (20 ml) containing glacial acetic acid (0.5 ml) is hydrogenated in presence of palladium on carbon containing 10% Pd (17 mg) at room temperature and under atmospheric pressure hydrogen for 12 to 24 hours. The catalyst is filtered off. The filtrate is evaporated to dryness and the residue is then dried by suction from a vacuum pump to provide N—[(R)-3-dodecanoyloxytetradecanoyl]-D-aspartic acid, α-N-{(4R)-5-hydroxy-4-[(R)-3-hydroxytetradecanoylamino]pentyl}-amide β-N—[(1S)-1-carboxy-5-aminopentyl]amide (71 mg, stoichiometric yield). C$_{55}$H$_{105}$N$_5$O$_{10}$: ES/MS: m/z ratio 996.9 ([M+H]$^+$); 1018.9 ([M+Na]$^+$) (FIG. 32).

Example 2.22

N—[(R)-3-dodecanoyloxytetradecanoyl]-D-aspartic acid, α-N-{(4R)-5-(6-aminohexanoyloxy)-4[(R)-3-hydroxytetradecanoylamino]-pentyl}amide β-N-[(1S)-1-carboxy-5-aminopentylamide (=OM-197-Lys-AC) (FIG. 31)

2.22.1. N—[(R)-3-dodecanoyloxytetradecanoyl]-D-aspartic acid, α-N-{(4R)-5-(6-benzyloxycarbonylaminohexanoyloxy)-4-[(R)-3-benzyloxytetradecanoylamino]pentyl}-amide β-N-[(1S)-1-benzyloxycarbonyl-5-benzyloxycarbonylaminopentyl]-amide To a solution of N—[(R)-3-dodecanoyloxytetradecanoyl]-D-aspartic acid, α-N-{(4R)-5-hydroxy-4-[(R)-3-benzyloxytetradecanoylamino]pentyl}-amide β-N-[(1S)-1-benzyloxycarbonyl-5-benzyloxycarbonylaminopentyl]-amide (Section 2.21.1.) (317 mg, 0.48 mmol.) and 6-(benzyloxycarbonylamino)hexanoic acid (128 mg, 0.48 mmol.) in dry CH$_2$Cl$_2$ (15 ml) at 0° C. and under argon flow, there are added in succession 1-(3-dimethylaminopropyl)-3-ethylcarbodiimide hydrochloride (93 mg, 0.48 mmol.) and 4-dimethylaminopyridine (12 mg, 0.98 μmol.). The reaction mixture is then stirred for 30 minutes at 0° C. and thereafter overnight at room temperature. The reaction medium is then washed with water and a solution of 1N HCl followed by layer separation. The organic layer is dried over MgSO$_4$, filtered and evaporated. By running a flash chromatography treatment on a silica gel (5/1 CH$_2$Cl$_2$/acetone eluent), there is recovered the coupling reaction product (226 mg; 71%) as a white solid.

2.22.2. N—[(R)-3-dodecanoyloxytetradecanoyl]-D-aspartic acid, α-N-{(4R)-5-(6-aminohexanoyloxy)-4-[(R)-3-hydroxytetradecanoylamino]pentyl}-amide β-N-[(1S)-1-carboxy-5-aminopentyl]amide (=OM-197-Lys-AC)

Figure 33:
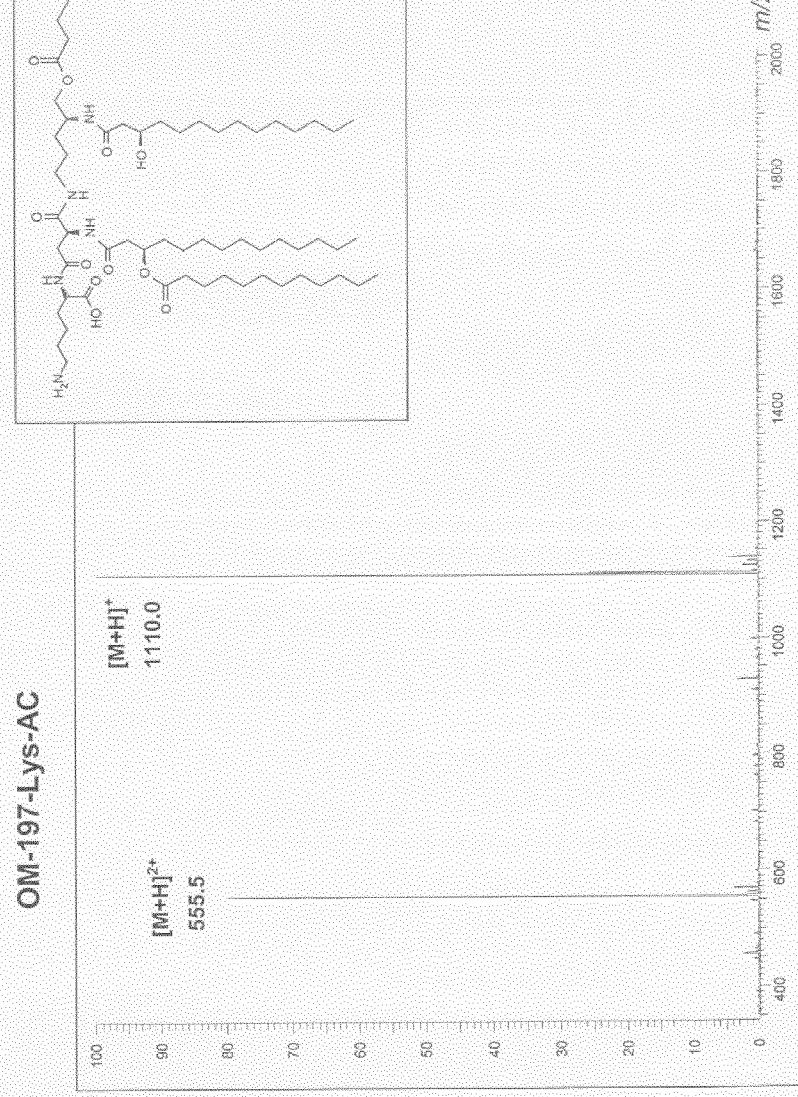
FIG. 33 shows the ionic cloud of LC/ES mass spectra analysis of the conjugate OM-197-Lys-AC.

A solution of the above prepared compound (236 mg; 151 μmol.) in an 1/1 CH$_2$Cl$_2$/isopropanol mixture (20 ml) containing acetic acid (1 ml) is hydrogenated in presence of palladium on carbon containing 10% Pd (100 mg) at room temperature and under atmospheric pressure hydrogen for 12 to 24 hours. The catalyst is filtered off. The filtrate is evaporated to dryness and the residue is then dried by suction from a vacuum pump to provide N—[(R)-3-dodecanoyloxytetradecanoyl]-D-aspartic acid, α-N-{(4R)-5-(6-aminohexanoyloxy)-4-[(R)-3-hydroxytetradecanoylamino]-pentyl}amide β-N-[(1S)-1-carboxy-5-aminopentyl]amide (140 mg, 83%). C$_{61}$H$_{116}$N$_6$O$_{11}$: ES/MS: m/z ratio 555.5 ([M+H]$^{+2}$); 1110.0 ([M+H]$^+$) (FIG. 33).

Example 2.23

Figure 34:
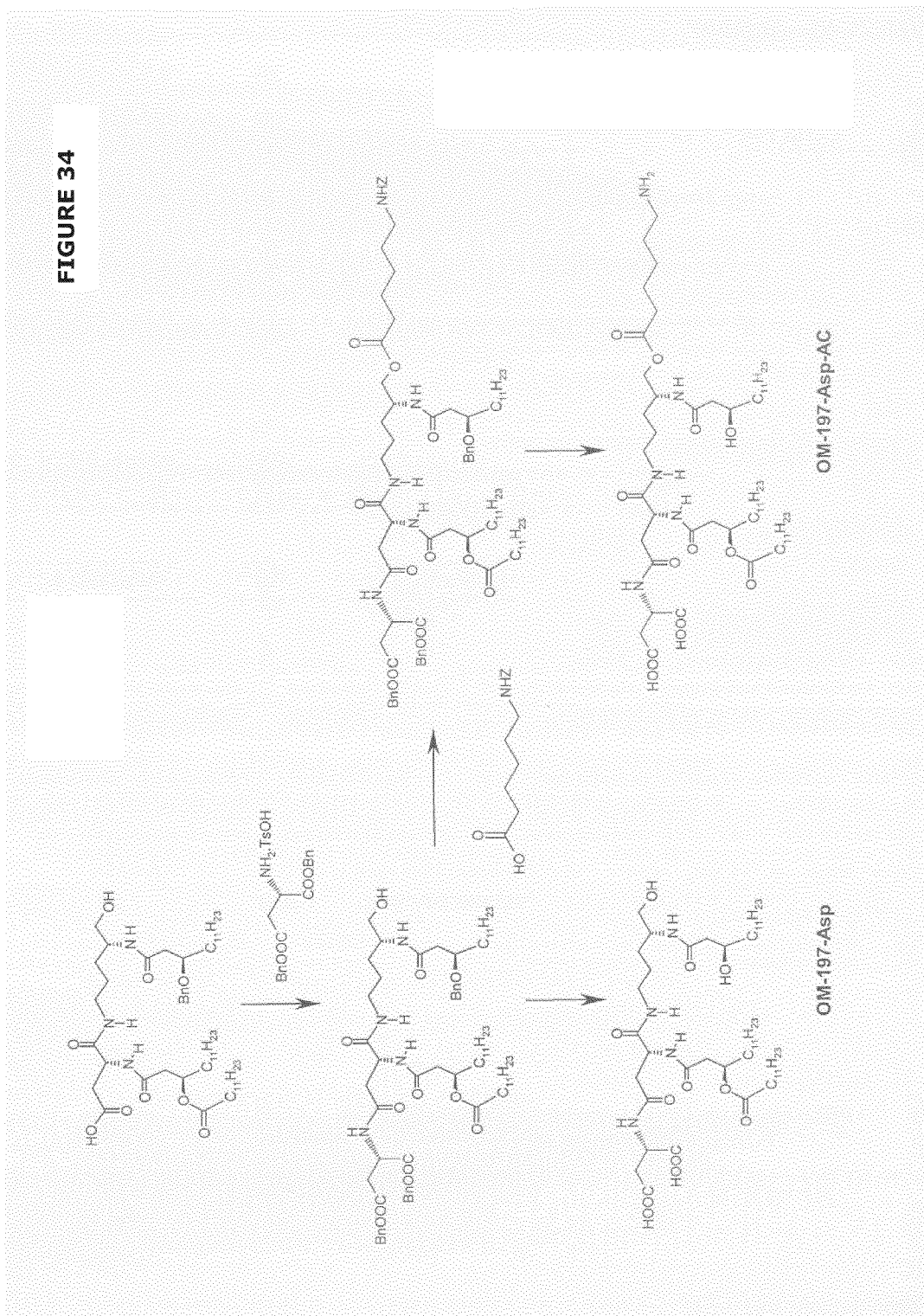
FIG. 34 shows the synthesis of the conjugates OM-197-Asp and OM-197-Asp-AC.

N—[(R)-3-dodecanoyloxytetradecanoyl]-D-aspartic acid, α-N-{(4R)-5-hydroxy-4-[(R)-3-hydroxytetradecanoylamino]-pentyl}Amide β-N-[(1S)-1,2-Dicarboxyethyl]Amide (=OM-197 Asp) (FIG. 34)

2.23.1. N—[(R)-3-dodecanoyloxytetradecanoyl]-D-aspartic Acid, α-N-{(4R)-5-hydroxy-4-[(R)-3-benzyloxytetradecanoylamino]pentyl}-amide β-N-[(1S)-1,2-bis(benzyloxycarbonyl)ethyl]amide A solution of IIDQ (2-isobutoxy-1-isobutoxycarbonyl-1,2-dihydroquinoline) (96 g; 0.32 mmol.) in anhydrous $CH_2Cl_2$ (5 ml) is added to a solution of N—[(R)-3-dodecanoyloxytetradecanoyl]-D-aspartic acid, α-N-{(4R)-5-hydroxy-4-[(R)-3-benzyloxytetradecanoylamino]-pentyl}amide (Section 2.20.1.) (252 mg, 0.26 mmol.) in anhydrous $CH_2Cl_2$ (20 ml) at room temperature and under argon flow. The reaction mixture is stirred for 15 minutes at room temperature and a solution of commercially available L-aspartic acid dibenzyl ester paratoluenesulfonate salt (141 mg, 0.29 mmol.) in anhydrous $CH_2Cl_2$ (5 ml) containing triethylamine (40 μl, 0.29 mmol.) is added. After stirring for 18 hours, the solution is evaporated to dryness. By running a flash chromatography purification on a silica gel (20/1 $CH_2Cl_2$/MeOH eluent), there is recovered the coupling reaction product (260 mg 78%).). $^{13}$C-NMR (62.89 MHz, $CDCl_3$), δ in ppm: 173.68, 171.92, 171.17, 170.60, 170.46, 170.37, 170.18, 170.06, 138.31, 138.19, 135.20, 135.12, 134.87, 128.48, 128.26, 128.18, 127.75, 127.63, 127.56, 76.66, 71.40, 71.19, 70.98, 68.79, 67.59, 66.85, 65.14, 64.73, 51.25, 50.17, 48.78, 48.67, 41.70, 39.37, 39.21, 37.50, 35.94, 34.48, 34.10, 31.81, 29.54, 29.25, 29.08, 27.93, 25.56, 25.14, 25.09, 24.91, 22.58, 14.02.

2.23.2. N—[(R)-3-dodecanoyloxytetradecanoyl]-D-aspartic acid, α-N-{(4R)-5-hydroxy-4-[(R)-3-hydroxytetradecanoylamino]-pentyl}amide β-N-[(1S)-1,2-dicarboxyethyl]amide (=OM-197-Asp)

Figure 35:
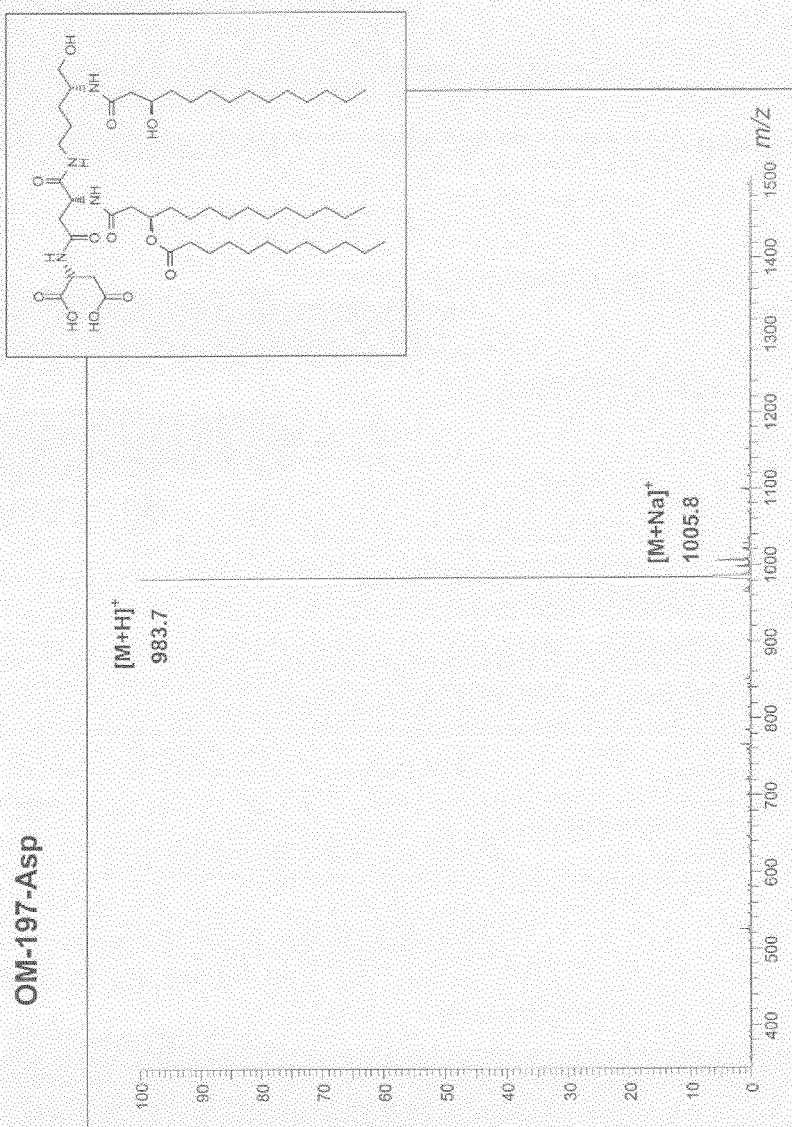
FIG. 35 shows the ionic cloud of LC/ES mass spectra analysis of the conjugate OM-197-Asp.

A solution of the above prepared compound (260 mg 207 μmol.) in a 1/1 $CH_2Cl_2$/isopropanol mixture (20 ml) is hydrogenated in presence of palladium on carbon containing 10% Pd (50 mg) at room temperature and under atmospheric pressure hydrogen for 4 hours. The catalyst is filtered off. The filtrate is evaporated to dryness and the residue is then dried by suction from a vacuum pump to provide the diacid (108 mg, 88%). $C_{53}H_{98}N_4O_{12}$: ES/MS: m/z ratio 983.7 ([M+H]$^+$); 1005.8 ([M+Na]$^+$); (FIG. 35).

Example 2.24

N—[(R)-3-dodecanoyloxytetradecanoyl]-D-aspartic acid, α-N-{(4R)-5-(6-aminohexanoyloxy)-4-[(R)-3-hydroxytetradecanoyl-amino]-pentyl}amide β-N-[(1S)-1,2-dicarboxyethyl]Amide (=OM-197-Asp-AC) (FIG. 34)

2.24.1. N—[(R)-3-dodecanoyloxytetradecanoyl]-D-aspartic acid, α-N-{(4R)-5-(6-benzyloxyaminohexanoyloxy)-4-[(R)-3-benzyloxytetra-dodecanoylmino]pentyl}amide β-N-[(1S)-1,2-bis(benzyloxycarbonyl)ethyl-amide To a solution of N—[(R)-3-dodecanoyloxytetradecanoyl]-D-aspartic acid, α-N-{(4R)-5-hydroxy-4-[(R)-3-benzyloxytetradecanoyl-amino]pentyl}amide β-N-[(1S)-1,2-bis(benzyloxycarbonyl)ethylamide (Section 2.23.1.) (158 mg, 0.13 mmol.) and 6-(benzyloxycarbonylamino)hexanoic acid (84 mg, 0.32 mmol.) in dry $CH_2Cl_2$ (6 ml) at 0° C. and under argon flow, there are added in succession commercially available 1-(3-dimethylaminopropyl)-3-ethylcarbodiimide hydrochloride (61 mg, 0.32 mmol.) and 4-dimethylaminopyridine (4 mg, 33 μmol.). The reaction mixture is then stirred for 30 minutes at 0° C. and thereafter overnight at room temperature. The reaction medium is then washed with water and a solution of 1N HCl followed by layer separation. The organic layer is dried over $MgSO_4$, filtered and evaporated. By running a flash chromatography purification on a silica gel (6/1 $CH_2Cl_2$/acetone eluent), there is recovered the coupling reaction product (83 mg; 44%). $^{13}$C-NMR (62.89 MHz, $CDCl_3$), δ in ppm: 173.69, 173.53, 173.26, 171.21, 171.11, 170.61, 170.38, 170.31, 170.22, 156.36, 138.26, 136.58, 135.20, 134.87, 128.48, 128.38, 128.31, 128.27, 128.19, 127.95, 127.55, 76.50, 71.24, 71.10, 67.58, 67.48, 66.79, 66.42, 65.69, 49.99, 48.77, 47.86, 41.70, 41.49, 40.70, 39.15, 37.50, 35.94, 34.44, 34.37, 33.97, 33.67, 31.80, 29.54, 29.24, 29.07, 28.37, 25.98, 25.55, 25.13, 25.08, 24.91, 24.28, 22.58, 14.02.

2.24.2. N—[(R)-3-dodecanoyloxytetradecanoyl]-D-aspartic acid, α-N-{(4R)-5-(6-aminohexanoyloxy)-4-[(R)-3-hydroxytetradecanoylamino]-pentyl}amide β-N-[(1S)-1,2-dicarboxyethyl]amide (=OM-197-Asp-AC)

Figure 36:
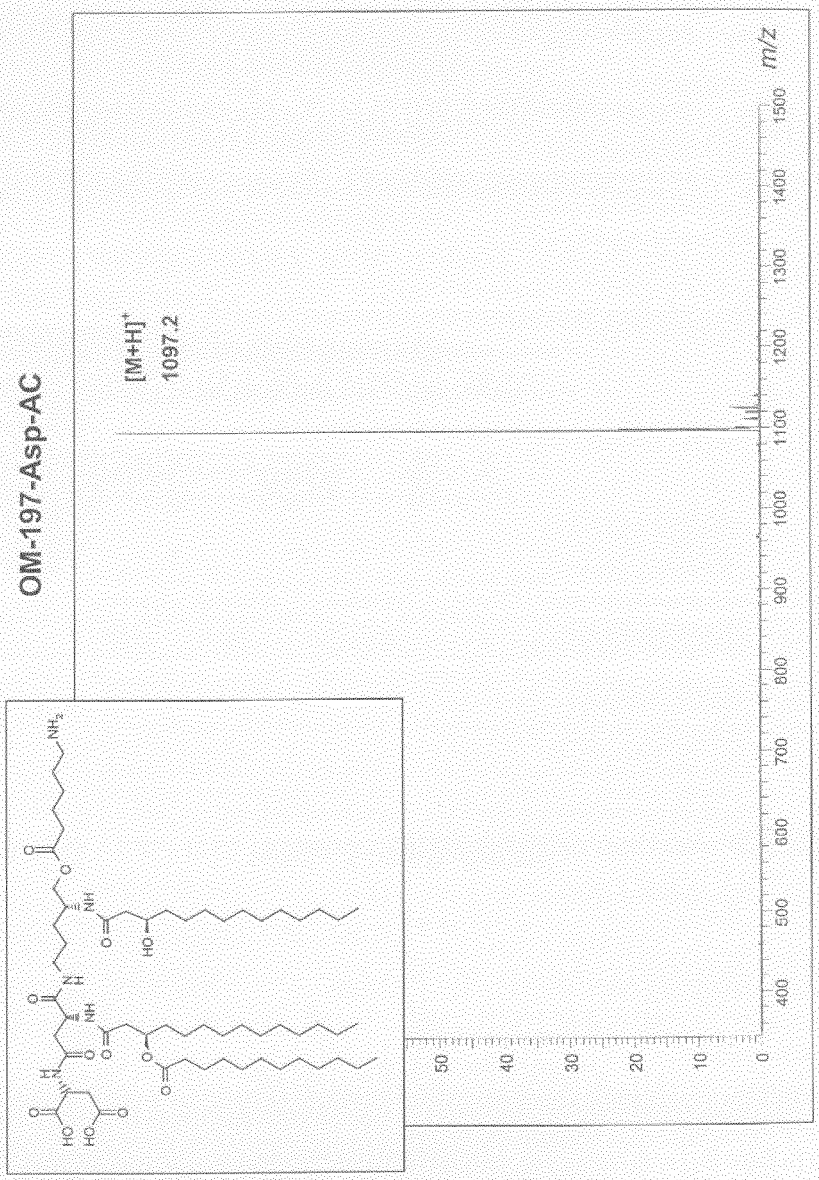
FIG. 36 shows the ionic cloud of LC/ES mass spectra analysis of the conjugate OM-197-Asp-AC.

A solution of the above prepared compound (80 mg 0.053 μmol.) in a 1/4 $CH_2Cl_2$/ethanol mixture (10 ml) containing acetic acid (1 ml) is hydrogenated in presence of palladium on carbon containing 10% Pd (50 mg) at room temperature and under atmospheric pressure hydrogen for 12 to 24 hours. The catalyst is filtered off. The filtrate is evaporated to dryness and the residue is then dried by suction from a vacuum pump to provide the diacid (61 mg, stoichiometric yield). Mass spectrometry MS: Calculated for $C_{59}H_{109}N_5O_{13}$: 1095.8. Found ES/MS: m/z ratio 1097.0 ([M+H]$^+$) (FIG. 36).

Example 2.25

Figure 37:
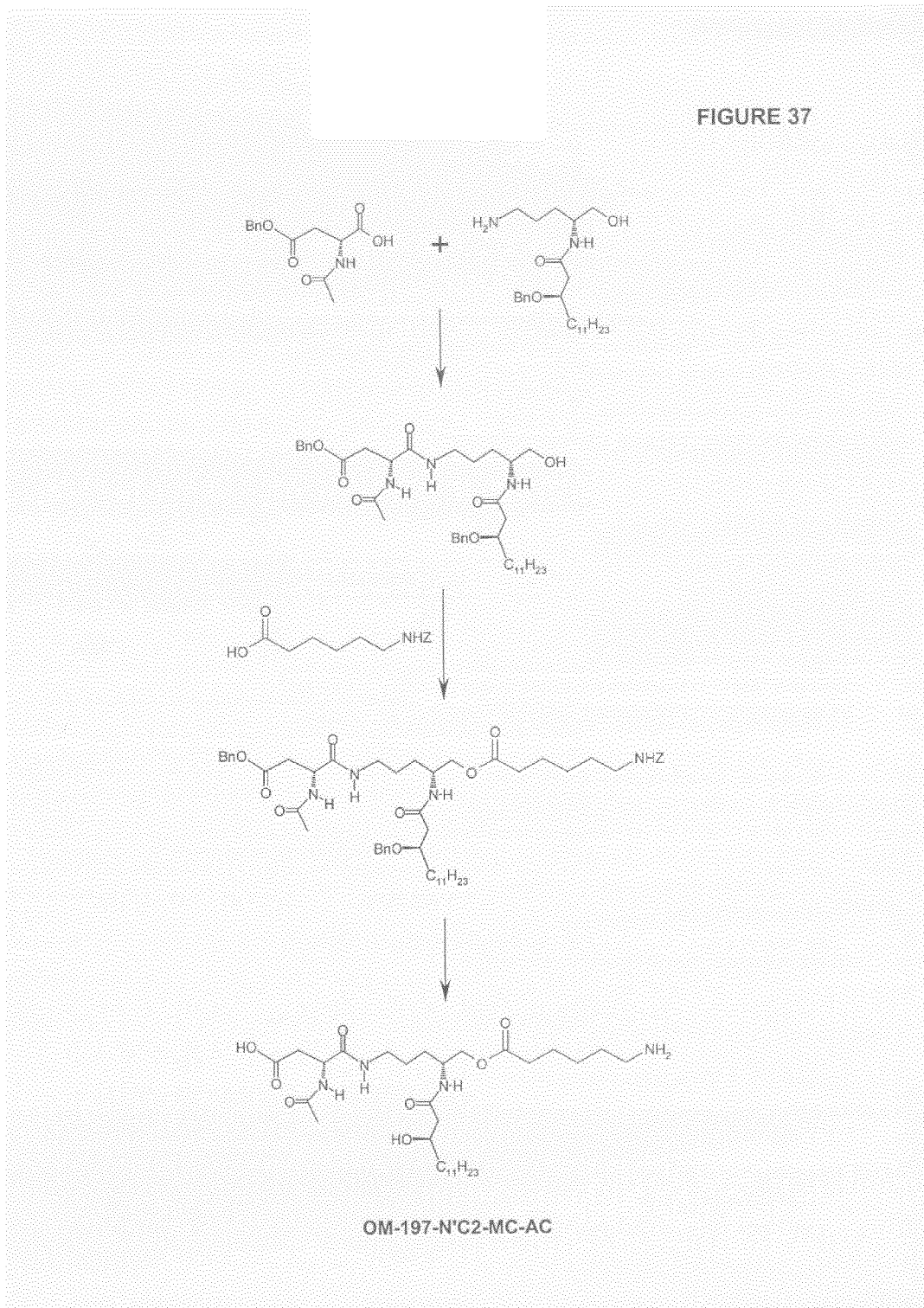
FIG. 37 shows the synthesis of the conjugate OM-197-N'$C_2$-MC-AC.

N-acetyl-D-aspartic acid, α-N-{(4R)-5-(6-aminohexanoyloxy)-4-[(R)-3-hydroxytetradecanoylamino]-pentyl}amide (=OM-197-N'C2-AC) (FIG. 37)

2.25.1. N-acetyl-D-aspartic acid, β-benzyl ester

To a solution of acetic anhydride (85 μl, 0.90 mmol.) in acetonitrile (1 ml), there is added a solution of commercially available H-D-Asp(OBn)-OH (Senn Chemicals, CH-Dielsdorf) (200 mg, 0.90 mmol.) in a $CH_3CN.H_2O/Et_3N$ (3.5/1.0/0.4 ml) mixture. The reaction mixture is stirred for 18 hours at room temperature. The organic solvent is evaporated and the remaining aqueous phase is cooled down to 0° C., acidified with a 10% aqueous solution of citric acid till pH=3 and extracted with EtOAc (2×). The organic layers are pooled and dried over $MgSO_4$, filtered and evaporated. The -benzyl ester of N-acetyl-D-aspartic acid obtained as a white crystalline solid (192 mg, 81%) is used in the next step with no further purification. (Rf=0.45 in 20/1 $CH_2Cl_2$/MeOH containing 2% of acetic acid, phosphomolybdinium compound and U.V. color development agent).

2.25.2. N]-acetyl-D-aspartic acid, α-N-{(4R)-5-hydroxy-4-[(R)-3-benzyloxytetradecanoylamino]pentyl}amide α-benzyl ester A solution of IIDQ (2-isobutoxy-1-isobutoxycarbonyl-1,2-dihydroquinoline) (254 g; 0.84 mmol., 1.2 eq.) in anhydrous CH$_2$Cl$_2$ (5 ml) is added to a solution of N-acetyl-D-aspartic acid β-benzyl ester prepared above (185 mg, 0.70 mmol.) in anhydrous CH$_2$Cl$_2$ (15 ml) at RT and under argon flow. The reaction mixture is stirred for 15 minutes and thereafter a solution of (2R)-5-amino-2-[(R)-3-benzyloxytetradecanoylamino]pentan-1-ol (Section 1.1.2.) (334 mg, 0.77 mmol., 1 eq.) in anhydrous CH$_2$Cl$_2$ (10 ml) is added. After stirring for 3 hours, the solution is evaporated to dryness. By subjecting the residual product to a flash chromatography purification on a silica gel (5/3 CH$_2$Cl$_2$/acetone then pure acetone eluent), there is recovered the coupling reaction product (369 mg; 78%). (R$_f$=0.22 in 5/2 CH$_2$Cl$_2$/acetone, phosphomolybdinium compound and U.V. color development agent). $^{13}$C-NMR (62.89 MHz, CD$_3$OD), δ in ppm: 171.92, 171.23, 171.07, 170.61, 170.35, 138.11, 135.24, 128.40, 128.24, 128.02, 127.69, 127.59, 71.25, 67.57, 64.56, 51.03, 49.41, 41.51, 39.21, 35.90, 33.88, 31.73, 29.46, 29.17, 28.32, 28.02, 25.35, 25.24, 24.97, 22.83, 22.51, 13.97, MS: Calc. for C$_{39}$H$_{59}$N$_3$O$_7$ 681.4. found: m/z 682.5 ([M+H]$^+$), 704.5 ([M+Na]$^+$).

2.25.3. N-acetyl-D-aspartic acid, α-N-{(4R)-5-(6-aminohexanoyloxy)-4-[(R)-3-benzyloxytetradecanoylamino]-pentyl}amide β-benzyl ester To a solution of N-acetyl-D-aspartic acid, α-N-{(4R)-5-hydroxy-4-[(R)-3-benzyloxytetradecanoylamino]-pentyl}amide β-benzyl ester (200 mg 0.29 mmol.) and 6-(benzyloxycarbanoylamino)hexanoic acid (156 mg 0.59 mmol.) in dry CH$_2$Cl$_2$ (8 ml) at 0° C. and under argon flow, there are added in succession commercially available 1-(3-dimethylaminopropyl)-3-ethylcarbodiimide hydrochloride (112 mg, 0.59 mmol.) and 4-dimethylaminopyridine (7 mg, 59 µmol.). The reaction mixture is then stirred for 30 minutes at 0° C. and thereafter overnight at room temperature. The reaction medium is then washed in succession with water and a solution of 1N HCl followed by layer separation. The organic layer is dried over MgSO$_4$, filtered and evaporated. By running a flash chromatography purification on a silica gel (6/1 CH$_2$Cl$_2$/acetone eluent), there is recovered the coupling reaction product (200 mg; 73%) as a white solid. $^{13}$C-NMR (62.89 MHz, CDCl$_3$), δ in ppm: 173.65, 171.71, 171.26, 170.30, 156.41, 138.16, 136.60, 135.33, 128.57, 128.46, 128.38, 128.20, 128.04, 127.76, 127.62, 71.21, 66.80, 66.53, 65.72, 65.63, 49.36, 47.80, 41.36, 40.76, 39.22, 39.13, 35.79, 33.75, 31.88, 29.61, 29.31, 28.58, 28.52, 26.04, 25.48, 25.11, 24.36, 23.13, 22.64, 14.09.

2.25.4. N-acetyl-D-aspartic acid, α-N-{(4R)-5-(6-aminohexanoyloxy)-4-[(R)-3-hydroxytetradecanoylamino]-pentyl}amide(OM-197-N'C2-AC)

Figure 38:
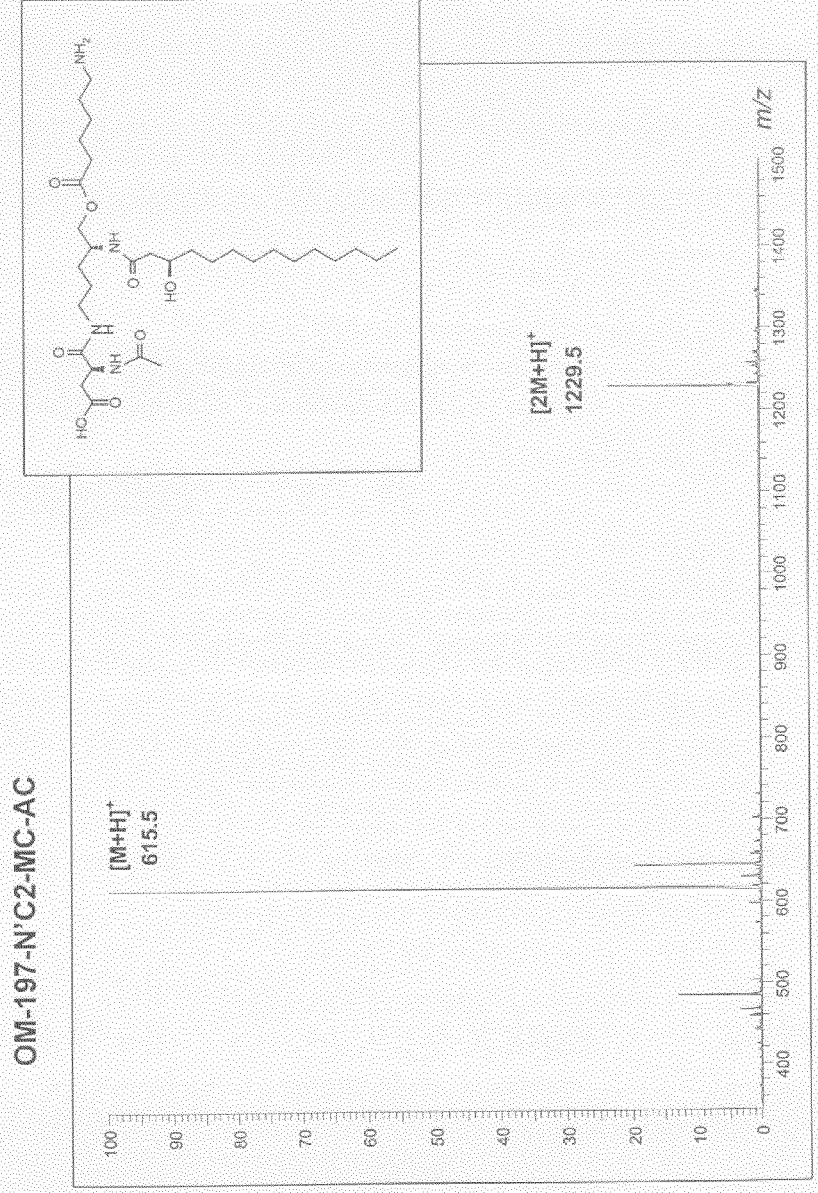
FIG. 38 shows the ionic cloud of LC/ES mass spectra analysis of the conjugate OM-197-N'$C_2$-MC-AC.

A solution of the compound obtained above (200 mg; 0.22 mmol.) in a 1/1 CH$_2$Cl$_2$/ethanol mixture (16 ml) containing acetic acid (2 ml) is hydrogenated in presence of Pd on carbon containing 10% Pd (40 mg) at room temperature and under atmospheric pressure hydrogen for 12 to 24 hours. The catalyst is filtered off and the filtrate is evaporated to dryness and then dried by suction from a vacuum pump to provide N-acetyl-D-aspartic acid, α-N-{(4R)-5-(6-aminohexanoyloxy)-4-[(R)-3-hydroxytetra-decanoylamino]pentyl}amide (132 mg, stoichiometric yield); MS: Calc. For C$_{31}$H$_{58}$N$_4$O$_8$ 614.43. Found: m/z 615.5 ([M+H]$^+$, 629.5 ([M+NH$_4$]$^+$), 637.5 ([M+Na]$^+$) (FIG. 38).

Example 2.26

Figure 39:
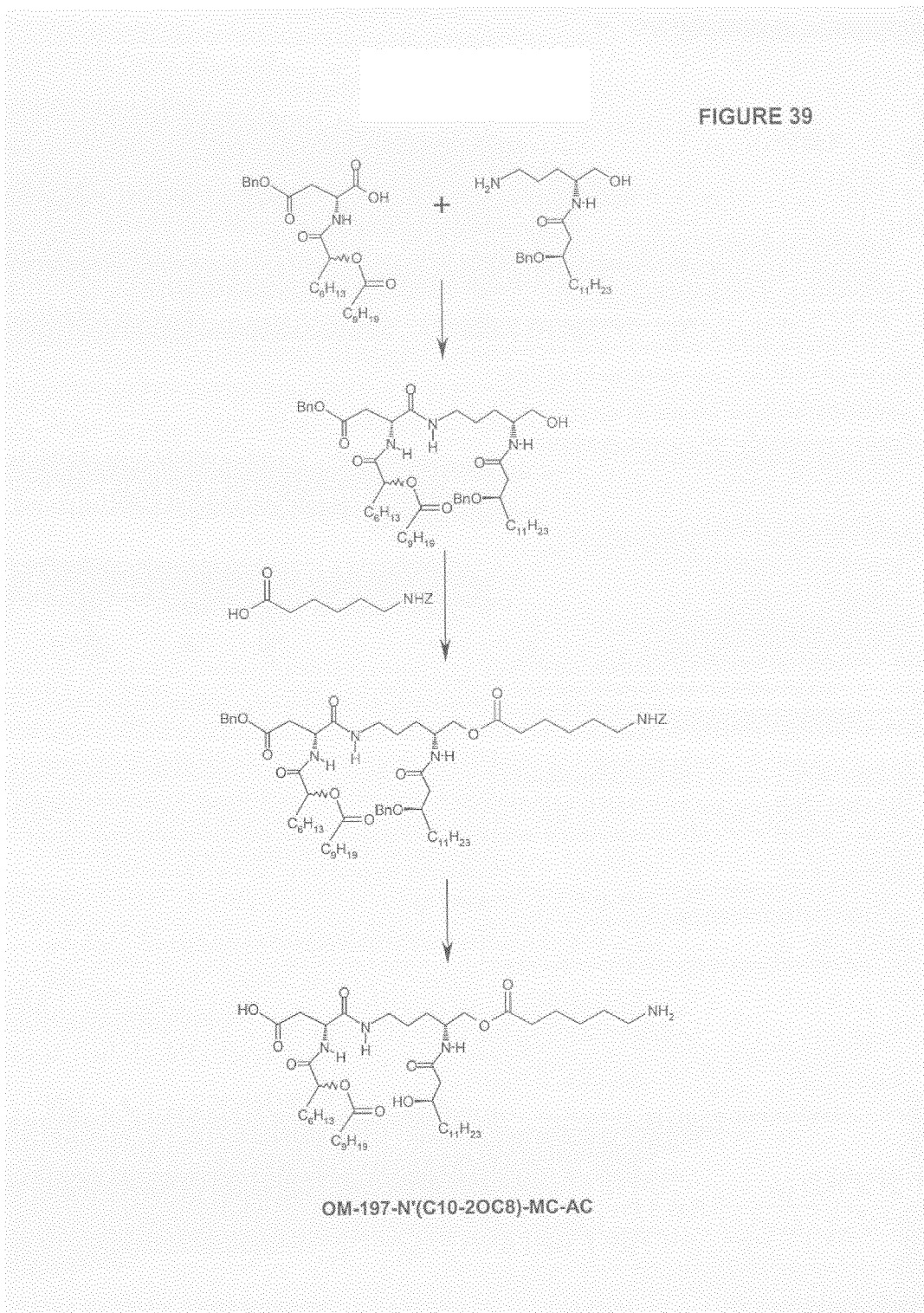
FIG. 39 shows the synthesis of the conjugate OM-197-N'($C_{10}$-2O$C_8$)-MC-AC.

N-(2-decanoyloxyoctanoyl)-D-aspartic acid, α-N-{(4R)-5-(6-aminohexanoyloxy)-4-[(R)-3-hydroxytetradecanoylamino]-pentyl}amide (=OM-197-N'(C10-2O8C)-AC) (FIG. 39)

2.26.1. Benzyl 2-hydroxyoctanoate

To a solution of a commercially available racemic 2-hydroxyoctanoic acid mixture (1.00 g, 6.2 mmol.) in HPLC-grade ethylacetate (30 ml), there are added in succession benzyl bromide (2.22 ml; 18.7 mmol.), triethylamine (2.6 ml, 18.7 mmol.) and tetrabutylammonium iodide (1.15 g; 3.12 mmol.). The solution is stirred for 18 hours at room temperature and the solvent is thereafter evaporated. The residue is taken up into ether and the organic layer is then washed with a saturated solution of NaHCO$_3$ and H$_2$O (2×). The organic layer is dried over MgSO$_4$, filtered and evaporated to yield crude benzyl 2-hydroxyoctanoate (Rf=0.57 in a 3/1 petroleum ether/EtOAc mixture; phosphomolybdinium compound and U.V. color development agent)

2.26.2. Benzyl 2-decanoyloxyoctanoate

To a solution of the ester as obtained above (780 mg; 3.12 mmol.) in dry CH$_2$Cl$_2$ (15 ml) at 0° C., there are added dropwise in succession pyridine (0.9 ml) and decanoyl chloride (654 mg; 3.43 mmol.). The mixture is stirred for 20 hours at room temperature and the reaction medium is then poured into ice-cold water containing (5%) NaHCO$_3$. The organic layer is separated, successively washed with a 1N HCl solution and water (2×). The organic layer is then dried over MgSO$_4$, filtered and evaporated. By running a flash chromatography purification on a silica gel (30/1 petroleum ether/EtOAc eluent), recovery of pure Benzyl 2-decanoyloxyoctanoate is achieved.

2.26.3. 2-decanoyloxyoctanoic acid solution of benzyl 2-hydroxyoctanoate as prepared above (515 mg; 1.27 mmol.) in HPLC-grade EtOH (40 ml) is hydrogenated in presence of Pd on carbon containing 10% Pd (100 mg) at room temperature and under atmospheric pressure hydrogen for 2 hours. The catalyst is filtered off on a millipore filter. The filtrate is evaporated to dryness and the residue is then dried under suction from a vacuum pump to obtain 2-decanoyloxyoctanoic acid (stoichiometric yield)

2.26.4. N-(2-decanoyloxyoctanoyl)-D-aspartic acid, β-benzyl ester

To a solution of 2-decanoyloxyoctanoic acid (317 mg; 1.01 mmol.) in anhydrous THF (2 ml) at −15° C. and under argon flow, there are added in succession N-methylmorpholin (111 µl; 1.01 mmol.; 1 eq.) and isobutyl chloroformate (131 µl; 1.01 mmol.; 1 eq.). Rapid formation of a N-methylmorpholin hydrochloride precipitate is observed. After stirring for 30 minutes at −15° C., a commercially available solution of H-D-Asp(OBn)-OH (Senn Chemicals AG, Switzerland-Dielsdorf) (225 mg 1.01 mmol.; 1 eq.) in a 3.5/1 CH$_3$CN/H$_2$O mixture (9 ml) containing Et$_3$N (0.4 ml) is added. The reaction mixture is then stirred overnight at room temperature. The organic layer is then evaporated and the aqueous layer is cooled down to 0° C., acidified with a 10% aqueous solution of citric acid down to pH=3 and extracted with EtOAc (2×). The organic layer is dried over MgSO$_4$, filtered and evaporated. By running a flash chromatography purification on a silica gel (2/1 petroleum ether/EtOAc eluent containing 2% acetic acid) followed by toluene coevaporation, there is recovered N-(2-decanoyloxyoctanoyl)-D-aspartic acid, β-benzyl ester (140 mg 27%).

2.26.5. N-(2-decanoyloxyoctanoyl)-D-aspartic acid, α-N-{(4R)-5-hydroxy-4-[(R)-3-benzyloxytetradecanoylamino]-pentyl}amide β-benzyl ester IIDQ (98 mg; 0.32 mmol.; 1.2 eq.) is added to a solution of N-(2-decanoyloxyoctanoyl)-D-aspartic acid, β-benzyl ester (140 g; 0.27 mmol.) in anhydrous $CH_2Cl_2$ (15 ml) at room temperature and under argon flow. After stirring for 15 minutes, addition was made of a solution of (2R)-5-amino-2-[(R)-benzyloxytetradecanoylamino]pentan-1-ol (Section 1.1.2.) (129 mg; 0.30 mmol.; 1.1 eq.) in anhydrous $CH_2Cl_2$ (5 ml). After stirring for 18 hours, the solution is evaporated to dryness. By running a flash chromatography purification on a silica gel (successively 5/1 $CH_2Cl_2$/acetone and 1/1 $CH_2Cl_2$/acetone eluent), there is recovered the coupling reaction product (197 mg; 78%). (Rf=0.30 in a 5/1 $CH_2Cl_2$/acetone mixture; phosphomolybdinium compound and U.V. color development agent).

2.26.6. N-(2-decanoyloxyoctanoyl)-D-aspartic acid, α-N-{(4R)-5-[6-(benzyloxycarbonylamino)hexanloxy]-4-[(R)-3-benzyloxytetradecanoyl-amino]pentyl}amide β-benzyl ester To a solution of N-(2-decanoyloxyoctanoyl)-D-aspartic acid, α-N-{(4R)-5-hydroxy-4-[(R)-3-benzyloxytetradecanoylamino]-pentyl}amide β-benzyl ester (97 mg; 0.21 mmol.) and 6-(benzyloxycarbanoylamino) hexanoic acid (112 mg, 0.42 mmol.) in dry $CH_2Cl_2$ (8 ml) at 0° C. and under argon flow, there are added in succession 1-(3-dimethylaminopropyl)-3-ethylcarbodiimide hydrochloride (81 mg, 0.42 mmol) and 4-dimethylaminopyridine (6 mg, 42 µmol.). The reaction mixture is next stirred for 30 minutes at 0° C. and thereafter overnight at room temperature. The reaction medium is then washed in succession with water and a 1N HCl solution; followed by layer separation. The organic layer is dried over $MgSO_4$, filtered and evaporated. By running a flash chromatography purification on a silica gel (6/1 $CH_2Cl_2$/acetone eluent), there is recovered the coupling reaction product (170 mg; 68%).

Figure 40:
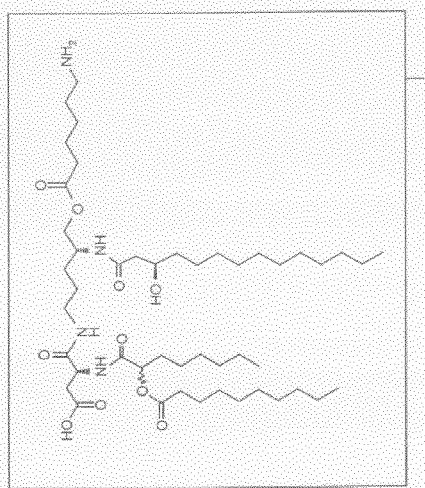
FIG. 40 corresponds to a mass spectra analysis of the conjugate OM-197-N'($C_{10}$-2O$C_8$)-MC-AC.

2.26.7. N-(2-decanoyloxyoctanoyl)-D-aspartic acid, α-N-{(4R)-5-[6-(aminohexanoyloxy]-4-[(R)-3-hydroxytetradecanoylamino]pentyl}amide A solution of the compound as prepared above (150 mg; 0.13 mmol.) in a 1/1 $CH_2Cl_2$/ethanol mixture (16 ml) containing acetic acid (2 ml) is hydrogenated in presence of Pd on carbon containing 10% Pd (40 mg) at room temperature and under atmospheric pressure hydrogen for 12 to 24 hours. The catalyst is filtered off. The filtrate is evaporated to dryness and the residue is then dried by suction from a vacuum pump to provide N-(2-decanoyloxyoctanoyl)-D-aspartic Acid, α-N-{(4R)-5-[6-(aminohexanoyloxy]-4-[(R)-3-hydroxytetradecanoylamino]pentyl}amide (110 mg, stoechiometric yield) MS (mass spectrometry) Calc. For $C_{47}H_{88}N_4O_{10}$: 868.65. Found: m/z ratio 870.0 ($[M+H]^+$); 884.0 ($[M+NH_4]^+$), 891.5 ($[M+Na]^+$) (FIG. 40).

Example 2.27

Purification and Analysis of Compounds in Accordance with the Invention

The synthesis product and acyl-dipeptide-like compounds bearing an accessory functional side chain spacer are dissolved in a (1:1 v/v) water-isopropanol mixture The required quantity of 2 M ammonium bicarbonate is then added up to a concentration of 50 mM.

2.27.1. Purification

Purification process is performed by reverse phase preparative HPLC according to the following conditions:
Column: Bondapack C18 PrepPak, 40×200 mm, 15-20 µm, 300 Å, Waters
Mobile phase:
A: (9:1 v/v) isopropanol-water, 50 mM ammonium bicarbonate
B: (2:8 v/v) isopropanol-water, 50 mM ammonium bicarbonate
Flow rate: 40 ml/min.
Elution: Isocratic adsorption on column: 40% B (60% A), 10 min.
Gradient: A:B: 40-80% B within 10 min.
Isocratic elution: 80% B, 30 min.
Washing step: 100% B, 10 min.
Detection: UV, 210 nm.

Should any aromatic products be observed (incomplete deprotection step), a finer purification step must be carried out. This further purification process is performed according to the following conditions:
Column: Kromasil C18, 21×250 mm, 5 µm, 100 Å, Macherey-Nagel.
[0442] Mobile phase:
A: (9:1 v/v) isopropanol-water 50 mM ammonium bicarbonate
B: (2:8 v/v) isopropanol-water, 50 mM ammonium bicarbonate
Flow rate: 5 ml/min.
Elution: Isocratic adsorption on column: 40% B (60% A), 10 min.
Isocratic elution: 84% B, 30 min.
Washing step: 100% B, 10 min.
Detection: UV, 210 nm.
System: Waters 2000
The fractions containing the relevant compounds in the form of ammonium salts are pooled and concentrated by adsorption on C18 Bondapack, 15-20 µm, 300 Å, Waters. The counter-ion can then be exchanged by washing with an aqueous solution of an alkaline metal salt (such as NaCl or KCl, for instance) at a concentration of 10 g/l in a water-isopropanol mixture (9:1, v/v). Upon removal of excess salt by flowing 5 volumes of a (9:1, v/v) water-isopropanol mixture over the column, the compound is eluted with pure isopropanol.

2.27.2. Purification Process Monitoring

After each step, the fractions are analyzed by analytical reverse phase HPLC chromatography according to the following conditions:
Column: Supelcosil C18, 3 µm, 4.6×150 mm, 100 Å, Supelco.
Mobile phase:
A: (1:1, v/v.) water-acetonitrile, 5 mM TBAP
B: (1:9, v/v) water-isopropanol 5 mM, TBAP
TBAP: tetrabutylammonium phosphate
Flow rate: 1 ml/min.
Elution step: (75:25 to 0:100 range) A:B Gradient within 37.5 min.
Detection: UV, 210 nm and 254 nm.
Chromatography apparatus: For these assays, different HPLC chromatography apparatus were used (HP1050 Ti series, HP1090 series M, LabChromShimadzu). Retention times read by the particular system being used may vary by about 1 minute for a given compound.

2.27.3. Assay and Purity Analysis of Final Products

Assay and purity analysis of the obtained products are performed by an HPLC/UV technique according to the chromatography operating conditions specified above. Based on these analysis, purity of products ranges from 97 to 100%. In order to demonstrate that inactive impurities are present as judged by UV detection, LC/ES-MS analysis were carried out (electrospray type ionization, positive mode). In order to fulfill ionization conditions, chromatographic separation was carried out according to the following conditions:
Column: Vydac C4, 5 µm, 4.6×150 mm, 300 Å
Mobile phase:
A: (1:1, v/v) water-acetonitrile, 0.05% TFA
B: (1:9, v/v) water-isopropanol, 0.05% TFA
Flow rate: 1 ml/min.
Elution: (80:20-0:100 range) A/B gradient within 20 minutes.
Temperature: 40° C.

2.27.4. Spectroscopic Analysis

Mass Spectrometry
ES/MS spectra (positive and negative modes) were recorded on a variety of mass spectrometers (Finnigan LCQ, ion trap; Micromass Quattro II, triple stage quadrupole; Micromass Z-Bio-Q, triple stage quadrupole). Additional analysis based on MS/MS measurements were carried out.
Nuclear Magnetic Resonance
$^1$H-NMR and $^{13}$C-NMR spectra were recorded on a DPX Bruker type apparatus at 250.13 and 62.89 MHz.

$3^{rd}$ Series of Examples Preparation of Conjugates

Example 3.1

FGFG Peptide Conjugates

As shown by synthesis schemes set forth on FIGS. 5, 8, 15, 17, 19, 21 and 23, a vicinal dihydroxylation reaction is performed on dipeptide-like compounds bearing an olefin type accessory side chain spacer to finally result into a stable diol functional group. A periodic oxidation reaction is then conducted to form an aldehyde functional group on the accessory side chain spacer. A reductive amination reaction may then carried out using this functional group to couple, for instance, a small size peptide such as FGFG (SEQUENCE NO 14) (Phenylalanine-Glycine-Phenylalanine-Glycine, Sigma). However, the aldehyde compound is preferably subjected to a purification step in order to remove salts present in the solution. This purification of the aldehyde compound is achieved on a C18 phase Bondapack (Waters), 15-20 µm, 300 Å, according to the following procedure:
  sample adsorption after dilution in a (1:3) isopropanol-water mixture.
    elution of salts with a (1:9) isopropanol-water mixture.
  elution of the aldehyde compound with the least volume of isopropanol
The coupling reaction based on reductive amination was carried out in an aqueous solution at a 1:1 stoechiometric ratio of aldehyde (accessory side chain spacer of the acyl-dipeptide-like compound) and amine functional groups available on the peptide or the protein to be coupled.

Figure 41:
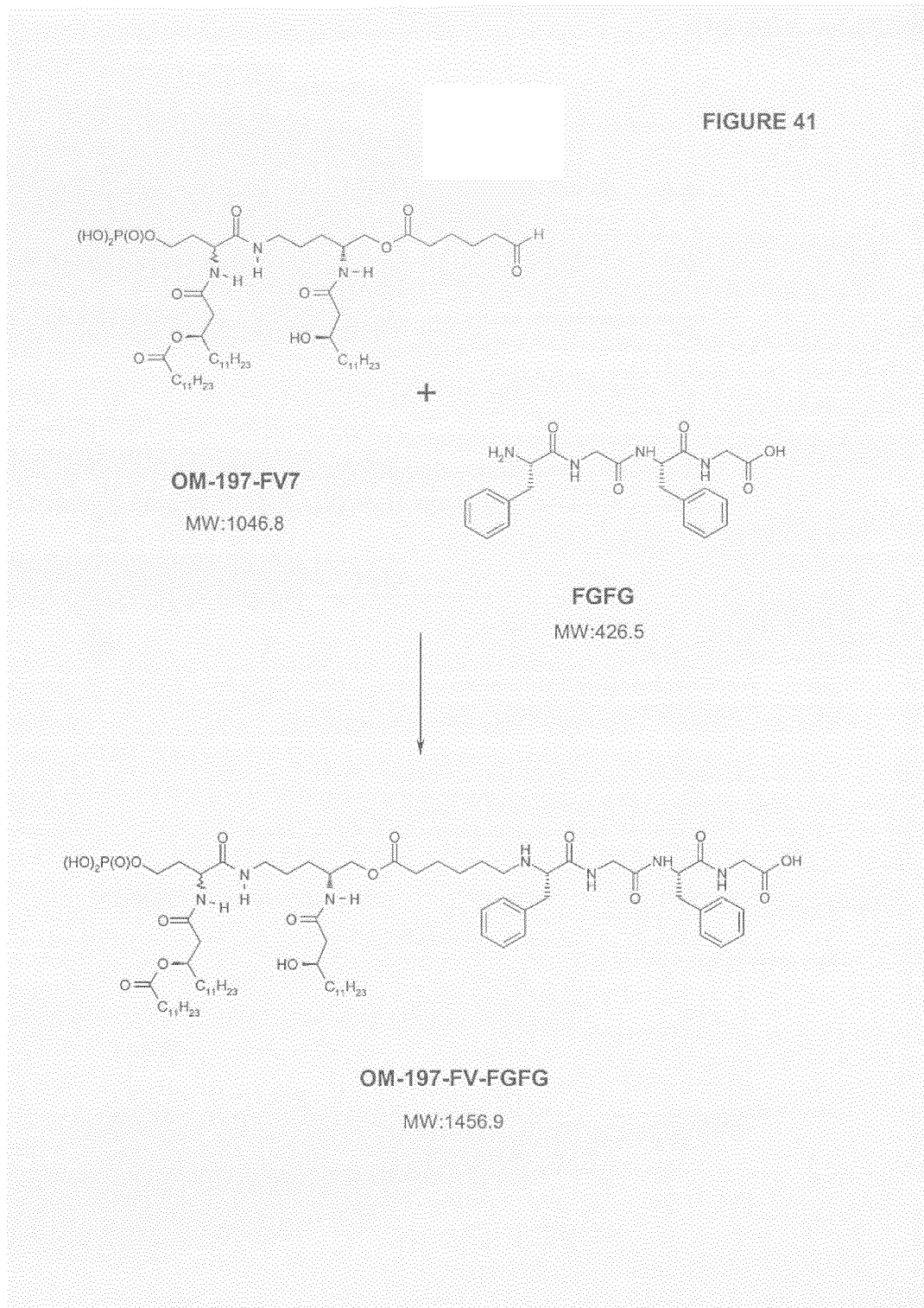
FIG. 41 shows the synthesis of the conjugate OM-197-FV-FGFG.
Figure 42:
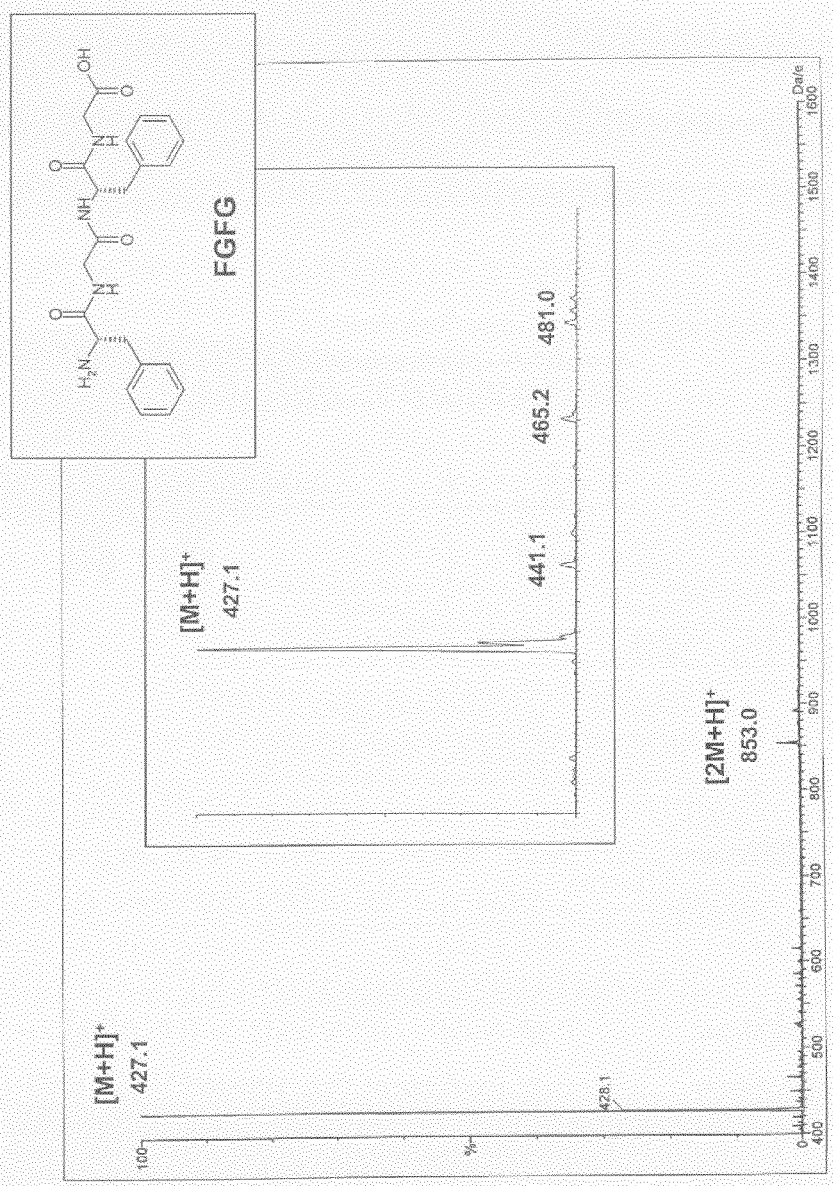
FIG. 42 shows the ionic cloud of LC/ES mass spectra analysis of the compound FGFG.
Figure 43:
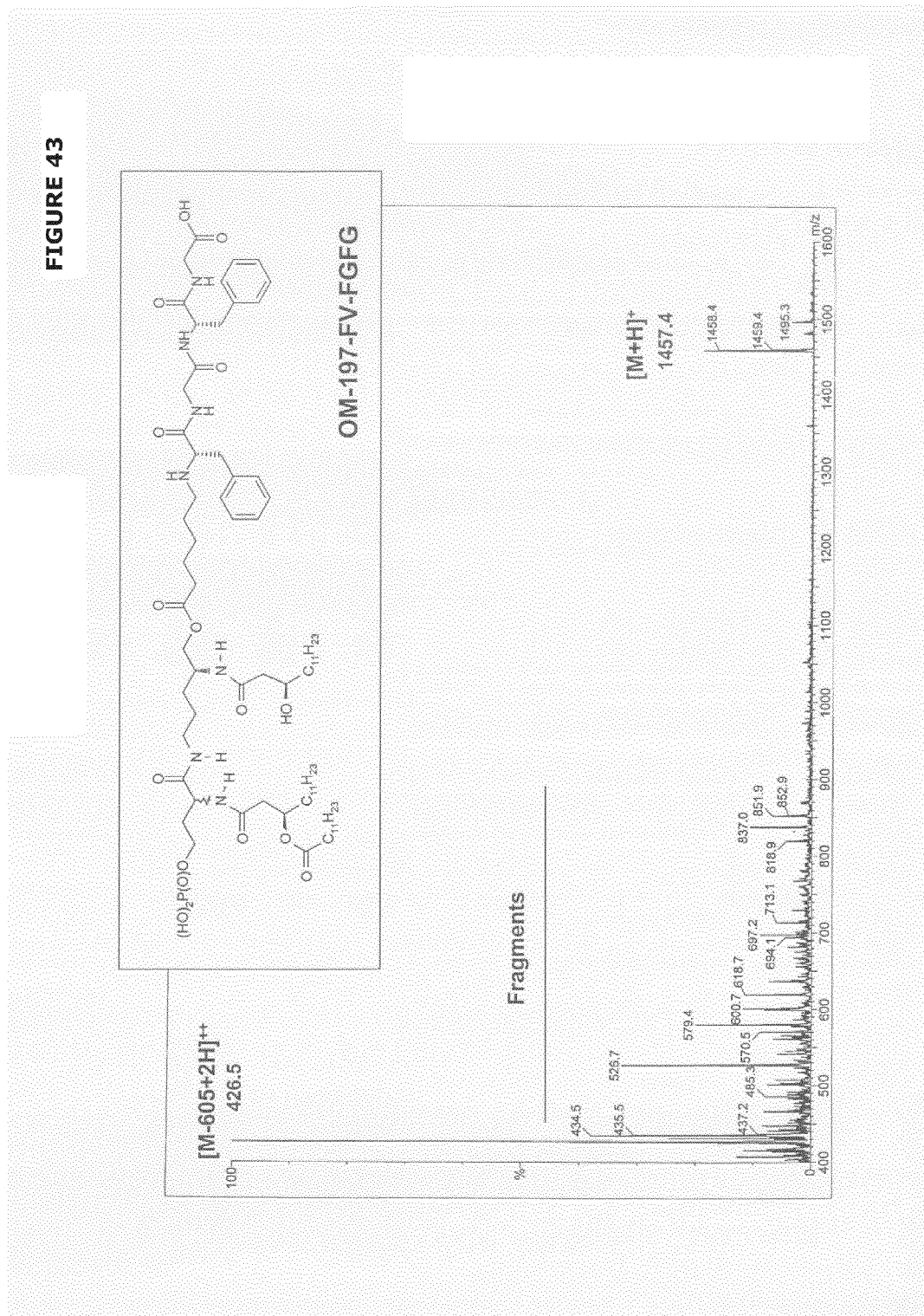
FIG. 43 shows the ionic cloud of LC/ES mass spectra analysis of the conjugate OM-197-FV-FGFG.

In case of an FGFG peptide (SEQ ID NO: 14), 2 mg of purified OM-197-FV7 (1.86 µmol., 1 eq.) were added to a solution of 0.8 mg FGFG (SEQ ID NO: 14), (1.86 µmol., 1 eq.) dissolved in 1 ml of (1:1) $H_2O$-MeCN. The solution was stirred for a period of 30 minutes at room temperature to form an imine. The reduction step was subsequently carried out by adding 92 µl of 1 M NaBH$_3$CN (5.77 mg, 50 eq.) to form a highly stable carbon-nitrogen bond (FIG. 41). The conjugate was subjected to a preliminary purification step on a Vydac C$_4$ column in order to remove the non reacted peptide, and thereafter on a Bondapack C18 phase (Waters) to obtain the sodium salt (see purification and analysis section of compounds according to the invention). Next, the conjugate was dissolved back in sterile $H_2O$/0.01% triethanolamine (TEoA) to meet the biological activity testing requirements. The ES/MS mass spectrum recorded after the purification process is shown on FIG. 43 and clearly demonstrates a $[M+H]^+$ molecular ion at 1457.4 m/z ratio, which provides evidence that the required coupling did occur. Visible ions between 400 and 900 m/z ratio were identified by MS/MS analysis as fragments arising from a molecular peak of the conjugated peptide. Ions corresponding to the initial FGFG peptide (SEQ ID NO: 14), (m/z ratio 427.1 $[M+H]^+$, m/z ratio 853.0 $[2M+H]^+$, FIG. 42) were not detected.

Example 3.2

$(NANP)_6P_2P_{30}$ Peptide Conjugates

Figure 44:
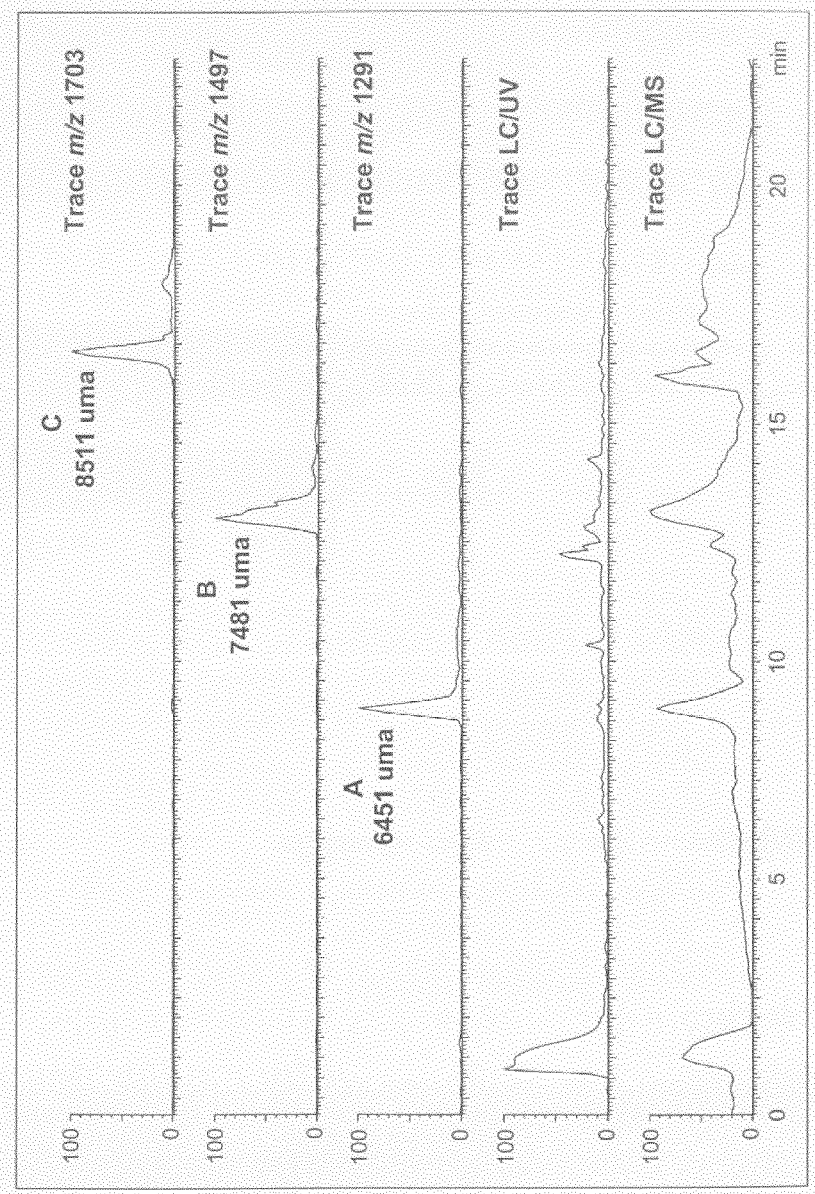
FIG. 44 shows the ionic cloud of LC/ES mass spectra analysis of the reaction mixture of compound of Example 3.2.
Figure 45:
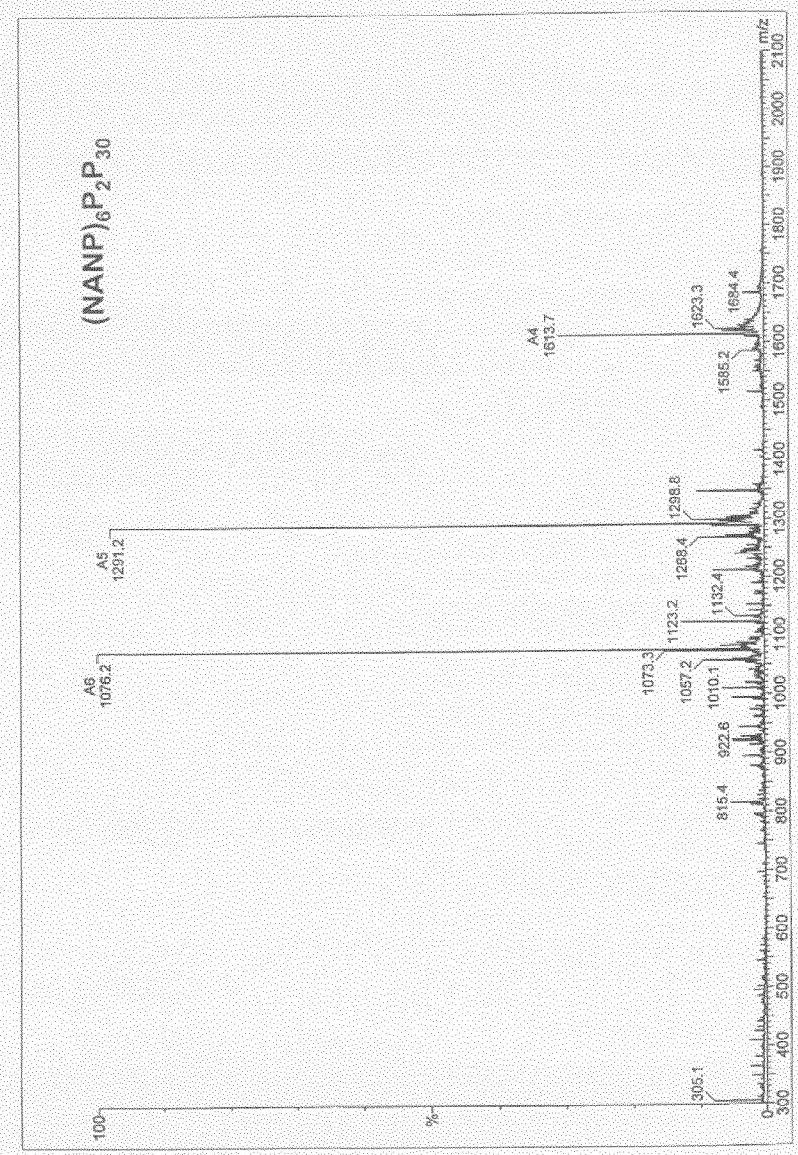
FIG. 45 shows the ionic cloud of LC/ES mass spectra analysis of the peptide (NANP)$_6$P$_2$P$_{30}$.
Figure 46:
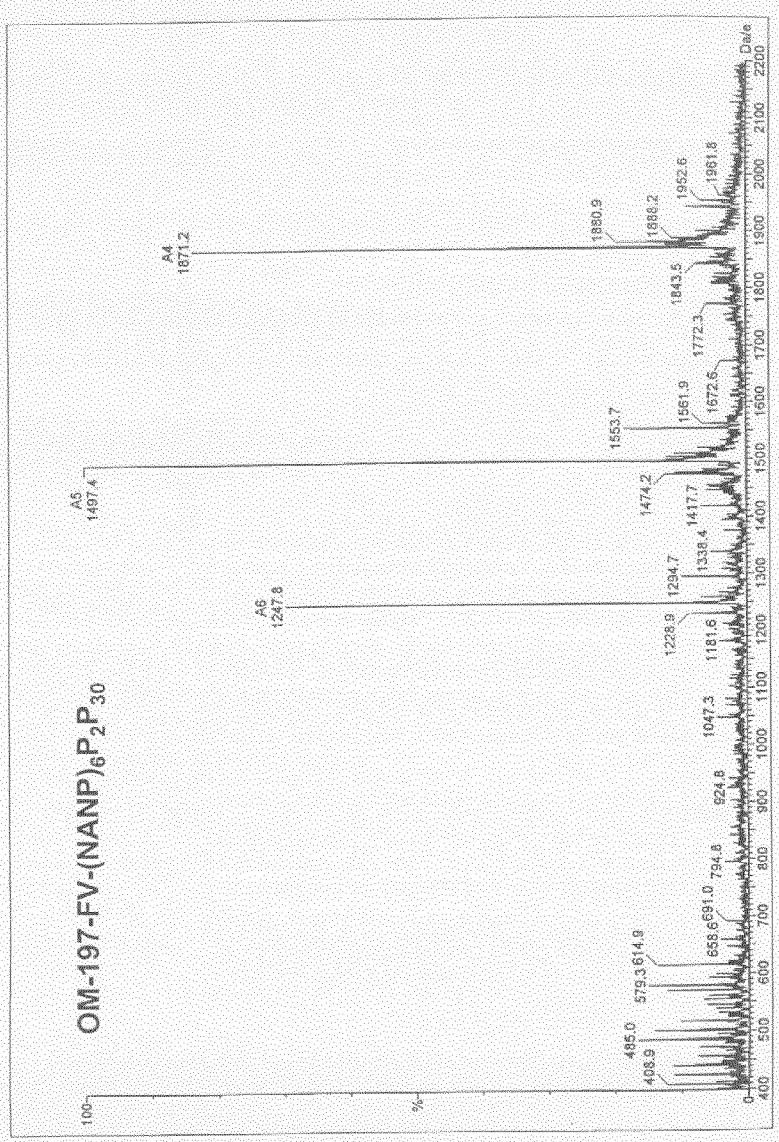
FIG. 46 shows the ionic cloud of LC/ES mass spectra analysis of the monoconjugate OM-197-FV-(NANP)$_6$P$_2$P$_{30}$.
Figure 47:
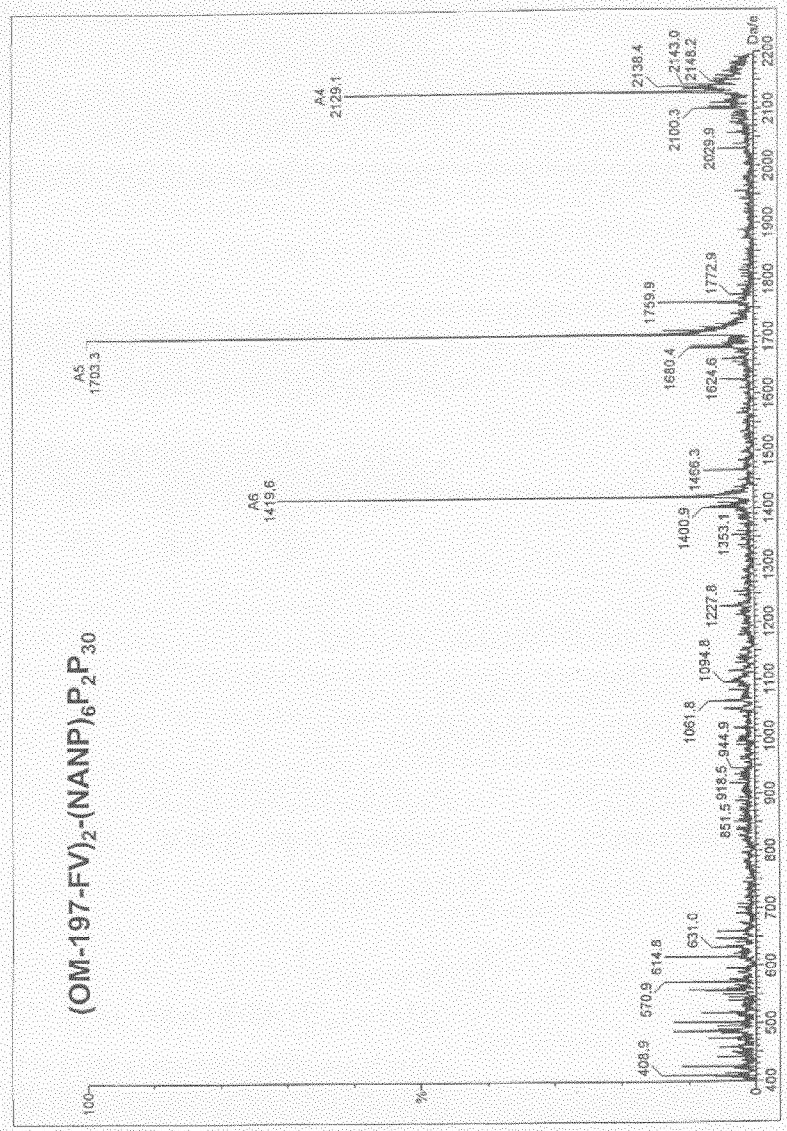
FIG. 47 shows the ionic cloud of LC/ES mass spectra analysis of the biconjugate (OM-197-FV)$_2$-(NANP)$_6$P$_2$P$_{30}$.

OM-197-FV7 compound obtained by the synthesis scheme set forth on FIG. 5 may be coupled, for instance, to a peptide of pharmaceutical interest such as $(NANP)_6P_2P_{30}$ [Valmori et al., 1992, *J. Immunol.*, 149:717-721] having the following sequence: (NANP)$_6$QYIKANSKFIGITEFNN-FTVSFWLRVPKVSASHLE (SEQ ID NO: 2) The (NANP)$_6P_2P_{30}$ peptide (SEQ ID NO: 2) shows four potential conjugation sites (terminal amine+three lysines). 5 mg of purified OM-197-FV7 (4.64 µmol., 4 eq.) were added to a solution of 7.49 mg (NANP)$_6P_2P_{30}$ (SEQ ID NO: 2) (1.16 µmol., 1 eq.) dissolved in 1 ml of a (1:1) $H_2O$-isopropanol mixture. The solution was stirred for 30 minutes at room temperature, and thereafter the reduction step was conducted by adding 230 µl of 1M NaBH$_3$CN (14.43 mg, 50 eq.). The solution was stirred for two hours at room temperature. The reaction mixture was then dialyzed against $H_2O$ for 24 hours (3.5 kDa dialysis cassette, Slide-A-Lyzer, Pierce). LC/ES-MS analysis of the reaction mixture demonstrates the presence of three molecular species, as shown by the chromatograms depicted on FIG. 44: Peaks corresponding to the free peptide (peak A), to the monoconjugated peptide (peak B) and the biconjugated peptide (peak C) are clearly visible. The ionic cloud recorded for each of these are depicted on FIGS. 45, 46 and 47 and provide evidence that covalent conjugation to one or two molecules of OM-197-FV has taken place as for the monoconjugate and biconjugate, respectively.
FIG. 45: Peptide $(NANP)_6P_2P_{30}$ (free peptide) (SEQ ID NO: 2) MW: 6451. Ions at an m/z ratio of 1076.2 (A6), 1291.2 (A5), 1613.7 (A4)
FIG. 46: Monoconjugate OM-197-FV-$(NANP)_6P_2P_{30}$ (SEQ ID NO: 2) MW: 7481 Ions at an m/z ratio of 1247.8 (B6), 1497.4 (B5), 1871.2 (B4)
FIG. 47: Biconjugate (OM-197-FV)$_2$-$(NANP)_6P_2P_{30}$ (SEQ ID NO: ID 2) MW: 8511 Ions at an m/z ratio of 1419.6 (C6), 1703.3 (C5), 2129.1 (C4)
SDS-PAGE analysis of OM-197-FV-$(NANP)_6P_2P_{30}$ (SEQ ID NO: 2) conjugates demonstrated various discrete bands corresponding to the unreacted peptide, the monoconjugate and the biconjugate. Under the electrophoretic conditions herein used (10-20% polyacrylamide gradient, tris-tricin buffer, Bio-Rad, #161-1108), the difference between the relevant bands was estimated at 1000 amu based on standard markers, which provides evidence that coupling of one or two molecules of OM-197-FV to the peptide did occur.

Example 3.3

$P_2P_{30}$ Peptide Conjugates

Other peptides can also be coupled by a reductive amination reaction to the compounds bearing an accessory aldehyde type side chain spacer. The example of coupling OM-197-FV with a $P_2O_{30}$ (SEQ ID NO: 3) peptide is given for the purpose of illustration. The latter corresponds to the T epitope portion of the tetanus toxoid and has the following sequence: KQYIKANSKFIGITEFNNFTVSFWLRVP-KVSASHLE (SEQ ID NO: 3)

Figure 48:
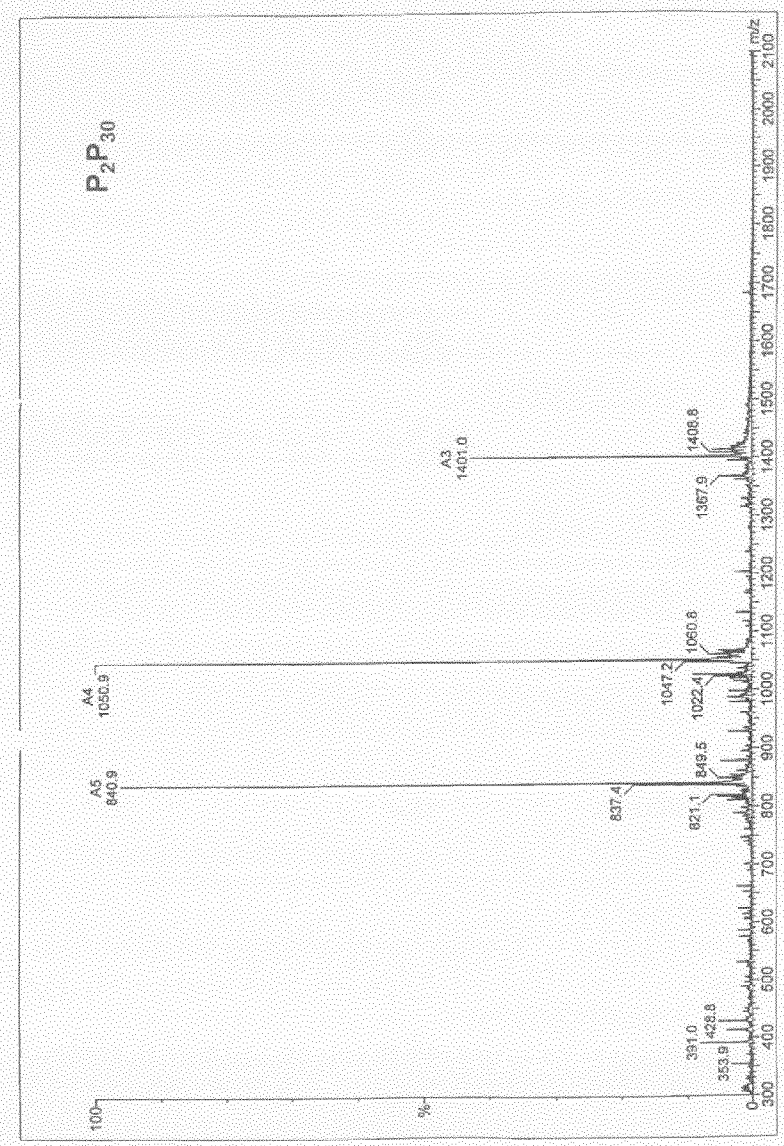
FIG. 48 shows the surrounding ionic charge of the peptide P$_2$P$_{30}$.
Figure 49:
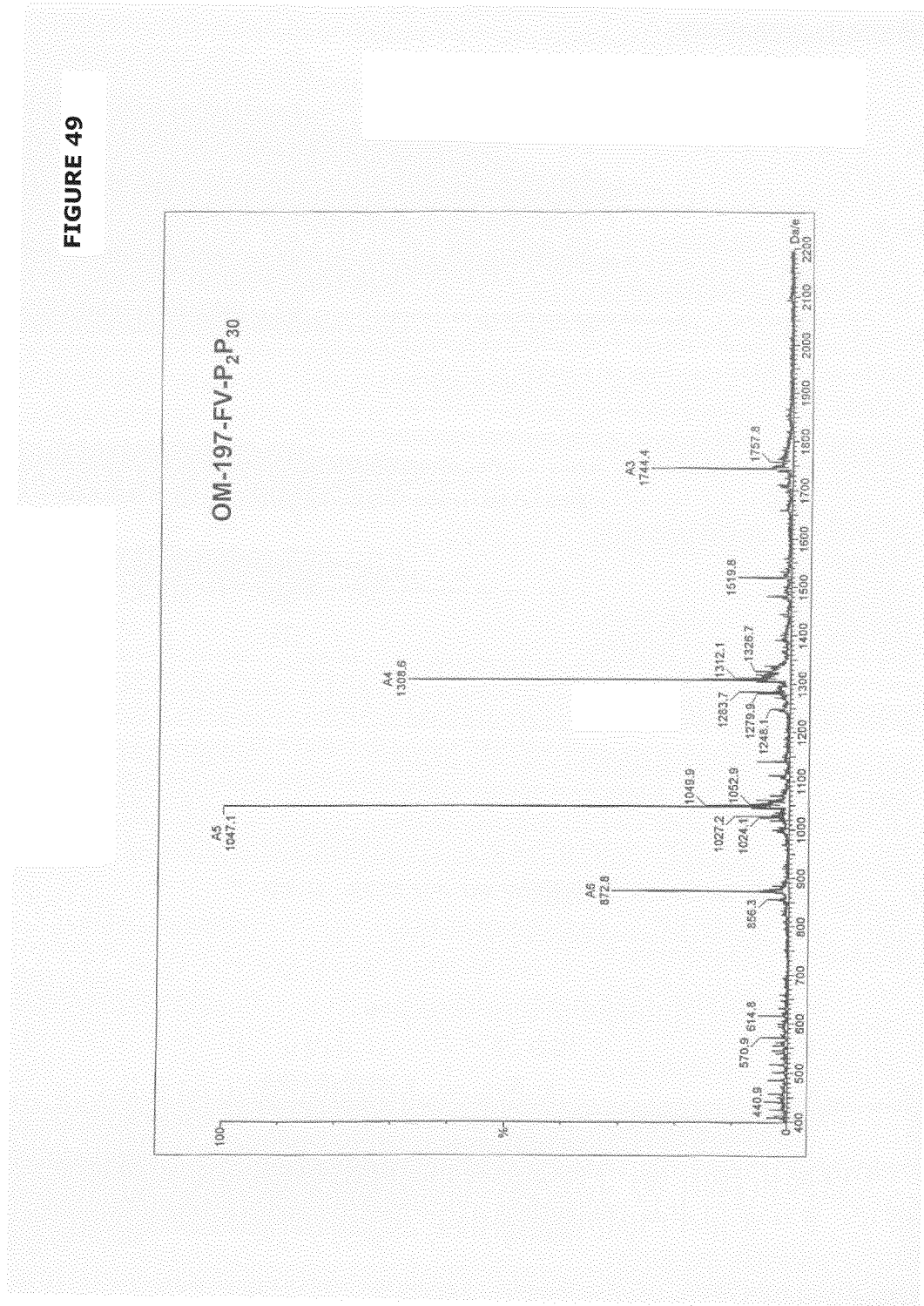
FIG. 49 shows the ionic cloud of LC/ES mass spectra analysis of OM-197-FV-P$_2$P$_{30}$.

The $P_2P_{30}$ (SEQ ID NO: 3) peptide displays five potential conjugation sites (terminal amine+four lysine residues) and a mass of 4200 amu. Hence, five equivalents of OM-197-FV7 were used up. Reaction conditions specified above were observed. After dialysis in $H_2O$ (3.5 kDa dialysis cassette, Slide-A-lyzer, Pierce), the mass spectra of the obtained conjugates were measured by an LC/ES-MS technique and compared to spectra recorded for the free peptide $P_2P_{30}$ (SEQ ID NO: 3) which displays polyvalent ions at an m/z ratio of 840.9 (A5) 1050.9 (A4) and 1401.0 (A3) which form the surrounding ionic charge (FIG. 48) of a peptide having a molecular mass of 4200 amu. The ES/MS spectrum of the OM-197-FV-$P_2$-$P_{30}$ (SEQ ID NO: 3) monoconjugate displays polyvalent ions at an m/z ratio of 872.8 (A6) 1047.1 (A5), 1308.6 (A4) and 1744.4 (A3) (FIG. 49) which constitute the surrounding ionic charges of the conjugate having a molecular mass of 5230 amu, which corresponds to the grafting of an OM-197-FV molecule on a $P_2P_{30}$ peptide (SEQ ID NO: 3) molecule by reductive amination.

Figure 50:
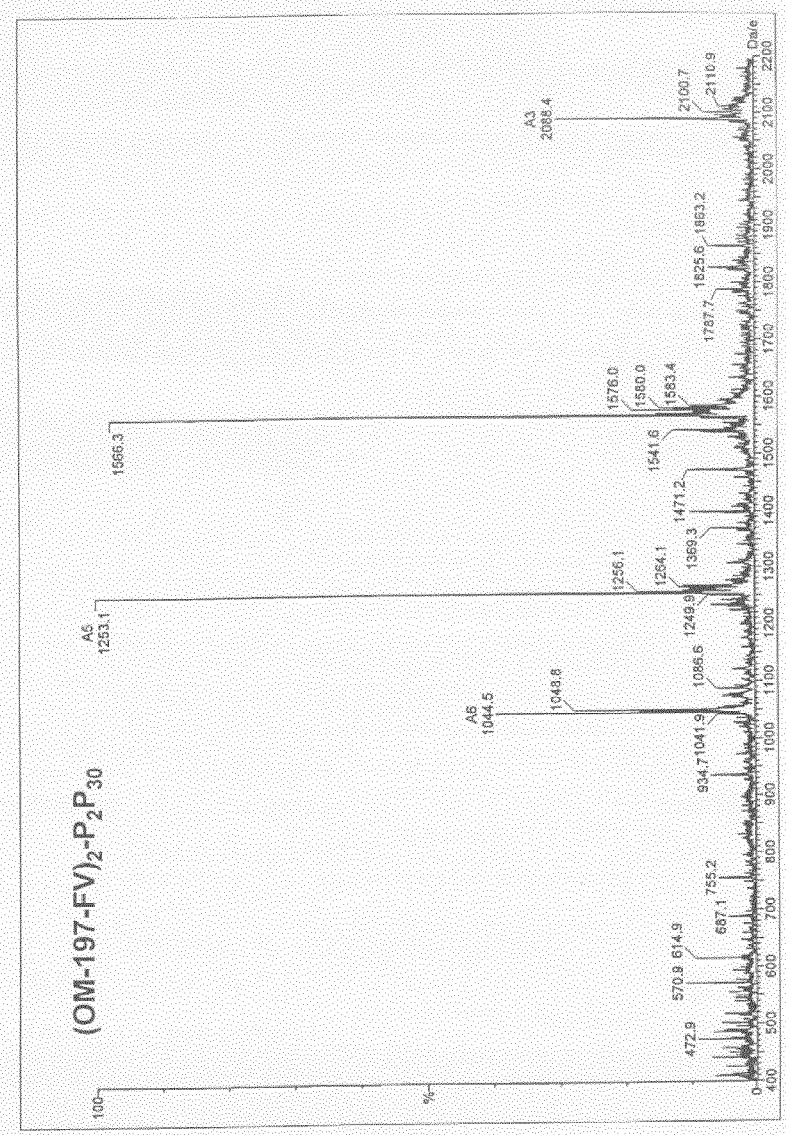
FIG. 50 shows to the mass spectrum analysis of the biconjugate (OM-197-FV)$_2$-P$_2$P$_{30}$.

Likewise, the mass spectrum obtained for the (OM-197-FV)$_2$-$P_2P_{30}$ (SEQ ID NO: 3) biconjugate ascertains the presence of two molecules of OM-197-FV per peptide unit. The surrounding ionic charge is formed by ions at an m/z ratio of 1044.5 (A6), 1253.1 (A5), 1566.3 (A4) and 2088.4 (A3) (FIG. 50), which after transform analysis verify with the expected molecular mass of the biconjugate (6261 amu).

Example 3.4

(NANP)$_3$CS.T3 Peptide Conjugates

A similar coupling procedure can be conducted for the (NANP)$_3$CS.T3 peptide (SEQ ID NO: 4) (TNO, MW: 3527 amu) having the following sequence:

NANPNANPNANPDIEKKIAKMEKASSVFNWNS (SEQ ID NO: 4)

Following $H_2O$ dialysis, the observed ions on the ES/MS spectra reflect a molecular mass of 4557 and 5587 amu, corresponding to the expected values for the mono- and biconjugate compounds.

Example 3.5

MR99B Peptide Conjugates

OM-197-MC-FV6 compound obtained through the reaction scheme shown on FIG. 8, can be coupled, for instance, to a peptide of pharmaceutical interest such as PyCS 245-253 (SEQ ID NO: 1). This peptide corresponding to the T-epitope portion of *Plasmodium yoelli* [Franke, E. D., et al., 1997, *J. Immunol.*, 159: 3424-3433] has the following sequence: SYVPSAEQI (PyCS 245-253) (SEQ ID NO: 1).

In order not to modify the T-epitope portion during the coupling step, amino acids SER were added to form a peptide referred to as MR99B (SEQ ID NO: 5), of the following sequence: SERSYVPSAEQI (MR99B) (SEQ ID NO: 5)

Figure 51:
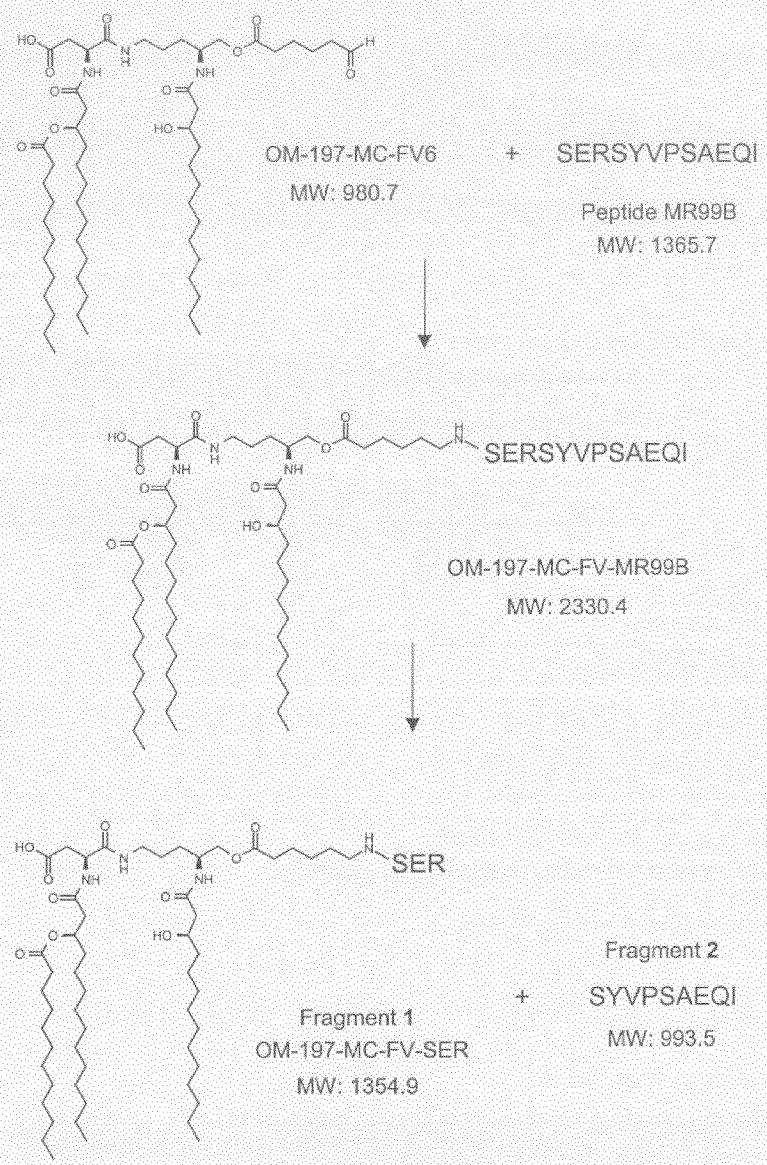
FIG. 51 shows the synthesis of the peptide conjugate OM-197-MC-FV6 with T-epitope portion of *Plasmodium yoelli*.
Figure 52:
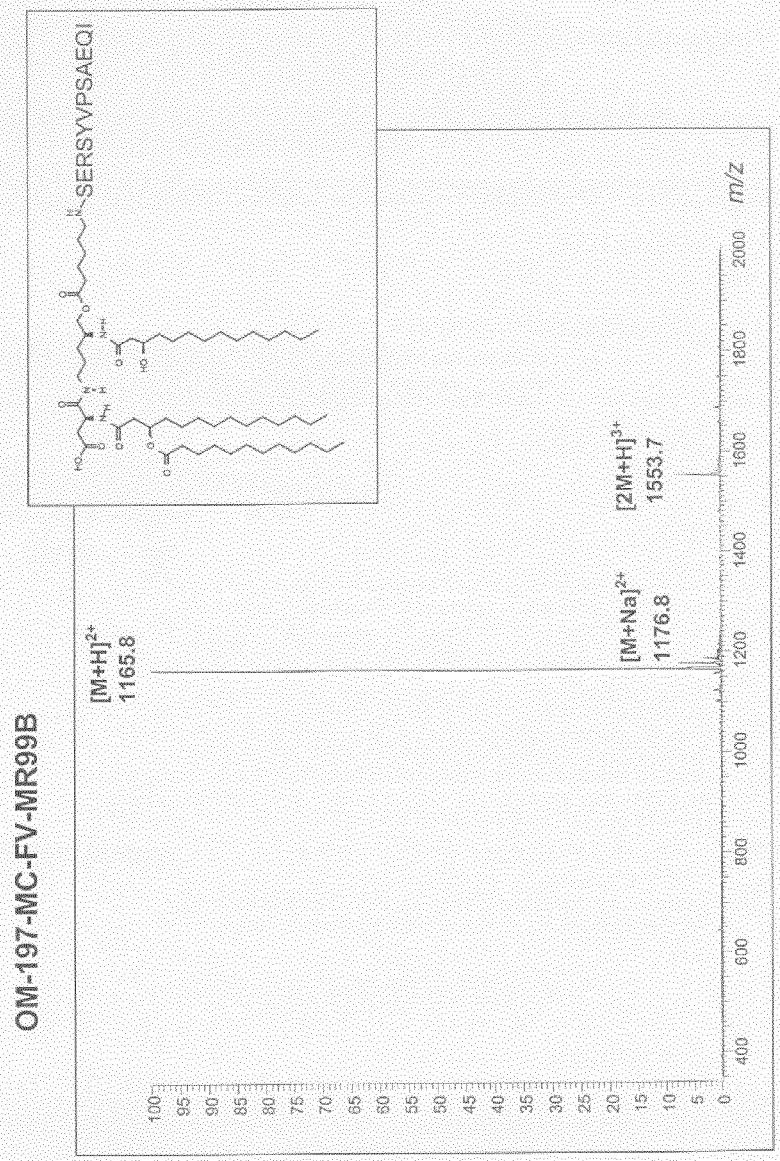
FIG. 52 corresponds to a mass spectrum analysis of the conjugate OM-197-MC-FV-MR99B.
Figure 53:
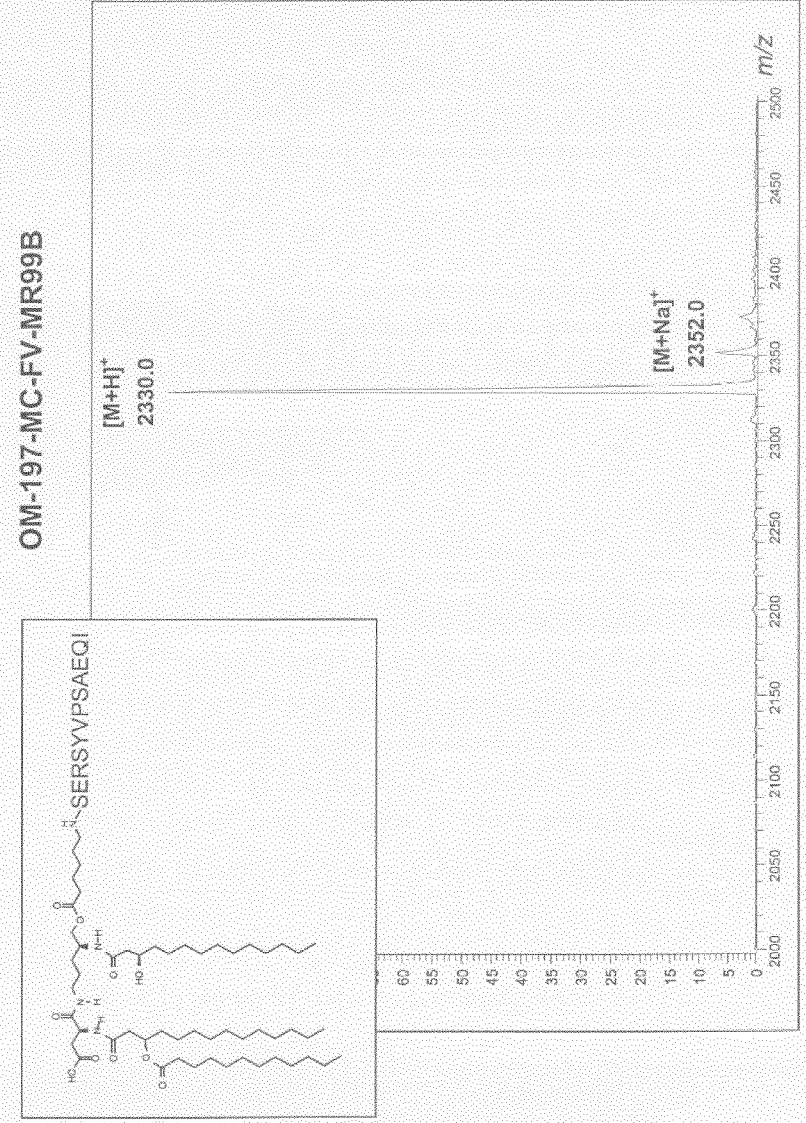
FIG. 53 corresponds to the mass spectrum analysis (transformed spectrum) of the conjugate OM-197-MC-FV-MR99B.

Since the present sequence is lysine-free, MR99B(SEQ ID NO: 5) peptide has a unique reductive amination coupling site (at the terminal amine). Thus, 2 mg of purified OM-197-MC-FV6 (2.04 µmol., 1.4 eq.) were added to a solution of 2 mg MR99B (SEQ ID NO: 5) (1.47 µmol., 1 eq.) dissolved into 1 ml of a 1:1 $H_2O$-isopropanol mixture. The solution is stirred for 30 minutes at room temperature, then the reduction step is carried out by adding 29.4 µml. (1M) NaBH$_3$CN (29.4 µmol., 2 eq.) The solution is stirred for two hours at room temperature. LC/ES-MS analysis of the reaction mixture provides evidence of the formation of an OM-197-MC-FV-MR99B (SEQ ID NO: 5) conjugate of an expected molecular mass (2330.4 amu, FIG. 51), as shown by spectra depicted on FIGS. 52 (surrounding ionic charge) and 53 (transformed spectrum).

Purification of OM-197-MC-FV-MR99B (SEQ ID NO: 5) conjugate is carried out by semi-preparative liquid chromatography on a C4 phase according to the following conditions.

Column: Vydac C4, 250×10 mm, 5 µm, 300 Å (Vydac)
Mobile phase:
A: (9:1, v/v) water-MeCN, 0.05% TFA
B: (9:1, v/v) isopropanol-water, 0.05% TFA
Flow rate: 2.5 ml/min.
Elution: Isocratic elution: 65% B, 20 minutes
Washing: 100% B, 10 minutes
Detection: UV, 210 nm
System: HPLC 1050

In order to demonstrate that the peptide antigenic portion is not altered by conjugation, a trypsin digestion of the OM-197-MC-FV-MR99B (SEQ ID NO: 5) is conducted. 0.5 mg of the conjugate is incubated for 24 hours with 83 µg of trypsin (Roche #109819) (substrate-enzyme ratio (6:1)) in 1 ml of 50 mM Tris-HCl buffer, 2 mM CaCl2, Ph 8.

Figure 54:
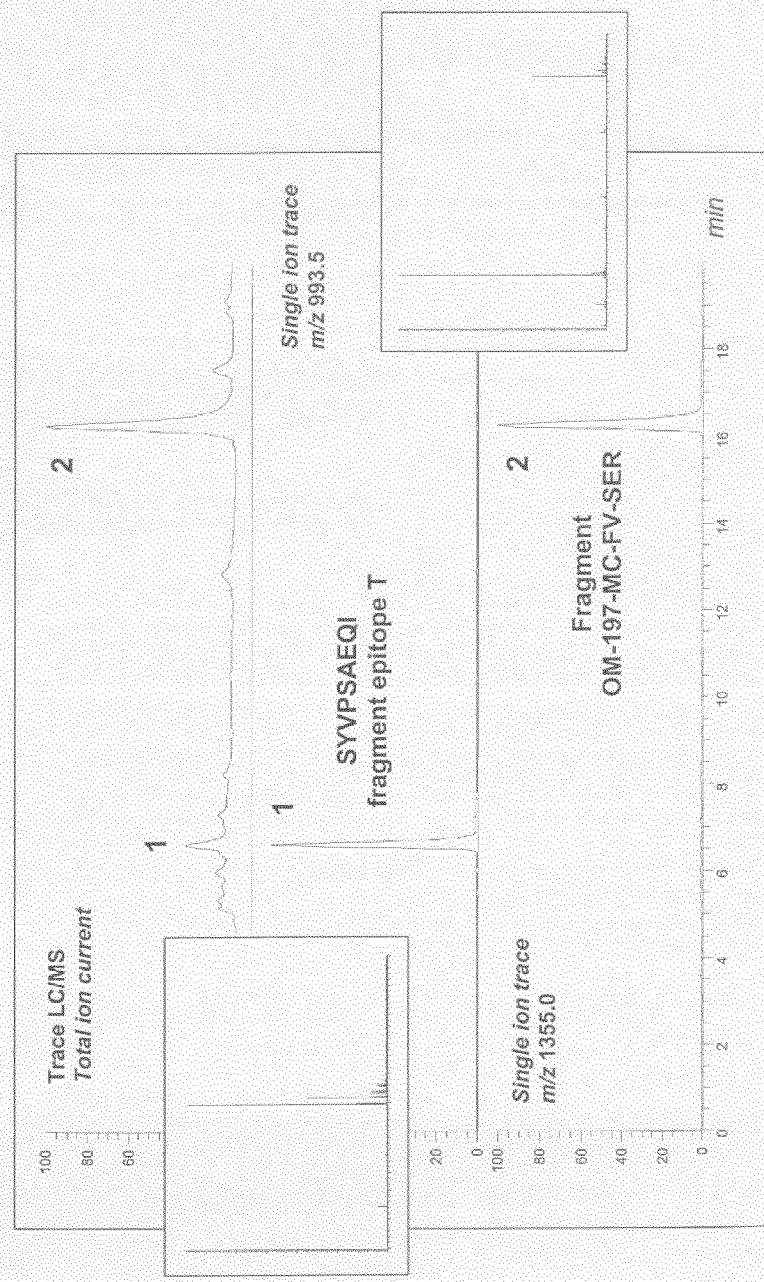
FIG. 54 corresponds to the LC/ES-MS analysis following the trypsic digestion of OM-197-MC-FV-MR99B.
Figure 55:
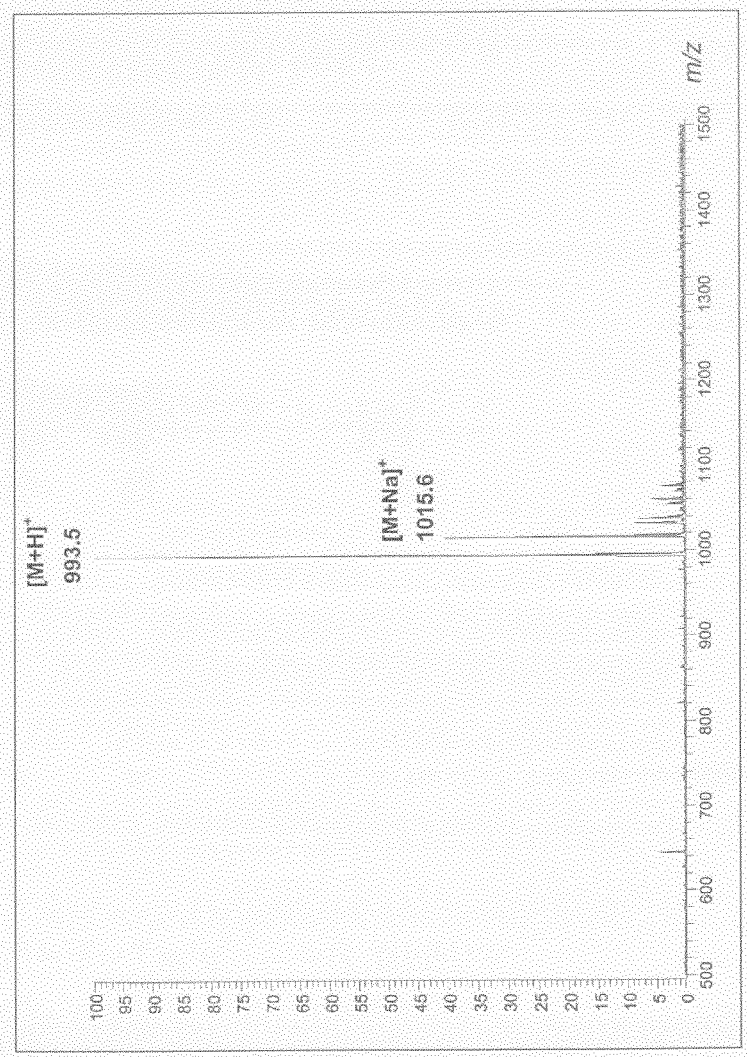
FIG. 55 corresponds to the LC/ES-MS analysis following the trypsic digestion of OM-197-MC-FV-MR99B.
Figure 56:
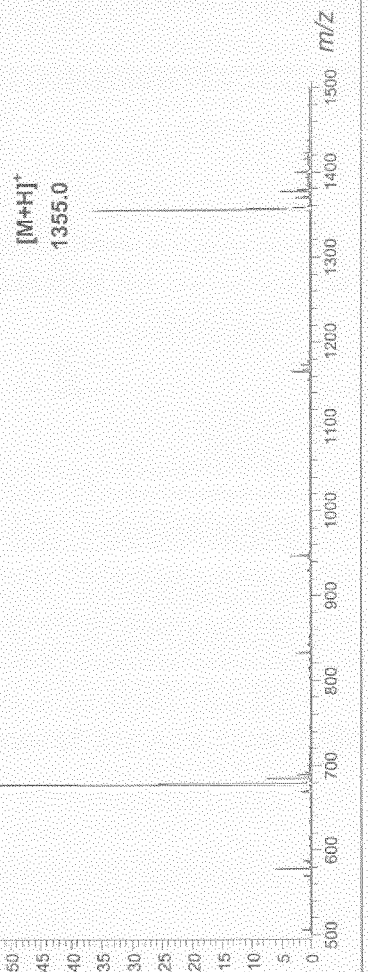
FIG. 56 corresponds to a mass spectrum analysis of OM-197-MC-FV-SER.

LC/ES-MS analysis following this reaction is shown on FIG. 54 and ascertains the presence of two fragments with the corresponding ES-MS spectra being shown on FIGS. 55 and 56. The first fragment clearly demonstrates ions at an m/z ration of 993.5 ([M+H]$^+$) and 1015.6 ([M+Na]$^+$) and corresponds to the CSPy 145-253 peptide (FIG. 55). The second fragment demonstrates ions at an m/z ration of 678.1 ([M+H]$^+$) and 1355.0 ([M+H]$^+$), demonstrating the presence of a OM-FV-SER type structure (FIG. 56). A third peak is also visible. This peak corresponds to both SYVPS and EQI fragments (co-eluents according to chromatography separation conditions herein used). This reaction is also observed when MR99B (SEQ ID NO: 5) is digested alone. These results clearly demonstrate that conjugation does not alter the T-epitope portion of the MR99B peptide (SEQ ID NO: 5), as schematically depicted on FIG. 51.

Example 3.6

MR99A Peptide Conjugates

In order to increase conjugation rate of OM-197-MR-FV to a given peptide and increase the adjuvant/antigen ration without altering the T-epitope portion, KGG type sequences can be grafted on the peptide to be grafted. Thus, a KGGKGGK (SEQ ID NO: 14) sequence can be, for example, grafted to MR99B (SEQ ID NO: 5) peptide, to yield the MR99A peptide as follows: KGGKGGKSERSYVVWPSAEQ (MR99A) (SEQ ID NO: 6)

Figure 57:
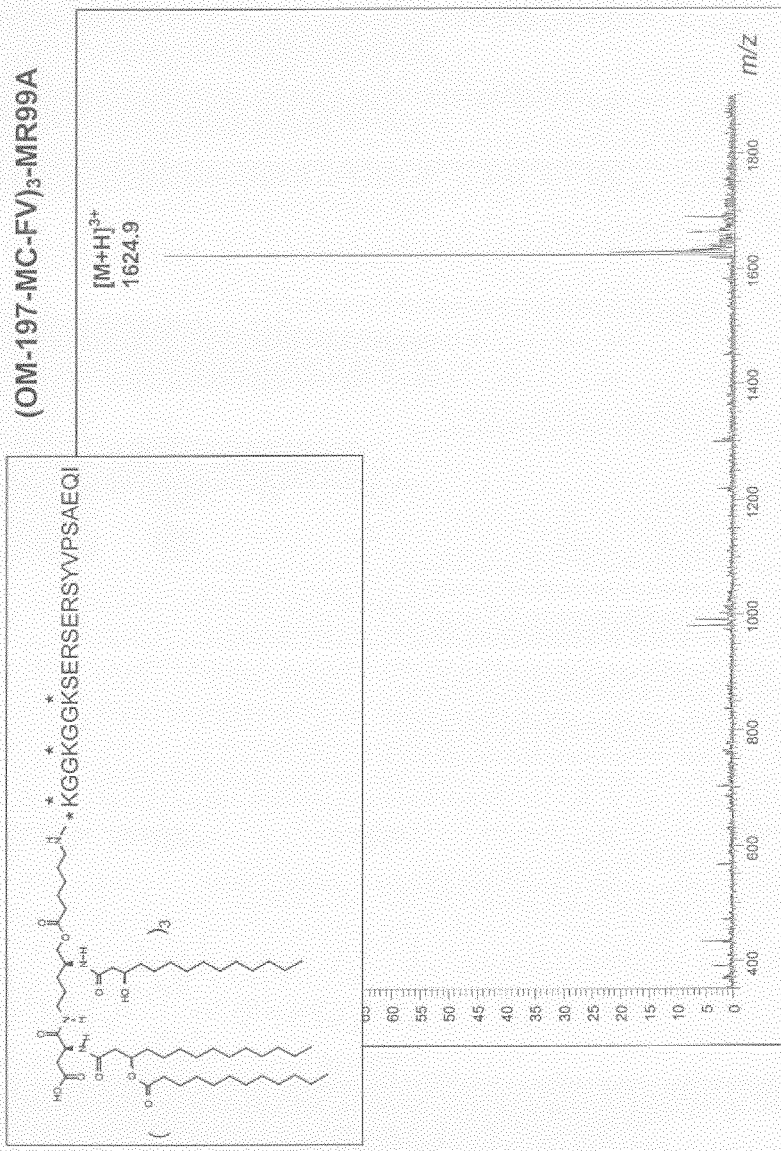
FIG. 57 corresponds to the mass spectra analysis (surrounding ionic charge) of the tri-conjugate (OM-197-MC-FV)$_3$-MR99A.
Figure 58:
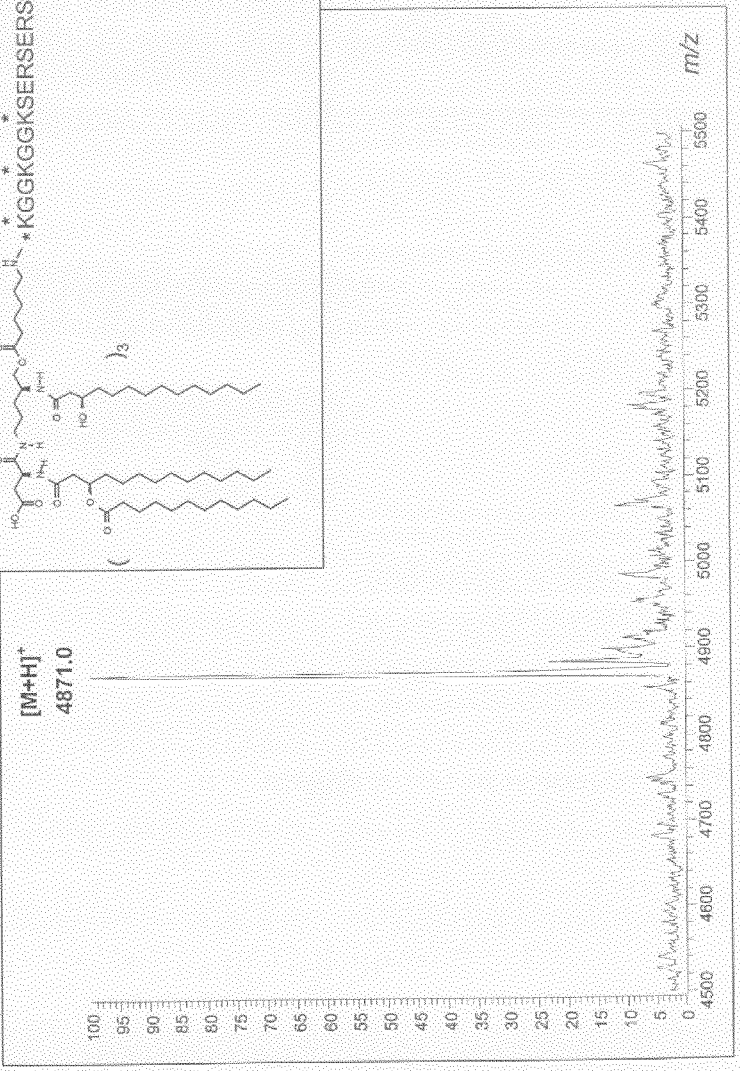
FIG. 58 corresponds to the mass spectrum analysis (transformed spectrum) of the tri-conjugate (OM-197-MC-FV)$_3$-MR99A.
Figure 59:
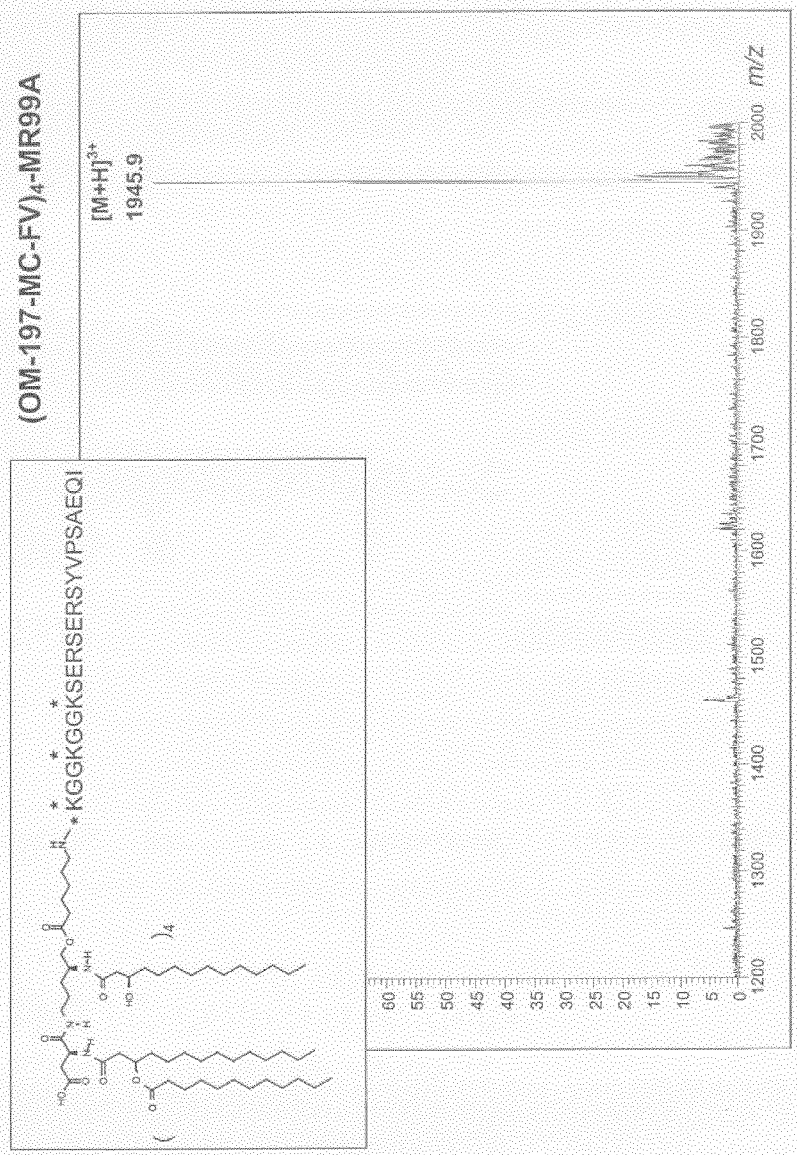
FIG. 59 corresponds to the mass spectrum analysis (ionic cloud) of the tetraconjugate (OM-197-MC-FV)$_4$-MR99A.
Figure 60:
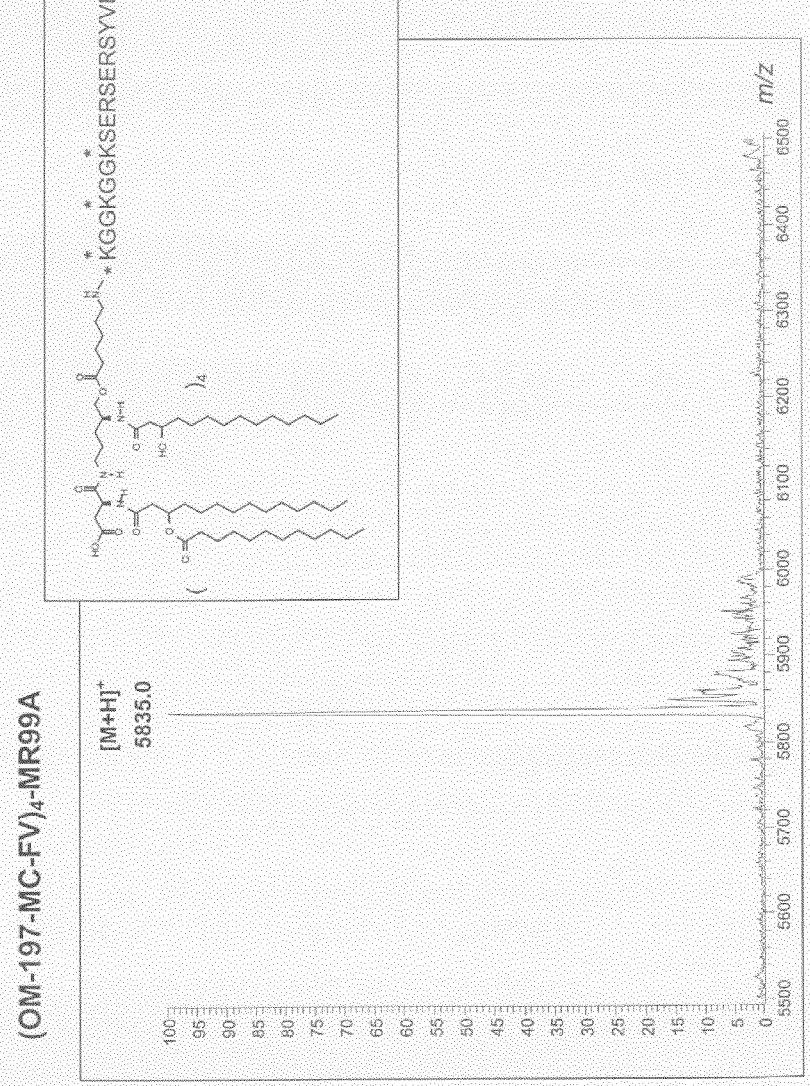
FIG. 60 corresponds to the mass spectrum analysis (transformed spectrum) of the tetraconjugate (OM-197-MC-FV)$_4$-MR99A.
Figure 61:
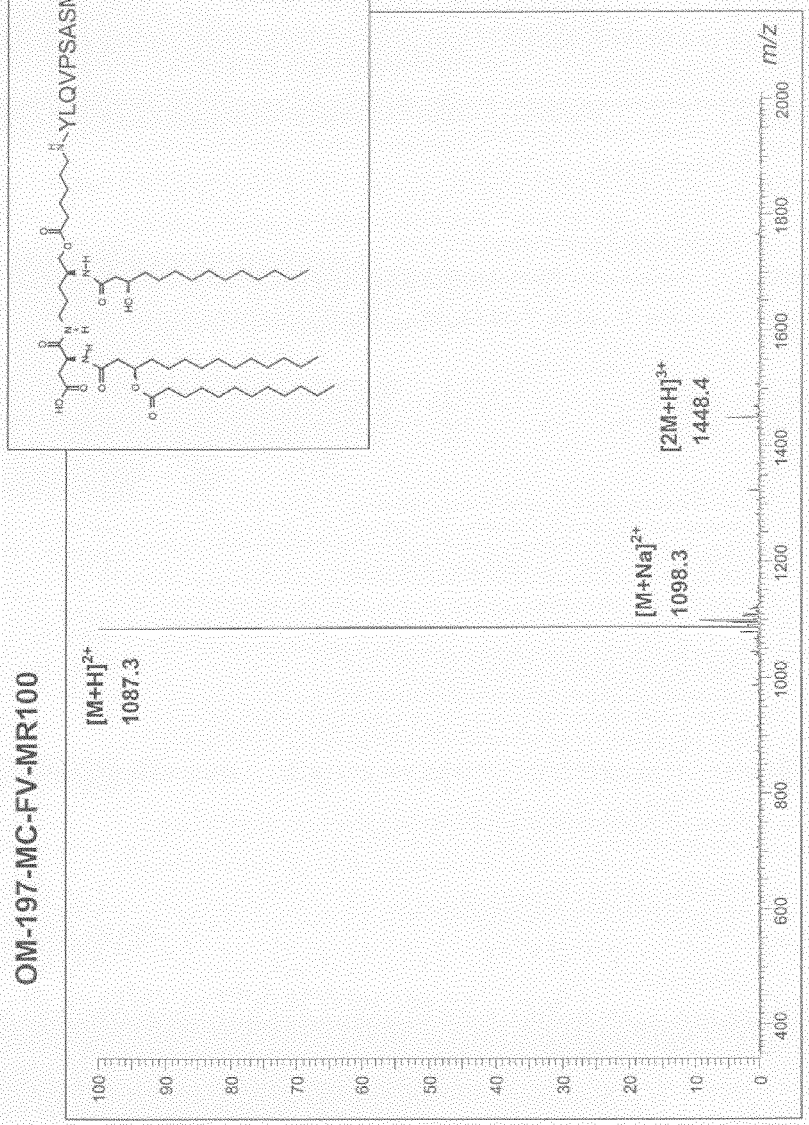
FIG. 61 corresponds to a mass spectrum analysis of the conjugate OM-197-MC-FV-MR100.
Figure 62:
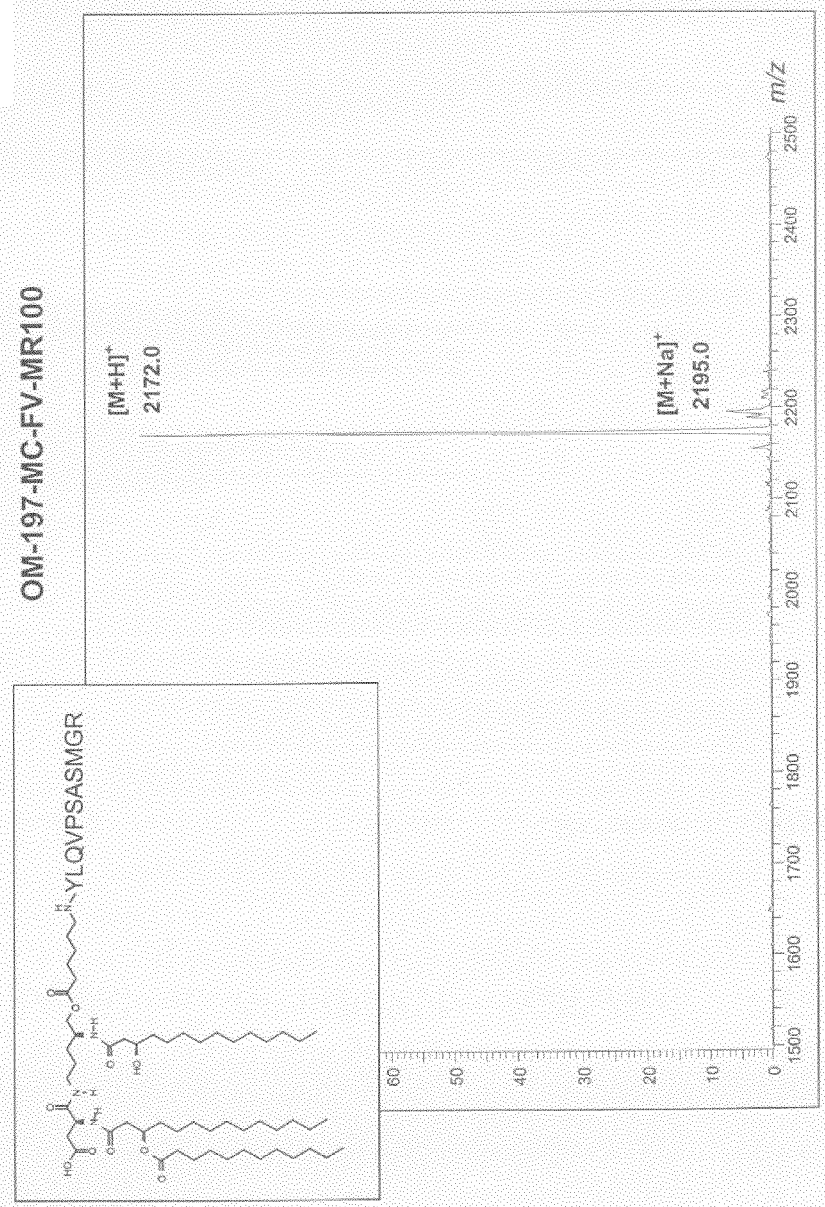
FIG. 62 corresponds to a mass spectrum analysis of the conjugate OM-197-MC-FV-MR100.
Figure 63:
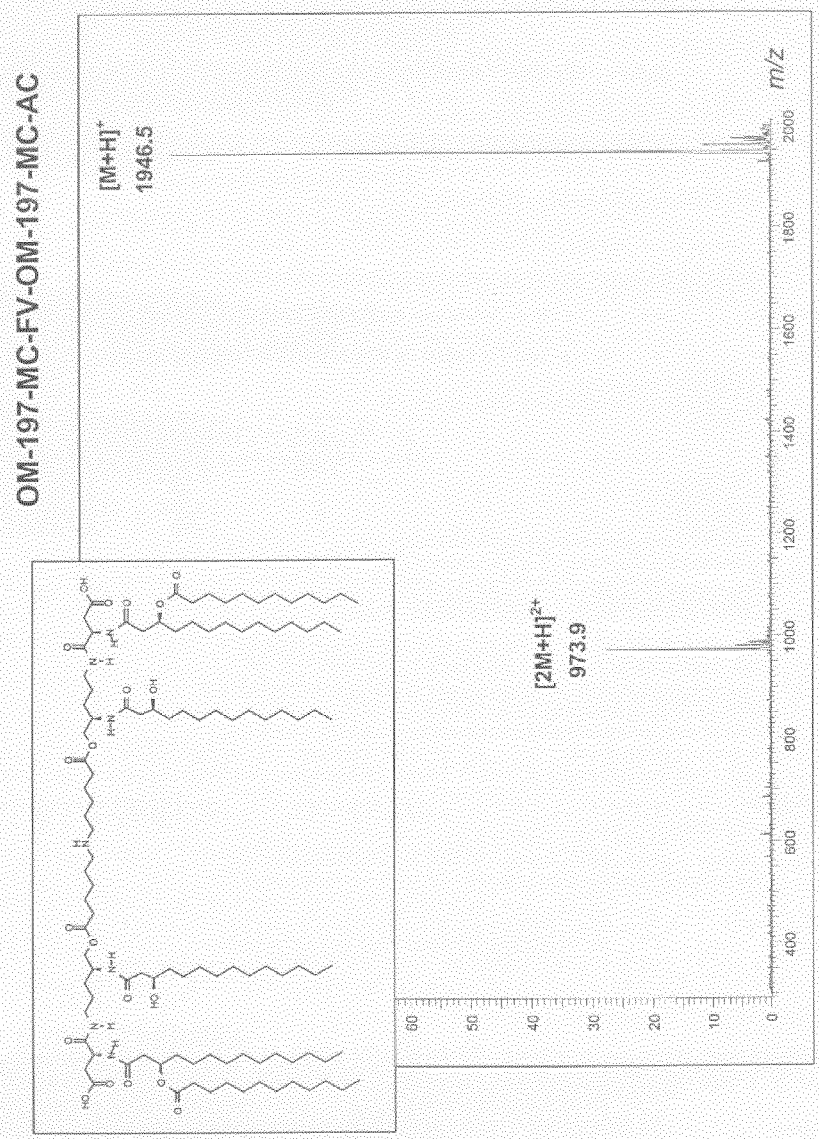
FIG. 63 corresponds to a mass spectrum analysis of the dimeric conjugate OM-197-MC-FV-OM-197-MC-AC.
Figure 64:
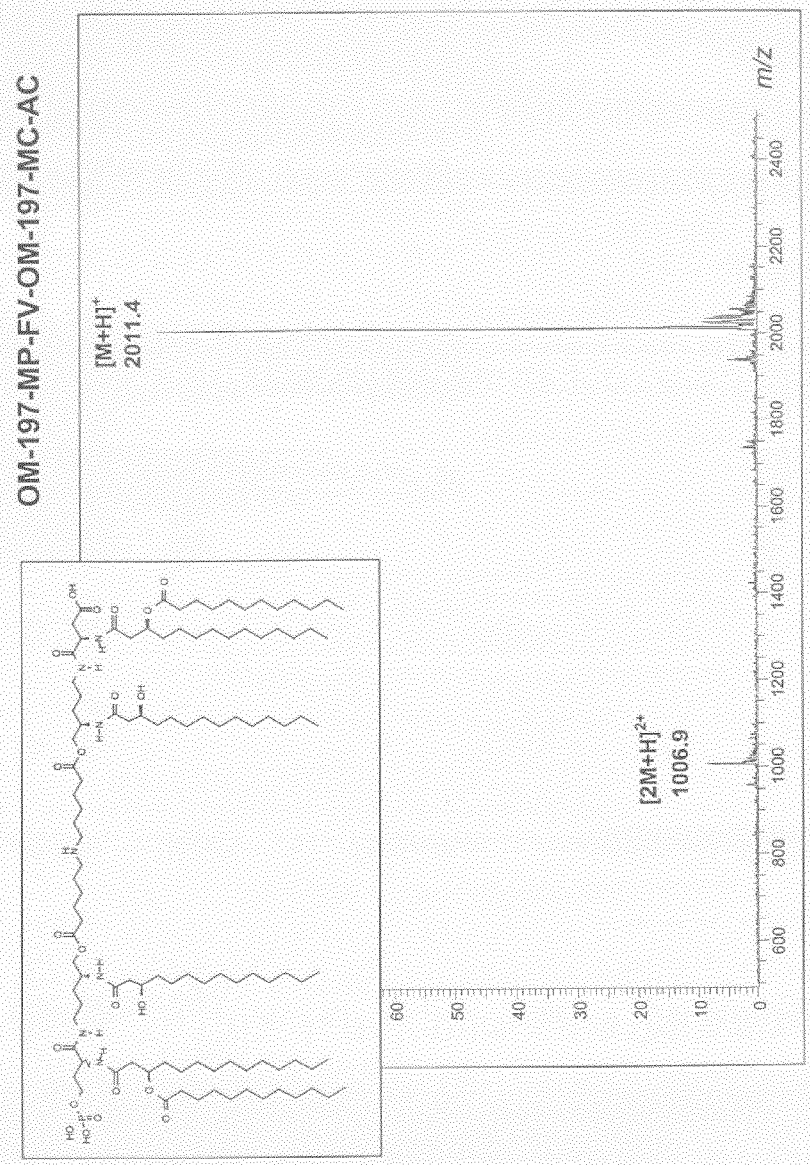
FIG. 64 corresponds to a mass spectrum analysis of the dimeric conjugate OM-197-MC-FV-OM-197-MC-AC.

Accordingly, this peptide has four potential conjugation sites for a reductive amination reaction (three lysines and the terminal amine). Thus, 12 mg of purified OM-197-MC-FV6 (12.2 µmol., 12 eq.) are added to a solution of 2 mg of MR99A (SEQ ID NO: 6) dissolved into 1 ml of 1:1 $H_2O$-isopropanol. The solution is stirred for 30 minutes at room temperature, then a reductive step is conducted by adding 242 µl of 1M $NaBH_3CN$ (244 µmol., 242 eq.). The solution is stirred for 2 hours at room temperature. LC/ES-MS analysis of the reaction mixture demonstrates different peaks corresponding to variable conjugation rates of OM-197-MC-FV molecules to the MR99A peptide (SEQ ID NO: 6). Mass spectra corresponding to -OM-197-MC-FV)$_3$-MR99A (SEQ ID NO: 6) triconjugate (4870 amu) are shown on FIGS. 57 (ionic cloud) and 58 (transformed spectrum) whereas spectra shown on FIGS. 59 (ionic cloud) and 60 (transformed spectrum) demonstrate formation of (OM-197-MC-FV) 4-MR99A (SEQ ID NO: 6) tetra conjugate (5834 amu). Ions corresponding to a pentaconjuguate form are equally observed. This result shows that lysine, under certain reaction conditions (excess OM-197-MC-FV), is not the only reactive amino acid in a reductive amination reaction.

Purification of the tri and tetra-conjugates (OM-197-MC-FV)$_{3,4}$-MR99A (SEQ ID NO: 6) is conducted by semi-preparative liquid chromatography on a C4 phase according to the following conditions:

Column: Vydac C4, 250×10 mm, 5 µm, 300 Å (Vydac)
Mobile phase:
A: (9:1, v/v) water-MeCN, 0.05% TFA
B: (9:1, v/v) isopropanol-water, 0.05% TFA
Flow rate: 2.5 ml/min.
Elution: Isocratic elution: 65% B, 20 minutes
Washing: 100% B, 10 minutes
Detection: UV, 210 nm
System: HPLC 1050

As for an OM-197MC-FV-MR99B (SEQ ID NO: 5) monoconjugate, (OM-197-MC-FV)n-MR99A (SEQ ID NO: 6) polyconjugates are submitted to a trypsin digestion to determine whether or not the antigenic portion (CSPy 245-253) is altered by conjugation. 1 mg of the polyconjugate is incubated for 24 hours at 25° C. with 166 µg of trypsin (Roche, #109819) (substrate-enzyme ratio (6:1)) in 1 ml of 50 mM Tris HCl buffer, 2 mM CaCl, pH 8.

LC/ES-MS analysis carried out after the reaction ascertains the presence of a great number of cleavage products at variable locations of the MR99A peptide (SEQ ID NO: 6). Among such products, a fragment at an m/z ratio of 993.5 ([M+H]$^+$) and 1015.6 ([M+Na]$^+$) is noted which corresponds to a CSPy 245-253 peptide. Presence of this peptide is a proof of the integrity of the T-epitope portion of the peptide even after a multiple conjugation reaction. Two fragments, detected through their triple charge ions at an m/z ratio of 1621.4 ([M+H]$^+$) and 1942.8 ([M+H]$^+$) are of special interest. In fact, such fragments correspond to fragments (OM-197-MC-FV)$_4$-KGGKGGKSER (SEQUENCE 7) and (OM-197-MC-FV)$_5$-KGGKGGKSER (SEQ ID NO: 7), respectively. Detection thereof shows that different molecules of OM-197-MC-FV are actually grafted onto the sequence added to CSPy 245-253 even in case amino acids other than lysine have reacted in the reductive amination step. It should be noted that presence of several sterically relevant molecules of OM-197-MC-FV on a peptide does not affect protease activity as in case of trypsin. This result is of remarkable interest when considering conjugation to a prodrug where the active ingredient can be released after selective cleavage of a cleavable bond, for example.

Example 3.7

Ag85c Peptide Conjugates

Structures bearing an accessory formylvaleryl type side chain spacer can be conjugated to a great number of peptides of pharmaceutical interest. Mention is made, for example, of grafting of OM-197-MC-FV molecules by reductive amination reaction to the terminal amine of synthetic peptides having sequences derived from an antigenic protein sequence of *Mycobacterium tuberculosis*. Peptides initially used were as follows

| | |
|---|---|
| MR 100 YLQVPSASMGR (SEQ ID NO: 8) | 1208.4 amu |
| MR 101 MVQIRPRLVANNTRIWVYC (SEQ ID NO: 9) | 2176.6 amu |
| LR72 PYAASLSGFLNPSEGWWPTLIGLAM (SEQ ID NO: ID10) | 2676.1 amu |

Following reaction with OM-197-MC-FV, the following conjugates were detected by LC/ES-MS analysis: for example, OM-197-FV-MR100 (SEQ ID NO: 8) which displays a molecular weight of 2171.0 amu (FIGS. 61 and 62). Alternatively, OM-197-MC-FV-MR101 (SEQ ID NO: 9) of 3140.0 amu and OM-197-MC-FV-LR72 (SEQ ID NO: 10) of 3643.0 amu were also obtained.

Example 3.8

Dimers Having an OM-197-Type Structure

The reductive amination method can be equally applied to the synthesis of dimers having an OM-197-type structure.

For example, a dimer can be formed starting from two compounds bearing an accessory functional side chain spacer such as OM-197-MC-FV and OM-197-MC-AC. Thus, 1 mg of purified OM-197-MC-FV6 (0.98 μmol., 1 eq.) is added to a solution of 1 mg of OM-197-MC-AC (0.98 μmol, 1 eq.) dissolved into 1 ml of (1:9) $H_2O$-isopropanol. The solution is stirred for 1 hour at room temperature, then the reductive step is carried out by adding 19.6 μl of 1M $NaBH_3CN$ (19.6 μmol., 20 eq.). The solution is thereafter stirred for 12 hours at room temperature. LC/ES-MS analysis of the reaction medium demonstrates formation of an OM-197-MC-FV-OM-197-MC-AC dimer of the expected molecular weight (1945.5 amu) as evidenced by the spectrum shown on FIG. 63. This molecule hence shows two carboxylic acid functional groups at the end portions of the main chain bearing acyl chains.

In structure shown on FIG. 63, one of the carboxylic groups can be replaced, for instance, by a phosphoryl group by conducting the above synthesis process starting from an OM-197-MP-FV or OM-197-MP-AC type compound. By performing a reductive amination similar to the one described above between two compounds bearing a functional side chain spacer (OM-197-MP-FV and OM-197-MC-AC), an OM-197-MP-FV-OM-197-MC-AC dimer can be obtained. The ES/MS spectrum depicted on FIG. 64 confirms the expected molecular mass for this compound. (2011.9 amu).

Example 3.9

Conjugation of Compounds Bearing an Amino-Type Accessory Side Chain Spacer

Compounds bearing an amino type accessory side chain spacer can also be conjugated to peptide antigens through a reductive amination reaction. It is further possible to make use of the presence of a terminal serine, for example, in the sequence of peptides to be conjugated. In a first step, a periodic oxidation reaction is conducted upon the peptide, leading to the formation of a highly reactive glyoxylyl group (—O—CHO). This group can then react through a reductive amination reaction with a primary amine born on the accessory functional side chain spacer of OM-197 type compounds.

Figure 65:
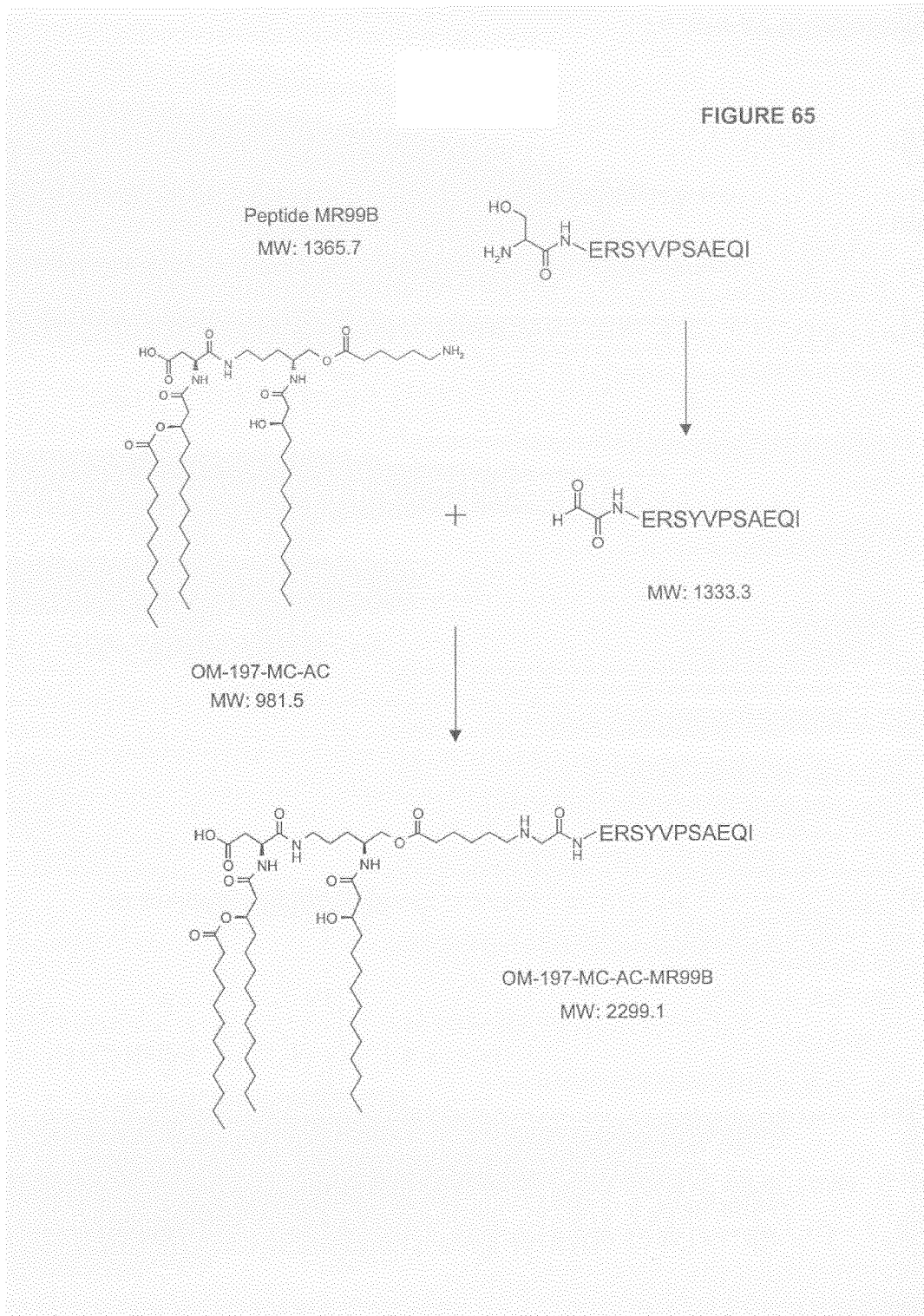
FIG. 65 shows the synthesis of OM-197-MC-AC-MR99B.

For example, the synthetic peptide MR99B (SEQ ID NO: 5) can be conjugated to an OM-197-MC-AC compound, as shown by the synthesis scheme of FIG. 65. To this end, 147 µl of 0.1 M NaIO$_4$ (14.6 µmol., 20 eq.) are added to a solution of 1 mg of MR99B peptide (SEQ ID NO: 5) (0.73 µmol., 1 eq.) dissolved into 1 ml of water. The solution is stirred for 2 hours at RT. The aldehyde compound thus formed is purified on a C18 phase and recovered into 1 ml of a (1:1) isopropanol-water mixture. 0.72 mg of the OM-197-MC-AC compound (0.73 µmol., 1 eq.) are then added, as well as 1 ml of a 0.2 M borate buffer, pH 9.2. After stirring at room temperature for 30 minutes, the reduction step is carried out by adding 14.6 µl of 1 M NaBH$_3$CN (14.6 µmol., 20 eq.). The solution is stirred for 24 hours at room temperature.

Figure 66:
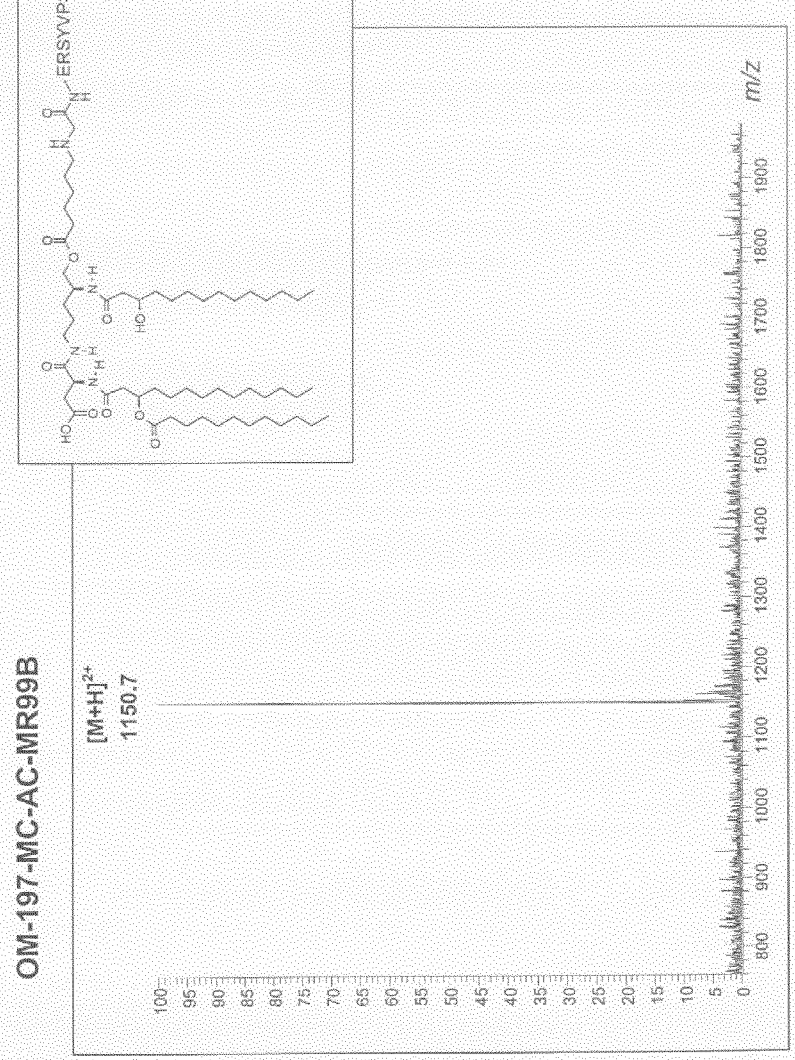
FIG. 66 corresponds to a mass spectrum analysis of the conjugate OM-197-MC-AC-MR99B.
Figure 67:
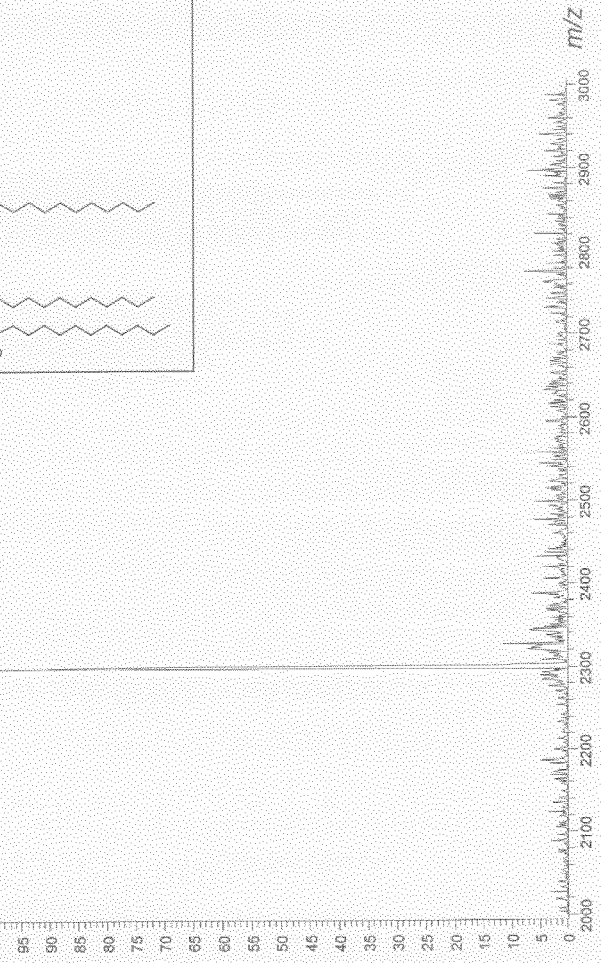
FIG. 67 corresponds to a mass spectrum analysis (transformed spectrum) of the conjugate OM-197-MC-AC-MR99B.

LC/ES-MS analysis of the reaction mixture demonstrates the formation of an OM-197-MC-AC-MR99B (SEQ ID NO: 5) conjugate of the expected molecular mass (2299.1 amu, FIG. 65) as evidenced by spectra depicted on FIGS. 66 (ionic cloud) and 67 (transformed spectrum).

Other compounds bearing an amino-type accessory functional side chain spacer can be conjugated in a similar fashion. Mention is made, for example, of OM-197-MC-AP, OM-197-MP-AC, OM-212-AH1, OM-197-MC-gly, OM-197-MC-Lys, OM-197-Lys-AC or OM-197-Asp-AC.

Example 3.10

Ovalbumin Conjugates

Proteins, such as ovalbumin for instance, are particularly adapted to reductive amination coupling. The great number of lysine residues contained in the sequence (20 lysine residues for ovalbumin) are all potential conjugation sites for the dipeptide-like compounds bearing an accessory functional side chain spacer with an aldehyde functional group. By varying the stoichiometric ratio of the reductive amination reaction (acyl-dipeptide-like compound/protein), conjugation to a variable extent can be achieved.

1 mg of purified OM-197-FV7 (0.928 µmol., 10 eq.) was added to a solution of 4 mg of ovalbumin (0.09 µmol., 1 eq.) dissolved in 5 ml of H$_2$O. The solution was stirred for 30 minutes at room temperature, before proceeding with a reduction step by adding 46 µl of 1M NaBH$_3$CN (2.89 mg, 50 eq.) The solution was stirred for two hours at room temperature. The reaction mixture was subsequently dialyzed against H$_2$O for a period of 24 hours (3.5 kDa dialysis cassette, Slide-A-Lyzer, Pierce).

Figure 68:
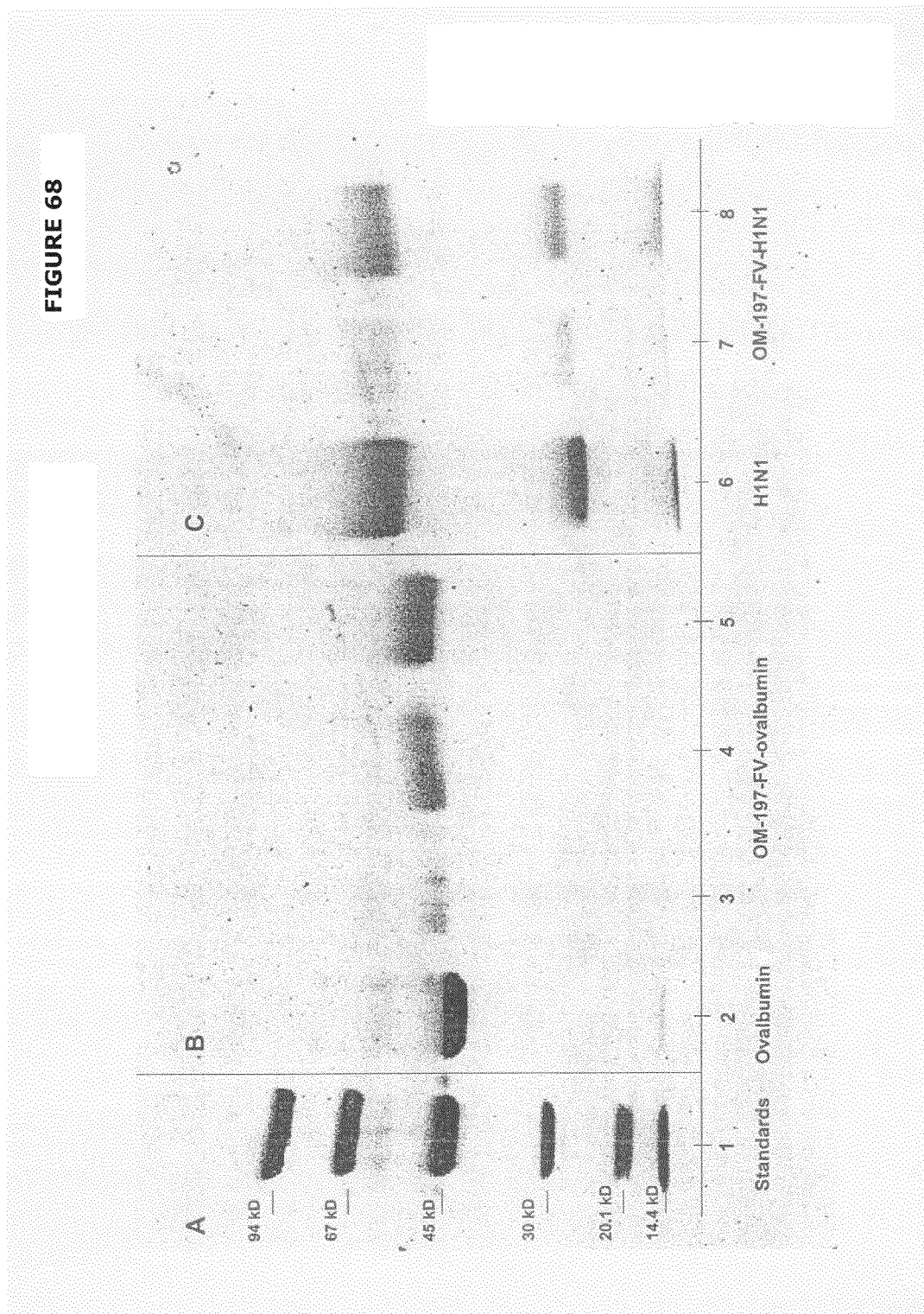
FIG. 68 is a polyacrylamide gel showing the SDS-PAGE analysis of the conjugate OM-197-FV-ovalbumine and of the conjugate OM-197-FV-H1N1.

Owing to its size and its inherent heterogenous character, ovalbumin raises a great number of analytical problems. As a result, characterization of an OM-1976FV-ovalbumin conjugate by mass spectrometry may prove a very difficult task. To show that a conjugation reaction did occur, SDS-PAGE analysis were conducted on different batches of OM-197-FV-ovalbumin conjugates. As is apparent from the gel shown on FIG. 68 (B) (4-20% polyacrylamide gel gradient), a mass exceeding the initial mass of ovalbumin by about 3000 amu (lane 2) is observed for OM-1976FV-ovalbumin conjugates (lanes 3, 4 and 5). This mass difference suggests that several molecules of OM-197-FV are present on each molecule of ovalbumin. LC/UV analysis conducted on a C$_4$ phase confirm this result. As a matter of fact, in these conditions, the initially used ovalbumin clearly appears at RT=11.3 min., whereas following the conjugation reaction, the peak corresponding to initially used ovalbumin is no longer visible, a fact which shows that reaction with ovalbumin was stoichiometric. The OM-197-FV-ovalbumin conjugate is however not eluted. This chromatographic profile also indicates that more than one single OM-197-FV molecule is present on ovalbumin, thus preventing the elution of the conjugate in such conditions.

Example 3.11

3.6. H1N1 Hemagglutinin Conjugates

H1N1 hemagglutinin protein also provides a fine example intended to illustrate coupling between OM-197 type molecules and a protein antigen.

1 mg of purified OM-197-FV7 (0.928 µmol., 15 eq.) is added to a solution of 5 mg of H1N1 (hemagglutinin A/Beijing 262/95, Solvay Duphar, Weesp, NL) (0.06 μmol., 1 eq.) dissolved in 8 ml of $H_2O$. The solution is stirred for 30 minutes at room temperature, then the reduction step is performed by adding 46 μl of 1 M $NaBH_3CN$ (2.89 mg, 50 eq.) The solution is stirred for 2 hours at room temperature. The reaction mixture is then dialyzed against $H_2O$ for 24 hours (3.5 kDa dialysis cassette).

The OM-197-FV-H1N1 conjugate is analyzed by SDS-PAGE in the same conditions used for OM-197-FV-ovalbumin conjugate (4-20% polyacrylamide gradient). The electrophoretic profiles obtained for the starting protein (lane 6) and the conjugate before and after dialysis (lanes 8 and 7, respectively) are shown on FIG. 68(C). H1N1 protein appears as three bands, two of which correspond to HA1 and HA2 subunits reported in the literature (Swiss-Prot, Swiss Institute of Biological Computer Science, Geneva). In case of OM-197-FV-H1N1 conjugates, a mass difference is observed for each band, demonstrating that coupling of OM-197-FV molecules with H1N1 protein was achieved.

Example 3.12

AZT Conjugates (FIG. 69)

To a solution of AZT (200 mg; 0.749 mmol.) in pyridine (4 ml), there are added in succession succinic anhydride (150 mg; 0.5 mmol.) and 4-dimethylaminopyridine (50 mg; 0.41 mmol.) After being allowed to stand for 12 hours at 50° C., methanol (2 ml) is added and the reaction medium is stirred for further 15 minutes at room temperature. The reaction medium is then concentrated and the product is purified by flash chromatography on a silica gel using the following eluent: 5/1 $CH_2Cl_2$/MeOH. As a result, the product is obtained as a white solid (266 mg; 97%). $C_{14}H_{17}N_5O_7$ (M=367 g/mol.); Rf=0.25 (4/1 $CH_2Cl_2$/MeOH).

To a solution of a succinyl-AZT derivative thus obtained (60 mg 0.163 mmol.) in THF (3 ml) at 0° C. and under argon flow, there are added in succession triethylamine (24 μl; 0.172 mmol.) and ethyl chloroformate (14 µl; 0.172 mmol.). Rapid formation of a triethylamine hydrochloride precipitate is observed. After stirring for 40 minutes, addition is made of an aminocaproyl derivative solution (Ex. 2.16.) (160 mg; 0.163 mmol.) in a 9/1 DMF:water mixture (10 ml) containing triethylamine (24 µl; 0.172 mmol.). The reaction mixture is then stirred for 15° C. at 0° C. and thereafter overnight at room temperature before being evaporated under partial vacuum. The crude product is then taken up into dichloromethane (15 ml) and water (5 ml). The organic layer is separated. The aqueous layer is acidified with a 10% citric acid aqueous solution then extracted by dichloromethane (2×). The organic layers are then pooled, dried over $MgSO_4$, filtered and concentrated. By running a flash chromatography purification on a silica gel with the following eluent (9/1 then 7/1 $CH_2Cl_2$/MeOH), there is recovered the AZT-conjugated compound (123 mg; 57%) as a white solid. Rf=0.2 (4/1 $CH_2Cl_2$/MeOH); $C_{69}H_{119}N_9O_{16}$ (M=1329 g/mol). Found: m/z 1330.9 ([M+H]$^+$).

Analytic HPLC: Retention time Tr=24.437 min., C18 Supelcosil Column (15 cm×4.6 mm, 3 µm, 100 Å); Solvent A=50% MeCN, 5 mM TBAP; Solvent B=90% 2-propanol, 5 mM TBAP. Gradient: 25-100% B within 37.5 min., UV detection at 210 nm.

Preparative HPLC: C18 Kromasil column (25 cm×21 mm, 5 µm, 100 Å), solvent A=50% MeCN, 5 mM TBAP; Solvent B=90% 2-propanol, 5 mM TBAP.

Product Elution with 80% B.

Figure 69:
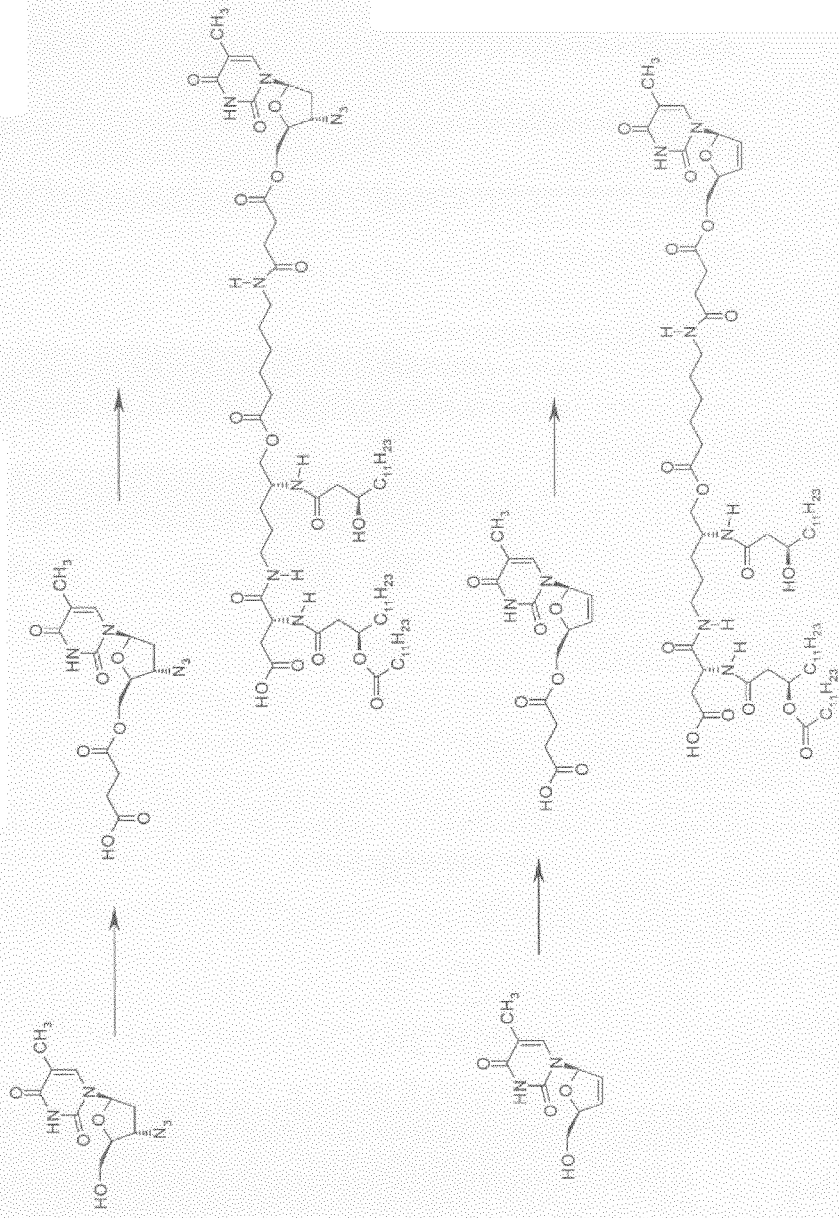
FIG. 69 shows the synthesis of d4T-OM-197-MC.

Final phase: flowing a Na$^+$ salt by SPE, C18 Bondapack phase 15 µm, elution by 90% 2-propanol.

d4T Conjugates (FIG. 69)

To a solution of d4T (200 mg; 0.89 mmol.) in pyridine (4 ml), there are added in succession succinic anhydride (179 mg; 0.786 mmol.) and 4-dimethylaminopyridine (109 mg; 0.89 mmol.) After stirring for 12 hours at room temperature, methanol (2 ml) is added and the reaction medium is stirred for further 15 minutes at room temperature and finally evaporated. The crude product is then purified by flash chromatography on a silica gel using the following eluent: 5/1 $CH_2Cl_2$/MeOH. The resulting product is obtained as a white solid (280 mg; 97%). $C_{24}H_{26}N_2O_7$ (M=324 g/mol.); Rf=0.25 (4/1 $CH_2Cl_2$/MeOH)

To a solution of a succinyl-d4T derivative thus obtained (60 mg 0.185 mmol.) in THF (3 ml) at 0° C. and under argon flow, there are added in succession triethylamine (27 µl; 0.194 mmol.) and ethyl chloroformate (16 µl; 0.194 mmol.). Rapid formation of a triethylamine hydrochloride precipitate is observed. After stirring for 40 minutes, addition is made at 0° C. of an aminocaproyl derivative (Ex. 2.16.) (181 mg; 0.185 mmol.) in a 9/1 DMF:water mixture (10 ml) containing triethylamine (27 µl; 0.194 mmol.). The reaction mixture is then stirred for 15 min. at 0° C. and thereafter at room temperature before being evaporated under partial vacuum. The crude product is then taken up into dichloromethane (15 ml) and water (5 ml). The organic layer is separated. The aqueous layer is acidified with a 10% citric acid aqueous solution then extracted by dichloromethane (2×). The organic layers are then pooled, dried over $MgSO_4$, filtered and concentrated. By running a flash chromatography purification on a silica gel with the following eluent (9/1 then 7/1 $CH_2Cl_2$/MeOH), there is recovered the d4T-conjugated compound (107 mg; 45%) as a white solid. Rf=0.2 (4/1 $CH_2Cl_2$/MeOH); $C_{69}H_{118}N_6O_{16}$ (M=1329 g/mol). Found: m/z 1288.9 (MH); 1310 (Na).

Analytic HPLC: Retention time Tr=24.455 min., C18 Supelcosil Column (15 cm×4.6 mm, 3 µm, 100 Å); Solvent A=50% MeCN, 5 mM TBAP; Solvent B=90% 2-propanol, 5 mM TBAP. Gradient: 25-100% B within 37.5 min., UV detection at 210 nm.

Preparative HPLC: C18 Kromasil column (25 cm×21 mm, 5 µm, 100 Å), solvent A=50% MeCN, 5 mM TBAP; Solvent B=90% 2-propanol, 5 mM TBAP.

Product Elution with 80% B.

Final phase: flowing a Na$^+$ salt by SPE, C18 Bondapack phase 15 µm, elution by 90% 2-propanol.

Example 4

4$^{th}$ Series of Examples

Pharmacological Study of Compounds in Accordance with the Invention (In Vitro)

Example 4.1

Endotoxicity Determination Assay

Endotoxicity levels were determined by a time-course chromogenic *Limulus* Amoebocyte Lysate test (Charles River Endosafe, product R1708K, batch EK2251 E).

This LAL test was used to demonstrate that antigens coupled to the inventive compounds have low endotoxicity.

The biological principle on which this test is based consists in priming of a proenzyme present in *Limulus* amoeboycte lysate (LAL) by bacterial endotoxins, which newly formed enzyme activates at its turn a serine-protease cascade. In presence of a colorless substrate (S-2834 peptide coupled with p-nitroaniline), cleavage of a chromophore finally results in the liberation of p-nitroaniline (pNA) and development of a yellow color which can be monitored with a spectrophotometer at 405 nm.

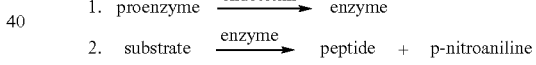

This time-course chromogenic test is based on the fact that endotoxin quantity is proportional to the reciprocal of the time period required to reach an optical density (O.D.) of 0.2. The concentration is determined in relation to a standard curve covering the 0.005-50 EU/ml range.

Products are tested using a (5-, 10-, 50-, 100-, 500- or 1000-fold) dilution of a 0.1 mg/ml product solution. LAL result corresponds to the lowest dilution which does no longer inhibit recovery of an LPS overload.

Results are expressed in EU (endotoxin unit) in relation to an international standard solution (EC-6). For this series of assays, 1 EU stands for 0.08 ng of *E. coli* strain 055:B5 LPS. LAL Values Obtained for Various acyl-dipeptide-like Compounds Bearing an Accessory Functional Side Chain Spacer Having the General Formula I (Table Listing)

| Tested Compounds | Dilution | EU/mg of product | ng of LPS equivalent per mg of product |
|---|---|---|---|
| OM-197-MC | 50 | 88.6 | 7.4 |
| OM-197-MC-MP | 50 | 210.5 | 16.8 |
| OM-197-FV6 | 50 | 540 | 43 |

-continued

| Tested Compounds | Dilution | EU/mg of product | ng of LPS equivalent per mg of product |
|---|---|---|---|
| OM-197-FV8 | 50 | 1820 | 145.6 |
| OM-197-MC-FV5 | 50 | 49.3 | 3.9 |
| OM-197-MC-FV7 | 10 | <0.05 | <0.004 |
| OM-197-MP-AC(R/S,R) | 25 | 0.14 | 0.011 |
| OM-197-MP-AC(R,R) | 25 | 0.15 | 0.012 |
| OM-197-MP-AC(S,R) | 25 | <0.125 | <0.01 |
| OM-197-MP-AC | 25 | 6 | 0.48 |
| OM-197-N'C2-MC-AC | 10 | <0.5 | <0.04 |
| OM-197-N'(C10-20C8)-MC-AC | 10 | <0.5 | <0.04 |
| OM-197-MC-Succ | 25 | 5.3 | 0.42 |
| OM-197-Lys | 25 | 3 | 0.24 |
| OM-197-AP | 10 | <0.5 | <0.04 |
| OM-197-Asp | 50 | <2.5 | <0.2 |
| OM-197-Asp-AC | 50 | 2307 | 184.6 |
| OM-197-Lys-AC | 50 | <2.5 | <0.2 |
| OM-197-MC-AC-Succ-AZT | 10 | 1.34 | 0.11 |
| OM-197-MC-AC-Succ-d4T | 10 | 1.05 | 0.08 |
| OM-197-MC-AC-Succ | 10 | <0.05 | <0.004 |

All tested dipeptide-like compounds show low endotoxicity levels. For many such products, this endotoxicity is even lower than assay sensitivity. Quantitative determination of endotoxicity is limited due to the fact that samples must be diluted in order to recover overload. Even the most active compounds in this LAL test display an endotoxicity level 5000-fold less than LPS.

Dipeptide-like compounds of the invention are interesting in view of their biological activities and low endotoxicity.

Table

LAL Results for Different Products Used in Immunization Experiments with Ovalbumin-Conjugated Products

| Tested compound or admixture | EU/mg | ng of LPS equivalent per mg of product |
|---|---|---|
| Ovalbumin | <0.8 | <0.064 |
| Ovalbumin + OM-197-MP | 5.8 | 0.48 |
| OM-197-FV-ovalbumin | 99 | 8.21 |

It is believed that coupling OM-197-FV to ovalbumin results in an increase in LAL activity actually detected. This increase may be ascribed to a change in how the OM-197-FV molecule is presented. The other products of the ovalbumin series all have equivalent LAL activities. LAL results are highly variable and a 3-fold to 4-fold difference between groups is non significant. Peak LAL activity is equal to 2.4 ng of LPS equivalent per injection (25 µg/shot) for the coupling reaction products, as for other groups, the peak LAL activity is equal to 0.012 ng of LPS equivalent per injection.

Table

LAL Results for Different Products Used in Immunization Experiments with H1N1 Hemagglutinin-Conjugated Products

| Tested compound or admixture | EU/mg | ng of LPS equivalent per mg of product |
|---|---|---|
| N1N1 | 2 | 0.17 |
| H1N1 + OM-197-MP | 20 | 1.67 |
| OM-197-FV-H1N1 | 15.6 | 1.30 |

Products of the H1N1 series all have comparable LAL activities. LAL results are highly variable and a 3-fold to 4-fold difference between groups is non significant. Coupling has no effect on LAL activity. Peak LAL activity is equal to 0.008 ng of LPS equivalent per injection (5 µg/shot).

Table

LAL Results for Different Products Used in Immunization Experiments with H1N1 Hemagglutinin-Conjugated Products

| Tested compound or admixture | EU/mg | ng of LPS equivalent per mg of product |
|---|---|---|
| $(NANP)_6P_2P_{30}$ (SEQ ID NO: 2) | 16 | 1.33 |
| $(NANP)_6P_2P_{30}$ (SEQ ID NO: 2) + IFA | n.d.* | n.d.* |
| $(NANP)_6P_2P_{30}$ (SEQ ID NO: 2) + OM-197-FV6 | 13 | 1 |
| $(NANP)_6P_2P_{30}$ (SEQ ID NO: 2) + OM-197-MC | 12 | 1 |
| (OM-197-FV)-1,2,3-$(NANP)_6P_2P_{30}$20 (SEQ ID NO: 2) | 2 | 0.17 |
| OM-197-FV-$(NANP)_6P_2P_{30}$ (SEQ ID NO: 2) | 9.4 | 0.78 |
| OM-197-FV-$(NANP)_6P_2P_{30}$ (SEQ ID NO: 2) + OM-197-MP | 17.4 | 1.45 |

*cannot be assayed by LAL as this test is unsuitable for emulsions

Products of the $(NANP)_6P_2P_{30}$ (SEQ ID NO: 2) series all have comparable LAL activities. LAL results are highly variable and a 3-fold to 4-fold difference between groups is non significant. Coupling has no effect on LAL activity. Maximum LAL activity is equal 0.03 ng of LPS equivalent per injection (20 µg/shot).

Example 4.2

Determination of the Bone Marrow Stem Cell Proliferation in Mice Challenged with the Inventive Products

4.2.1. Proliferation Experiment 6-week old male C57/BL6 mice are killed by $CO_2$ inhalation. The hip, femur, tibia and hind leg bones are removed. The marrow is extracted from the bone lumen by injecting Dulbecco's Modified Eagle Medium (DH medium) from the end portions which had been excised. The stem cells are washed and suspended again in DH medium supplemented with 20% foetal calf serum (FCS) The cell concentration is adjusted to 500000 cells/ml.

Products previously dissolved in DH medium supplemented with 20% FCS, amino acids and antibiotics are serially diluted directly into a microtiter plate. The products are tested in triplicate and each microtiter plate includes a negative control containing plain medium. The final volume in each well is 100 µl.

100 µl of the cell suspension are added to diluted solutions of products and the cells are incubated for 7 days in an incubator at 37° C., under 8% $CO_2$ and a moisture saturated atmosphere. Cell proliferation is determined by measuring the oxidation of a chromogenic substrate XTT (2,3-bis[2-methoxy-4-nitro-5-sulphophenyl]-2H-tetrazolium-5-carboxanilide) in mitochondria of viable cells.

At the end of the incubation period, 50 µl of the XTT substrate solution (1 mg/ml XTT+0.008 mg/ml phenazine methosulfate) are added to each well. After an 8 hour incubation period at 37° C. under 8% $CO_2$ in a moisture saturated incubator, the microtiter plates are read with a spectrophotometer at 492 nm against a reference sample at 690 nm.

Results are expressed as mean value±standard deviation and plotted as a dose versus response curve. Values for a negative control composed of DH medium (mean±standard deviation) are also graphically shown.

From this dose versus response curve, 3 curve variables are computed:
Max: maximum curve amplitude and corresponding concentration
$EC_{50}$: concentration corresponding to 50% of maximum amplitude
Min: lowest concentration inducing a significant proliferation corresponding to the blank±3× standard deviation value Concentration values corresponding to $EC_{50}$ and Min are determined from line segments joining different points on the curve.

If the curve has no plateau phase but an ascending configuration for the highest concentration being tested, a ">" sign is shown before Max and $EC_{50}$ values.

If the curve does not drop below the blank±3× standard deviation value, minimum concentration value is shown as "<" lowest concentration being tested.

4.2.2. Results

Figure 70:
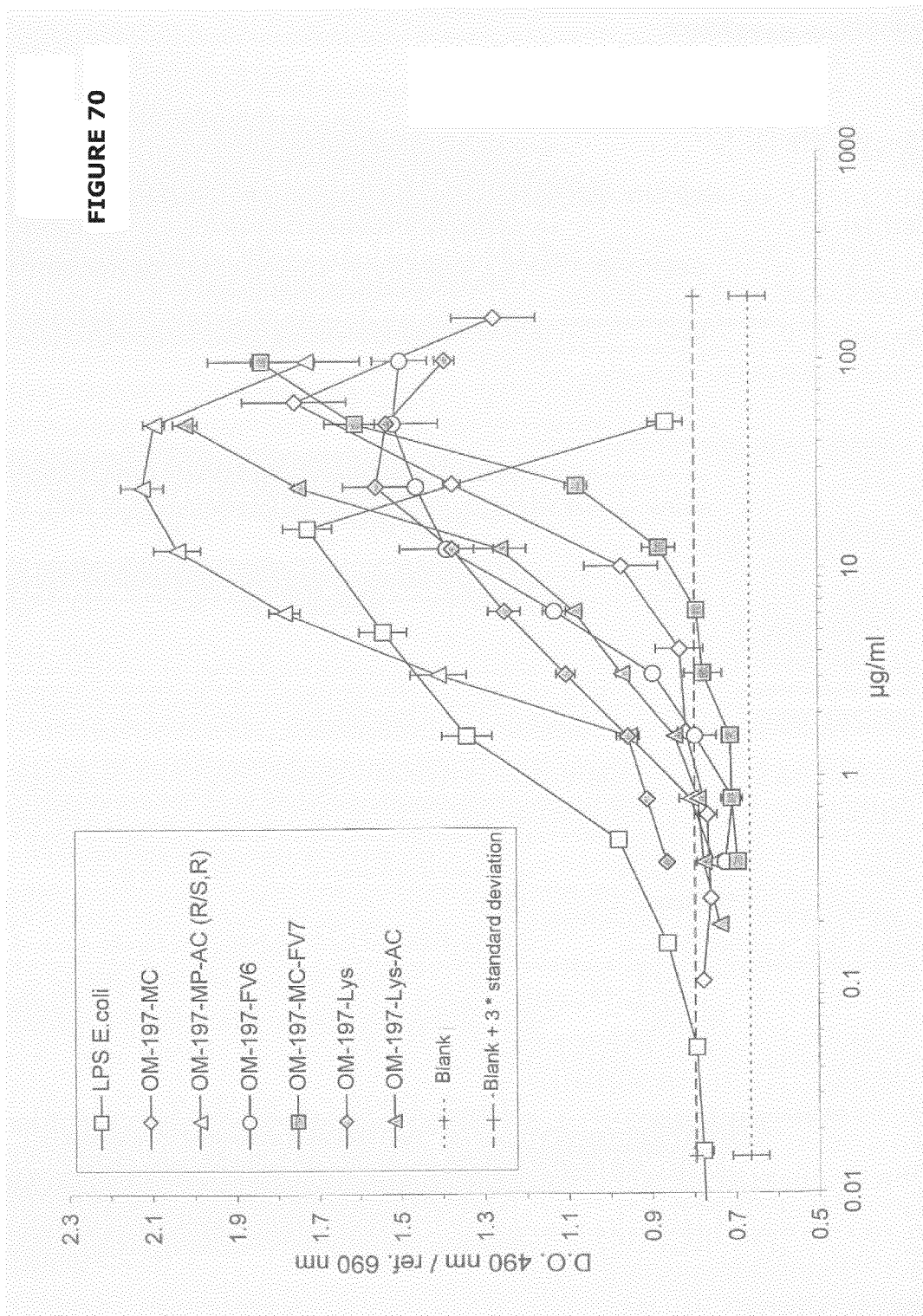
FIG. 70 are graphs showing the effect of the various acylated pseudodipeptides on the proliferation of stem cells of bone marrow of mice.

Proliferation of Bone Marrow Stem Cells Induced by Acyl-Dipeptide-Like Compounds Bearing an Accessory Functional Side Chain Spacer FIG. 70 displays the activity of different acyl dipeptide-like compounds and clearly shows the influence of accessory functional side chain spacer on the ability to induce bone marrow stem cell proliferation in mice.

Certain acyl-dipeptide-like compounds are able to induce proliferation to a greater extent than positive control, made up of *E. coli* LPS. Minimal product concentration capable of inducing a significant proliferation is higher than concentration used in positive control. This minimal product concentration is greatly affected by the particular accessory functional side chain spacer being used.

Figure 71:
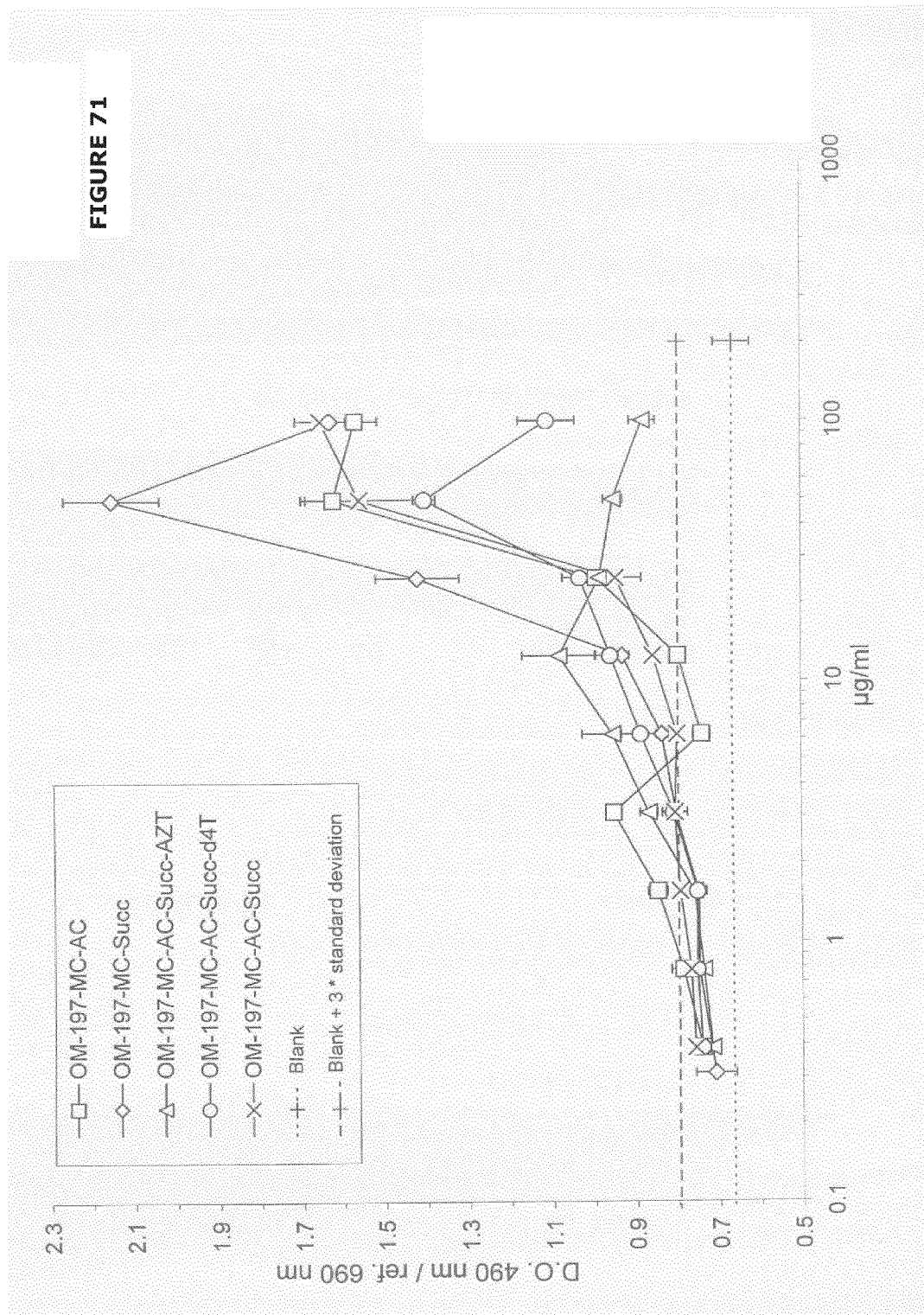
FIG. 71 are graphs showing the effect of the various acylated pseudodipeptides conjugated with an antiviral drug (AZT or D4T) on the proliferation of stem cells of bone marrow of mice.

FIG. 71 shows the activity of acyl dipeptide-like compounds coupled to a given drug. This activity provides evidence that compounds remain partially active in spite of the coupling process. It has not been possible to discriminate between intrinsic activity and activity resulting from coupling of the ester bond by intracellular esterases. Antiviral activity of these products strongly suggests that ester bonds undergo at least partial cleavage. Whatever the underlying mechanism, retention of biological activity underscores the full potential of combining antiviral activity and product activity. Bone Marrow Stem Cell Proliferation Induction Results by Various Acyl-Dipeptide-Like Compounds Bearing an Accessory Functional Side Chain Spacer Having the General Formula I (Table Listing)

| Products | Max amplitude/ concentration O.D/µg/ml | $EC_{50}$ amplitude/conc O.D/µg/ml | Min amplitude/ concentration O.D/µg/ml |
| --- | --- | --- | --- |
| DH Medium (negative control) | 0.67 ± 0.04 | | |
| *E. coli* LPS (positive control) | 1.75/16 | 1.19/1.2 | 0.80/0.06 |
| OM-197-MC | 1.75/64 | 1.21/19.4 | 0.80/1.25 |
| OM-197-MC-MP | >1.60/>160 | >1.13/>6.5 | 0.80/0.77 |
| OM-197-FV6 | 1.52/50 | 1.10/5.7 | 0.80/1.60 |
| OM-197-FV8 | 1.07/25 | 0.87/1.8 | 0.80/1.24 |
| OM-197-MC-FV5 | 1.75/50 | 1.21/32.0 | 0.80/8.20 |
| OM-197-MC-FV7 | >1.83/>100 | >1.25/>33.1 | 0.80/6.58 |
| OM-197-MP-AC (R/S, R) | 2.12/25 | 1.39/3.1 | 0.80/0.71 |
| OM-197-MP-AC (S, R) | 1.22/6.25 | 0.94/2.62 | 0.80/1.17 |
| OM-197-MC-AC | 1.62/50 | 1.15/31.0 | 0.80/0.92 |
| OM-197-N'C2-MC-AC | 0.75/1.56 | 0.71/nd | 0.80/nd |
| M-197-N'(C10-20C8)-MC-AC | 0.75/6.25 | 0.71/nd | 0.80/nd |
| OM-197-MC-Succ | 2.16/50 | 1.41/24.7 | 0.80/2.95 |
| OM-197-Lys | 1.56/25 | 1.11/3.3 | <0.86/<0.39 |
| OM-197-AP | 1.49/25 | 1.08/2.2 | 0.80/0.41 |
| OM-197-Asp | 1.22/25 | 0.94/5.0 | 0.80/1.89 |
| OM-197-Asp-AC | 1.33/50 | 0.10/2.8 | 0.80/1.27 |
| OM-197-Lys-AC | >2.02/>50 | >1.34/>14.6 | 0.80/0.90 |
| OM-197-MC-AC-Succ-AZT | 1.08/12.5 | 0.87/3.3 | 0.80/2.11 |
| OM-197-MC-AC-Succ-d4T | 1.40/50 | 1.03/25.4 | 0.80/2.81 |
| OM-197-MC-AC-Succ | >1.65/>100 | >1.16/33.7 | 0.80/2.04 | nd = undetermined

All acyl-dipeptide-like compounds of the invention except compounds with short chains are capable of inducing significant bone marrow stem cell proliferation.

Example 4.3

Determining the Production of Nitric Oxide by Murine Macrophage Cells Challenged with Products of the Invention

4.3.1. Experimental Assay of Nitric Oxide Production

Six-week old male C57/BL6 mice are killed by $CO_2$ inhalation. The hip, femur, tibia and posterior appendage bones are removed. The bone marrow is extracted from the bone lumen by injecting Dulbecco's Modified Eagle Medium (DH medium) from the end portions which had been excised. The stem cells are washed and resuspended (approximate cell concentration 4000 cells/ml) in DH medium supplemented with 20% equine serum (SH) and 30% L929 cell supernatant. L929 is a murine fibroblast cell line the supernatant fluid of which is rich in growth factor for macrophage cells (M-CSF). The cell suspension is divided into Petri dishes which are incubated for 8 days in an incubator at 37° C. under 8% $CO_2$ and a moisture saturated atmosphere.

After 8 days, the stem cells have differentiated into mature macrophage cells. The macrophage cells are scraped off by rapid cooling, washed and resuspended in DH medium supplemented with 5% foetal calf serum (FCS), amino acids and antibiotics. The cell density is adjusted to 700 000 cells/ml.

Products previously dissolved in DH medium supplemented with 5% FCS, amino acids and antibiotics are serially diluted directly in microtiter plates. The products are tested in triplicates and each microtiter plate comprises a negative control containing plain medium. The final volume in each well is 100 µl.

100 µl of cell suspension are added to diluted solutions of such products and the cells are incubated for 22 hours in an incubator at 37° C., under 8% $CO_2$ and a moisture saturated atmosphere. At the end of the incubation period with the products, 100 µl of supernatant are withdrawn and the nitrite concentration is determined by running a Griess reaction.

100 µl of Griess reagent (5 mg/ml of sulfanilamide+0.5 mg/ml of N-(1-naphtylethylene diamine hydrochloride)) in 2.5% aq. phosphoric acid, are added to each well. The microtiter plates are read with a spectrophotometer at 562 nm wavelength against a reference sample at 690 nm. The nitrite concentration is proportional to nitric oxide content being formed. The nitrite content is determined based on a standard curve.

The results are given as mean value±standard deviation and plotted as a dose versus response curve.

From this dose versus response curve, 3 curve variables are computed:
Max: maximum curve amplitude and corresponding concentration
$EC_{50}$: concentration corresponding to 50% of maximum amplitude
Min: lowest concentration inducing a significant proliferation corresponding to the blank±3× standard deviation value Concentration values corresponding to $EC_{50}$ and Min are determined from line segments joining different points on the curve.

If the curve has no plateau phase but an ascending configuration for the highest concentration being tested, a ">" sign is shown before "Max" and "$EC_{50}$" values.

If the curve does not drop below the blank±3× standard deviation, minimum concentration value is shown as "<" lowest concentration being tested.

4.3.2. Results

Figure 72:
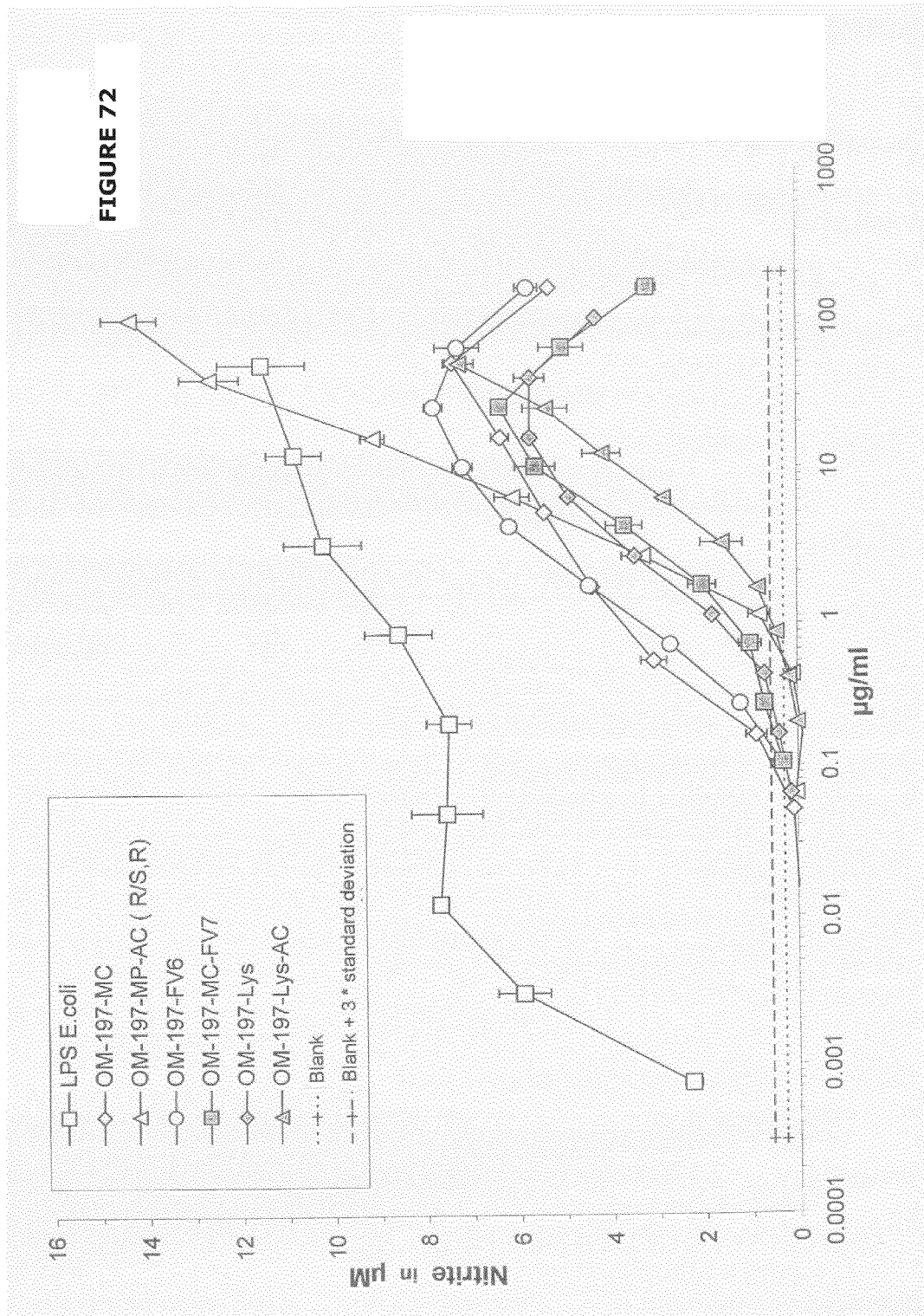
FIG. 72 are graphs showing the activity of the various acylated pseudodipeptides on the capacity to induce murine bone marrow stem cell proliferation.

Nitric Oxide Production by Murine Macrophage Cells Induced by Acyl Dipeptide-Like Compounds Bearing an Accessory Functional Side Chain Spacer FIG. 72 shows the activity of different acyl-dipeptide-like compounds and demonstrates the influence of the accessory functional side chain spacer on the ability to induce murine bone marrow stem cell proliferation.

OM-197-MP-AC (R/S, R) is capable of inducing a higher proliferation response as compared to positive control made up of E. coli LPS. Minimal product concentration capable of inducing a significant proliferation is nonetheless far lower than positive control concentration. NO production by murine macrophage cells challenged by acyl dipeptide-like compounds is greatly affected by the particular accessory functional side chain spacer being used.

Figure 73:
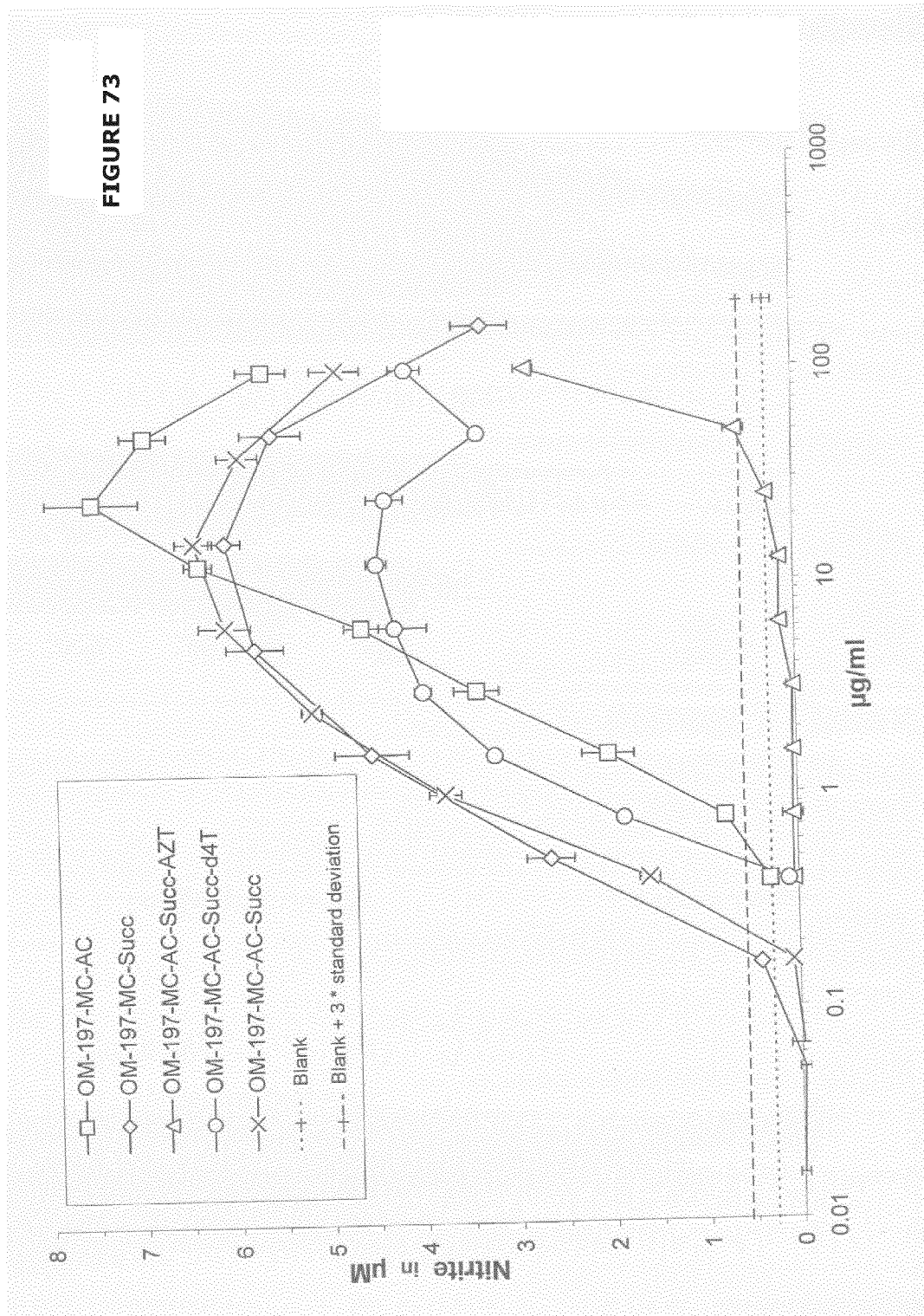
FIG. 73 are graphs showing the nitric oxide production as Induced by the N-acylated pseudodipeptides conjugated with an antiviral drug such as AZT or d4T.

FIG. 73 shows the activity of acyl dipeptide-like compounds coupled to a given drug. This activity is regarded as evidence that compounds remain partially active in spite of the coupling step. It has not been possible to discriminate between intrinsic activity and activity resulting from coupling of the ester bond by intracellular esterases. Antiviral activity of these products strongly suggests that ester bonds undergo at least partial cleavage. Whatever the underlying mechanism, retention of biological activity demonstrates the full potential of combining antiviral activity and product activity. Nitric Oxide Induced Production Results in Murine Macrophage Cells by Various Acyl-Dipeptide-like Compounds Bearing an Accessory Functional Side Chain Spacer Having the General Formula I (Table Listing)

| Products | Max amplitude/ concentration O.D/µg/ml | $EC_{50}$ amplitude/conc O.D/µg/ml | Min amplitude/ concentration O.D/µg/ml |
| --- | --- | --- | --- |
| DH Medium (negative control) | 0.29 ± 0.09 | | |
| E. coli LPS (positive control) | >10.37/>50 | >5.33/>0.01 | <1.41/<0.001 |
| OM-197-MC | 7.16/51 | 3.73/1.23 | 0.57/0.15 |
| OM-197-MC-MP | 7.94/51 | 4.12/1.18 | 0.57/0.11 |
| OM-197-FV6 | 7.48/25.6 | 3.89/1.49 | 0.57/0.20 |
| OM-197-FV8 | 8.00/51 | 4.15/7.89 | 0.57/1.45 |
| OM-197-MC-FV5 | 5.64/16 | 2.97/2.56 | 0.57/0.67 |
| OM-197-MC-FV7 | 6.17/>25.6 | 3.23/>3.70 | 0.57/0.36 |
| OM-197-MP-AC(R/S, R) | >14.09/>100 | >7.19/>10.69 | 0.57/1.04 |
| OM-197-MP-AC (S, R) | 7.56/40 | 3.93/3.28 | 0.57/0.59 |
| OM-197-MC-AC (R, R) | >8.31/>100 | >4.3/>15.32 | 0.57/3.35 |
| OM-197-MC-AC | 7.08/25 | 3.69/4.91 | 0.57/0.91 |
| OM-197-N'C2-MC-AC | >0.24/200 | nd | nd |
| OM-197-N'(C10-2OC8)-MC-AC | >0.96/>100 | 0.63/61.05 | 0.57/54.3 |
| OM-197-MC-Succ | 5.84/16 | 3.07/0.89 | 0.57/0.22 |
| OM-197-Lys | 5.50/40 | 2.90/2.23 | 0.57/<0.47 |
| OM-197-AP | >9.64/>100 | >4.97/>13.69 | 0.57/1.87 |
| OM-197-Asp | 8.26/51 | 4.28/0.95 | 0.57/0.086 |
| OM-197-Asp-AC | >7.97/>100 | >4.13/>7.04 | 0.57/2.00 |
| OM-197-Lys-AC | >7.04/>50 | >3.67/>11.06 | 0.57/1.46 |
| OM-197-MC-AC-Succ-AZT | >2.53/>100 | >1.41/>74.89 | 0.57/55.98 |
| OM-197-MC-AC-Succ-d4T | 4.17/12.5 | 2.23/1.15 | 0.57/0.56 |
| OM-197-MC-AC-Succ | 6.17/>16 | 3.23/0.72 | 0.57/0.28 | nd = undetermined

All acyl-dipeptide-like compounds of the invention except compounds with short chains (minor production for OM-197-N'(C10-2OC8)-MC-AC) are capable of inducing a significant nitric oxide production by murine macrophage cells.

Example 4.4

Differentiation Test of Dendritic Cells

The ability of products of the invention to induce maturation of predendritic cells into dendritic cells was assessed.

The following parameters were measured: FITC-Dextran conjugate take-up and expression of CD83, CD86 surface markers.

4.4.1. Experimental Procedure

Mononucleated cells of peripheral blood are isolated from buffy coats of healthy donors. Purified monocytes by adherence selection are resuspended in RPMI-1640 medium containing 10% of foetal calf serum (FCS), GM-CSF and IL-4 (10 ng/ml) at a density of $1\times10^6$ cells/ml. Cells are divided into Petri Dishes ($10\times10^6$ cells per dish) and cultured for 6 days with a change to fresh medium after 3 days. Cells thus obtained are called predendritic cells (DC-6). Maturation of predendritic cells into mature dendritic cells is achieved by incubating cells with diluted solutions of the products or LPS (positive control) for 3 more days (see product section below). At day 9 (DC-9), cells are harvested and analyzed for different indicators of dendritic cell maturation: assessment of CD83, CD86 surface marker expression as well as of their ability to take up FITC-Dextran conjugate. All these parameters are analyzed by an EPICS-XL-MCL model FACS (Coulter Immunology, Hialeah, Finland).

Expression of surface markers is given as % of mean fluorescence of LPS-activated cells (positive control); FITC-Dextran conjugate take-up rate is calculated based on take-up of cells maintained in basic medium and is expressed in %. Products: Stock solutions of OM-197-MC, OM-197-FV6 and OM-197-MP-AC (R/S, R) are prepared at a concentration of 0.5 mg/ml in 0.9% NaCl/water, with addition of 0.1% triethanolamine. Solutions are incubated at 37° C. for 20 minutes, subjected to vigorous stirring during 3 minutes and then diluted to 100 µg/ml in RPMI-1640 culture medium and used in diluted state at concentrations ranging from 10 µg/ml to 0.03 µg/ml.

Reference Product: *E. coli* lipopolysaccharide (LPS, DIFCO, Detroit, Mich., U.S.A.), as a 5 mg/ml stock solution in PBS. An intermediate 100 µg/ml solution is prepared in RPMI 1640 culture medium. Concentrations of dilute solutions being tested range from 1 µg/ml to 0.03 µg/ml.

In another series of experiments, all acyl dipeptide-like compounds were freeze-dried and directly redissolved into pyrogen-free water. Different products as well as LPS control are tested at a concentration of 10 µg/ml. Results are given as % of dendritic cells and mean fluorescence value for dextran phagocytosis or CD86 surface marker expression. These results stand for the mean value of 2 to 6 experiments depending on the product being used.

4.4.2. Result Analysis

Immature dendritic cells (DC-6) resulting from monocyte differentiation, through the joint action of GM-CSF and IL-4, are able to incorporate FITC-Dextran conjugate. During the maturation process, cells lose their ability to incorporate the FITC-Dextran conjugate. Assays are conducted upon reaching the DC-9 differentiation stage.

Figure 74:
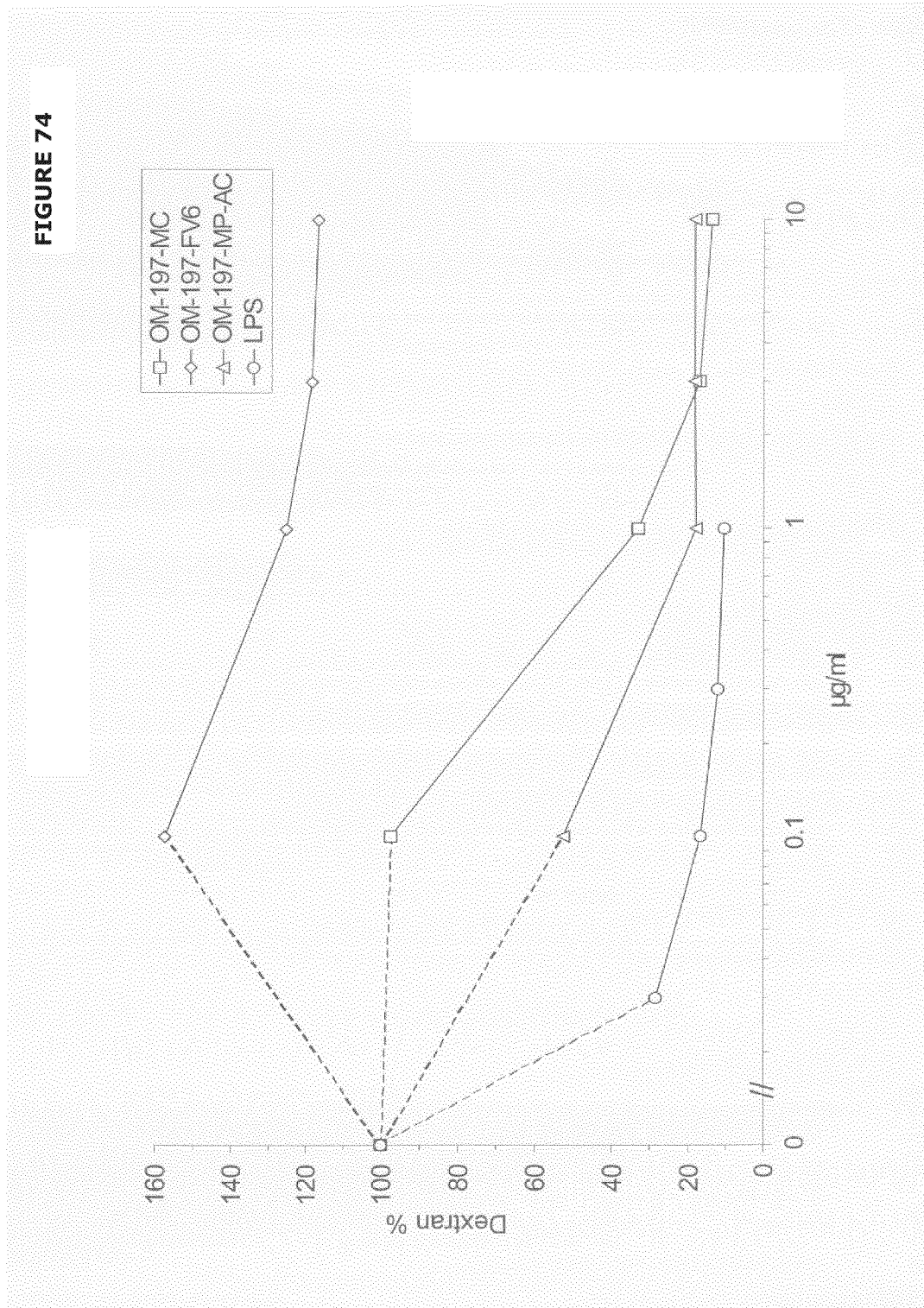
FIG. 74 are graphs showing the incorporation of dextran-FITC in the unstimulated cells incubated in the culture medium in the presence of various acylated pseudodipeptides.

Results (FIG. 74) are expressed in terms of % incorporation of FITC-Dextran conjugate observed in unchallenged cells incubated in basic medium. Cells treated with LPS or OM-197-AC (R/S, R) retain only 15% and 22% of their phagocytic capacity, respectively. It should be noted that at least 1 µg/ml of OM-197-MP-AC (R/S, R) is required to induce full decrease of Dextran take-up whereas 0.1 µg/ml of LPS results in a similar decrease. 10 µg/ml of OM-197-MC are required to induce a 22% decrease of phagocytic capacity. Furthermore, for concentrations lower than 3 µg/ml, OM-197-MC has no effect on phagocytosis. OM-197-FV6 has apparently no effect on maturation of dendritic cells.

Figure 75:
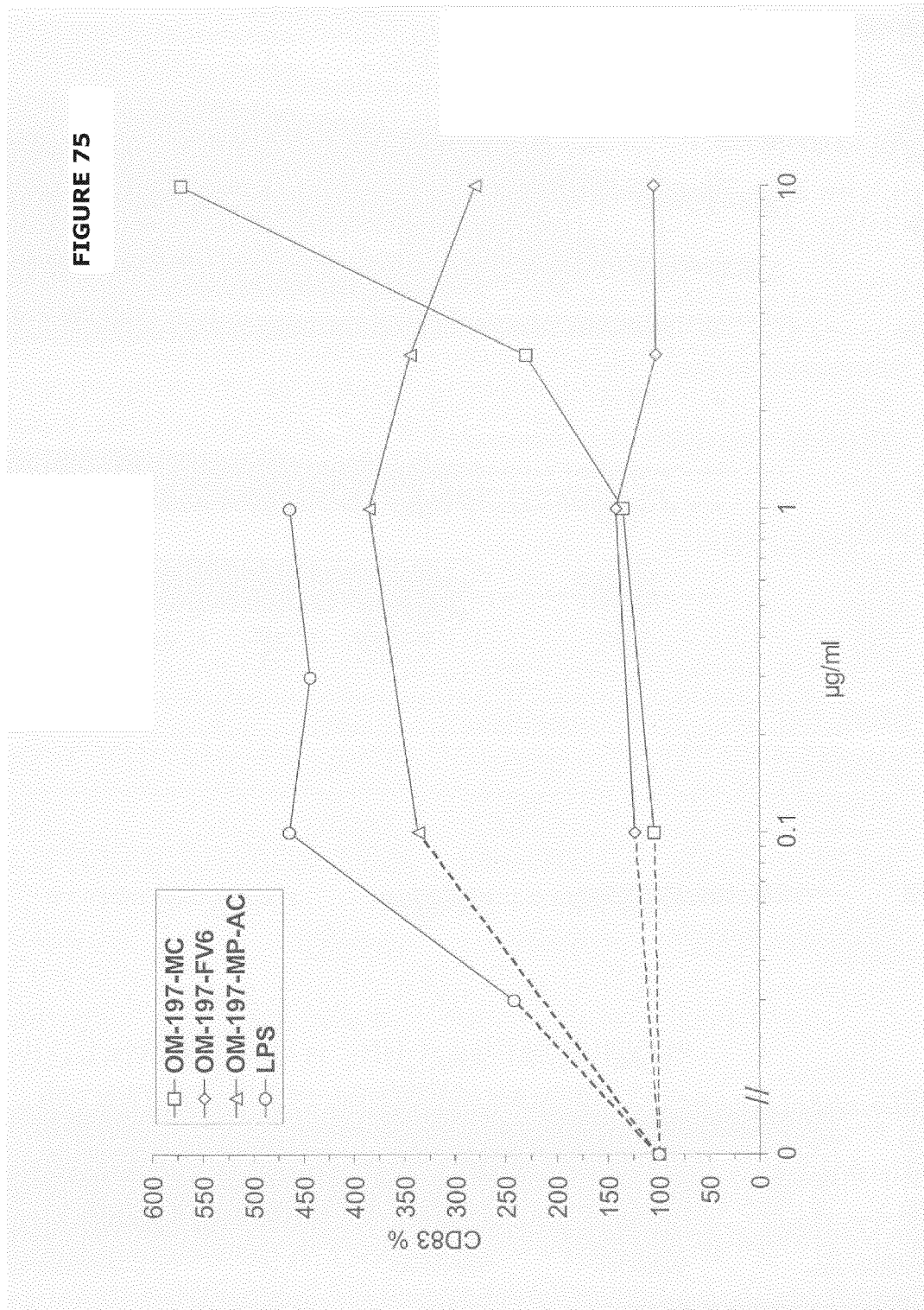
FIG. 75 are graphs showing the increase of the expression of surface molecule CD83 in the presence of N-acylated pseudodipeptides and the conjugates thereof.
Figure 76:
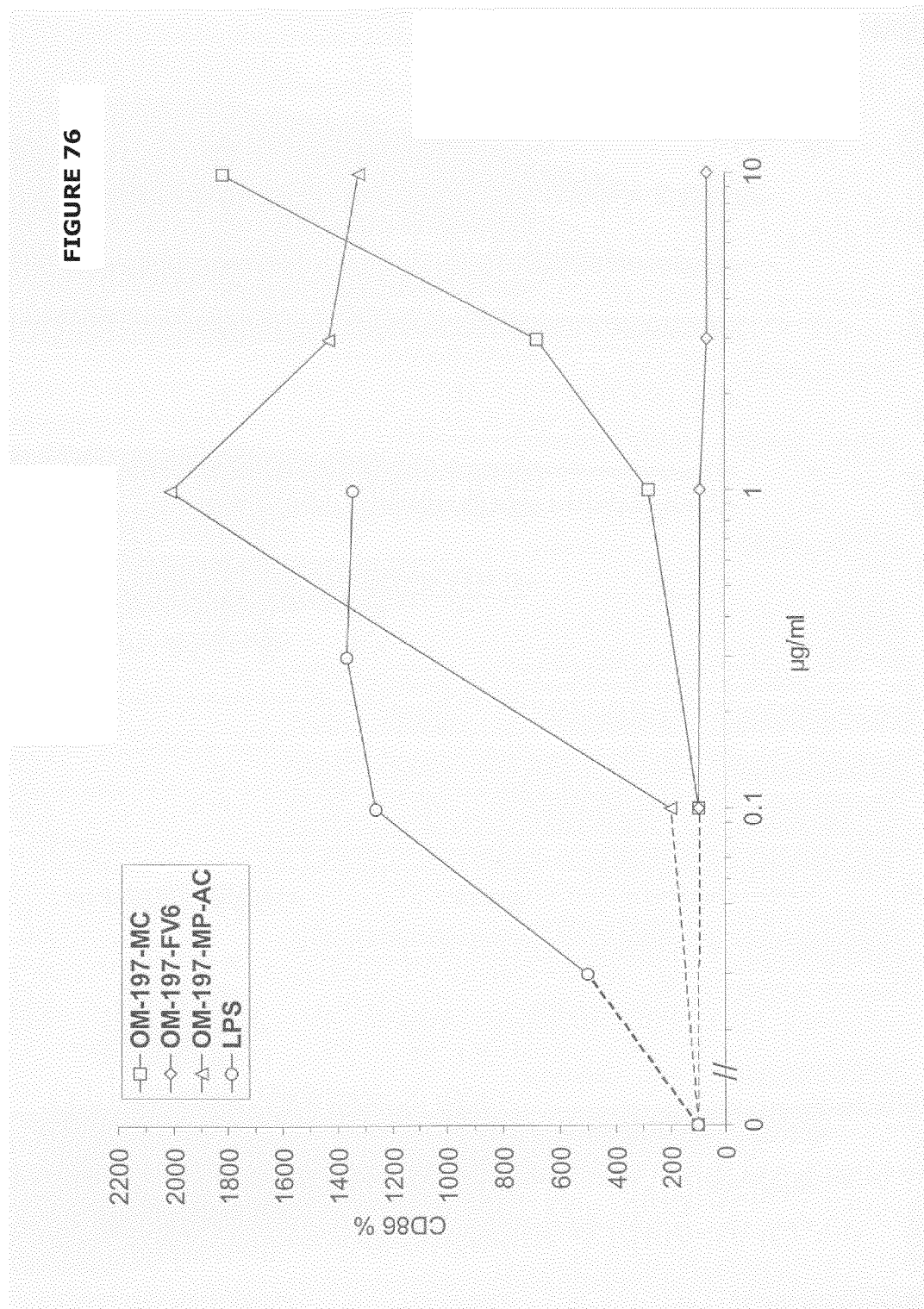
FIG. 76 are graphs showing the increase of the expression of surface molecule CD86 in the presence of the N-acylated pseudodipeptides and the conjugates thereof.

Expression of co-stimulation surface markers is another criterion to assess DC maturation. Rise in expression of CD83, CD86 (FIGS. 75 & 76, respectively) is tested. Results are expressed in terms of % of mean fluorescence based on LPS-induced expression of these markers. These results are fully consistent with those obtained from phagocytosis studies. OM-197-MP-AC (R/S, R) induces an increase in expression of surface markers at concentrations as low as 0.1 µg/ml, while at least 1 µg/ml is needed in case of OM-197-MC to initiate a rise in expression of CD83 and CD86 markers. OM-197-FV6 has no effect at all on expression of surface markers which are typical of dendritic cells.

The foregoing data show that acyl-dipeptide-like compounds act very differently depending on the selected accessory side chain spacer. OM-197-MP-AC (R/S, R) displays an outstanding ability to induce differentiation of DC-6 cells into DC-9 cells in concentrations as low as 0.1 µg/ml, whereas concentrations greater than 1 µg/ml are required for OM-197-MC to initiate differentiation, and OM-197-FV6 does totally lack such an activity.

Fluorescein-Labelled Dextran Phagocytosis and CD86 Expression after Predendritic Cell (CD6) Stimulation by Acyl Dipeptide-Like Compounds Bearing an Accessory Functional Side Chain Spacer Having the General Formula I Differentiation of Predendritic Cells into Mature Dendritic Cells

| Products | Dextran % CD/Fluorescence | CD86 % CD/Fluorescence |
| --- | --- | --- |
| 37° C. | 18.3/0.9 | 33.5/2.9 |
| LPS *E. Coli* | 100/7.3 | 100/7.3 |
| OM-197-FV6 | 84.5/6.3 | 62.9/4.9 |
| OM-197-MC-FV5 | 86.5/6.4 | 74.5/5.6 |
| OM-197-MP-AC (R/S, R) | 84.6/6.3 | 80.0/6.0 |
| OM-197-MC-AC | 68.3/5.2 | 67.4/5.2 |
| OM-197-MC-MC-Succ | 35.5/3.0 | 34.9/3.0 |
| OM-197-Lys | 12.1/0.5 | 21.2/2.1 |
| OM-197-AP | 56.1/4.4 | 62.0/4.8 |
| OM-197-Asp | 26.4/2.4 | 29.0/2.6 |
| OM-197-Asp-AC | 22.0/22.1 | 26.7/2.4 |
| OM-197-Lys-AC | 92.2/6.8 | 93.5/6.9 |
| OM-197-MC-AC-Succ-AZT | 62.2/4.8 | 81.4/6.1 |
| OM-197-MC-AC-Succ-d4T | 11.6/0.5 | 25.9/2.4 |

At a concentration of 10 µg/ml, a great number of acyl dipeptide-like compounds are able to induce differentiation of predendritic cells into dendritic cells. The functional group born by the accessory side chain spacer regulates this ability to activate predendritic cells.

Acyl-dipeptide-like compound OM-197-MC-AC-Succ-AZT coupled to a drug has a significant ability to induce differentiation into dendritic cells. The way acyl-dipeptide-like compounds are formulated has a determining effect on their ability to induce predendritic cell differentiation into dendritic cells. The activity of certain products varies to a great extent depending on whether said products are dissolved in presence or absence of 0.1% TEOA.

Example 4.5

Analysis of MxA Protein Induction in Dendritic Cells

The ability of products of the invention to induce production of antiviral MxA protein by predendritic cells has been assessed. MxA production by cells was measured after an SDS-PAGE electrophoretic separation by a Western Blot assay

4.5.1. Experimental Procedure

DC-6 Staged dendritic cells obtained as described above were either activated or not with α IFN (500 U/ml), LPS (1 µg/ml), TRANCE (100 ng/ml), CD40L (1 µg/ml), OM-197-MP-AC (1 µg/ml) or OM-197-FV6 (1 µg/ml) for 48 hours. Extraction and analysis of protein was conducted as follows: cells were harvested, then washed 3 times with PBS (phosphate buffered saline) and lyzed with a 100 Mm Tris-HCl buffer, 150 mM NaCl, 5 mM EDTA, 1% Triton-100 containing 1 mM PMSF (phenylmethylsulphonyl fluoride) and 1 µ/ml of pepstatin as protease inhibitors. Lysis was carried out at a density of $10^6$ cells for 100 µl of (5×) buffer containing 60 mM Tris-HCl (pH 6.8), 10% glycerol, 2% SDS, 14.4 mM 2-mercaptoethanol and 0.1% bromophenol). Samples were heated up to 95° C. for 5 min. in sealed Eppendorf tubes. Electrophoresis was performed on a 10 cm×10 cm 12% acrylamide minigel by running a sample having the same number of cells. Migration was effected with the following buffer: 25 mM Tris, 192 mM glycine, 0.1% SDS, pH 8.3.

Blotting: Protein are blotted from an SDS-PAGE gel to a nitrocellulose membrane (blotting buffer 25 mM Tris, 192 mM glycine, methanol pH 8.3)

Incubation with Antibodies—Blotting was demonstrated by dyeing the membrane with Ponceau Red. Non specific bonding sites on the membrane were blocked with 5% skimmed milk in TBS (10 mM Tris-HCl, 150 Mm NaCl, pH 7.4) and allowing to stand for 1 hour at room temperature. The membrane was washed 3 times with TBS-0.1% Tween 20. The membrane was incubated with an anti-MxA monoclonal antibody solution (clone 143) previously diluted 100-fold (vol./vol.) in TBS-milk. The membrane was incubated with a second peroxidase coupled anti-mouse antibody (HRP, Sigma) previously diluted 1000-fold (vol./vol.). The membrane was washed three times with TBS-Tween. Bands containing MxA were revealed by incubation of the membrane with chemiluminescent reagents (ECL, Amersham Pharmacia). In this system, HRP catalyzes a luminol-mediated chemiluminescent reaction which can be detected on a photographic film.

4.5.2. Results

Figure 77:
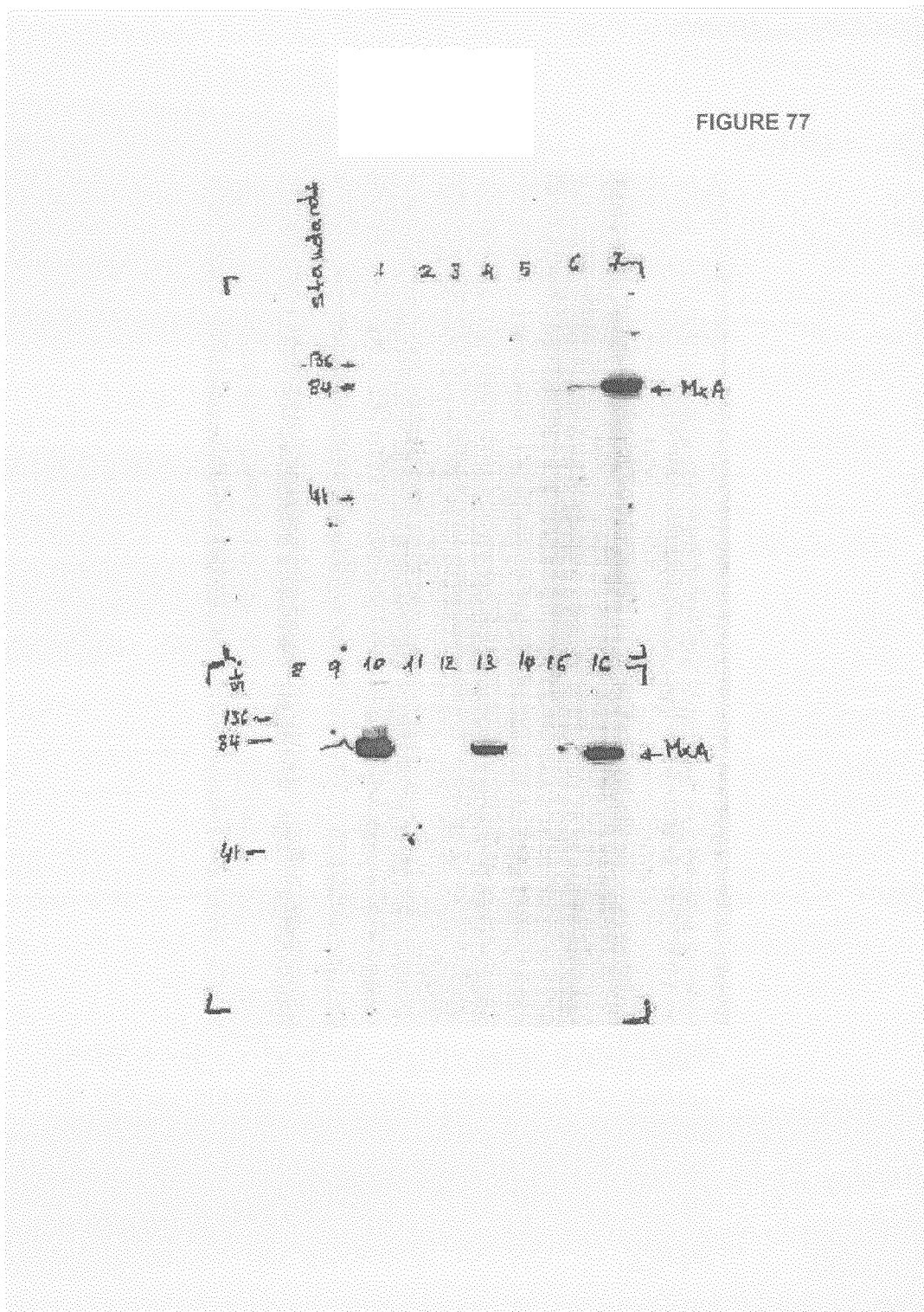
FIG. 77 is a Western blot analysis showing a significant increase in the production of MxA protein as a function of time induced by the acylated pseudodipeptides after 24 h.
Figure 78:
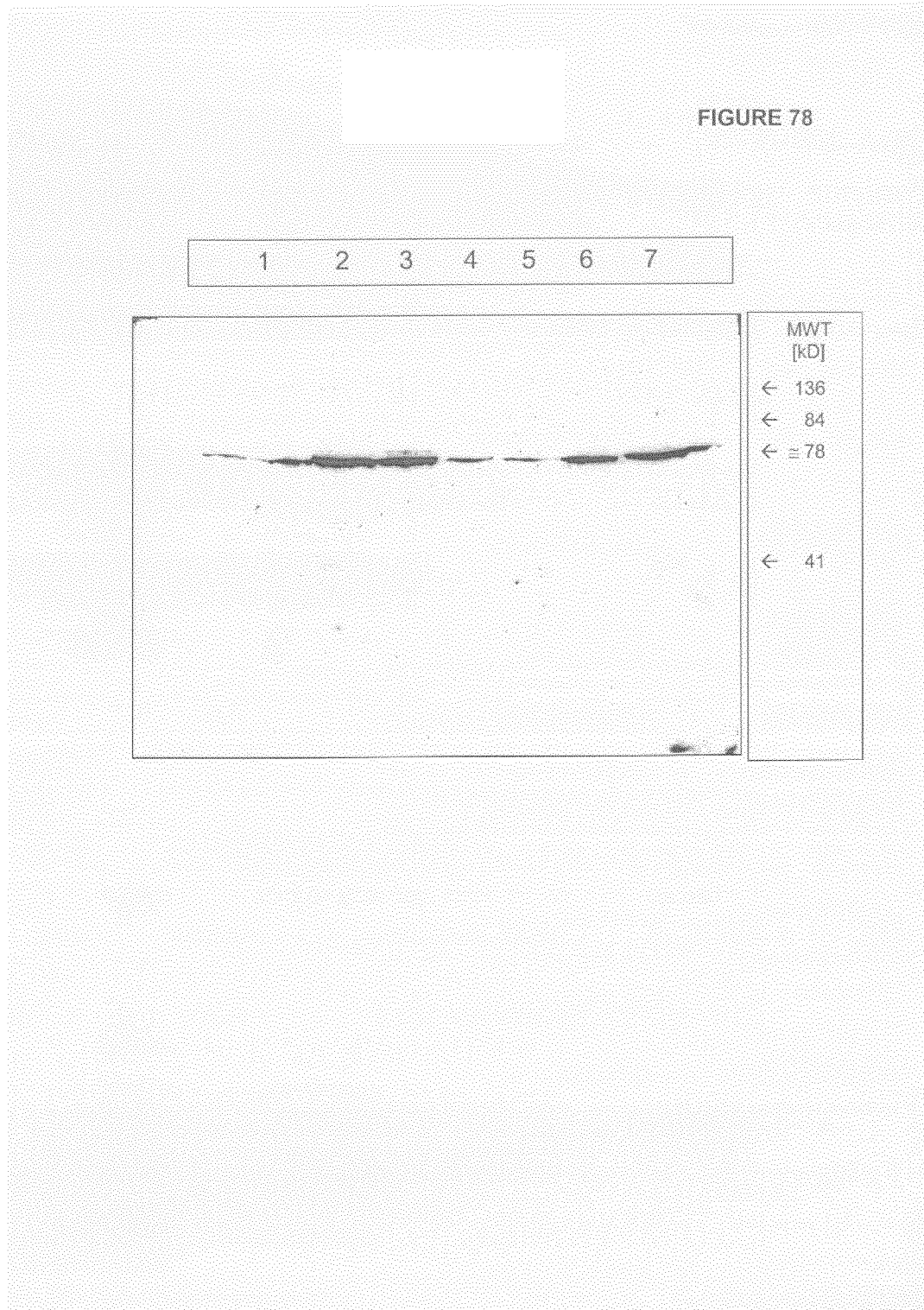
FIG. 78 is a Western blot analysis showing the increase in the production of the MxA protein 48 h after induction by the acylated pseudodipeptides.

DC-9 cells were activated for 0, 2 hr, 4 hr, 24 hr (FIG. 77) or 48 hr. FIG. 78) as follows:

| Assay: culture Sample- medium | | FIG. 77 | | | | FIG. 78 | Location on Western Blot Location on |
|---|---|---|---|---|---|---|---|
| | GMCSF/IL-40 | OH | 2 h | 4 h | 24 h | 48 h | Western Blot |
| 1. | +NaCl (negative control) | 1 | 2 | 3 | 4 | 1 | Location on Western Blot |
| 2. | +LPS (1 µg/ml) | | 5 | 6 | 7 | 2 | Location on Western Blot |
| 3. | +IFN-α (500 U/ml) (positive control) for 89103"M × A protein induction | | 8 | 9 | 10 | 3 | Location on Western Blot Western Blot |
| 4. | +TRANCE (1 ng/ml) | | | | | 4 | Location on Western Blot |
| 5. | +CD40 (1 µg/ml) | | | | | 5 | Location on Western Blot |

| Assay: culture Sample- medium | | FIG. 77 | | | | FIG. 78 | Location on Western Blot Location on |
|---|---|---|---|---|---|---|---|
| | GMCSF/IL-40 | OH | 2 h | 4 h | 24 h | 48 h | Western Blot |
| 6. | +OM-197-MP-AC (1 µg/ml) | | 11 | 12 | 13 | 6 | Location on Western Blot |
| 7. | +OM-197-FV6 (1 µg/ml) | | 14 | 15 | 16 | 7 | Location on Western Blot |

Western Blots shown on FIGS. 77 and 78 illustrate the time-course production of MxA: induction of a significant rise of MxA protein by IL-197-AC5 and OM-197-FV6 products after 24 hr. (FIG. 77) and after 48 hours, respectively (FIG. 78). MxA production noted herein is comparable to the one induced by LPS positive control or α IFN with production level being higher than the level induced by negative control, by TRANCE (a cytokine belonging to the family of α TNF which induces maturation of dendritic cells) or by CD40L (another agent promoting maturation of dendritic cells), respectively.

Compounds according to the invention OM-197-MP-AC and OM-197-FV6 show antiviral properties by virtue of their capacity to induce MxA-protein production

Example 4.6

Determining the Ability of Compounds According to the Invention to Elicit α TNF Production by Human Peripheral Blood Mononuclear Cells

4.6.1. Procedure

Mononuclear cells of peripheral blood are recovered from buffy coats of 6 healthy donors. Such buffy coat cells are resuspended and mononuclear cells are isolated by centrifugation on a Ficoll-Paque gradient (Amersham Pharmacia). Purified mononuclear cells are resuspended into RPMI-1640 medium supplemented with 10% FCS, antibiotics, mercaptoethanol and L-glutamine. Cell concentration is adjusted to $2\times10^6$ viable cells/ml 100 µl of each one of these solutions of acyl dipeptide-like compounds bearing an accessory functional side chain spacer, diluted 100-, 10- or 1-fold in RPMI medium 1640, are dispensed into a microtiter plate. Samples are tested in triplicates, and each microtiter plate includes a negative control made up of plain medium. Dilutions of E. coli LPS (ranging grom 1 to 0.00001 µg/ml) are used as a positive control.

100 µl of the cell suspension are added to each well containing product dilute solutions or control. Cells are incubated with the products for 18 hours in an incubator at 37° C., under 5% $CO_2$ and a moisture saturated atmosphere.

At the end of the incubation period, microtiter plates are centrifuged, and the supernatant fluids are pooled and frozen at −80° C. as aliquots until time of ELISA assay.

Concentration of α TNF secreted by mononuclear cells is determined by chemiluminescent ELISA (QuantiGlo #QTAOO R&D kit). 4-fold supernatant fluid dilutions are dispensed into each well of the microtiter plate to which anti-αTNF antibodies are bound. The microtiter plate is incubated for 4 hours at room temperature. After washing, peroxidase-conjugated anti-human a TNF antibody is added. Following a 2 hour incubation period and thorough washing, a chemiluminescent substrate is added and chemilunescence is read after 20 minutes. α TNF content in the supernatant fluid is determined with respect to a standard curve covering the 7000 to 0.7 pg/ml range.

Results are expressed in pg/ml of α TNF produced. Results derive from an experiment representative of acyl-dipeptide-like compound activity

4.6.2. Results

Induction of α TNF production by acyl dipeptide-like compounds bearing an accessory functional side chain spacer having the general formula I in peripheral blood mononuclear cells

| Product | 100 μg/ml | 10 μg/ml | 1 μg/ml |
|---|---|---|---|
| OM-197-MC | 12 | 0 | 0 |
| OM-197-MC-MP | 72 | 0 | 0 |
| OM-197-FV6 | 88 | 104 | 0 |
| OM-197-FV8 | 252 | 100 | 12 |
| OM-197-MC-FV5 | 116 | 104 | 0 |
| OM-197-MC-FV7 | 76 | 80 | 0 |
| OM-197-MP-AC(R/S, R) | 160 | 156 | 244 |
| OM-197-MP-AC (R, R) | 84 | 88 | 0 |
| OM-197-MC-AC (S, R) | 80 | 124 | 488 |
| OM-197-MC-AC | 144 | 140 | 12 |
| OM-197-N'C2-MC-AC | 0 | 0 | 0 |
| OM-197-N'(C10-20C8)-MC-AC | 0 | 0 | 0 |
| OM-197-MC-Succ | 176 | 96 | 0 |
| OM-197-Lys | 20 | 164 | 284 |
| OM-197-AP | 84 | 116 | 428 |
| OM-197-Asp | 80 | 28 | 0 |
| OM-197-Asp-AC | 132 | 172 | 20 |
| OM-197-Lys-AC | 256 | 184 | 232 |
| OM-197-MC-AC-Succ-AZT | 64 | 224 | 108 |
| OM-197-MC-AC-Succ-d4T | 52 | 40 | 0 |
| OM-197-MC-AC-Succ | 40 | 32 | 0 |

Negative control comprised of RPMI medium induced a baseline α-TNF production below test sensitivity level of 0.7 mg/ml.

Induction of TNF production by *E. coli*. LPS in peripheral blood mononuclear cells.

| | *E. coli* LPS in μg/ml | | | | | |
|---|---|---|---|---|---|---|
| Product | 1 | 0.1 | 0.01 | 0.001 | 0.0001 | 0.00001 |
| TNF-α (pg/ml) | 404 | 436 | 356 | 276 | 132 | 0 |

Positive control made up of *E. coli* LPS elicits high production of αTNF even for the lowest concentrations tested.

Most acyl-dipeptide-like compounds induce substantial α TNF-production even though production level is less than what is seen for the positive control. Greater concentrations are required with respect to LPS to induce a significant production of αTNF.

Certain compounds like OM-197-MC and OM-197-MC-MP induce a significant production level only at a concentration of 100 μg/ml.

Amine functional group is of particular interest for inducing αTNF production as seen on one hand, by increasing amplitude and decreasing minimal product concentration required to induce a significant production on the other.

Short chain acyl-dipeptide-like compounds OM-197-N'C2-MC-AC and OM-197-N'(C10-20C8)-MC-AC do not induce any αTNF production even at a concentration of 100 μg/ml.

Example 4.7

Determining the Capacity of Compounds in Accordance with the Invention to Inhibit α TNF Production in Human Peripheral Blood Mononuclear Cells in Response to *E. coli* Lipopolysaccharide (LPS)

4.7.1. Procedure

Mononuclear cells of peripheral blood are recovered from buffy coats of 6 healthy donors. Such buffy coat cells are resuspended and mononuclear cells are isolated by centrifugation on a Ficoll-Paque gradient (Amersham Pharmacia). Purified mononuclear cells are resuspended into RPMI-1640 medium supplemented with 10% FCS, antibiotics, mercaptoethanol and L-glutamine. Cell concentration is adjusted to $2 \times 10^6$ viable cells/ml.

Product mediated Inhibition is determined by preincubating those products with mononuclear cells, and adding, 1 hour later, serially diluted solutions of LPS capable of inducing α TFN production. Inhibitory concentration of different acyl dipeptide-like products bearing an accessory functional side chain spacer was found to be 10 μg/ml. *E. coli* LPS is serially diluted (10-fold dilution) to be in the range of 1 to 0.00001 μg/ml 50 μl of 10 μg/ml dilute product solutions in RPMI 1640 medium are dispensed into a microtiter plate. Each assay (10 μg/ml product concentration+dilute *E. coli* LPS) is run in triplicates and each microtiter plate includes a negative control comprised of plain medium. LPS-induced α TNF production (without inhibitor) is determined by adding *E. coli* LPS dilutions to RPMI medium.

100 μl of the cell suspension are added to each well containing dilutions of either product or control. Cells are incubated with the products for 1 hour in an incubator at 37° C., under 5% $CO_2$ and a moisture saturated atmosphere.

At the end of the pre-incubation period, 50 μl of serially diluted solutions of *E. coli* LPS are added. Incubation of mononuclear cells with the product and LPS is extended for 18 hours. At the end of the cell activation period, the microtiter plates are centrifuged, and the supernatants are pooled and frozen at −80° C. as aliquots until time of ELISA assay.

Concentration of αTNF secreted by mononuclear cells is determined by chemiluminescent ELISA (QuantiGlo # QTAOO R&D kit). 4-fold dilutions of supernatant fluid are dispensed into each well of the microtiter plate to which anti-human αTNF antibodies are bound. The microtiter plate is incubated for 4 hours at room temperature. After washing, peroxidase-conjugated anti-human αTNF antibody is added. Following a 2 hour incubation period and a thorough washing, a chemiluminescent substrate is added and chemilunescence is read after 20 minutes. αTNF content in the supernatant fluid is determined with respect to a standard curve covering the 7000 to 0.7 pg/ml range.

Inhibition is characterized by the *E. coli* LPS concentration which elicits 50% production of α TNF during co-incubation in comparison to a control including only RPMI. This concentration increases as product inhibition activity becomes stronger. Knowing inhibition values of α TNF production, this concentration is given by calculating 100-(αTNF production induced by product and LPS)/(αTNF production induced by LPS alone)*100. From these inhibition data, concentration is determined by linear regression along the line segment which joins 2 LPS dilutions giving approx. 50% inhibition.

Product ability to inhibit α TNF production in mononuclear cells in response to LPS is further characterized by maximum inhibition. LPS concentration corresponding to this maximum inhibition level (inhibition>95%) is also representative of product inhibitory potency. Results are calculated from a representative experience using all products.

4.7.2. Results

Inhibition of α TNF production in response to LPS in human mononuclear cells by acyl dipeptide-like compounds bearing an accessory functional side chain spacer having the general formula I

| Products | 50% inhibition LPS in μg/ml | max. Inhibition in % | max. Inhibition LPS in μg/ml |
|---|---|---|---|
| OM-197-MC | 1 | 100 | 0.0043 |
| OM-197-MC-MP | 0.19 | 100 | 0.001 |
| OM-197-FV6 | >1 | 100 | 0.014 |
| OM-197-FV8 | >1 | 100 | 0.0033 |
| OM-197-MC-FV5 | >1 | 100 | 0.016 |
| OM-197-MC-FV7 | >1 | 100 | 0.00035 |
| OM-197-MP-AC (R/S, R) | >1 | 100 | 0.00002 |
| OM-197-MP-AC (R, R) | 0.68 | 100 | 0.0013 |
| OM-197-MP-AC (S, R) | >1 | 100 | 0.00002 |
| OM-197-MC-AC | 0.88 | 100 | 0.00003 |
| OM-197-N'C2-MC-AC | 0.0003 | 100 | 0.00001 |
| OM-197-N'(C10-20C8)-MC-AC | 0.0009 | 85 | <0.00001 |
| OM-197-MC-Succ | 1 | 100 | 0.018 |
| OM-197-Lys | 0.70 | 100 | 0.0055 |
| OM-197-AP | >1 | 100 | 0.016 |
| OM-197-Asp | >1 | 100 | 0.00036 |
| OM-197-Asp-AC | 0.29 | 100 | 0.0058 |
| OM-197-Lys-AC | >1 | 100 | 0.001 |
| OM-197-MC-AC-Succ-AZT | 0.45 | 100 | 0.0005 |
| OM-197-MC-AC-Succ-d4T | 0.64 | 100 | 0.00016 |
| OM-197-MC-AC-Succ | >1 | 100 | 0.044 |

Negative control comprised of RPMI medium induced a baseline α-TNF production below test sensitivity level of 0.7 mg/ml.

All acyl-dipeptide-like compounds are able to induce inhibition of TNF production in response to *E. coli* LPS. Product concentration required to achieve this inhibition depends on the particular accessory functional side chain spacer and length of fatty acid chains. Even acyl-dipeptide-like compounds coupled to a drug by an ester bond are able to induce such an inhibition.

Example 4.8

Determining Capacity of Compounds in Accordance with the Invention to Activate of NK Cell Cytotoxicity Against Target Cells of K562 Cell Line

4.8.1. Procedure

PBMC were recovered from buffy coats according to the procedure previously described in example 4.6. Briefly stated, after centrifugation over a Ficoll gradient and 3 washing steps, PBMC were divided into a 6-well plate at a density of $3 \times 10^6$ cells/ml in 3 ml of RPMI containing 10% FCS and incubated either in medium alone or stimulated with γ IFN (1000 U/ml), LPS (1 μg/ml), OM-197-AC5 (1 μg/ml), or OM-197-FV6 (1 μg/ml). Cells were incubated under such conditions for 24 hours. K562 cells (human leukemia cell line, ATCC #CCL 243, 20110-2209 Manassas (Va.), U.S.A.) were maintained in culture using RPMI medium containing 10% FCS and subjected to 2 passages per week.

In order to make cytotoxicity measurement, PBMC and K562 cells were washed twice in HBSS and resuspended in Phenol Red-free RPMI medium containing 5% FCS. PBMC were divided into a round bottom 96-well plate so as to achieve a PBMC/target ratio of 20/1, 10/1 and 5/1 in 50 μl volume. 5000 K562 cells (target) were added in each well using 50 μl of Phenol Red-free RPMI. Final volume was 100 μl. The plate was centrifuged to promote contact then incubated at 37° C. for 4 hours.

Cytotoxicity was assayed using a non radioactive CytoTox 96 kit based on measuring LDH release during cell lysis (kit #G1780, batch #124100, Promega, Madison, Wis.) according to the supplier's instructions.

The percentage of cytotoxicity was calculated according to the following equation:

$$\% \text{ cytotoxicity} = \frac{O.D.(K562 + PBMC) - O.D.PBMC + O.D.K562.\text{alone}}{O.D.(K562.\text{total.lysis}) - O.D.K562.\text{alone}} \times 100$$

4.8.2. Results

Compounds OM-197-AC5 and OM-197-FV6 induce an NK activity level which is comparable or slightly inferior to that induced by LPS when tested at the same concentration (1 μg/ml).

| Stimulus | Ratio PBMC:K562 | Optical density at 490 nm PBMC alone | Optical density at 490 nm K562 + PBMC | % cytotoxicity |
|---|---|---|---|---|
| Medium | 20.1 | 0.141 | 1.5 | 0.5 |
|  | 10.1 | 0.073 | 1.55 | 7.7 |
|  | 5.1 | 0.055 | 1.4 | 0 |
| IFN-γ | 20.1 | 0.101 | 2.1 | 39.3 |
|  | 10.1 | 0.064 | 1.9 | 29.4 |
|  | 5.1 | 0.035 | 1.68 | 17.9 |
| LPS | 20.1 | 0.17 | 2.2 | 42 |
|  | 10.1 | 0.122 | 1.9 | 26 |
|  | 5.1 | 0.035 | 1.7 | 19 |
| OM-197-MP-AC | 20.1 | 0.084 | 1.8 | 22 |
|  | 10.1 | 0.084 | 1.66 | 13.7 |
|  | 5.1 | 0.027 | 1.5 | 7.4 |
| 4OM-197-MC-FV6 | 20.1 | 0.11 | 2.1 | 38.8 |
|  | 10.1 | 0.087 | 1.65 | 12.9 |
|  | 5.1 | 0.079 | 1.4 | 0 |
| Controls | plain culture medium | K562 alone | K562 full lysis |  |
| Optical density at 490 nm |  | 0.048 | 1.35 | 3 |

Example 4.9

Determining the Capacity of Compounds in Accordance with the Invention to Induce Lymphocyte Proliferation in Mice

4.9.1. Experiment Outline

Spleenic cells derived from a group of 4 naive CBA mice are pooled, cultured in quadriplicate either in absence or presence of OM-197-MP-AC adjuvant (0.1 to 10 μg/ml). Cell proliferation response is assessed by measuring triturated thymidine ($^3$H-TdR) take-up after 1 or 2 days of culture. Values reported in the table stand for the arithmetic mean±standard deviation of 4 cultures.

Adjuvants: OM-197-MP-AC stock solution is prepared at a concentration of 0.9 mg/ml in water for injection to which 0.1% triethanolamine is added.

Results

OM-197-MP-AC product triggers spleenic cell proliferation in vitro. This effect which is seen to be at a peak level after one day of culture, results in a 5-fold increase of thymidine take-up at a concentration of 1 μg/ml and a 12-fold increase of thymidine take-up at a concentration of 10 μg/ml After one day of culture, OM-197-MP-AC product, at a concentration of 1 μg/ml, exerts a powerful mitogenic effect of the same magnitude as Concanavalin A at 5 μg/ml. (see Table 1).

TABLE 1

Measuring proliferation response of murine spleenic cells to OM-197-MP-AC adjuvant

| Adjuvant | $^3$H-TdR take-up (CPM × $10^{-3}$) Incubation time (days) | |
|---|---|---|
| | 1 | 2 |
| No adjuvant | 6.4 ± 1.0 | 14.3 ± 0.8 |
| OM-197-MP-AC (μg/ml) - 0.1 | 8.7 ± 0.7 | 21.1 ± 1.3 |
| 1 | 34.3 ± 2.6 | 55.6 ± 5.2 |
| 10 | 79.0 ± 12 | 92.7 ± 8.8 |

Data reported in the above table stand for mean±SD of take-measurements for quadriplicate cultures. (5 μg/ml) concanavaline A used as a positive control results in a thymidine take-up of 37.5±6.2×$10^3$ cpm after one day of culture.

Example 4.10

Determining Antiviral Activity of Compound Conjugates in Accordance with the Invention Obtained Through Coupling to AZT and d4T as a Prodrug 4.10.1. Procedure T MT-4 lymphocyte cell line which had been transformed into a continuous cell line by an HTLV infection, a virus associated with one form of leukemia, was used to test the antiviral activity (anti-HIV) of AZT- and d4T-conjugated compounds according to the invention, respectively. A characteristic feature of such cells is lack of survival following an HIV infection. The test is based on protection provided by the product (like AZT) against this viral destructive effect. Products were tested in serially diluted solutions in a 96-well plate. In the upper portion of the microplate, products were tested by incubation at various concentrations with cells and virus (in triplicate), so as to determine the concentration of product which affords cell protection against the viral destructive effect. IC$_{50}$ of the product is taken as the concentration where a 50% loss of viable cell count is recorded. Viable cell count was done with MTT, a yellow tetrazolium compound which undergoes enzymatic reduction (at the mitochondrial level in viable cells) into a purple colored formazan compound. Wells containing viable cells are purple in colour, whereas dead cells give a persistent yellow color. Measurement of optical density (O.D.) allows this effect to be quantified.

Cytotoxicity of a given product is assessed in the same manner in the lower portion of the plate where the test is conducted by incubating serially diluted products over virus-free cells, to thereby determine the toxic effect of products on cells. The result is given as CC$_{50}$, i.e. the concentration at which 50% of cells are dead due to product toxicity. Selectivity (selectivity index, SI) of a given product is defined as a CC$_{50}$/IC$_{50}$ ratio. This parameter is of great importance since the selectivity index of a fairly efficient product is high.

4.10.2. Results

Conjugates obtained by coupling products according to the invention to AZT (OM-197-LC-succ-AZT) or d4T have antiviral activities directed against HIV 1 IIIB and HIV 2 ROD. Results of two experiments (run in triplicates) on MT-4 cells are given below:

| Product | HIV strain | IC$_{50}$ (μM) | CC$_{50}$ (μM) |
|---|---|---|---|
| AZT | HIV-1 IIIB | 0.0029 | 187 |
| OM-197-MC-Succ-AZT | HIV-1 IIIB | 0.0519 | >94 |
| D4T | HIV-1 IIIB | 0.107 | 321 |
| OM-197-MC-Succ-d4T | HIV-1 IIIB | 0.963 | +/−97 |
| AZT | HIV-2 ROD | 0.0018 | 187 |
| OM-197-MC-Succ-AZT | HIV-2 ROD | 0.061 | >94 |
| D4T | HIV-2 ROD | 0.22 | 321 |
| OM-197-MC-Succ-d4T | HIV-2 ROD | 0.51 | +/−97 |

AZT or d4T-conjugated inventive compounds display antiviral activities in this MT-4 cell model. One advantage of such prodrugs lies on one hand in that conjugates have a lipid structure which makes it possible to target compounds to the infected cells by releasing antiviral substances into the virus reservoir and in their ability to regulate the immunological activity of target cells on the other.

Example 4.11

Determining Ability of Compounds in Accordance with the Invention to Activate Maturation of Murine Predendritic Cells into Dendritic Cells 4.11.1. Procedure Preparation of Dendritic Cells The marrow was aspirated from the femur and tibia bones of (C57Bl/6, 6 to 8 week-old) mice. The marrow suspension was screened through a 70 μm cell sieve in order to obtain a single cell suspension. Marrow cells were resuspended into Isocove's modified Dulbecco medium (IMDM) supplemented with 10% of heat inactivated foetal calf serum (iFCS) and antibiotics. Cells were incubated overnight at 37° C., under CO$_2$ and a moisture saturated atmosphere, inside 6-well microtiter plates. Next day (day 0), non adherent cells were collected and washed. Viable cells were counted by trypan blue dye exclusion test. Cell concentration was adjusted to 2×10$_5$ cells/ml in IMDM containing ng/ml of murine recombinant GM-CSF and 20 ng/ml of murine recombinant IL-4 (rmIL-4) and plates were further incubated. On the 3$^{rd}$ day, there were added freshly prepared mGM-CSF and rmIL-4 at a concentration of 10 ng/ml. On the 6$^{th}$ day, non adherent cells were collected, washed and counted by trypan blue dye exclusion. Cell concentration was adjusted to 2×10$^5$ cells/ml in IMDM containing 10 ng/ml of rmGM-CSF and rmIL-4, and plates were further incubated. On the 8$^{th}$ day, non adherent cells made up of both mature and immature dendritic cells (CD-DM) were collected and used in product co-incubation experiments.

Incubation with products according to the invention: CD-DM were incubated at a concentration of $5 \times 10^5$ cells/ml in 24-well microtiter plates in presence of the following activators: *Esherichia coli* strain 0111:B4 LPS as positive control, IMDM as negative control; as well as 2 compounds in go accordance with the invention: OM-197-MC-FV5 and OM-197-PM-AC at a concentration of 0.1, 1 and 10 μg/ml. After a 48 hour incubation period, cells were collected and stored for flow cytometry analysis Flow cytometry analysis CD-DM were washed with PBS containing 2% iFCS and 0.01% sodium azide (FACS buffer). Then, cells were incubated on ice for 30 minutes with optimal concentrations of anti-CD86 antibody; anti-CD40 antibody, FITC conjugated anti-MCHII antibody, and peroxidase-conjugated anti-CD80 antibody. Then, cells were washed 3 times. Labeling of anti-CD86 and anti-CD40 antibodies was performed by incubating cells on ice for 30 minutes with peroxidase-conjugated donkey anti-rat immunoglobulins. Following incubation, cells were washed and resuspended into FACS medium. Fluorescence was measured with the aid of FACScan® flow cytometry. 15000 pulse events were analyzed per sample. Cells which had been incubated with the conjugate alone were used as a negative control.

14.11.2. Results

Cell Expression

| | | Surface Markers | | | | | | |
|---|---|---|---|---|---|---|---|---|
| | | CD40 | | C80 | | CD86 | | MHCII |
| μg/ml | MFI | % cells | MFI | % cells | MFI | % cells | MFI | % cells |
| OM-197-MC-FV5  10 | 630 | 54 | 97 | 48 | 4097 | 51 | 1681 | 48 |
|  1 | 517 | 44 | 84 | 45 | 3888 | 43 | 1691 | 43 |
|  0.1 | 442 | 33 | 66 | 42 | 3437 | 37 | 1689 | 40 |
| OM-197-MC-AC  10 | 605 | 55 | 97 | 53 | 4162 | 52 | 1622 | 49 |
|  1 | 493 | 48 | 73 | 47 | 3791 | 45 | 1607 | 45 |
|  0.1 | 446 | 34 | 66 | 41 | 3504 | 37 | 1597 | 38 |
| LPS 0.1 | 539 | 51 | 95 | 51 | 3445 | 50 | 1546 | 51 |
| Negative control 0 | 431 | 29 | 74 | 41 | 3011 | 34 | 1553 | 41 |

MFI: Mean fluorescence intensity

Products in accordance with the invention are capable of inducing maturation of predendritic cells into dendritic cells. These results obtained in vitro are consistent with observations made in mice in vivo.

In vivo, i.v. and s.c. administration of OM-197-MP-AC at a concentration of 20 μg and 5 μg per mouse, respectively, induce maturation and migration of dendritic cells into the spleen, from the marginal zone (located between red and white pulp) to the white pulp where T cells are found. Immunostaining of histological slides taken from spleen of animals treated with products of the invention reveal colocalization of mature dendritic cells and T cells in the white cortex, as is seen with LPS treatment, whereas in untreated animals, no migration and maturation are observed.

5th Series of Examples

Pharmacological Study of Compounds in Accordance with the Invention (In Vivo)

Example 5.1

Assessing Properties of Dipeptide-Like Compounds Bearing an Accessory Functional Side Chain Spacer in Admixture or Coupled with (NANP)$_6$P$_2$P$_{30}$ (SEQ ID NO:2) in a Murine Immunization Model 5.1.1. Experimental Procedure Antigen: (NANP)$_6$P$_2$P$_{30}$ (SEQ ID NO:2) peptide comprises a recurrent (NANP) (SEQ ID NO:12) sequence of *Plasmodium falciparum* and two sequences of tetanus toxin (P$_2$: 830-843 and P$_{30}$: 947-967). This peptide is known as a T helper epitope and has shown its capacity to induce a strong prolonged immune response in presence of common adjuvants. Such a peptide has been obtained by synthesis means according to a method disclosed in the literature (Valmori et al., 1992, *J. Immunol.*, 149: 717-721). Antigen stock solution is prepared at a concentration of 0.4 mg/ml in a 0.9% NaCl/water mixture at pH 8.0.

Adjuvants: Stock solutions of dipeptide-like compounds (OM-197-MP, OM-197-FV6 and OM-197-MC) are prepared at a concentration of mg/ml in 0.9% NaCl-water, to which 0.1% triethanolamine is added. The positive control is comprised of Incomplete Freund's Adjuvant (IFA from Difco, Detroit, Mich., U.S.A.) with the negative control being a 0.9% NaCl/water solution.

Throughout this experimental procedure, the antigen and adjuvant are formulated in the form of a mixture or conjugates as previously described. Two types of conjugates (OM-197-FV)$_n$-(NANP)$_6$P$_2$P$_{30}$ (SEQ ID NO:2) were tested. The extent of coupling of such products is variable, i.e. 1, 2 or 3 molecules of OM-197-FV may be found on a single peptide molecule (mixture of mono-, bi- and triconjugates, n=1, 2, and 3, respectively), i.e., 1 molecule of OM-197-FV per one peptide molecule (monoconjugate, n=1).

Immunization schedule: 6-week old female BALB/c mice (6 mice per group) are immunized twice, with a subcutaneous shot in the tail end containing 0.1 ml. Amounts administered are 20 μg of antigen plus 50 μg of adjuvant during the first shot and 10 μg of antigen plus 50 μg of adjuvant during the second shot. In case of conjugates, the antigen portion is critical in determining the injected dose. 18

Table Listing of Experimental Groups:

| Group | Adjuvant | Antigen | Number of mice |
|---|---|---|---|
| 1 | | NaCl | 6 |
| 2 | | (NANP)$_6$P$_2$P$_{30}$ (SEQ ID NO: 2) | 6 |
| 3 | IFA + | (NANP)$_6$P$_2$P$_{30}$ (SEQ ID NO: 2) | 6 |
| 4 | OM-197-FV6 + | (NANP)$_6$P$_2$P$_{30}$ (SEQ ID NO: 2) | 6 |
| 5 | OM-197-MC + | (NANP)$_6$P$_2$P$_{30}$ (SEQ ID NO: 2) | 6 |
| 6 | | (OM-197-FV)$_{1,2,3}$-(NANP)$_6$P$_2$P$_{30}$ (SEQ ID NO: 2) | 6 |
| 7 | | OM-197-FV-(NANP)$_6$P$_2$P$_{30}$ (SEQ ID NO: 2) | 6 |

-continued

| Group | Adjuvant | Antigen | Number of mice |
|---|---|---|---|
| 8 | OM-197-MP + OM-197-(FV(NANP)$_6$P$_2$P$_{30}$ SEQ ID NO: 2) | | 6 |

Immunization and Sampling Schedule:

| | Weeks | | |
|---|---|---|---|
| | 0 | 3 | 5 |
| Immunization shots (N$^b$) | ↑ (1) | ↑ (2) | |
| specific antibody response | ↑ | | ↑ |

Blood Sampling:
Serum Preparation:

Blood sampling is conducted at weeks 0 & 5. Blood is allowed to stand for 60 min. at 37° C., and then is kept overnight at 4° C. Serum is subsequently frozen at −80° C. until time of antibody assay.

5.1.2. Determination of Anti-(NANP)$_6$P$_2$P$_{30}$ IgG Antibody Titer

Assay of IgG antibodies specifically raised against (NANP)$_6$P$_2$P$_{30}$ (SEQ ID NO: 2) antigen is performed by an ELISA technique. Binding of antigen is done in 96-well microtiter plates (Maxisorp F96, Nunc, DK) by conducting an overnight incubation in a moist chamber at 4° C. with each well containing 0.1 ml of PBS (phosphate buffered saline) containing 0.001 mg/ml (NANP)$_6$P$_2$P$_{30}$ (SEQ ID NO: 2) antigen. Blocking of the microtiter plate is performed with PBS containing 1% of bovine serum albumin (BSA, Fluka, Switzerland). Plates are washed with PBS containing 0.05% Tween 20 (Sigma, St. Louis, Mo., U.S.A.). Serum samples collected at 5 weeks are serially diluted with dilution buffer (PBS containing 2.5% of skimmed milk powder and 0.05% of Tween 20), then transferred into a microtiter plate and allowed to stand for 1 hr. at room temperature (RT). Plates are then washed with PBS. A dilute solution containing mouse polyclonal anti-immunoglobulin G antibody coupled to alkaline phosphatase (Sigma, St. Louis, Mo., U.S.A.) is then dispensed into those plates and incubated for 1 hr. at RT. Plates are washed with PBS and specific antibodies are revealed by a color reaction involving addition of an alkaline phosphatase substrate, p-nitrophenylphosphate (Sigma, St. Louis, Mo., U.S.A.). Absorbance at 405 nm is read with a microtiter plate reader (Dynatech 25000 ELISA reader, Ashford, Middlesex, UK), each serum sample is measured in duplicate. Results stand for the mean of all absorbance measurements at 405 nm relating to mice in each group.

5.1.3. Results: Specific Response

Figure 79:
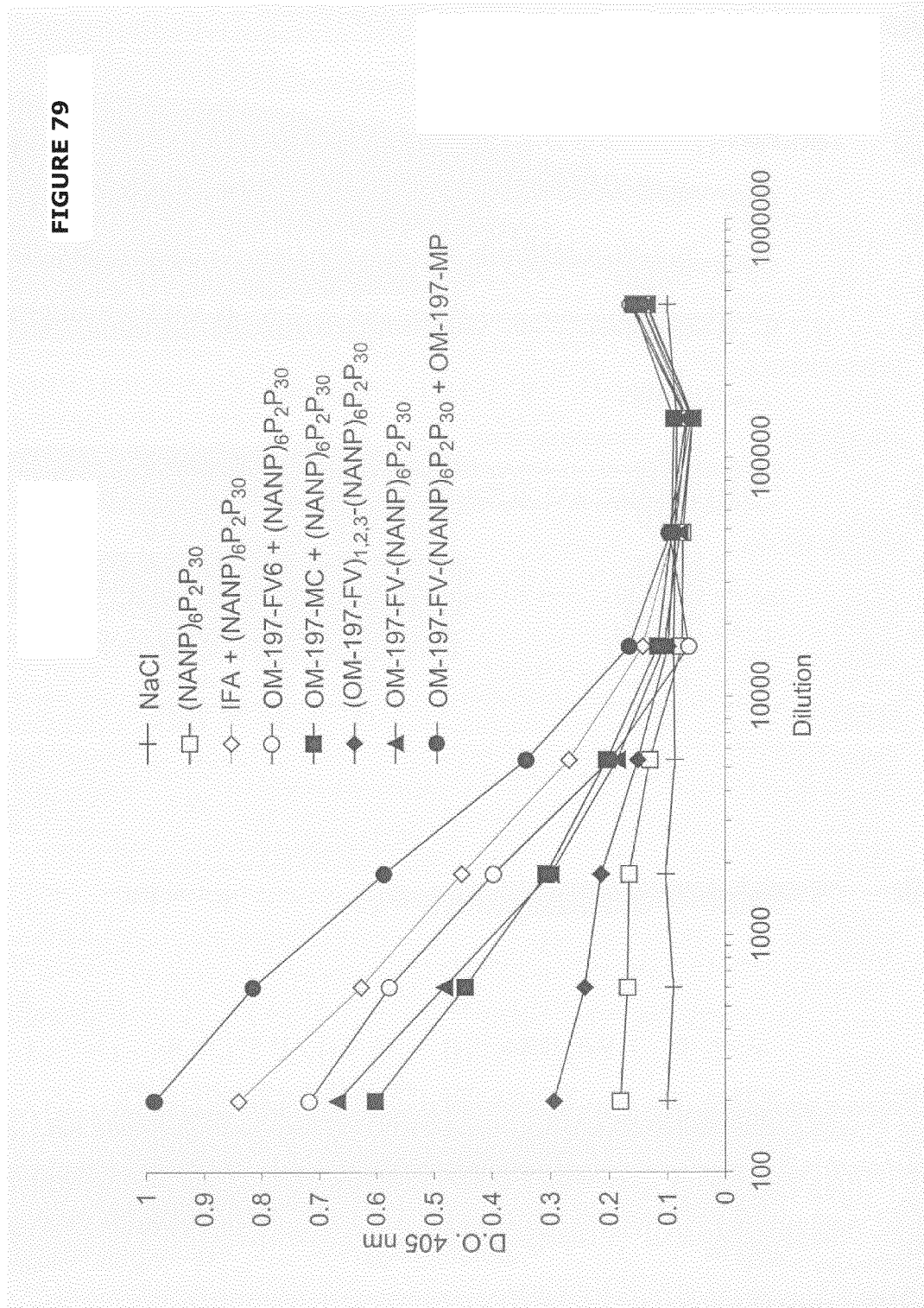
FIG. 79 are graphs showing the specific production of anti (NANP)$_6$P$_2$P$_{30}$ IgG antibody in mice having received two immunizations of a mixture antigen and adjuvant.

Production of IgG antibodies specifically directed to (NANP)$_6$P$_2$P$_{30}$ (SEQ ID NO:2) antigen, as determined by ELISA, is graphically shown for mice administered one, two and three immunization shots (FIG. 79)

Two shots of an antigen+adjuvant mixture (OM-197-FV or OM-197-MC) induce a serologic response which is greatly superior to the one observed when injecting antigen alone. Immunization with the OM-197-FV-(NANP)$_6$P$_2$P$_{30}$ (SEQ ID NO:2) monoconjugate induces an IgG response which is slightly greater than the one obtained with the antigen+OM-197-FV6 mixture. Higher coupling rate for (OM-197-FV)$_{1,2,3}$-(NANP)$_6$P$_2$P$_{30}$ (SEQ ID NO: 2) does not improve the serologic response directed to this antigen. The mixture containing OM-197-MP adjuvant and OM-197-FV-(NANP)$_6$P$_2$P$_{30}$ (SEQ ID NO: 2) monoconjugate does result in a significantly higher serologic response against this antigen that exceeds values obtained for the positive control consisting of (NANP)$_6$P$_2$P$_{30}$ (SEQ ID NO: 2)+IFA.

Figure 80:
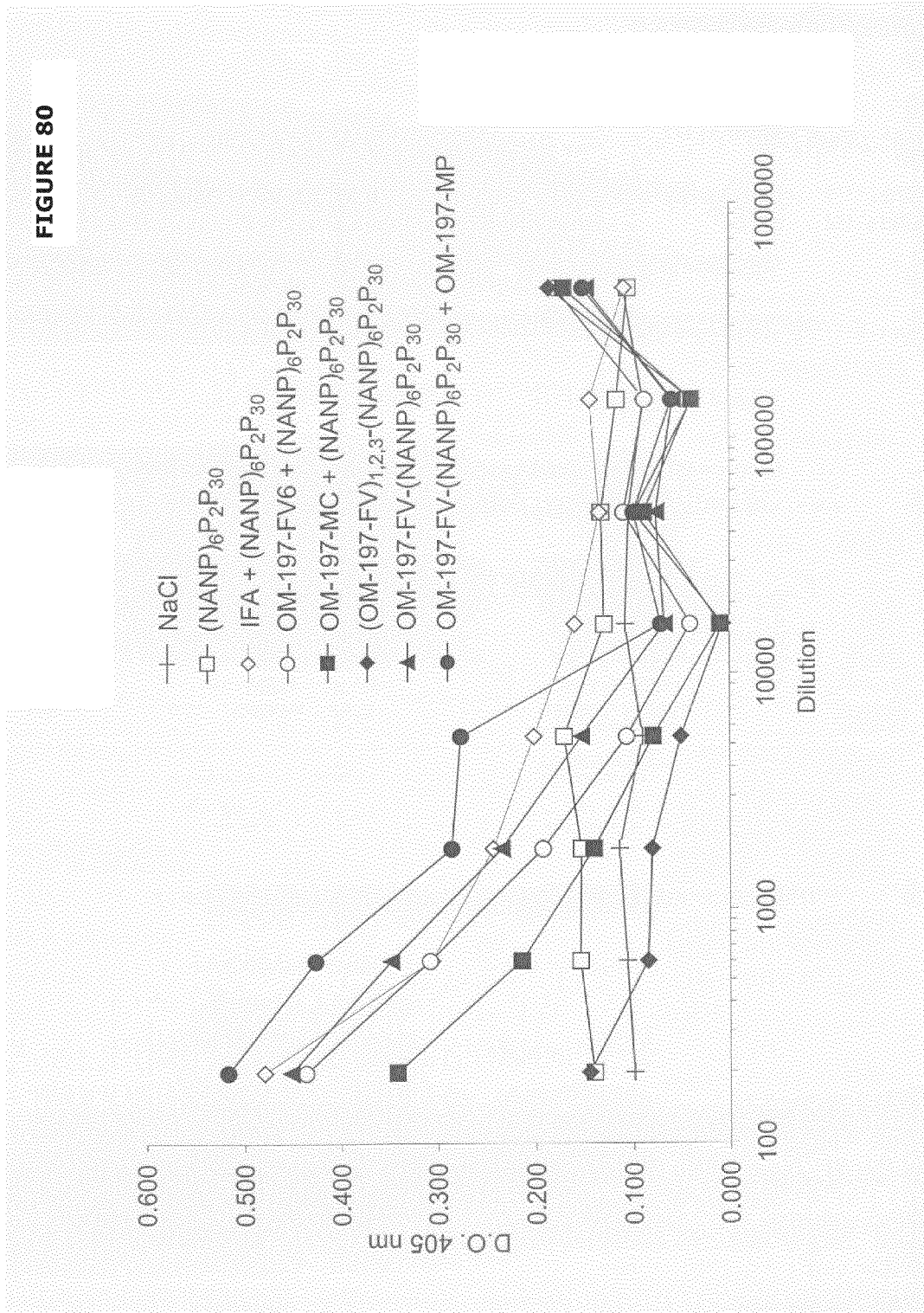
FIG. 80 is graphs showing the serological antibody response after injection of the various N-acylated pseudo-dipeptides conjugated or in mixture with peptide (NANP)$_6$P$_2$P$_{30}$.

Similar results are obtained when the antibody is captured by an ELISA technique using (NANP)$_6$NA (SEQ ID NO: 13) peptide as antigen (FIG. 80).

Example 5.2

Ovalbumin Immunization Group: Determining Specific Antibodies Raised in Mice Following 1 and 2 Subcutaneous Injections

5.2.1. Experiment Outline

This study is aimed at comparing the serologic response induced by injecting an adjuvant+antigen mixture (OM-197-MP+ovalbumin) with the one elicited by a conjugate based on the same antigen (OM-197-FV-ovalbumin). To this end, 30 BALB/c mice (females, aged 8 weeks at the beginning of treatment) were divided into 3 groups as follows

| Groups | Adjuvant-antigen 25 μgprot/animal/injection | Adjuvant (unbound) 50 μg/animal/injection | Injected volume μl |
|---|---|---|---|
| A | Ovalbumin | — | 200 |
| B | Ovalbumin | OM-197-MP | 200 |
| C | OM-197-FV-Ovalbumin | — | 200 |

Solutions:
Group A: A stock solution of antigen alone (ovalbumin, Fluka AG, Buchs, Switzerland) was prepared at a concentration of 125 μg/ml in H$_2$O+0.01% thiomersal.
Group B: Stock solution of an antigen+adjuvant mixture (ovalbumin+OM-197-MP) contains 125 μg/ml of ovalbumin and 250 μg/ml of OM-197-MP in H$_2$O+0.01% thiomersal.
Group C: Stock solution of OM-197-FV-ovalbumin conjugate at a concentration of 125 μg/ml of protein in H$_2$O+0.01% thiomersal.

Preparation of Injection Solutions: Each Stock Solution is incubated for 15 minutes at 37° C., then an adequate volume of NaCl (14%) is systematically added to each solution to obtain an isotonic solution (0.9% NaCl). The whole mixture is vortexed for 3 minutes.

Immunization schedule: Injections are scheduled at days 0 and 14. The solutions are administered subcutaneously (100 μl at 2 different sites, with a total of 200 μl per animal). Blood sampling occurred at days 14 and 28 (retro-orbital puncture).

Assay for anti-ovalbumin immunoglobulins: The following serum Immunoglobulins which are specifically directed against ovalbumin were assayed in duplicate by ELISA: IgG1, IgG2a, and IgM. Briefly stated, microtiter plates (NUNC Immunoplate, Roskilde, DK) were incubated (overnight coating) at 4° C. together with 100 μl ovalbumin (0.5 μg) in bicarbonate buffer pH 9.6). After washing with 0.5% Tween-20 (Merck Hohenbrunn, D), sera were diluted 50-, 200- and 800-fold (diluting solution: phosphate buffered saline (PBS)+1% bovine serum albumin (BSA, Sigma, St. Louis, Mo., U.S.A.)+0.02% Tween-20)). 100 μl of each dilute serum sample were added to the wells. Incubation lasted 45 minutes at 37° C.

After a second washing step, IgG1, IgG2a and IgM specifically directed to ovalbumin were incubated for 30 minutes at 37° C. together with 100 μl of anti-IgG1 antibodies (anti-mouse rat antibody)-peroxidase conjugate (Serotec, Oxford, UK), IgG2a-peroxidase conjugate (Pharmingen, San Diego, Calif., U.S.A.) and IgM-biotin conjugate (Pharmingen, San Diego, Calif., U.S.A.), diluted beforehand in PBS/BSA/Tween buffer (250-, 1000-, 500-fold dilutions, respectively). For IgM, after an extra washing step, a $3^{rd}$ incubation step was required (30 min. at 37° C.) with a 1:100 dilute solution of streptavidin-peroxidase conjugate (Dako, Glostrup, DK).

After the washing step, 100 μl of a phenylene 1,2-diamine solution (OPD, Merck, Darmstadt, GFR) were added to detect peroxidase-coupled anti-IgG1 secondary antibodies whereas for IgG2a and IgM, the reagent used was 3',3',5',5'-tetramethylbenzidine (TMB, Sigma, St. Louis, Mo., U.S.A.). After a 20 minute incubation period at room temperature, the reaction was stopped by adding 100 μl of $2NH_2SO_4$. Absorbance values were read at 490 nm with a Bio-Rad 3550 model plate reader.

5.2.2. Results

Figure 81:
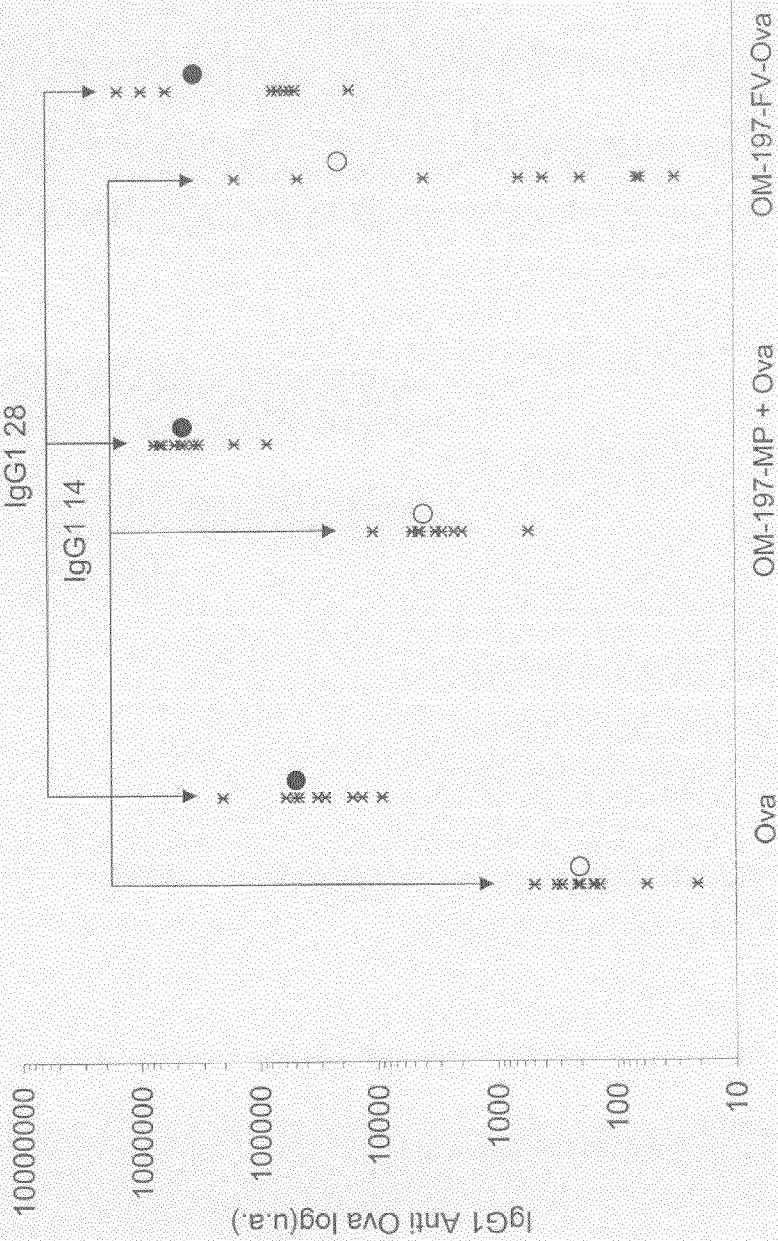
FIG. 81 shows the induction of anti-ovalbumine IgG1 antibody 14 days and 28 days after injection of ovalbumine, of the mixture of ovalbumine and OM-197-MP, and of the conjugate OM-197-FV-Ova.
Figure 82:
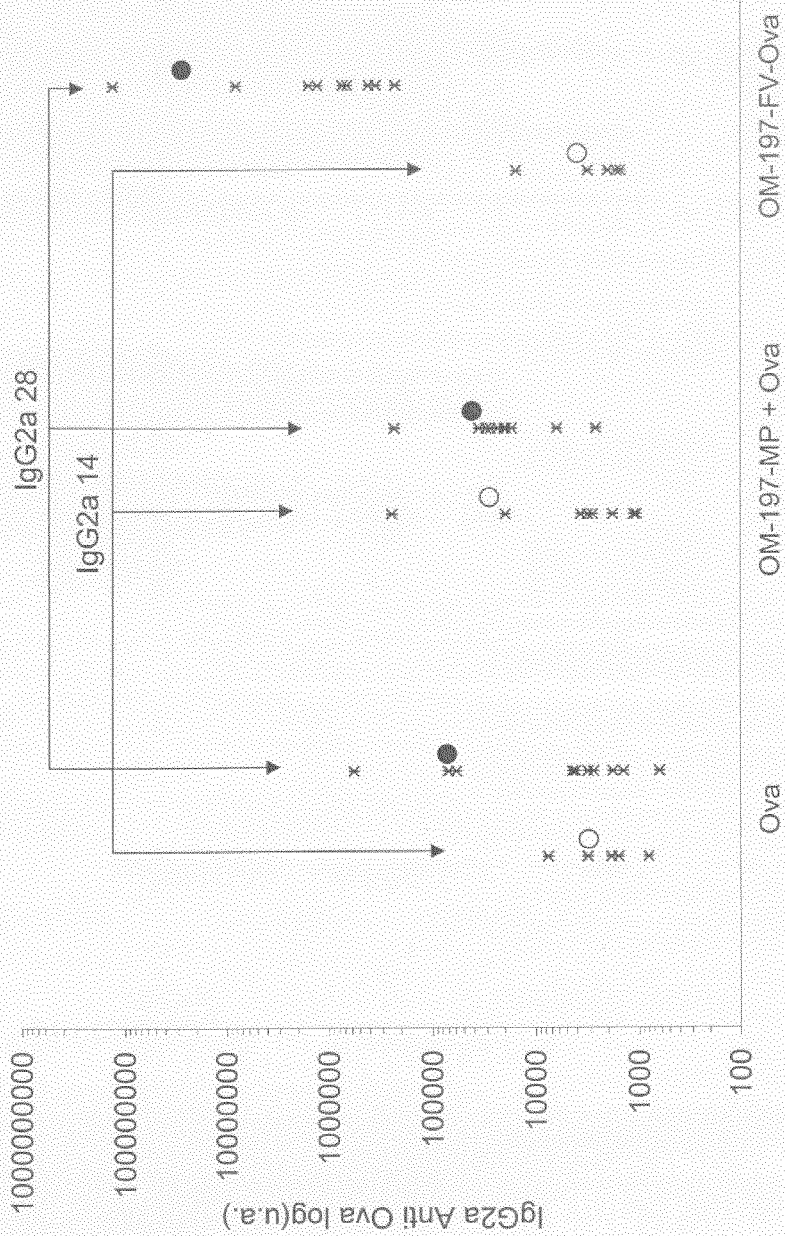
FIG. 82 shows the induction of anti-ovalbumine IgG2a antibody 14 days and 28 days after injection of ovalbumine, of the mixture of ovalbumine and OM-197-MP, and of the conjugate OM-197-FV-Ova.
Figure 83:
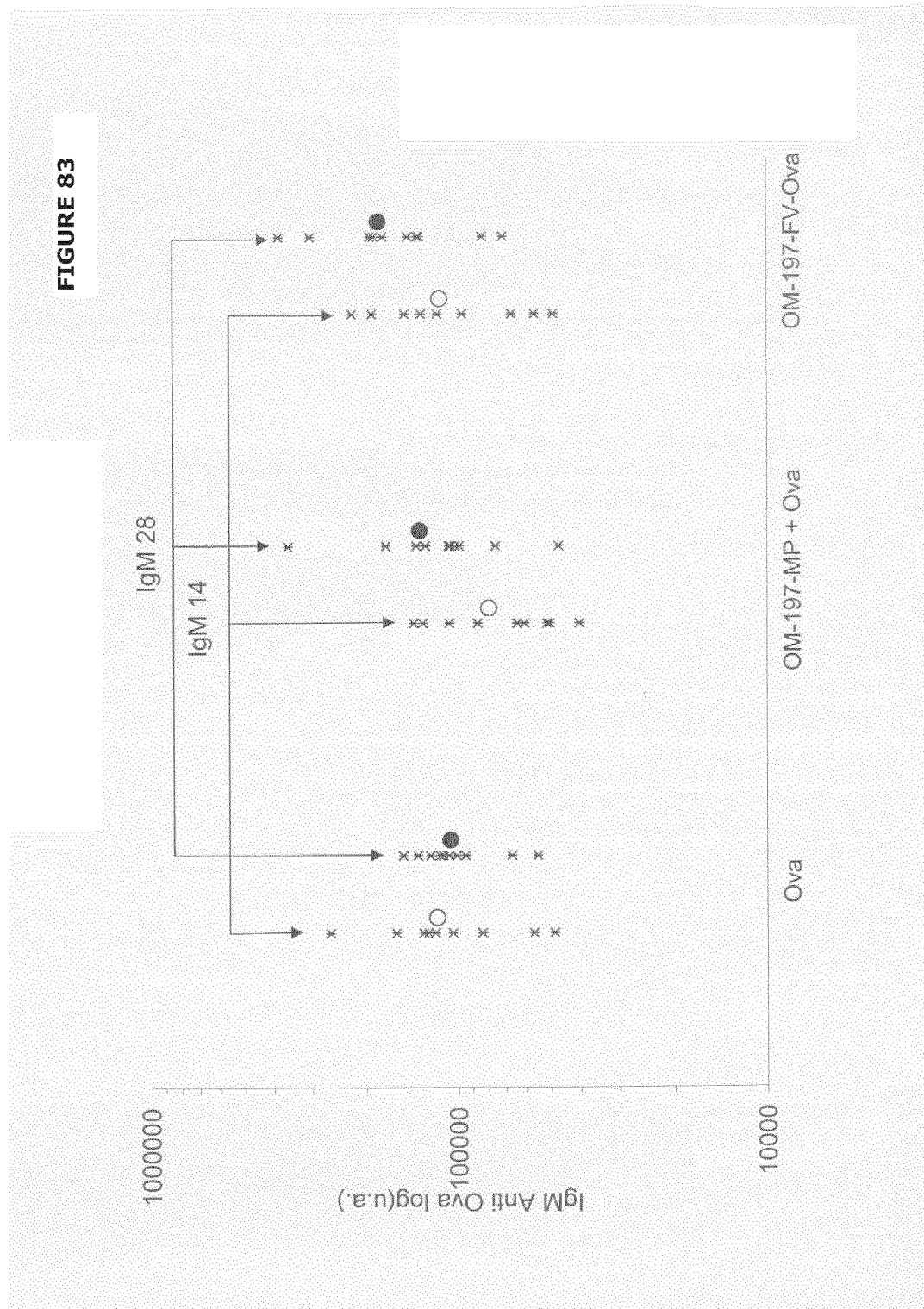
FIG. 83 shows the induction anti-ovalbumine IgM antibody 14 days and 28 days after injection of ovalbumine, of the mixture of ovalbumine and OM-197-MP, and of the conjugate OM-197-FV-Ova.

Results of each 490 nm reading are given in arbitrary units (A.U.) per ml. This is achieved by comparing each sample with a standard sample prepared from different dilutions of a sample pool collected from group A at 28 days (animals injected with ovalbumin alone). As clearly understood by this term, the sample pool diluted 50-fold is at a concentration of 1000 A.U./ml. Individual results are then corrected for the corresponding dilution factor (50-, 200-, or 800-fold) and are shown at FIGS. 81, 82 and 83. Void circles correspond to the mean value at 14 days while black circles correspond to the mean value at 28 days; Ova stands for ovalbumin in short.

These results indicate that the OM-137-FV-ovalbumin conjugate is a particularly effective immunogen in the model under study, since it increases significantly the titer of specific antibody to ovalbumin in mice after the second injection, irrespective of the immunoglobulin subclass being analyzed (IgG1, IgG2a and IgM). In particular, there is a striking increase of anti-ovalbumin IgG2a (FIG. 84) which suggests that a TH1 immune reaction is favoured.

Ovalbumin+OM-197-MP non covalent mixture gives rise to an IgG2a response lower than what is seen with the conjugate.

Example 5.3

H1N1 Hemagglutinin Immunization Group: Determining Specific Antibodies Raised in Mice Following 1 and 2 Subcutaneous Injections

5.3.1. Experiment Outline

This study is designed to compare the serologic response induced by injecting an adjuvant+antigen mixture (OM-197+H1N1) to that elicited by a conjugate based on the same antigen (OM-197-FV-H1N1). To this end, 30 BALB/c mice (females, 8 weeks-old at the beginning of treatment) are divided into 3 groups as follows:

| Groups | Adjuvant-antigen H1N1 2.5 μg/animal/injection | Adjuvant (unbound) 50 μg/animal/injection | Injected volume μl |
|---|---|---|---|
| A | H1N1 | — | 100 |
| B | H1N1 | OM-197-MP (50 μg) | 100 |
| C | OM-197-FV-H1N1 | — | 100 |

5.3.2. Preparation of Injection Solutions

Group A: The stock solution of H1N1 (A/Beijing 262/95 hemagglutinin, Solvay Duphar, Weesp, NL) is prepared at a concentration of 25 μg/ml in $H_2O$.

Group B: The stock solution of H1N1+OM-197-MP contains 25 μg/ml of H1N1 and 500 μg/ml of OM-197-MP in $H_2O$.

Group C: The stock solution of OM-197-FV-H1N1 (H1N1 covalently bound to OM-197-FV) is at a concentration of 25 μg/ml in $H_2O$).

Each stock solution is incubated for 15 minutes at 37° C. and 135 μl of (14%) NaCl are then added to 2 ml of each solution. The whole mixture is vortexed for 3 minutes.

5.2.3. Injection Schedule and Anti-H1N1 Immunoglobulin Assay

Injections are scheduled on days 0 and 14. Solutions are administered subcutaneously (50 μl at 2 different sites, with a total of 100 μl per animal). Blood sampling is scheduled on day 14 (retro-orbital puncture).

IgM antibodies specifically directed to H1N1 were assayed in duplicate by ELISA. Briefly stated, microtiter plates (NUNC Immunoplate, Roskilde, DK) were incubated (overnight coating) at 4° C. with 100 μl H1N1 (0.5 μg) in bicarbonate buffer (pH 9.6). After washing with 0.5% Tween-20 (Merck Hohenbrunn, D), sera were diluted 50-, 200-, and 800-fold (diluting solution: phosphate buffered saline (PBS)+1% bovine serum albumin (BSA, Sigma, St. Louis, Mo., U.S.A.)+0.02% Tween-20)). 100 μl of each dilute serum sample were added to the wells. Incubation lasted 45 minutes at 37° C.

After a second washing step, IgM specifically directed to H1N1 are incubated for 30 minutes at 37° C. together with 100 μl of anti-IgM antibody (rat anti-mouse antibody)-biotin conjugate (Pharmingen, San Diego, Calif., U.S.A.), diluted beforehand in a Tween buffer (500-fold dilution). After an extra washing step, a $3^{rd}$ incubation period is required (30 min. at 37° C.) with a 1:100 dilute solution of streptavidin-peroxidase conjugate (Dako, Glostrup, DK).

After the washing step, 100 μl of a 3',3',5',5'-tetramethylbenzidine solution (TMB, Sigma, St. Louis, Mo., U.S.A.) are added to detect peroxidase-coupled anti-IgM secondary antibodies. After a 20 minute incubation period at room temperature, the reaction is stopped by adding 100 μl of $2NH_2SO_4$. Absorbance values are read at 490 nm with a Bio-Rad 3550 model plate reader.

5.3.4. Results

Results of each 490 nm reading are given in arbitrary units (A.U.) per ml. This is achieved by comparing each sample with a standard prepared from variable dilutions of a sample pool collected from group A (animals injected with H1N1 alone) at 28 days. As the term implies, the sample pool diluted 50-fold is at a concentration of 1000 A.U./ml. Individual results are then corrected for the corresponding dilution factor (50, 200, or 800-fold) and are shown on FIG. 84: black circles correspond to the mean value at 28 days.

Mice immunized with an OM-197-FV-H1N1 conjugate show an anti-H1N1 IgM antibody titer greater than control consisting either of H1N1 antigen alone, or of an OM-197-MP+H1N1 mixture.

Example 5.4

Evaluation of the Adjuvant Properties of OM-294-MP-AC in a Mouse Immunization Model by Subcutaneous Administration of *Leishmania* LmCPb Antigen 5.4.1. Experiment Outline CBA mice were administered through the tail a single subcutaneous injection (100 μl) of *Leishmania* parasite LmCPb antigen (3 μg per mouse)±adjuvant. Two groups of 6 mice each were formed and received the following treatments: antigen alone (control group) and antigen+50 μg OM-197-MP-AC respectively. Eleven days after injection, inguinal and periaortic lymph node cells (2 groups of 3 mice each) were cultured in triplicate in presence of purified LmCPb antigen or whole extract of the parasite (amastigote). At day 4, a supernatant sample is withdrawn and stored at −20° C. for IL-4 and γ IFN assay. Finally, tritiated thymidine ($^3$H-TdR) is added to the cultures to measure the proliferation reaction.

Cytokine assay is carried out by a sandwich ELISA assay (OptEIA®) kits for γ IFN and IL-4, BD, PharMingen, Basel, Switzerland) and the proliferation response is determined by measuring thymidine take-up ($^3$H-TdR). $^3$H-TdR take-up given in cpm as the arithmetic mean value±standard deviation (8 pools of 3 mice each) and IL-4 concentration given in pg/ml are individually reported for each pool of 3 mice as the arithmetic mean of two measurements (cytokine assay).

Antigen:

An LmCPb stock solution is prepared at a concentration of 150 μg/ml in PBS

Adjuvants: The stock solution of OM-294-MP-AC is prepared at a concentration of 0.9 mg/ml in water for injection, with addition of 0.1% triethanolamine.

Antigen-adjuvant mixture: Adjuvant preparation (4 volumes), which had been adjusted to an adequate final concentration in sterile PBS, is mixed just prior to injection with the antigen stock solution (1 volume).

5.4.2. Results

In CBA mice immunized with *Leishmania* LmCPb antigen, a single 50 μg dose of OM-197-MP-AC is sufficient to induce an increase (2 to 6-fold) in lymph node cell proliferation as measured in vitro in response to purified antigen (in the range of 0.6 to 15 μg/ml) or a whole extract of amastigote stage parasite (in the range of 2 to 50×10$^{-6}$/ml). These results are reported in Table 1. Furthermore, treatment of mice by OM-197-MC-AC reveals substantial quantities of IL-4 in the supernatant fluid of lymph node cell cultures challenged with the parasite antigen (see Table 2) whereas γ IFN production was undetected (<100 pg/ml).

TABLE 1

In vitro Proliferation response of lymph node lymphocytes in CBAmice immunized with LmCPb: Effect of OM-197-MP-AC adjuvant alone or in combination with CpG-DNA

| | | triturated thymidine take-up (CPM) | |
|---|---|---|---|
| In vitro challenge | | Without adjuvant | OM-197-MP-AC |
| No challenge | | 0.7 ± 0.2 | 0.7 ± 0.1 |
| LmCPb (μg/ml) | 15 | 2.8 ± 0.8 | 7.0 ± 0.7 |
| | 5 | 1.6 ± 0.4 | 3.0 ± 1.1 |
| | 1.7 | 1.1 ± 0.3 | 1.9 ± 0.5 |
| | 0.6 | 0.9 ± 0.2 | 1.3 ± 0.5 |
| Amastigotes (×10$^{-6}$/ml) | 50 | 5.1 ± 1.4 | 32.6 ± 5.2 |
| | 17 | 2.8 ± 1.0 | 12.6 ± 2.5 |
| | 6 | 1.1 ± 0.6 | 5.3 ± 1.5 |
| | 2 | 0.9 ± 0.4 | 1.6 ± 0.3 |
| Con A (μg/ml) | 5 | 124.3 ± 48.9 | 208.5 ± 56.0 |

Values reported in this table stand for the arithmetic mean ± standard deviation of take up measurements conducted on two pools of lymph nodes (3 mice per pool; triplicate cultures of each pool)

TABLE 2

In vitro IL-4 production by CBA mouse lymphocytes challenged with LmCPb: Effect of OM-197-MP-AC adjuvant alone or in combination with CpG-DNA

| | | IL-4 production (pg/ml) | |
|---|---|---|---|
| In vitro challenge | | Without adjuvant | OM-197-MP-AC |
| No challenge | a | <8 | <8 |
| | b | <8 | <8 |
| LmCPb (μg/ml) | a | <8 | 12 |
| | b | <8 | 13 |
| Amastigotes (×10$^{-6}$/ml) | a | <8 | 55 |
| | b | <8 | 70 |
| | a | <8 | 29 |
| | b | <8 | 28 |
| Con A (μg/ml) | a | 117 | 103 |
| | b | 168 | 102 |

Values reported in this table stand for the arithmetic mean ± standard deviation 2 cytokine measurements conducted on 2 pools of lymph node cell supernatant fluids (a & b; 3 mice per pool) cultured in triplicates.

Conclusion

OM-294-MP-AC adjuvant potentiates specific T response in vitro in CBA mice which have been immunized with LmCPb (an abundant protease during the amastigote stage of the *Leishmania* parasite) as assayed by lymphocyte proliferation in vitro. Moreover, this adjuvant promotes development of anti-LmCPb lymphocytes which secrete substantial quantities of IL-4.

Example 5.5

Evaluation of the Properties of Acyl-Dipeptide-Like Compounds Bearing an Accessory Functional Side Chain Spacer Either Coupled or in Admixture with Synthetic Peptides Derived from the Circumsporozoite Protein of *Plasmodium yoelii* (PyCS-252-260) in a Murine Immunization Model This experiment is aimed at evaluating the capacity of acyl dipeptide-like compounds bearing an accessory side chain spacer when grafted or in admixture with a PyCS 252-260 synthetic peptide derived from the circumsporozoite protein of *Plasmodium yoelli*, to induce a humoral or cell mediated immune response specifically directed against this peptide

5.5.1. Experimental Procedure

Formulation of antigens with adjuvants: Synthetic peptide PyCS 252-260 corresponding to the T cell epitope of circumsporozoite protein of *Plasmodium yoelli* has the following sequence SYVPSAEQI (SEQ ID NO: 1) (Table 1). Peptide 2 MR99B (SERSYVPSAEQI) (SEQ ID NO: 5) was obtained by adding SER amino acids to the N-terminal end and peptide 1 MR99A (KGGKGGKSERSYVPSAEQI) (SEQ ID NO: 11) was obtained by adding lysine-glycine-glycine amino acids to the N-terminal end of the previously disclosed MR99B (SEQ ID NO: 5) peptide. Peptides were obtained by solid phase synthesis (F-moc, according to the Merrifield and Atherton synthesis method (Atherton et al., Bioorg Chem., 8: 350-351, 1979) using reagents and solvents purchased from Bachem Feinchemikallien (Buddendorf, Switzerland), Novabiochem (Laufelfingen, Switzerland) and Fluka (Buchs, Switzerland). Peptides were purified by reverse phase HPLC.

Mono- and polypeptide conjugates with acyl dipeptide-like compounds bearing an accessory side chain spacer (OM-197-MC-FV)$_4$ peptides were obtained as described above in Example 3.6. ([OM-197-MC-FV) and Example 3.5. (OM-197-MC-FV-peptide 2). Final sterile solutions of the peptide conjugates were freeze-dried.

Mouse immunization regimen: Antigen dose corresponds to 20 μg of peptide 2 per mouse and per injection (Table 2). Before injection, freeze-dried preparations are taken up into 0.9% NaCl, vortexed for 3 min. and sonicated for 10 min. at 50° C. Formulations incorporating IFA are prepared by mixing one volume of antigen (14.5 μg of peptide PyCS 252-260 plus 50 μg of P30 (universal T cell epitope) in PBS) and one volume of adjuvant.

4-week old BALB/c mice (Harlan, Zeist, NL) received one subcutaneous shot in the tail end. Formulations are injected with a 23" gauge needle using a final volume of 50 μl. Animals received a second shot of antigen at the beginning of the 5$^{th}$ week and a third shot during the 9$^{th}$ week. 23.

TABLE 1

Antigens

| Synthetic peptides | Sequences | Molecular mass | Dose/shot (μg) |
| --- | --- | --- | --- |
| Peptide 1 | KGGKGGKSERSYVPSAEQI (SEQ ID NO: 11) | 1978.2 | 29.0 |
| Peptide 2 | SERSYVPSAEQI (SEQ ID NO: 5) | 1365.5 | 20 |
| PyCS 252-260 | SYVPSAEQI (SEQ ID NO: 1) | 993.1 | 14.5 |

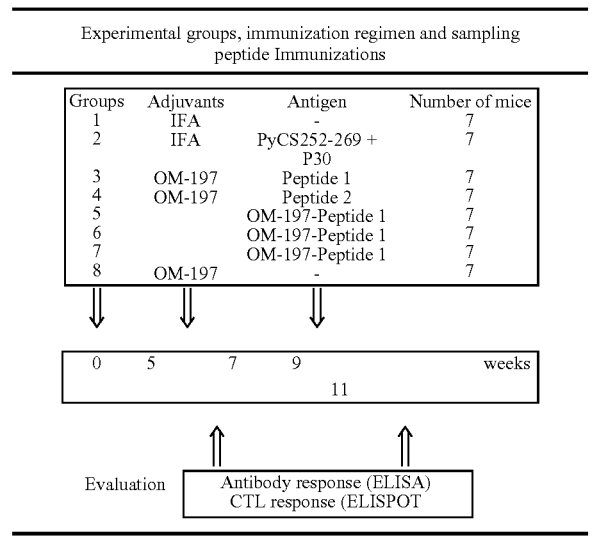

TABLE 2

Experimental groups, immunization regimen and sampling peptide Immunizations

| Groups | Adjuvants | Antigen | Number of mice |
| --- | --- | --- | --- |
| 1 | IFA | - | 7 |
| 2 | IFA | PyCS252-269 + P30 | 7 |
| 3 | OM-197 | Peptide 1 | 7 |
| 4 | OM-197 | Peptide 2 | 7 |
| 5 | | OM-197-Peptide 1 | 7 |
| 6 | | OM-197-Peptide 1 | 7 |
| 7 | | OM-197-Peptide 1 | 7 |
| 8 | OM-197 | - | 7 |

Lymphoid Organ and Blood Sampling:

Serum sampling: Blood sampling is performed on all mice after 7 and 11 weeks. Blood is allowed to stand for 6 min. at 37° C., then is kept overnight at 4° C. Serum is subsequently frozen at −80° C. until time of antibody assay.

Recovery of inguinal lymph nodes and spleen: Two animals belonging to each group are killed after 7 and 11 weeks, respectively. Inguinal lymph nodes and the spleen are surgically removed and the cells are cultured to assay CTL activity by ELISPOT (γ IFN response)

Determination of Anti-Peptide 1 Antibody Titer

Assay of antibodies specifically raised against peptide 1 (KGGKGGKSERSYVPSAEQI) (SEQ ID NO: 11) is performed by ELISA. Binding of antigen is done in 96-well microtiter plates (Maxisorp F96, Nunc, DK) by conducting an overnight incubation in a moist chamber at 4° C. with each well containing 0.05 ml of PBS (phosphate buffered saline) containing 0.001 mg/ml of peptide 1. Plates are washed with PBS-0.05% Tween 20 (Sigma, St-Louis, Mo., U.S.A.) (PBS-T) and blocking of the plate is made with 5% skimmed milk in PBS-T for 1 hour at room temperature. Individual serum samples (A, B, C, D, E, F, G) of mice taken at weeks 9 and 11 are serially diluted with dilution buffer (PBS containing 2.5% of skimmed milk powder and 0.05% of Tween 20), then transferred into the microtiter plate and allowed to stand for 1 hr. at room temperature (RT). Plates are then washed with PBS and a diluted solution containing goat polyclonal anti-mouse immunoglobulin antibody coupled to alkaline phosphatase (Sigma, St. Louis, Mo., USA) is then dispensed into those plates and incubated for 1 hr. at RT. Plates are washed with PBS and specific antibodies are revealed by a color reaction through adding the alkaline phosphatase substrate, p-nitrophenylphosphate (Sigma, St. Louis, Mo., USA). Absorbance at 405 nm is read with a microtiter plate reader (Dynatech 25000 ELISA reader, Ashford, Middlesex, UK), each serum sample is measured in duplicate. Results stand for the mean of all measurements relating to mice in each group. The antibody titer is given by the highest dilution resulting in a significantly positive response, i.e. an OD greater to background noise level±3SD.

γ-IFN ELISPOT Assay

Antibodies specifically directed to murine γ-interferon (O1E703B2) are bound by running an overnight incubation at 4° C. in a moist chamber, adding an antibody solution at 50

μg/ml in an ELISPOT microtiter plate with the well bottom being covered by nitrocellulose (Millipore, Molsheim, France). The blocking step is effected by adding DMEM medium (Life Technologies, Grand Island, N.Y., U.S.A.) containing 10% of foetal calf serum (FCS, Fakola, Switzerland) and letting stand for 2 hours at 37° C. Cells obtained from lymphoid organs (inguinal lymph nodes and spleen) are cultured in microtiter plates at a density of 200 000 or 400 000 cells/well, then co-cultured during 24 hours at 37° C. with 100 000 antigen presenting cells (which had been primed with PyCS 252-260 peptide at 37° C. for 1 hr. and irradiated (10 Krad) and washed 3 times) or in presence of Concanavalin A as control. After incubation, cells are removed and following the washing step, a second anti-mouse γ IFN antibody-biotin complex (ANI, 2 μg/ml in PBS with 1% BSA) is added and incubated for 2 hr. A streptavidin-alkaline phosphatase conjugate (Boehringer Mannheim, Mannheim, GFR) diluted 1000-fold is added and incubated for 1 hr at 37° C., and thereafter 3 washings are effected with PBS containing 0.05% Tween 20, followed by 3 washings with PBS. Presence of anti-γ IFN immune complexes is demonstrated by adding BCIP/NBT substrate (Sigma, St. Louis, Mo., U.S.A.). This reaction is stopped by washing with tap water. Spots which are positive for γ IFN are then counted under a Biosys GmbH model automatic reader (Karben, Germany). Specific spot count is the difference between spots counted in presence of cells primed with the peptide and spots counted in absence of peptide. Results are given as mean measurement values recorded for mice in each group. They are expressed as the number of spots per million of cultured cells.

Results

The antibody response is depicted on FIG. 85 (2 weeks after the $2^{nd}$ shot) and on FIG. 86 (2 weeks after the $3^{rd}$ shot). After 2 immunization shots, positive responses are observed in 5 out of 7 animals for group 5 (animals previously immunized with peptide 1 coupled to 4 units of acyl-dipeptide-like compound through an accessory side chain spacer). In this group, the percentage of responsive mice increases following the $3^{rd}$ injection since mice B and D show a moderate but significant antibody titer.

Group 3 immunized with the same peptide in admixture with the same adjuvant does not show any significant antibody titer. A nascent response is observed after 3 immunizations shots in group 7 (peptide 2 monoconjugate supplemented with free OM-197 adjuvant). Other groups which were administered the short peptide or no peptide did not display any antibody response.

In conclusion, OM-197-peptide 2 tetraconjuguate is capable of inducing a low to moderate titer antibody response in all immunized mice Cell activity assay is based on the frequency of CTL secreting γIFN, specifically directed to PyCS 252-260 epitope. Results are recorded in Table 3. The positive control is represented by group 2 and the negative control is represented by adjuvant alone (groups 1 and 8). Cell stimulation control based on Concanavalin A is positive for all mice.

Groups 5 (tetraconjugate) and 7 (monoconjugate+adjuvant) show positive CTL responses.

In conclusion, the peptide conjugated to 4 molecules of acyl dipeptide-like compound (OM-197-peptide 1) is effective whereas the monoconjugate (OM-197-peptide 2) induces no CTL response. By contrast, the monoconjugate supplemented with free OM-197 does induce a CTL response, whereas it does not elicit an antibody response, which fact is probably due to the small size of peptide 2 (12 amino acids).

TABLE 3

CTL Response to PyCS 252-260 peptide

| | | CTL number per million of splenic cells | |
|---|---|---|---|
| GROUP | Adjuvant . . . Antigen | After $2^{nd}$ injection | After $3^{rd}$ injection |
| 1 | IFA (Freund's incomplet adjuvant) | 0.0 ± 0.0 | 0.2 ± 0.2 |
| 2 | IFA + PyCS 252-260 + P30 | 36.9 ± 2.7 | 4.4 ± 6.2 |
| 3 | OM-197 + Peptide 1 | 0.0 ± 0.0 | 0.7 ± 1.0 |
| 4 | OM-197 + Peptide 2 | 0.0 ± 0.0 | 0.0 ± 0.0 |
| 5 | OM-197 – Peptide 1 | 11.3 ± 12.4 | 36.9 ± 25.6 |
| 6 | OM-197 – Peptide 2 | 0.0 ± 0.0 | 0.6 ± 0.9 |
| 7 | OM-197 + OM-197-Peptide | 28.8 ± 7.1 | 20.0 ± 14.1 |
| 8 | OM-197 | 0.0 ± 0.0 | 0.6 ± 0.9 |

Example 5.6

Assessing Pyrogenicity of Acyl-Dipeptide-Like Compounds in the Rabbit Model

This experiment is aimed at determining the highest concentration of acyl-dipeptide-like compound bearing a grafted accessory side chain spacer which does not induce fever in rabbits administered an iv. injection of the compound.

Procedure:

15 New Zealand white rabbits are divided into the following groups:

Group 1: 1.0 mg/kg
Group 2: 0.1 mg/kg
Group 3: 0.01 mg/kg
Group 4: 0.001 mg/kg
Group 5: water for injection On the day of testing, rabbits are tightly held and weighed in boxes designed for this purpose. Temperature probes are inserted in the rectum are 1 hour after probe insertion, temperatures (preinjection) are recorded for 90 minutes and the mean value is calculated.

Each rabbit is then administered an i.v. injection of product or control (sterile water in 0.9% NaCl) via the marginal (lateral) ear vein. Temperature is measured at 30 minute intervals for 3 hours. Difference between the preinjection average temperature and maximum temperature is calculated and reported.

Taking 3 rabbits per group, test products are considered non pyrogenic if the sum of 3 responses does not exceed 1.15° C., or else pyrogenic if said sum exceeds 2.650° C. If the result obtained lies in-between, the test is repeated with 3 more rabbits.

Results

The results of pyrogenicity testing conducted on OM-197-MC-MP and OM-197-MC-MP compounds are reported hereinafter:

| OM-197-MC-MP dose | response in ° C. average (individual values) | Results |
|---|---|---|
| 1 mg/Kg | 3.40 (1.50, 0.60, 1.30) | pyrogenic |
| 0.1 mg/Kg | 2.00 (1.45, 0.05, 0.50) | non pyrogenic (1 high value recorded) |

| OM-197-MC-MP dose | response in °C. average (individual values) | Results |
| --- | --- | --- |
| 0.01 mg/Kg | 0.65 (0.00, 0.45, 0.20) | non pyrogenic |
| 0.001 mg/Kg | 0.35 (0.10, 0.05, 0.20) | non pyrogenic |
| Control | 0.20 (0.20, 0.00, 0.00) | non pyrogenic |

| OM-197-MC-MP dose | response in °C. average (individual values) | Results |
| --- | --- | --- |
| 1 mg/Kg | 3.25 (1.25, 1.45, 0.55) | pyrogenic |
| 0.1 mg/Kg | 2.85 (1.10, 1.20, 0.55) | pyrogenic |
| 0.01 mg/Kg | 0.35 (0.20, 0.15, 0.00) | non pyrogenic |
| 0.001 mg/Kg | 0.25 (0.00, 0.10, 0.15) | non pyrogenic |
| Control | 0.40 (0.25, 0.05, 0.10) | non pyrogenic |

Compounds in accordance with the invention are non pyrogenic at doses below 0.1 mg/kg.

What is claimed is:

1. An immunomodulatory composition comprising N-acyl-dipeptide-like adjuvant bearing an acid group in neutral or charged state, at one end portion of said dipeptide-like adjuvant and bearing an accessory functional side chain spacer at the other end portion thereof, having the general formula I:

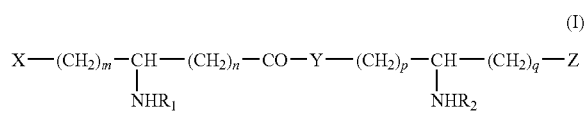

$$X-(CH_2)_m-\underset{NHR_1}{CH}-(CH_2)_n-CO-Y-(CH_2)_p-\underset{NHR_2}{CH}-(CH_2)_q-Z \quad (I)$$

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from a group consisting of hydroxyl, alkyl, alkoxy, acyloxy, amino, acylamino, acylthio and $(C_{1-24})$ alkylthio groups, subscripts m, n are integers ranging from 0 to 10,
subscripts p, q are integers ranging from 1 to 10,
Y designates O or NH, and wherein one of X or Z designates an acid group either in neutral or charged state selected from the a group consisting of
carboxyl,
carboxy [$(C_{1-5})$alkoxy],
carboxy [$(C_{1-5})$alkylthio],
phosphono [$(C_{1-5})$alkoxy],
phosphono [$(C_{1-5})$alkylthio],
dihydroxyphosphoryloxy[$C_{1-5}$)alkoxy],
dihydroxyphosphoryloxy[$C_{1-5}$)alkylthio],
dihydroxyphosphoryloxy,
hydroxysulfonyloxy,
hydroxysulfonyl[$(C_{1-5})$alkoxy],
hydroxysulfonyl [$(C_{1-5})$ alkylthio],
hydroxysulfonyloxy [$(C_{1-5})$alkoxy],
hydroxysulfonyloxy [$(C_{1-5})$alkylthio],
[carboxy($C_{1-5}$)alkyl]aminocarbonyl,
[dicarboxy($C_{1-5}$)alkyl]aminocarbonyl,
[ammonio($C_{1-5}$)alkyl]aminocarbonyl, and
{carboxy[amino($C_{1-5}$)alkyl]aminocarbonyl,
and the other X or Z designates an accessory functional side chain spacer having the formula (II)

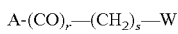

$$A\text{-}(CO)_r\text{---}(CH_2)_s\text{---}W \quad (II)$$

wherein A designates either O, S or NH,
subscript r is an integer equal to 0 or 1,
subscript s is an integer ranging from 1 to 10, and
W is selected from a group consisting of
Formyl,
acetyl,
cyano,
halogeno,
amino,
bromo- or iodo-acetamido,
acylamido,
diacylimido,
sulfhydril,
alkylthio,
hydroxyl,
1,2-dihydroxyethyl,
alkoxy,
acyloxy,
vinyl,
ethynyl,
free carboxyl,
esterified carboxyl or in the form of a mixed anhydride, amide or hydrazide,
azido, and
thiocyano,
provided that one of substituents X or Z designates said accessory functional side chain spacer, and the pharmaceutically acceptable salts, enantiomers and diastereomers of the N-acyl-dipeptide-like adjuvant.

2. The immunomodulatory composition according to claim 1, wherein the composition comprises
(a) one or more antigens, and
(b) an effective amount of at least one N-acyl-dipeptide-like adjuvant bearing an acid group in neutral or charged state, at one end portion of said dipeptide-like adjuvant and bearing an accessory functional side chain spacer at the other end portion thereof, having the general formula (I):

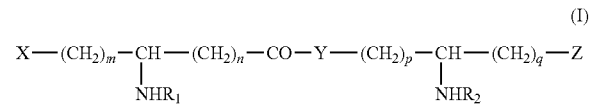

$$X-(CH_2)_m-\underset{NHR_1}{CH}-(CH_2)_n-CO-Y-(CH_2)_p-\underset{NHR_2}{CH}-(CH_2)_q-Z \quad (I)$$

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from a group consisting of hydroxyl, alkyl, alkoxy, acyloxy, amino, acylamino, acylthio and $(C_{1-24})$ alkylthio groups, subscripts m, n are integers ranging from 0 to 10,
subscripts p, q are integers ranging from 1 to 10,
Y designates O or NH, X and Z each designate an accessory functional side chain spacer or an acid group either in neutral or charged state selected from a group consisting of
carboxyl,
carboxy [$(C_{1-5})$alkoxy],
carboxy [$(C_{1-5})$alkylthio],
phosphono [$(C_{1-5})$alkoxy],
phosphono [$(C_{1-5})$alkylthio], dihydroxyphosphoryloxy[$C_{1-5}$)alkoxy],
dihydroxyphosphoryloxy[$C_{1-5}$)alkylthio],
dihydroxyphosphoryloxy,
hydroxysulfonyloxy,
hydroxysulfonyl[($C_{1-5}$)alkoxy],
hydroxysulfonyl [($C_{1-5}$) alkylthio],
hydroxysulfonyloxy [($C_{1-5}$)alkoxy],
hydroxysulfonyloxy [($C_{1-5}$)alkylthio],
[carboxy($C_{1-5}$)alkyl]aminocarbonyl,
[dicarboxy($C_{1-5}$)alkyl]aminocarbonyl,
[ammonio($C_{1-5}$)alkyl]aminocarbonyl, and
{carboxy[amino($C_{1-5}$)alkyl]aminocarbonyl,
provided that one of substituents X or Z designates an accessory functional side chain spacer, and the pharmaceutically acceptable salts, enantiomers and diastereomers of the N-acyl-dipeptide-like adjuvant.

3. The immunomodulatory composition according to claim 1, wherein said adjuvant is selected from a group consisting of:

N—-[(R)-3-dodecanoyloxytetradecanoyl]-D-aspartic acid, α-N-{(4R)-5-hydroxy-4-[(R)-3-hydroxytetradecanoylamino]pentyl}amide and addition salts with a mineral or an organic base thereof, 3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6,7-dihydroxyheptanoate) and addition salts with a mineral or an organic base thereof, 3-[(R)-3-dodecanoyloxytétradecanoylamino]-4-oxo-5-aza-9-[(R)-3-hydroxytetradecanoylamino]-decan-1,10-diol 1-dihydrogenphosphate 10-(6-oxohexanoate) and addition salts with a mineral or an organic base thereof, N—[(R)-3-dodecanoyloxytetradecanoyl]-D-aspartic acid, α-N-{(4R)-5-hydroxy-4-[(R)-3-hydroxytetradecanoylamino]pentyl}amide 5-O-(6,7-dihydroxyheptanoate) and addition salts with a mineral or an organic base thereof, N—[(R)-3-dodecanoyloxytetradecanoyl]-D-aspartic acid, α-N-{(4R)-5-hydroxy-4-[(R)-3-hydroxytetradecanoylamino]pentyl}amide 5-O-(6-oxohexanoate) and addition salts with a mineral or an organic base thereof, N—[(R)-3-dodecanoyloxytetradecanoyl]-D-aspartic acid, α-N-{(4R)-5-hydroxy-4-[(R)-3-hydroxytetradecanoylamino]pentyl}amide 5-O-(6-hydroxyhexanoate) and addition salts with a mineral or an organic base thereof, (3RS,9R)-3-[(R)-3-dodecanoyloxytetradecanoylamino]-4-oxo-5-aza-9-[(R)-3-hydroxy-tetra-decanoylamino]-decan-1,10-diol 1-dihydrogenphosphate 10-(6-aminohexanoate) and addition salts with a mineral or an organic base thereof, (3R,9R)-3-[(R)-3-dodecanoyloxytetradecanoylamino]-4-oxo-5-aza-9-[(R)-3-hydroxy-tetra-decanoylamino]-decan-1,10-diol 1-dihydrogenphosphate 10-(6-aminohexanoate) and addition salts with a mineral or an organic base thereof, (3S,9R)-3-[(R)-3-dodecanoyloxytetradecanoylamino]-4-oxo-5-aza-9-[(R)-3-hydroxy-tetra-decanoylamino]-decan-1,10-diol 1-dihydrogenphosphate 10-(6-aminohexanoate) and addition salts with a mineral or an organic base thereof, 3-[(R)-3-dodecanoyloxytetradecanoylamino]-4-oxo-5-aza-9-[(R)-3-hydroxytetradecanoylamino]-decan-1,10-diol 1-dihydrogenphosphate 10-(6-hydroxyhexanoate) and addition salts with a mineral or an organic base thereof, 2-[(R)-3-hydroxytetradecanolamino]-5-(6-oxohexyl)amino}pentyl 2-[(R)-3-dodecanoyloxytetradecanoylamino]-4-(dihydroxyphosphoryloxy)-butanoate and addition salts with a mineral or an organic base thereof, (2R,8R)-2-[(R)-3-dodecanoyloxytetradecanoylamino]-3-oxo-4-aza-8-[(R)-3-hydroxytetradecanoylamino]-nonane-1,9-diol 1-O-carboxymethyl ether 9-O-(6-oxohexanoate) and addition salts with a mineral or an organic base thereof, (2S,8R)-1-(carboxymethyl)-thio-2-[(R)-3-tetra-decanoyloxy-tetradecanoylamino]-3-oxo-4-aza-8-[(R)-3-hydroxytetradecanoylamino]-nonan-9-ol 9-O-(7-aminoheptanoate) and addition salts with a mineral or an organic base thereof, (2R,8R)-2-[(R)-3-dodecanoyloxytetradecanoylamino]-3-oxo-4-aza-8-[(R)-3-hydroxytetradecanoylamino]-nonan-1,9-ol 1-O-(2,2-dicarboxyethyl)ether 9-O(6-hexanoate) and addition salts with a mineral or an organic base thereof, 3-[(R)-3-dodecanoyloxytetradecanoylamino]-4-oxo-5-aza-9-[(R)-3-hydroxytetradecanoylamino]-1,10-diol 1-dihydrogenphosphate 10-(6-bromoacetamidohexanoate) and addition salts with a mineral or an organic base thereof, (3RS,9R)-3-[(R)-3-hydroxytetradecanoylamino]-4-oxo-5-aza-9-[(R)-3-dodecanoyloxytetradecanoylamino]-decan-1,10-diol 1-dihydrogenphosphate 10-O-(6-oxohexanoate) and addition salts with a mineral or an organic base thereof, N—[(R)-3-dodecanoyloxytetradecanoyl]-D-aspartic acid, α-N-{(4R)-5-(6-aminohexanoyloxy)-4-[(R)-3-hydroxytetradecanoylamino]pentyl}amide and addition salts with a mineral or an organic base thereof, N—[(R)-3-dodecanoyloxytetradecanoyl]-D-aspartic acid, α-N-{(4R)-5-(6-succinylamidohexanoyloxy)-4-[(R)-3-hydroxytetradecanoyl-amino]pentyl}amide and addition salts with a mineral or an organic base thereof, N—[(R)-3-dodecanoyloxytetradecanoyl]-D-aspartic acid, α-N-{(4R)-5-glycinyloxy-4-[(R)-3-hydroxytetradecanoylamino]pentyl}amide and addition salts with a mineral or an organic base thereof, N—[(R)-3-dodecanoyloxytetradecanoyl]-D-aspartic acid, α-N-{(4R)-5-succinyloxy-4-[(R)-3-hydroxytetradecanoylamino]pentyl}amide and addition salts with a mineral or an organic base thereof, N—[(R)-3-dodecanoyloxytetradecanoyl]-D-aspartic acid, α-N-{(4R)-5-hydroxy-4-[(R)-3-hydroxytetradecanoylamino]pentyl}amide β-N-(3-aminopropyl)amide and addition salts with a mineral or an organic base thereof, N—[(R)-3-dodecanoyloxytetradecanoyl]-D-aspartic acid, α-N-{(4R)-5-hydroxy-4-[(R)-3-hydroxytetradecanoylamino]pentyl}amide β-N-[(1S)-1-carboxy-5-aminopentyl]amide and addition salts with a mineral or an organic base thereof, N—[(R)-3-dodecanoyloxytetradecanoyl]-D-aspartic acid, α-N-{(4R)-5-(6-aminohexanoyloxy)-4-[(R)-3-hydroxytetradecanoylamino]pentyl}amide β-N-[(1S)-1-carboxy-5-aminopentyl]amide and addition salts with a mineral or an organic base thereof, N—[(R)-3-dodecanoyloxytetradecanoyl]-D-aspartic acid, α-N-{(4R)-5-hydroxy-4-[(R)-3-hydroxytetradecanoylamino]pentyl}amide β-N-[(1S)-1,2-dicarboxyethyl]amide and addition salts with a mineral or an organic base thereof, N—[(R)-3-dodecanoyloxytetradecanoyl]-D-aspartic acid, α-N-{(4R)-5-(6-aminohexanoyloxy)-4-[(R)-3-hydroxytetradecanoylamino]pentyl}amide β-N-[(1S)-1,2-dicarboxyethyl]amide and addition salts with a mineral or an organic base thereof, N-acetyl-D-aspartic acid, α-N-{(4R)-5-(6-aminohexanoyloxy)-4-[(R)-3-hydroxytetradecanoylamino]pentyl}amide and addition salts with a mineral or an organic base thereof, and N-(2-decanoyloxyoctanoyl)-D-aspartic acid, α-N-{(4R)-5-(6-aminohexanoyloxy)-4-[(R)-3-hydroxytetradecanoylamino]pentyl}amide and addition salts with a mineral or an organic base thereof.

4. The composition according to claim 2 wherein said antigen may be obtained from one or more bacteria, fungus, virus, parasite or protozoa, protein, polysaccharide, lipoprotein, enzyme, or components produced by micro-organisms.

5. The composition of claim 1, further comprising a drug, an antibiotic or substances which act on the central nervous system.

6. The composition of claim 5, wherein the drug is AZT or d4T, and wherein the antibiotic is a macrolid.

7. The composition of claim 5 as a prodrug, wherein the drug is conjugated to the N-acyl-dipeptide-like adjuvant, and is released after cleavage.

8. The composition of claim 4, wherein the antigen, protein, polysaccharide, lipoprotein, drug, enzyme, or said other component produced by microorganisms is conjugated to the N-acyl-dipeptide-like adjuvant, and is released after cleavage.

9. The composition of claim 8, wherein the antigen is Influenza Hemagglutinin $H_1N_1$, *Plasmodium* nonapeptide SYVPSAEQI from *Plasmodium*, peptide FGFG, peptide $(NANP)_6P_2P_{30}$, peptide $P_2P_{30}$, peptide $(NANP)_3CS.T3$, peptide MR99B, or an epitope T of *Plasmodium yoelii*, peptide of Ag85c.

10. The composition according to claim 2 wherein the dose of the N-acyl-dipeptide-like adjuvant is 0.005 mg to 200 mgs per unit dosage.

11. The composition according to claim 1 further comprising one or more excipients.

12. The composition according to claim 2 further comprising one or more excipients.

13. A method of eliciting an immune response in a subject, said method comprising the step of administering to said patient a therapeutically effective amount of a composition according to claim 1.

14. A method of eliciting an immune response in a subject, said method comprising the step of administering to said patient a therapeutically effective amount of the composition of claim 2.

15. The method according to claim 14 wherein one or more antigens or drugs are conjugated to N-acyl-dipeptide-like adjuvant with the proviso that any one of X or Z in the adjuvant is not phosphono [$(C_{1-5})$alkoxy],
phosphono [$(C_{1-5})$alkylthio],
dihydroxyphosphoryloxy[$C_{1-5}$)alkoxy],
dihydroxyphosphoryloxy[$C_{1-5}$)alkylthio],
dihydroxyphosphoryloxy,
wherein X or Z designates an accessory side chain spacer
A-$(CO)_r$—$(CH_2)_s$—W as defined in claim 1.

16. The method of claim 15, wherein said antigen may be obtained from one or more bacteria, fungus, virus, parasite or protozoa, protein, polysaccharide, lipoprotein, enzyme, or components produced by micro-organisms.

17. The method of claim 15, wherein said drug is AZT or d4T, an antibiotic or substances which act on the central nervous system.

18. The method according to claim 14 wherein one or more antigens and the N-acyl-dipeptide-like adjuvant are first combined and the combination is administered to the subject.

19. The method according to claim 14, wherein said composition is administered via mucosal, submucosal, parenteral, rectal, topical, subcutaneous, transcutaneous, oral, digestive route, inhalation or by way of oral or nasal delivery.

20. A kit containing a composition comprising an effective amount of at least one N-acyl-dipeptide-like adjuvant bearing an acid group in neutral or charged state, at one end portion of said dipeptide-like adjuvant and bearing an accessory functional side chain spacer at the other end portion thereof, having the general formula I:

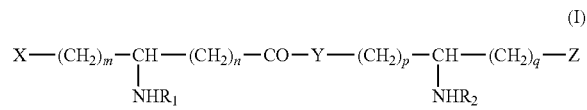

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from a group consisting of hydroxyl, alkyl, alkoxy, acyloxy, amino, acylamino, acylthio and ($C_{1-24}$) alkylthio groups, subscripts m, n are integers ranging from 0 to 10,
subscripts p, q are integers ranging from 1 to 10,
wherein Y designates O or NH, and wherein one of X or Z designates an acid group either in neutral or charged state selected from a group consisting of
carboxyl,
carboxy [($C_{1-5}$)alkoxy],
carboxy [($C_{1-5}$)alkylthio],
phosphono [($C_{1-5}$)alkoxy],
phosphono [($C_{1-5}$)alkylthio],
dihydroxyphosphoryloxy[$C_{1-5}$)alkoxy],
dihydroxyphosphoryloxy[$C_{1-5}$)alkylthio],
dihydroxyphosphoryloxy,
hydroxysulfonyloxy,
hydroxysulfonyl[($C_{1-5}$)alkoxy],
hydroxysulfonyl [($C_{1-5}$) alkylthio],
hydroxysulfonyloxy [($C_{1-5}$)alkoxy],
hydroxysulfonyloxy [($C_{1-5}$)alkylthio],
[carboxy($C_{1-5}$)alkyl]aminocarbonyl,
[dicarboxy($C_{1-5}$)alkyl]aminocarbonyl,
[ammonio($C_{1-5}$)alkyl]aminocarbonyl, and
{carboxy[amino($C_{1-5}$)alkyl]aminocarbonyl,
and the other X or Z designates an accessory functional side chain spacer having the formula (II)

wherein A designates either O, S or NH,
subscript r is an integer equal to 0 or 1,
subscript s is an integer ranging from 1 to 10,
W is selected from a group consisting of,
formyl,
acetyl,
cyano,
halogeno,
amino,
bromo- or iodo-acetamido,
acylamido,
diacylimido,
sulfhydril,
alkylthio,
hydroxyl,
1,2-dihydroxyethyl,
alkoxy, acyloxy,
vinyl,
ethynyl,
free carboxyl,
esterified carboxyl or in the form of a mixed anhydride, amide or hydrazide,
azido, and
thiocyano,
provided that one of substituents X or Z designates said accessory functional side chain spacer, and their pharmaceutically acceptable salts, enantiomers and diastereomers of the N-acyl-dipeptide-like adjuvant.

* * * * *

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial sequence
<220> FEATURE:
<223> OTHER INFORMATION: Partially synthesized and protozoa

<400> SEQUENCE: 1

Ser Tyr Val Pro Ser Ala Glu Gln Ile
1               5

<210> SEQ ID NO 2
<211> LENGTH: 59
<212> TYPE: PRT
<213> ORGANISM: Artificial sequence
<220> FEATURE:
<223> OTHER INFORMATION: Partially synthesized and recombinant
      bacteria/protozoa

<400> SEQUENCE: 2

Asn Ala Asn Pro Asn Ala Asn Pro Asn Ala Asn Pro Asn Ala Asn
1               5                   10                  15

Pro Asn Ala Asn Pro Asn Ala Asn Pro Gln Tyr Ile Lys Ala Asn
                20                  25                  30

Ser Lys Phe Ile Gly Ile Thr Glu Phe Asn Asn Phe Thr Val Ser
                35                  40                  45

Phe Trp Leu Arg Val Pro Lys Val Ser Ala Ser His Leu Glu
                50                  55

<210> SEQ ID NO 3
<211> LENGTH: 36
<212> TYPE: PRT
<213> ORGANISM: Artificial sequence
<220> FEATURE:
<223> OTHER INFORMATION: Partially synthesized and bacteria

<400> SEQUENCE: 3

Lys Gln Tyr Ile Lys Ala Asn Ser Lys Phe Ile Gly Ile Thr Glu
1               5                   10                  15

Phe Asn Asn Phe Thr Val Ser Phe Trp Leu Arg Val Pro Lys Val
                20                  25                  30

Ser Ala Ser His Leu Glu
                35

<210> SEQ ID NO 4
<211> LENGTH: 32
<212> TYPE: PRT
<213> ORGANISM: Artificial sequence
```

```
<220> FEATURE:
<223> OTHER INFORMATION: Partially synthesized and recombinant
      bacteria/protozoa

<400> SEQUENCE: 4

Asn Ala Asn Pro Asn Ala Asn Pro Asn Ala Asn Pro Asp Ile Glu
1               5                   10                  15

Lys Lys Ile Ala Lys Met Glu Lys Ala Ser Ser Val Phe Asn Trp
                20                  25                  30

Asn Ser

<210> SEQ ID NO 5
<211> LENGTH: 12
<212> TYPE: PRT
<213> ORGANISM: Artificial sequence
<220> FEATURE:
<223> OTHER INFORMATION: Synthetic

<400> SEQUENCE: 5

Ser Glu Arg Ser Tyr Val Pro Ser Ala Glu Gln Ile
1               5                   10

<210> SEQ ID NO 6
<211> LENGTH: 20
<212> TYPE: PRT
<213> ORGANISM: Artificial sequence
<220> FEATURE:
<223> OTHER INFORMATION: Synthetic

<400> SEQUENCE: 6

Lys Gly Gly Lys Gly Gly Lys Ser Glu Arg Ser Tyr Val Val Trp
1               5                   10                  15

Pro Ser Ala Glu Gln
                20

<210> SEQ ID NO 7
<211> LENGTH: 10
<212> TYPE: PRT
<213> ORGANISM: Artificial sequence
<220> FEATURE:
<223> OTHER INFORMATION: Synthetic

<400> SEQUENCE: 7

Lys Gly Gly Lys Gly Gly Lys Ser Glu Arg
1               5                   10

<210> SEQ ID NO 8
<211> LENGTH: 11
<212> TYPE: PRT
<213> ORGANISM: Artificial sequence
<220> FEATURE:
<223> OTHER INFORMATION: Partially synthesized and bacteria

<400> SEQUENCE: 8

Tyr Leu Gln Val Pro Ser Ala Ser Met Gly Arg
1               5                   10

<210> SEQ ID NO 9
<211> LENGTH: 19
<212> TYPE: PRT
<213> ORGANISM: Artificial sequence
<220> FEATURE:
<223> OTHER INFORMATION: Partially synthesized and bacteria

<400> SEQUENCE: 9

Met Val Gln Ile Arg Pro Arg Leu Val Ala Asn Asn Thr Arg Ile
```

```
                1               5                  10                  15
Trp Val Tyr Cys

<210> SEQ ID NO 10
<211> LENGTH: 25
<212> TYPE: PRT
<213> ORGANISM: Artificial sequence
<220> FEATURE:
<223> OTHER INFORMATION: Partially synthesized and bacteria

<400> SEQUENCE: 10

Pro Tyr Ala Ala Ser Leu Ser Gly Phe Leu Asn Pro Ser Glu Gly
1               5                   10                  15

Trp Trp Pro Thr Leu Ile Gly Leu Ala Met
                20                  25

<210> SEQ ID NO 11
<211> LENGTH: 19
<212> TYPE: PRT
<213> ORGANISM: Artificial sequence
<220> FEATURE:
<223> OTHER INFORMATION: Synthetic

<400> SEQUENCE: 11

Lys Gly Gly Lys Gly Gly Lys Ser Glu Arg Ser Tyr Val Pro Ser
1               5                   10                  15

Ala Glu Gln Ile

<210> SEQ ID NO 12
<211> LENGTH: 4
<212> TYPE: PRT
<213> ORGANISM: Artificial sequence
<220> FEATURE:
<223> OTHER INFORMATION: Partially synthesized and protozoa

<400> SEQUENCE: 12

Asn Ala Asn Pro
1

<210> SEQ ID NO 13
<211> LENGTH: 26
<212> TYPE: PRT
<213> ORGANISM: Artificial sequence
<220> FEATURE:
<223> OTHER INFORMATION: Partially synthesized and protozoa

<400> SEQUENCE: 13

Asn Ala Asn Pro Asn Ala Asn Pro Asn Ala Asn Pro Asn Ala Asn
1               5                   10                  15

Pro Asn Ala Asn Pro Asn Ala Asn Pro Asn Ala
                20                  25

<210> SEQ ID NO 14
<211> LENGTH: 4
<212> TYPE: PRT
<213> ORGANISM: Artificial sequence
<220> FEATURE:
<223> OTHER INFORMATION: Synthetic

<400> SEQUENCE: 14

Phe Gly Phe Gly
1

<210> SEQ ID NO 15
<211> LENGTH: 7
```

```
<212> TYPE: PRT
<213> ORGANISM: Artificial sequence
<220> FEATURE:
<223> OTHER INFORMATION: Synthetic

<400> SEQUENCE: 15

Lys Gly Gly Lys Gly Gly Lys
1               5
```